United States Patent
Zhang

(10) Patent No.: US 9,918,983 B2
(45) Date of Patent: Mar. 20, 2018

(54) SUICIDAL LSD1 INHIBITORS TARGETING SOX2-EXPRESSING CANCER CELLS

(71) Applicant: THE BOARD OF REGENTS OF THE NEVADA SYSTEM OF HIGHER EDUCATION on behalf of THE UNIVERSITY OF NEVADA, LAS VEGAS, Las Vegas, NV (US)

(72) Inventor: Hui Zhang, Las Vegas, NV (US)

(73) Assignee: THE BOARD OF REGENTS OF THE NEVADA SYSTEM OF HIGHER EDUCATION ON BEHALF OF THE UNIVERSITY OF NEVADA, LAS VEGAS, Las Vegas, NV (US)

( * ) Notice: Subject to any disclaimer, the term of this patent is extended or adjusted under 35 U.S.C. 154(b) by 19 days.

(21) Appl. No.: 14/894,893

(22) PCT Filed: May 30, 2014

(86) PCT No.: PCT/US2014/040368
§ 371 (c)(1),
(2) Date: Nov. 30, 2015

(87) PCT Pub. No.: WO2014/194280
PCT Pub. Date: Dec. 4, 2014

(65) Prior Publication Data
US 2016/0120862 A1    May 5, 2016

Related U.S. Application Data

(60) Provisional application No. 61/828,749, filed on May 30, 2013, provisional application No. 61/937,394, filed on Feb. 7, 2014.

(51) Int. Cl.
| | |
|---|---|
| C07C 217/74 | (2006.01) |
| A61K 31/495 | (2006.01) |
| A61K 45/06 | (2006.01) |
| A61K 31/135 | (2006.01) |
| A61K 31/137 | (2006.01) |
| A61K 31/15 | (2006.01) |
| A61K 31/165 | (2006.01) |
| A61K 31/167 | (2006.01) |
| A61K 31/19 | (2006.01) |
| A61K 31/20 | (2006.01) |
| A61K 31/27 | (2006.01) |
| A61K 31/785 | (2006.01) |
| C07C 271/24 | (2006.01) |
| C07D 207/14 | (2006.01) |
| C07D 295/13 | (2006.01) |
| A61K 31/185 | (2006.01) |
| A61K 31/325 | (2006.01) |
| A61K 31/40 | (2006.01) |
| A61K 31/4406 | (2006.01) |

(52) U.S. Cl.
CPC .......... *A61K 31/495* (2013.01); *A61K 31/135* (2013.01); *A61K 31/137* (2013.01); *A61K 31/15* (2013.01); *A61K 31/165* (2013.01); *A61K 31/167* (2013.01); *A61K 31/185* (2013.01); *A61K 31/19* (2013.01); *A61K 31/20* (2013.01); *A61K 31/27* (2013.01); *A61K 31/325* (2013.01); *A61K 31/40* (2013.01); *A61K 31/4406* (2013.01); *A61K 31/785* (2013.01); *A61K 45/06* (2013.01); *C07C 217/74* (2013.01); *C07C 271/24* (2013.01); *C07D 207/14* (2013.01); *C07D 295/13* (2013.01); *C07C 2101/02* (2013.01)

(58) Field of Classification Search
CPC ........................... C07C 217/74; A61K 31/495
See application file for complete search history.

(56) References Cited

U.S. PATENT DOCUMENTS

| | | | | |
|---|---|---|---|---|
| 8,853,408 B2* | 10/2014 | Johnson | ............... | C07D 401/04 546/235 |
| 9,006,449 B2* | 4/2015 | Fyfe | ..................... | C07D 409/10 546/276.4 |
| 9,181,198 B2* | 11/2015 | Ortega Munoz | .... | C07D 213/73 |
| 9,278,931 B2* | 3/2016 | Tomita | ................. | A61K 31/167 |
| 2010/0324147 A1 | 12/2010 | McCafferty et al. | | |

FOREIGN PATENT DOCUMENTS

| | | |
|---|---|---|
| GB | 933168 A | 8/1963 |
| WO | WO-2011/035941 A1 | 3/2011 |
| WO | WO-2012/135113 A2 | 10/2012 |
| WO | WO-2013/057320 A1 | 4/2013 |

OTHER PUBLICATIONS

Neelamegam et al (2011): STN International, HCAPLUS database,(Columbus, Ohio), Accession No. 2011: 1488108.*
Suzuki et al (2012): STN International HCAPLUS database, (Columbus, Ohio), Accession No. 2012: 261326.*
Johnson et al (2012): STN International HCAPLUS database, (Columbus, Ohio), Accession No. 2012: 1443168.*
Adamo, A., et al. (20 11) LSD1 regulates the balance between self-renewal and differentiation in human embryonic stem cells, Nat. Cell Biol. vol. 13, No. 6, pp. 652-659.

(Continued)

*Primary Examiner* — Golam M M Shameem
(74) *Attorney, Agent, or Firm* — Ballard Spahr LLP

(57) ABSTRACT

Disclosed are inhibitors of lysine-specific demethylase I (LSD1); synthetic methods for making the compounds; pharmaceutical compositions comprising the compounds; and methods of treating cancers characterized by the presence of Sox2 using the compounds and compositions Also disclosed are methods of treating cancers characterized by the presence of Sox2 using inhibitors of LSD1 and/or histone deacetylation I (HDAC1). This abstract is intended as a scanning tool for purposes of searching in the particular art and is not intended to be limiting of the present invention.

20 Claims, 84 Drawing Sheets

(56) References Cited

OTHER PUBLICATIONS

Almarasson, O., et. al. (2004) Do Pharmaceutical Co-crystals Represent a New Path to Improved Medicines? The Royal Society of Chemistry, 1889-1896.
Alonso, M.M., et al. (2011) Genetic and Epigenetic Modifications of Sox2 Contribute to the Invasive Phenotype of Malignant Gliomas, PLoS One vol. 6, Issue 11, e26740, pp. 1-11.
Bass, A. J. et al., (2009) SOX2 is an amplified lineage-survival oncogene in lung and esophageal squamous cell carcinomas, Nature Genetics, vol. 41, pp. 1238-1242.
Dou, Y., et al. (2005) Physical Association and Coordinate Function of the H3 K4 Methyltransferase MLL1 and the H4 K16 Acetyltransferase MOF, Cell vol. 121, pp. 873-885.
Dovey, 0. M., et al. (2010) Histone deacetylase 1 (HDAC1), but not HDAC2, controls embryonic stem cell differentiation, PNAS USA vol. 107, No. 18 pp. 8242-8247.
Fantes, J., et al. (2003) Mutations in SOX2 cause anophthalmia, Nat. Genet. vol. 33, pp. 461-463.
Ferri, A. L., et al. (2004) Sox2 deficiency causes neurodegeneration and impaired neurogenesis in the adult mouse brain, Development vol. 131, 3805-3819.
Haberland, M., et al. (2009) Genetic dissection of histone deacetylase requirement in tumor cells, PNAS USA vol. 106, No. 19, pp. 7751-7755.
Harris, W. J., et al. (2012) The Histone Demethylase KDM1A Sustains the Oncogenic Potential of MLL-AF9 Leukemia Stem Cells, Cancer Cell vol. 21, pp. 473-487.
Hu, N., et al. (2010) Genome wide analysis of DNA copy number neutral loss of heterozygosity (CNNLOH) and its relation to gene expression in esophageal squamous cell carcinoma, BMC Genomics vol. 11, No. 1, p. 576-587.
Huang, Y., et al. (2007) Inhibition of lysine-specific demethylase 1 by polyamine analogues results in reexpression of aberrantly silenced genes, PNAS vol. 104, No. 19, pp. 8023-8028.
Jin, J., eta. (2006) A family of diverse Cul4-Ddb1-interacting proteins includes Cdt2, which is required for S phase destruction of the replication factor Cdt1, Mol. Cell vol. 23, No. 5, pp. 709-721.
Jurkin, J., et al. (20 11) Distinct and redundant functions of histone deacetylases HDAC1 and HDAC2 in proliferation and tumorigenesis, Cell Cycle vol. 10, pp. 406-412.
Lengerke, C., et al. (2011) Expression of the embryonic stem cell marker SOX2 in early-stage breast carcinoma, BMC Cancer vol. 11, pp. 42-52.
Miller, K.M., et al. (2010) Human HDAC1 and HDAC2 function in the DNA-damage response to promote DNA nonhomologous end-joining, Nature Struct. Mol. Bioi. vol. 17, pp. 1144-1151.
Neumann, J., et al. (2011) SOX2 expression correlates with lymph-node metastases and distant spread in right-sided colon cancer, BMC Cancer vol. 11, pp. 518.
PubChem. Compound Summary for: CID 51034697. Create Date: Apr. 18, 2011. [retrieved on Sep. 2014]. Retrieved from the Internet. <URL: https://pubchem.ncbi.nlm.nih.gov/compound/51034697?from=summary>.
PubChem. Compound Summary for: CID 69685062. Create Date: Dec. 1, 2012. [retrieved on Sep. 2014]. Retrieved from the Internet. <URL: https://pubchem.ncbi.nlm.nih.gov/compound/69685062?from=summary>.
Rudin. et al., (2012) Comprehensive genomic analysis identifies SOX2 as a frequently amplified gene in small-cell lung cancer, Nature Genetics, vol. 44, No. 10, pp. 1111-1116.
Scotto, L., et al. (2008) Identification of copy number gain and overexpressed genes on chromosome arm 20q by an integrative genomic approach in cervical cancer: potential role in progression, Genes Chromosomes Cancer, vol. 47, No. 9, pp. 755-765.
Shi, Y. (2007) Histone lysine demethylases: emerging roles in development, physiology and disease, Nat. Rev. Genet. vol. 8, No. 11, pp. 829-833.
Shi, Y. J., et al. (2005) Regulation of LSD1 histone demethylase activity by its associated factors, Mol. Cell vol. 19, No. 6, pp. 857-864.
Shi, Y., et al. (2003) Coordinated histone modifications mediated by a CtBP co-repressor complex, Nature vol. 422, No. 6933, pp. 735-738.
Sorlie, T., et al. (2003) Repeated observation of breast tumor subtypes in independent gene expression data sets, PNAS USA vol. 100, No. 14, pp. 8418-8423.
Wang, J. et al. (2011) Novel Histone Demethylase LSD1 Inhibitors Selectively Target Cancer Cells with Pluripotent Stem Cell Properties, Cancer Research, vol. 71, pp. 7238-7249.
Wang, Y., et al. (2009) LSD1 Is a Subunit of the NuRD Complex and Targets the Metastasis Programs in Breast Cancer, Cell vol. 138, pp. 660-672.
Whyte, W. A., et al. (2012) Enhancer decommissioning by LSD1 during embryonic stem cell differentiation, Nature vol. 482, pp. 221-225.
Williamson, K. A., et al. (2006) Mutations in SOX2 cause anophthalmia-esophageal-genital (AEG) syndrome, Hum. Mol. Genet. vol. 15, pp. 1413-1422.
Yang et al. (2007) Structural basis for the inhibition of the LSD1 histone demethylase by the antidepressant trans-2-phenylcyclopropylamine, Biochemistry vol. 46, pp. 8058-8065.
Zhong, X., et al. (2010) Identification of MicroRNAs Regulating Reprogramming Factor LIN28 in Embryonic Stem Cells and Cancer Cells, J. Bioi. Chern. vol. 285, No. 53 pp. 41961-41971.
Interntional Search Report and Written Opinion were mailed on Dec. 10, 2014 for Application No. PCT/US2014/040368, which was filed on May 30, 2014 nd published as WO2014/194280 on Dec. 4, 2014 (Applicant—Univerity of Nevada).
International Preliminary Report on Patentability was mailed on Dec. 1, 2015 for Application No. PCT/US2014/040368, which was filed on May 30, 2014 nd published as WO2014/194280 on Dec. 4, 2014 (Applicant—Univerity of Nevada).
Communication pursuant to Rules 161(2) and 162 EPC was issued on Jan. 29, 2016 by the Europen Patent Office for EP Application 14804229.4, which was filed on May 30, 2014 and published as 3003301 on Apr. 13, 2016 (Inventor—Hui Zhang; Applicant—University of Nevada) (2 pages).
Dawn, M. Z., et al. (2007) Trans-2-Phenylcyclopropylamine Is a Mechanism-Based Inactivator of the Histone Demethylase LSD1, Biochemistry vol. 46, pp. 4408-4416.
Episkopou, V. (2005) SOX2 functions in adult neural stem cells, Trends Neurosci. vol. 28, pp. 219-221.
Khan, 0. and LaThangue, N. B. (2012) HDAC inhibitors in cancer biology: emerging mechanisms and clinical applications, Immunology and Cell Biology vol. 90, No. 1, pp. 85-94.
Lee, M.G., et al. (2005) An essential role for CoREST in nucleosomal histone 3 lysine 4 demethylation, Nature vol. 437, pp. 432-435.
Leis, 0., et al. (2012) Sox2 expression in breast tumours and activation in breast cancer stem cells, Oncogene vol. 31, No. 11, pp. 1354-1365.
Peng, S., et al. (2008) Pluripotency factors Lin28 and Oct4 identify a sub-population of stem cell-like cells in ovarian cancer, Oncogene vol. 29, pp. 2153-2159.
Witt, O. et al. (2009) HDAC family: What are the cancer relevant targets?, Cancer Lett. vol. 277, pp. 8-21.
Partial European Search Report dated Dec. 20, 2016, by the EPO for application EP 14804229.4, filed on May 30, 2014 and published as EP 3003301 on Apr. 13, 2016 (Applicant—U. of Nevada, Las Vegas//Inventor—Zhang, et al.) (10 pages).
Benelkebir, et al., "Enantioselective synthesis of tranylcypromine analogues as 14,15 lysine demethylase (LSD1) inhibitors", Bioorganic & Medicinal Chemistry,. vol. 19, No. 12, 2011, pp. 3789-3716.

\* cited by examiner

FIG. 27A  FIG. 27B

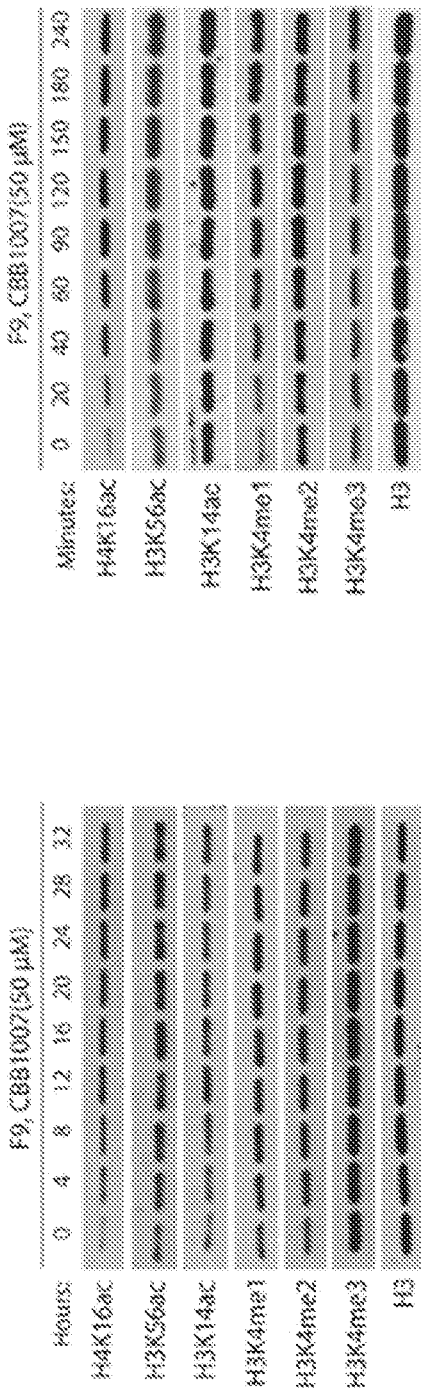
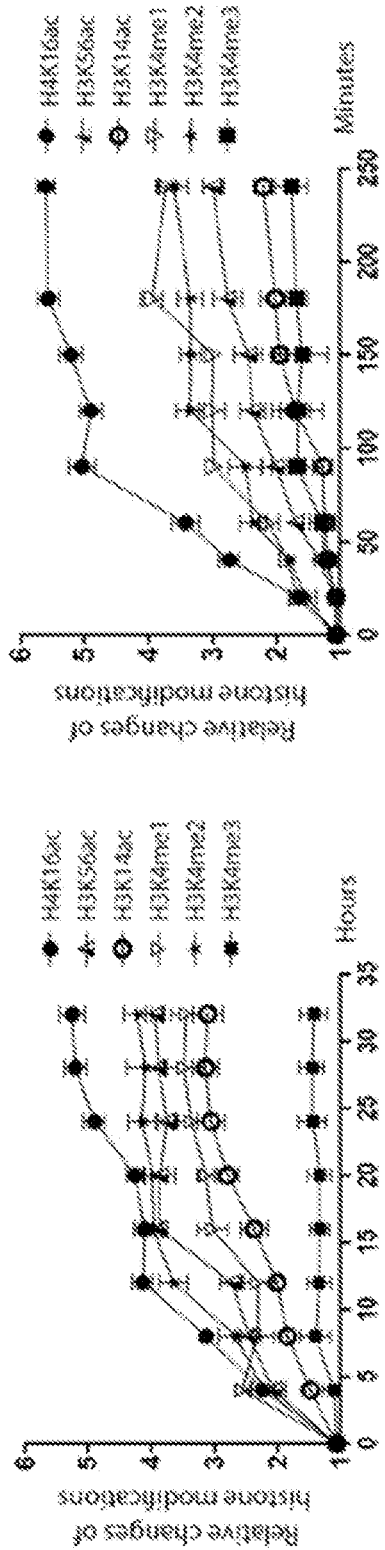
FIG. 28C
FIG. 28D

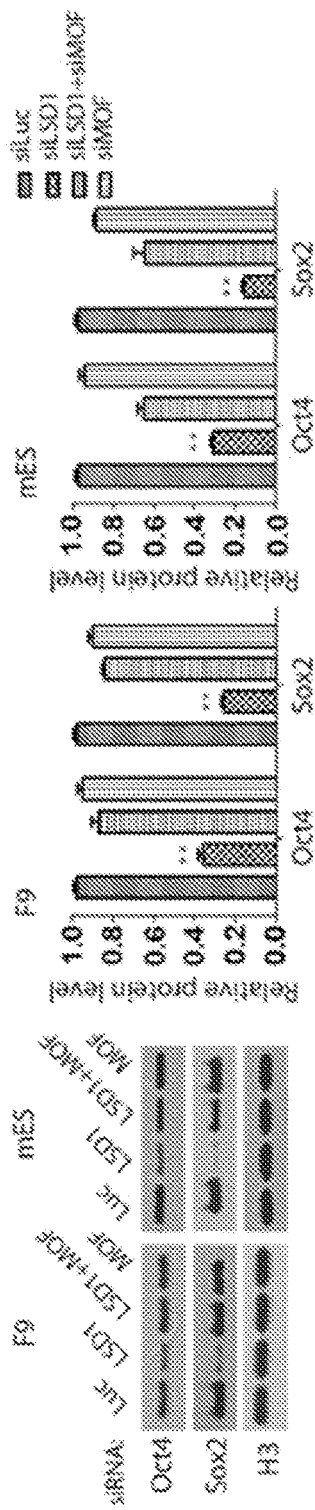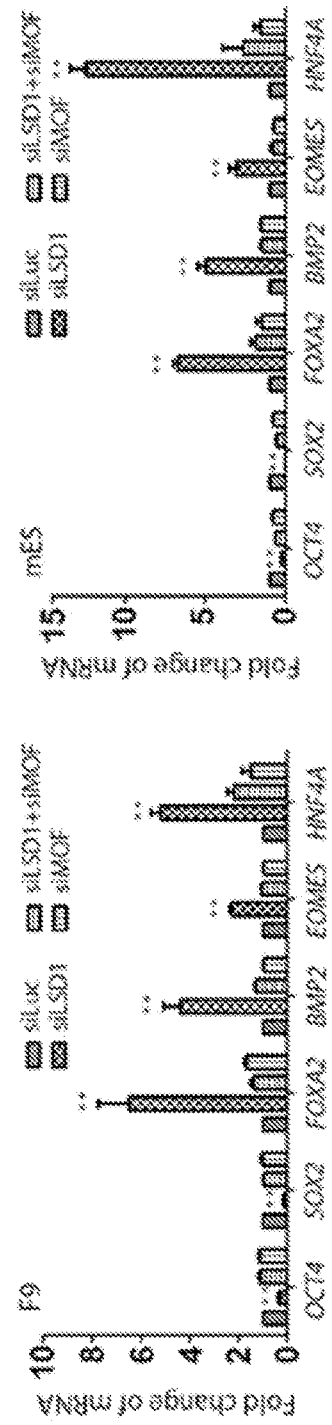
FIG. 37B
FIG. 37C

SEQUENCE LISTING

<160> NUMBER OF SEQ ID NOS: 374

<210> SEQ ID NO 1
<211> LENGTH: 19
<212> TYPE: RNA
<213> ORGANISM: Artificial Sequence
<220> FEATURE:
<223> OTHER INFORMATION: synthetic construct; human LSD1 siRNA

<400> SEQUENCE: 1
ggaagaagau agugaaaac                                              19

<210> SEQ ID NO 2
<211> LENGTH: 19
<212> TYPE: RNA
<213> ORGANISM: Artificial Sequence
<220> FEATURE:
<223> OTHER INFORMATION: synthetic construct; human Sox2 siRNA

<400> SEQUENCE: 2
cgcucaugaa gaaggauaa                                              19

<210> SEQ ID NO 3
<211> LENGTH: 19
<212> TYPE: DNA
<213> ORGANISM: Artificial Sequence
<220> FEATURE:
<223> OTHER INFORMATION: synthetic contruct; Mouse-HDAC1 siRNA

<400> SEQUENCE: 3
gcaagcagat gcagagatt                                              19

<210> SEQ ID NO 4
<211> LENGTH: 19
<212> TYPE: DNA
<213> ORGANISM: Artificial Sequence
<220> FEATURE:
<223> OTHER INFORMATION: synthetic construct; Human-HDAC1 siRNA

<400> SEQUENCE: 4
gcaagcagat gcagagatt                                              19

<210> SEQ ID NO 5
<211> LENGTH: 19
<212> TYPE: DNA
<213> ORGANISM: Artificial Sequence
<220> FEATURE:
<223> OTHER INFORMATION: synthetic construct; Mouse-HDAC2 siRNA

<400> SEQUENCE: 5
ccagaacact ccagaatat                                              19

<210> SEQ ID NO 6
<211> LENGTH: 19
<212> TYPE: DNA
<213> ORGANISM: Artificial Sequence
<220> FEATURE:
<223> OTHER INFORMATION: synthetic construct; Human-HDAC2 siRNA

<400> SEQUENCE: 6
agactgatat ggctgttaa                                              19

<210> SEQ ID NO 7
<211> LENGTH: 19
<212> TYPE: DNA
<213> ORGANISM: Artificial Sequence

```
<220> FEATURE:
<223> OTHER INFORMATION: synthetic construct; Mouse-HDAC3 siRNA

<400> SEQUENCE: 7
gcattgatga ccagagtta                                                    19

<210> SEQ ID NO 8
<211> LENGTH: 19
<212> TYPE: DNA
<213> ORGANISM: Artificial Sequence
<220> FEATURE:
<223> OTHER INFORMATION: synthetic construct; Human-HDAC3 siRNA

<400> SEQUENCE: 8
aaagcgatgt ggagattta                                                    19

<210> SEQ ID NO 9
<211> LENGTH: 19
<212> TYPE: DNA
<213> ORGANISM: Artificial Sequence
<220> FEATURE:
<223> OTHER INFORMATION: synthetic construct; Mouse-HDAC6 siRNA

<400> SEQUENCE: 9
ggatgttcat catggtaat                                                    19

<210> SEQ ID NO 10
<211> LENGTH: 19
<212> TYPE: DNA
<213> ORGANISM: Artificial Sequence
<220> FEATURE:
<223> OTHER INFORMATION: synthetic construct; Human-HDAC6 siRNA

<400> SEQUENCE: 10
tgaccaaaat atgatgaat                                                    19

<210> SEQ ID NO 11
<211> LENGTH: 19
<212> TYPE: DNA
<213> ORGANISM: Artificial Sequence
<220> FEATURE:
<223> OTHER INFORMATION: synthetic construct; Mouse-Sirt1 siRNA

<400> SEQUENCE: 11
ccatgaagta tgacaaaga                                                    19

<210> SEQ ID NO 12
<211> LENGTH: 19
<212> TYPE: DNA
<213> ORGANISM: Artificial Sequence
<220> FEATURE:
<223> OTHER INFORMATION: synthetic construct; Human-Sirt1 siRNA

<400> SEQUENCE: 12
cctcaaagta agaccagta                                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic construct; Mouse-LSD1 siRNA

<400> SEQUENCE: 13
aaggaaagcu agaagaaaa                                                    19
```

```
<210> SEQ ID NO 14
<211> LENGTH: 19
<212> TYPE: RNA
<213> ORGANISM: Artificial Sequence
<220> FEATURE:
<223> OTHER INFORMATION: synthetic construct; Human-LSD1 siRNA

<400> SEQUENCE: 14
aaggaaagcu agaagaaaa                                                   19

<210> SEQ ID NO 15
<211> LENGTH: 19
<212> TYPE: DNA
<213> ORGANISM: Artificial Sequence
<220> FEATURE:
<223> OTHER INFORMATION: synthetic construct; Mouse-MOF siRNA

<400> SEQUENCE: 15
gatccagtct cgagtgaac                                                   19

<210> SEQ ID NO 16
<211> LENGTH: 19
<212> TYPE: DNA
<213> ORGANISM: Artificial Sequence
<220> FEATURE:
<223> OTHER INFORMATION: synthetic construct; Human-MOF siRNA

<400> SEQUENCE: 16
gatccagtct cgagtgaac                                                   19

<210> SEQ ID NO 17
<211> LENGTH: 19
<212> TYPE: RNA
<213> ORGANISM: Artificial Sequence
<220> FEATURE:
<223> OTHER INFORMATION: synthetic construct; Mouse-HDAC1 5'-UTR siRNA

<400> SEQUENCE: 17
gcaagauggc gcagacuca                                                   19

<210> SEQ ID NO 18
<211> LENGTH: 19
<212> TYPE: RNA
<213> ORGANISM: Artificial Sequence
<220> FEATURE:
<223> OTHER INFORMATION: synthetic construct; Human-HDAC1 3'-UTR siRNA

<400> SEQUENCE: 18
aagacaaacu ccugaaaug                                                   19

<210> SEQ ID NO 19
<211> LENGTH: 19
<212> TYPE: DNA
<213> ORGANISM: Artificial Sequence
<220> FEATURE:
<223> OTHER INFORMATION: synthetic construct; Mouse-LSD1 3'-UTR siRNA

<400> SEQUENCE: 19
aagcaagtgg tgtgagata                                                   19

<210> SEQ ID NO 20
<211> LENGTH: 19
<212> TYPE: RNA
<213> ORGANISM: Artificial Sequence
<220> FEATURE:
<223> OTHER INFORMATION: synthetic construct; Human-LSD1 3'-UTR siRNA
```

-continued

<400> SEQUENCE: 20
gggaggaacu uguccauua                                                  19

<210> SEQ ID NO 21
<211> LENGTH: 19
<212> TYPE: DNA
<213> ORGANISM: Artificial Sequence
<220> FEATURE:
<223> OTHER INFORMATION: synthetic construct; Mouse-MOF 3'-UTR siRNA

<400> SEQUENCE: 21
tctgggtttc ctggcctct                                                  19

<210> SEQ ID NO 22
<211> LENGTH: 19
<212> TYPE: RNA
<213> ORGANISM: Artificial Sequence
<220> FEATURE:
<223> OTHER INFORMATION: synthetic construct; Human-MOF 3'-UTR siRNA

<400> SEQUENCE: 22
gggaagggga ggccaagaa                                                  19

<210> SEQ ID NO 23
<211> LENGTH: 19
<212> TYPE: RNA
<213> ORGANISM: Artificial Sequence
<220> FEATURE:
<223> OTHER INFORMATION: synthetic construct; Mouse-Tip60 siRNA

<400> SEQUENCE: 23
gacggaguau gacugcaaa                                                  19

<210> SEQ ID NO 24
<211> LENGTH: 19
<212> TYPE: RNA
<213> ORGANISM: Artificial Sequence
<220> FEATURE:
<223> OTHER INFORMATION: synthetic construct; Human-Tip60 siRNA

<400> SEQUENCE: 24
cuccaggcaa ugagauuua                                                  19

<210> SEQ ID NO 25
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 25
aatactggtg gtcgtcaaac                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 26
tgagaactag ccaagcatct                                                 20

<210> SEQ ID NO 27

-continued

```
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 27
tgctggattg aaatagagtg                                          20

<210> SEQ ID NO 28
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 28
taagcctgct gtacttatcg                                          20

<210> SEQ ID NO 29
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 29
cttagacgag gctttgtttg                                          20

<210> SEQ ID NO 30
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 30
gggttagagg aggatgagat                                          20

<210> SEQ ID NO 31
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 31
tttgggtctc ctaacttcta                                          20

<210> SEQ ID NO 32
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 32
gtcattgttc tcccgctcat                                          20

<210> SEQ ID NO 33
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 33
```
caggagttgt caaggcagag                              20

<210> SEQ ID NO 34
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 34
ggaaaatcag gcgaagaata                              20

<210> SEQ ID NO 35
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 35
catcacccac agcaaatgac                              20

<210> SEQ ID NO 36
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 36
ttcctgcaaa gctcctaccg                              20

<210> SEQ ID NO 37
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 37
tactgtgctc agccaagaaa                              20

<210> SEQ ID NO 38
<211> LENGTH: 20
<212> TYPE: DNA
<213> ORGANISM: Artificial Sequence
<220> FEATURE:
<223> OTHER INFORMATION: synthetic construct; human SOX2 reverse primer

<400> SEQUENCE: 38
gcaacaagtg gcataaatca                              20

<210> SEQ ID NO 39
<211> LENGTH: 20
<212> TYPE: DNA
<213> ORGANISM: Artificial Sequence
<220> FEATURE:
<223> OTHER INFORMATION: synthetic construct; human SOX2 forward primer

<400> SEQUENCE: 39
tcccggaatt tgaggcagtc                              20

<210> SEQ ID NO 40
<211> LENGTH: 20
<212> TYPE: DNA

```
<213> ORGANISM: Artificial Sequence
<220> FEATURE:
<223> OTHER INFORMATION: synthetic construct; human SOX2 reverse primer

<400> SEQUENCE: 40
ttggctcggc gatatgaagg                                                     20

<210> SEQ ID NO 41
<211> LENGTH: 20
<212> TYPE: DNA
<213> ORGANISM: Artificial Sequence
<220> FEATURE:
<223> OTHER INFORMATION: synthetic construct; human FOXA2 forward primer

<400> SEQUENCE: 41
caaccttcgg cacaacgatc                                                     20

<210> SEQ ID NO 42
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 42
gaagccacca tacaaactga                                                     20

<210> SEQ ID NO 43
<211> LENGTH: 20
<212> TYPE: DNA
<213> ORGANISM: Artificial Sequence
<220> FEATURE:
<223> OTHER INFORMATION: synthetic construct; human FOXA2 forward primer

<400> SEQUENCE: 43
aatagtgctg tggtggaggt                                                     20

<210> SEQ ID NO 44
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 44
tttgtgagct tatgtgggtg                                                     20

<210> SEQ ID NO 45
<211> LENGTH: 20
<212> TYPE: DNA
<213> ORGANISM: Artificial Sequence
<220> FEATURE:
<223> OTHER INFORMATION: synthetic construct; human FOXA2 forward primer

<400> SEQUENCE: 45
cctgtgccta ctgctacctc                                                     20

<210> SEQ ID NO 46
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 46
gttagcctgt gagcccagat                                                     20
```

<210> SEQ ID NO 47
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 47
gcttctcccg aggccgttcc                    20

<210> SEQ ID NO 48
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 48
actcgcccgc tgctgctcct                    20

<210> SEQ ID NO 49
<211> LENGTH: 20
<212> TYPE: DNA
<213> ORGANISM: Artificial Sequence
<220> FEATURE:
<223> OTHER INFORMATION: synthetic construct; human FOXA2 forward primer

<400> SEQUENCE: 49
ccgcccactt ccaactaccg                    20

<210> SEQ ID NO 50
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 50
gtcagccaaa gcaccgtccc                    20

<210> SEQ ID NO 51
<211> LENGTH: 20
<212> TYPE: DNA
<213> ORGANISM: Artificial Sequence
<220> FEATURE:
<223> OTHER INFORMATION: synthetic construct; human FOXA2 forward primer

<400> SEQUENCE: 51
ggtgtactcc cggcccatta                    20

<210> SEQ ID NO 52
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 52
atttcttctc ccttgcgtct                    20

<210> SEQ ID NO 53
<211> LENGTH: 20
<212> TYPE: DNA
<213> ORGANISM: Artificial Sequence
<220> FEATURE:

<223> OTHER INFORMATION: synthetic construct; human FOXA2 forward primer

<400> SEQUENCE: 53
ccaggtctcg ggtccgatta                                               20

<210> SEQ ID NO 54
<211> LENGTH: 20
<212> TYPE: DNA
<213> ORGANISM: Artificial Sequence
<220> FEATURE:
<223> OTHER INFORMATION: synthetic construct; human FOXA2 reverse primer

<400> SEQUENCE: 54
ccctccctcc ttcttgaaat                                               20

<210> SEQ ID NO 55
<211> LENGTH: 18
<212> TYPE: DNA
<213> ORGANISM: Artificial Sequence
<220> FEATURE:
<223> OTHER INFORMATION: synthetic construct; human Lin28A forward
      primer

<400> SEQUENCE: 55
gggtggatca cgaggtca                                                 18

<210> SEQ ID NO 56
<211> LENGTH: 18
<212> TYPE: DNA
<213> ORGANISM: Artificial Sequence
<220> FEATURE:
<223> OTHER INFORMATION: synthetic construct; human Lin28A reverse
      primer

<400> SEQUENCE: 56
ccaggttcaa gccattct                                                 18

<210> SEQ ID NO 57
<211> LENGTH: 18
<212> TYPE: DNA
<213> ORGANISM: Artificial Sequence
<220> FEATURE:
<223> OTHER INFORMATION: synthetic construct; human Lin28A forward
      primer

<400> SEQUENCE: 57
ttgcagcgag ccaagatc                                                 18

<210> SEQ ID NO 58
<211> LENGTH: 20
<212> TYPE: DNA
<213> ORGANISM: Artificial Sequence
<220> FEATURE:
<223> OTHER INFORMATION: synthetic construct; human Lin28A reverse
      primer

<400> SEQUENCE: 58
tgtaaagggt taggaaagaa                                               20

<210> SEQ ID NO 59
<211> LENGTH: 20
<212> TYPE: DNA
<213> ORGANISM: Artificial Sequence
<220> FEATURE:
<223> OTHER INFORMATION: synthetic construct; human Lin 28A forward
      primer

<400> SEQUENCE: 59
taaatgggtt gtagtggtgg                                               20

<210> SEQ ID NO 60
<211> LENGTH: 18
<212> TYPE: DNA
<213> ORGANISM: Artificial Sequence
<220> FEATURE:
<223> OTHER INFORMATION: synthetic construct; human Lin28A reverse
      primer

<400> SEQUENCE: 60
tactgccctg gtcggaga                                                 18

<210> SEQ ID NO 61
<211> LENGTH: 21
<212> TYPE: DNA
<213> ORGANISM: Artificial Sequence
<220> FEATURE:
<223> OTHER INFORMATION: synthetic construct; human Lin28A forward
      primer

<400> SEQUENCE: 61
aggcagacat tcagatgtag t                                             21

<210> SEQ ID NO 62
<211> LENGTH: 21
<212> TYPE: DNA
<213> ORGANISM: Artificial Sequence
<220> FEATURE:
<223> OTHER INFORMATION: synthetic construct; human Lin28A reverse
      primer

<400> SEQUENCE: 62
gtgcttagat agacctggag t                                             21

<210> SEQ ID NO 63
<211> LENGTH: 19
<212> TYPE: DNA
<213> ORGANISM: Artificial Sequence
<220> FEATURE:
<223> OTHER INFORMATION: synthetic construct; human Lin28A forward
      primer

<400> SEQUENCE: 63
aaagggaggg gaaaggaga                                                19

<210> SEQ ID NO 64
<211> LENGTH: 18
<212> TYPE: DNA
<213> ORGANISM: Artificial Sequence
<220> FEATURE:
<223> OTHER INFORMATION: synthetic construct; human Lin28A reverse
      primer

<400> SEQUENCE: 64
gcacaatagc ggtgggag                                                 18

<210> SEQ ID NO 65
<211> LENGTH: 20
<212> TYPE: DNA
<213> ORGANISM: Artificial Sequence
<220> FEATURE:
<223> OTHER INFORMATION: synthetic construct; human Lin28A forward
      primer

<400> SEQUENCE: 65
tgcgccaagg cggcagaaga                                              20

<210> SEQ ID NO 66
<211> LENGTH: 19
<212> TYPE: DNA
<213> ORGANISM: Artificial Sequence
<220> FEATURE:
<223> OTHER INFORMATION: synthetic construct; human Lin28A reverse
      primer

<400> SEQUENCE: 66
tggacaggaa gccgaaccc                                               19

<210> SEQ ID NO 67
<211> LENGTH: 18
<212> TYPE: DNA
<213> ORGANISM: Artificial Sequence
<220> FEATURE:
<223> OTHER INFORMATION: synthetic construct; human Lin28A forward
      primer

<400> SEQUENCE: 67
ggggcgtaaa gccgagaa                                                18

<210> SEQ ID NO 68
<211> LENGTH: 20
<212> TYPE: DNA
<213> ORGANISM: Artificial Sequence
<220> FEATURE:
<223> OTHER INFORMATION: synthetic construct; human Lin28A reverse
      primer

<400> SEQUENCE: 68
acgggaactg gacagcaaag                                              20

<210> SEQ ID NO 69
<211> LENGTH: 19
<212> TYPE: DNA
<213> ORGANISM: Artificial Sequence
<220> FEATURE:
<223> OTHER INFORMATION: synthetic construct; human Lin28A forward
      primer

<400> SEQUENCE: 69
atggcatgat ctccactca                                               19

<210> SEQ ID NO 70
<211> LENGTH: 19
<212> TYPE: DNA
<213> ORGANISM: Artificial Sequence
<220> FEATURE:
<223> OTHER INFORMATION: synthetic construct; human Lin28A reverse
      primer

<400> SEQUENCE: 70
cctgtaatcc cagcacttt                                               19

<210> SEQ ID NO 71
<211> LENGTH: 19
<212> TYPE: DNA
<213> ORGANISM: Artificial Sequence
<220> FEATURE:
<223> OTHER INFORMATION: synthetic construct; human KLF4 forward primer

<400> SEQUENCE: 71
gagccaagat cacgccact                                               19

<210> SEQ ID NO 72
<211> LENGTH: 18
<212> TYPE: DNA
<213> ORGANISM: Artificial Sequence
<220> FEATURE:
<223> OTHER INFORMATION: synthetic construct; human KLF4 reverse primer

<400> SEQUENCE: 72
tgccgcagga ctcaagaa                                                 18

<210> SEQ ID NO 73
<211> LENGTH: 20
<212> TYPE: DNA
<213> ORGANISM: Artificial Sequence
<220> FEATURE:
<223> OTHER INFORMATION: synthetic construct; human KLF4 forward primer

<400> SEQUENCE: 73
gatcttagag ggattcctgg                                               20

<210> SEQ ID NO 74
<211> LENGTH: 18
<212> TYPE: DNA
<213> ORGANISM: Artificial Sequence
<220> FEATURE:
<223> OTHER INFORMATION: synthetic construct; human KLF4 reverse primer

<400> SEQUENCE: 74
tgtttgaacc ctgcgatt                                                 18

<210> SEQ ID NO 75
<211> LENGTH: 18
<212> TYPE: DNA
<213> ORGANISM: Artificial Sequence
<220> FEATURE:
<223> OTHER INFORMATION: synthetic construct; human KLF4 forward primer

<400> SEQUENCE: 75
tggcgcacgc ctgtaatc                                                 18

<210> SEQ ID NO 76
<211> LENGTH: 18
<212> TYPE: DNA
<213> ORGANISM: Artificial Sequence
<220> FEATURE:
<223> OTHER INFORMATION: synthetic construct; human KLF4 reverse primer

<400> SEQUENCE: 76
catctcgaag cccttttcc                                                18

<210> SEQ ID NO 77
<211> LENGTH: 19
<212> TYPE: DNA
<213> ORGANISM: Artificial Sequence
<220> FEATURE:
<223> OTHER INFORMATION: synthetic construct; human KLF4 forward primer

<400> SEQUENCE: 77
ggagatggag ggctggatg                                                19

<210> SEQ ID NO 78
<211> LENGTH: 19
<212> TYPE: DNA
<213> ORGANISM: Artificial Sequence
<220> FEATURE:

<223> OTHER INFORMATION: synthetic construct; human KLF4 reverse primer

<400> SEQUENCE: 78
gcgaagactg gtggggtca                                                19

<210> SEQ ID NO 79
<211> LENGTH: 18
<212> TYPE: DNA
<213> ORGANISM: Artificial Sequence
<220> FEATURE:
<223> OTHER INFORMATION: synthetic construct; human KLF4 forward primer

<400> SEQUENCE: 79
acgctgctga gtggaaga                                                 18

<210> SEQ ID NO 80
<211> LENGTH: 18
<212> TYPE: DNA
<213> ORGANISM: Artificial Sequence
<220> FEATURE:
<223> OTHER INFORMATION: synthetic construct; human KLF4 reverse primer

<400> SEQUENCE: 80
aattggccga gatccttc                                                 18

<210> SEQ ID NO 81
<211> LENGTH: 18
<212> TYPE: DNA
<213> ORGANISM: Artificial Sequence
<220> FEATURE:
<223> OTHER INFORMATION: synthetic construct; human KLF4 forward primer

<400> SEQUENCE: 81
tgtatgcccg tggtgcga                                                 18

<210> SEQ ID NO 82
<211> LENGTH: 18
<212> TYPE: DNA
<213> ORGANISM: Artificial Sequence
<220> FEATURE:
<223> OTHER INFORMATION: synthetic construct; human KLF4 reverse primer

<400> SEQUENCE: 82
tctggcccag ccagtgtc                                                 18

<210> SEQ ID NO 83
<211> LENGTH: 20
<212> TYPE: DNA
<213> ORGANISM: Artificial Sequence
<220> FEATURE:
<223> OTHER INFORMATION: synthetic construct; human KLF4 forward primer

<400> SEQUENCE: 83
gagaccgagg agttcaacga                                               20

<210> SEQ ID NO 84
<211> LENGTH: 18
<212> TYPE: DNA
<213> ORGANISM: Artificial Sequence
<220> FEATURE:
<223> OTHER INFORMATION: synthetic construct; reverse primer

<400> SEQUENCE: 84
gcgacgacga agaggagg                                                 18

```
<210> SEQ ID NO 85
<211> LENGTH: 18
<212> TYPE: DNA
<213> ORGANISM: Artificial Sequence
<220> FEATURE:
<223> OTHER INFORMATION: synthetic construct; human KLF4 forward primer

<400> SEQUENCE: 85
ggtgtaggtg gtggttgt                                                 18

<210> SEQ ID NO 86
<211> LENGTH: 20
<212> TYPE: DNA
<213> ORGANISM: Artificial Sequence
<220> FEATURE:
<223> OTHER INFORMATION: synthetic construct; human KLF4 reverse primer

<400> SEQUENCE: 86
tgaccctatc ctaaagaaat                                               20

<210> SEQ ID NO 87
<211> LENGTH: 20
<212> TYPE: DNA
<213> ORGANISM: Artificial Sequence
<220> FEATURE:
<223> OTHER INFORMATION: synthetic construct; human BMP2 forward primer

<400> SEQUENCE: 87
cccagcgggg aaataagagg                                               20

<210> SEQ ID NO 88
<211> LENGTH: 18
<212> TYPE: DNA
<213> ORGANISM: Artificial Sequence
<220> FEATURE:
<223> OTHER INFORMATION: synthetic construct; human BMP2 reverse primer

<400> SEQUENCE: 88
cgcctccact ccctgctc                                                 18

<210> SEQ ID NO 89
<211> LENGTH: 20
<212> TYPE: DNA
<213> ORGANISM: Artificial Sequence
<220> FEATURE:
<223> OTHER INFORMATION: synthetic construct; human BMP2 forward primer

<400> SEQUENCE: 89
tcctaaggag gacgacagca                                               20

<210> SEQ ID NO 90
<211> LENGTH: 18
<212> TYPE: DNA
<213> ORGANISM: Artificial Sequence
<220> FEATURE:
<223> OTHER INFORMATION: synthetic construct; human BMP2  reverse primer

<400> SEQUENCE: 90
tcggagatgg cgaagcag                                                 18

<210> SEQ ID NO 91
<211> LENGTH: 18
<212> TYPE: DNA
<213> ORGANISM: Artificial Sequence
<220> FEATURE:
<223> OTHER INFORMATION: synthetic construct; human BMP2 forward primer
```

```
<400> SEQUENCE: 91
tcttccaccc ctctttct                                                18

<210> SEQ ID NO 92
<211> LENGTH: 18
<212> TYPE: DNA
<213> ORGANISM: Artificial Sequence
<220> FEATURE:
<223> OTHER INFORMATION: synthetic construct; human BMP2 reverse primer

<400> SEQUENCE: 92
agggatttct ttgaccca                                                18

<210> SEQ ID NO 93
<211> LENGTH: 18
<212> TYPE: DNA
<213> ORGANISM: Artificial Sequence
<220> FEATURE:
<223> OTHER INFORMATION: synthetic construct; human BMP2 forward primer

<400> SEQUENCE: 93
gagggcaaat cccaaatc                                                18

<210> SEQ ID NO 94
<211> LENGTH: 18
<212> TYPE: DNA
<213> ORGANISM: Artificial Sequence
<220> FEATURE:
<223> OTHER INFORMATION: synthetic construct; human BMP2 reverse primer

<400> SEQUENCE: 94
ggtaagaccg accgaagc                                                18

<210> SEQ ID NO 95
<211> LENGTH: 18
<212> TYPE: DNA
<213> ORGANISM: Artificial Sequence
<220> FEATURE:
<223> OTHER INFORMATION: synthetic construct; human BMP2 forward primer

<400> SEQUENCE: 95
agtaactccg caccctct                                                18

<210> SEQ ID NO 96
<211> LENGTH: 20
<212> TYPE: DNA
<213> ORGANISM: Artificial Sequence
<220> FEATURE:
<223> OTHER INFORMATION: synthetic construct; human BMP2 reverse primer

<400> SEQUENCE: 96
ttgcacgttt agctgactag                                              20

<210> SEQ ID NO 97
<211> LENGTH: 18
<212> TYPE: DNA
<213> ORGANISM: Artificial Sequence
<220> FEATURE:
<223> OTHER INFORMATION: synthetic construct; human BMP2 forward primer

<400> SEQUENCE: 97
ataaaagcgt ttgtagca                                                18

<210> SEQ ID NO 98
<211> LENGTH: 18
```

```
<212> TYPE: DNA
<213> ORGANISM: Artificial Sequence
<220> FEATURE:
<223> OTHER INFORMATION: synthetic construct; human BMP2 reverse primer

<400> SEQUENCE: 98
caagcagaaa tatcccac                                                   18

<210> SEQ ID NO 99
<211> LENGTH: 18
<212> TYPE: DNA
<213> ORGANISM: Artificial Sequence
<220> FEATURE:
<223> OTHER INFORMATION: synthetic construct; human BMP2 forward primer

<400> SEQUENCE: 99
ccaggtgctt cttgttct                                                   18

<210> SEQ ID NO 100
<211> LENGTH: 18
<212> TYPE: DNA
<213> ORGANISM: Artificial Sequence
<220> FEATURE:
<223> OTHER INFORMATION: synthetic construct; human BMP2 reverse primer

<400> SEQUENCE: 100
tttgtggaaa gagggtta                                                   18

<210> SEQ ID NO 101
<211> LENGTH: 18
<212> TYPE: DNA
<213> ORGANISM: Artificial Sequence
<220> FEATURE:
<223> OTHER INFORMATION: synthetic construct; human TP63 forward primer

<400> SEQUENCE: 101
agtggctacc acatcaga                                                   18

<210> SEQ ID NO 102
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 102
cacattagac accgagta                                                   18

<210> SEQ ID NO 103
<211> LENGTH: 18
<212> TYPE: DNA
<213> ORGANISM: Artificial Sequence
<220> FEATURE:
<223> OTHER INFORMATION: synthetic construct; human TP63 forward primer

<400> SEQUENCE: 103
gctcatgcct gtaatccc                                                   18

<210> SEQ ID NO 104
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 104
```

```
tctgcctcag cttcctgt                                                   18

<210> SEQ ID NO 105
<211> LENGTH: 18
<212> TYPE: DNA
<213> ORGANISM: Artificial Sequence
<220> FEATURE:
<223> OTHER INFORMATION: synthetic construct; human TP63 forward primer

<400> SEQUENCE: 105
tctcgggcta agtaaagg                                                   18

<210> SEQ ID NO 106
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 106
agttcacatc ttcccttc                                                   18

<210> SEQ ID NO 107
<211> LENGTH: 20
<212> TYPE: DNA
<213> ORGANISM: Artificial Sequence
<220> FEATURE:
<223> OTHER INFORMATION: synthetic construct; human TP63 forward primer

<400> SEQUENCE: 107
taaagaatag agtggagccg                                                 20

<210> SEQ ID NO 108
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 108
tttgcctgac ccgaataa                                                   18

<210> SEQ ID NO 109
<211> LENGTH: 19
<212> TYPE: DNA
<213> ORGANISM: Artificial Sequence
<220> FEATURE:
<223> OTHER INFORMATION: synthetic construct; human TP63 forward primer

<400> SEQUENCE: 109
aaaatcaaga aacgctccg                                                  19

<210> SEQ ID NO 110
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 110
gcaatagggt caaatgct                                                   18

<210> SEQ ID NO 111
<211> LENGTH: 18
<212> TYPE: DNA
<213> ORGANISM: Artificial Sequence
```

```
<220> FEATURE:
<223> OTHER INFORMATION: synthetic construct; human TP63 forward primer

<400> SEQUENCE: 111
cagcacctac tcactcaa                                                 18

<210> SEQ ID NO 112
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 112
aatgacaagc cacaatct                                                 18

<210> SEQ ID NO 113
<211> LENGTH: 18
<212> TYPE: DNA
<213> ORGANISM: Artificial Sequence
<220> FEATURE:
<223> OTHER INFORMATION: synthetic construct; human TP63 forward primer

<400> SEQUENCE: 113
ggggtctcca aggtttca                                                 18

<210> SEQ ID NO 114
<211> LENGTH: 18
<212> TYPE: DNA
<213> ORGANISM: Artificial Sequence
<220> FEATURE:
<223> OTHER INFORMATION: synthetic construct; human TP63 reverse primer

<400> SEQUENCE: 114
aacccaatcc tcaactgc                                                 18

<210> SEQ ID NO 115
<211> LENGTH: 18
<212> TYPE: DNA
<213> ORGANISM: Artificial Sequence
<220> FEATURE:
<223> OTHER INFORMATION: synthetic construct; human TP63 forward primer

<400> SEQUENCE: 115
gggacttcat cctctgtt                                                 18

<210> SEQ ID NO 116
<211> LENGTH: 22
<212> TYPE: DNA
<213> ORGANISM: Artificial Sequence
<220> FEATURE:
<223> OTHER INFORMATION: synthetic construct; human TP63 reverse primer

<400> SEQUENCE: 116
ggtaatgtga ttttatccaa ct                                            22

<210> SEQ ID NO 117
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 117
ccttcgtgct tctgtcta                                                 18
```

```
<210> SEQ ID NO 118
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 118
ttcagtgcct aatcttgc                                                 18

<210> SEQ ID NO 119
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 119
accacctttc cttccaat                                                 18

<210> SEQ ID NO 120
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 120
caggcttgtg ccacatta                                                 18

<210> SEQ ID NO 121
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 121
cttgccagac gctgagtt                                                 18

<210> SEQ ID NO 122
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 122
agcagtccca tttctcca                                                 18

<210> SEQ ID NO 123
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 123
tggcagaagt caggtctc                                                 18

<210> SEQ ID NO 124
<211> LENGTH: 20
<212> TYPE: DNA
<213> ORGANISM: Artificial Sequence
<220> FEATURE:
<223> OTHER INFORMATION: synthetic construct; human KRT6A reverse primer
```

<400> SEQUENCE: 124
ctttacactg taggagcaac					20

<210> SEQ ID NO 125
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 125
gctggaaggc aggagaat					18

<210> SEQ ID NO 126
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 126
ggtgagcttg caggttgg					18

<210> SEQ ID NO 127
<211> LENGTH: 18
<212> TYPE: DNA
<213> ORGANISM: Artificial Sequence
<220> FEATURE:
<223> OTHER INFORMATION: synthetic construct; human KRT6A forward primer

<400> SEQUENCE: 127
gaggtcaccg tcaaccag					18

<210> SEQ ID NO 128
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 128
cgatgaagga ggcaaact					18

<210> SEQ ID NO 129
<211> LENGTH: 19
<212> TYPE: DNA
<213> ORGANISM: Artificial Sequence
<220> FEATURE:
<223> OTHER INFORMATION: synthetic construct; human KRT6A forward primer

<400> SEQUENCE: 129
tgttcgagca gtacatcaa					19

<210> SEQ ID NO 130
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 130
cctggtcacc caatagtc					18

<210> SEQ ID NO 131

```
<211> LENGTH: 19
<212> TYPE: DNA
<213> ORGANISM: Artificial Sequence
<220> FEATURE:
<223> OTHER INFORMATION: synthetic construct; human KRT6A forward primer

<400> SEQUENCE: 131
gaacttatgc ccaagtcaa                                                19

<210> SEQ ID NO 132
<211> LENGTH: 18
<212> TYPE: DNA
<213> ORGANISM: Artificial Sequence
<220> FEATURE:
<223> OTHER INFORMATION: synthetic construct; human KRT6A reverse primer

<400> SEQUENCE: 132
cctcattatg gcaccact                                                 18

<210> SEQ ID NO 133
<211> LENGTH: 20
<212> TYPE: DNA
<213> ORGANISM: Artificial Sequence
<220> FEATURE:
<223> OTHER INFORMATION: synthetic construct; human SOX17 forward primer

<400> SEQUENCE: 133
acgctgctga taaggctgtc                                               20

<210> SEQ ID NO 134
<211> LENGTH: 20
<212> TYPE: DNA
<213> ORGANISM: Artificial Sequence
<220> FEATURE:
<223> OTHER INFORMATION: synthetic construct; human SOX 17 reverse
      primer

<400> SEQUENCE: 134
tgggctgtgg aacctcatac                                               20

<210> SEQ ID NO 135
<211> LENGTH: 20
<212> TYPE: DNA
<213> ORGANISM: Artificial Sequence
<220> FEATURE:
<223> OTHER INFORMATION: synthetic construct; Sox17_human forward primer

<400> SEQUENCE: 135
ccaagaacaa gggcaaataa                                               20

<210> SEQ ID NO 136
<211> LENGTH: 20
<212> TYPE: DNA
<213> ORGANISM: Artificial Sequence
<220> FEATURE:
<223> OTHER INFORMATION: synethetic construct; Sox17_human reverse
      primer

<400> SEQUENCE: 136
tcaagcgatt ctcctgtctc                                               20

<210> SEQ ID NO 137
<211> LENGTH: 20
<212> TYPE: DNA
<213> ORGANISM: Artificial Sequence
<220> FEATURE:
<223> OTHER INFORMATION: synthetic construct; Sox17_human forward primer
```

<400> SEQUENCE: 137
ggaggctgag acaggagaat                                        20

<210> SEQ ID NO 138
<211> LENGTH: 20
<212> TYPE: DNA
<213> ORGANISM: Artificial Sequence
<220> FEATURE:
<223> OTHER INFORMATION: synthetic construct; Sox17_human reverse primer

<400> SEQUENCE: 138
ggagccaaga aggtggagaa                                        20

<210> SEQ ID NO 139
<211> LENGTH: 20
<212> TYPE: DNA
<213> ORGANISM: Artificial Sequence
<220> FEATURE:
<223> OTHER INFORMATION: synthetic construct; Sox17_human forward primer

<400> SEQUENCE: 139
tctttgctaa tgctggaggg                                        20

<210> SEQ ID NO 140
<211> LENGTH: 20
<212> TYPE: DNA
<213> ORGANISM: Artificial Sequence
<220> FEATURE:
<223> OTHER INFORMATION: synthetic construct; Sox17_human reverse primer

<400> SEQUENCE: 140
aaatgtccga gtttgtttgg                                        20

<210> SEQ ID NO 141
<211> LENGTH: 20
<212> TYPE: DNA
<213> ORGANISM: Artificial Sequence
<220> FEATURE:
<223> OTHER INFORMATION: synthetic construct; Sox17_human forward primer

<400> SEQUENCE: 141
cagtgcctca ctccccaccc                                        20

<210> SEQ ID NO 142
<211> LENGTH: 20
<212> TYPE: DNA
<213> ORGANISM: Artificial Sequence
<220> FEATURE:
<223> OTHER INFORMATION: synthetic construct; Sox17_human reverse primer

<400> SEQUENCE: 142
gcctcgccct tcaccttcat                                        20

<210> SEQ ID NO 143
<211> LENGTH: 20
<212> TYPE: DNA
<213> ORGANISM: Artificial Sequence
<220> FEATURE:
<223> OTHER INFORMATION: synthetic construct; Sox17_human forward primer

<400> SEQUENCE: 143
ttcccatagt tggattgtca                                        20

<210> SEQ ID NO 144

```
<211> LENGTH: 20
<212> TYPE: DNA
<213> ORGANISM: Artificial Sequence
<220> FEATURE:
<223> OTHER INFORMATION: synthetic construct; Sox17_human reverse primer

<400> SEQUENCE: 144
gcatttatgt tcacccttt                                           20

<210> SEQ ID NO 145
<211> LENGTH: 20
<212> TYPE: DNA
<213> ORGANISM: Artificial Sequence
<220> FEATURE:
<223> OTHER INFORMATION: synthetic construct; Sox17_human forward primer

<400> SEQUENCE: 145
tgtcccaaga gttcccagta                                          20

<210> SEQ ID NO 146
<211> LENGTH: 20
<212> TYPE: DNA
<213> ORGANISM: Artificial Sequence
<220> FEATURE:
<223> OTHER INFORMATION: synthetic construct; Sox17_human reverse primer

<400> SEQUENCE: 146
aacaccaatc cctccatcca                                          20

<210> SEQ ID NO 147
<211> LENGTH: 18
<212> TYPE: DNA
<213> ORGANISM: Artificial Sequence
<220> FEATURE:
<223> OTHER INFORMATION: synthetic construct; CyclinA_human forward
      primer

<400> SEQUENCE: 147
agggaaagaa ggagtgag                                            18

<210> SEQ ID NO 148
<211> LENGTH: 18
<212> TYPE: DNA
<213> ORGANISM: Artificial Sequence
<220> FEATURE:
<223> OTHER INFORMATION: synthetic construct; CyclinA_human reverse
      primer

<400> SEQUENCE: 148
accttgcaga gctattgt                                            18

<210> SEQ ID NO 149
<211> LENGTH: 18
<212> TYPE: DNA
<213> ORGANISM: Artificial Sequence
<220> FEATURE:
<223> OTHER INFORMATION: synthetic construct; CyclinA_human forward
      construct

<400> SEQUENCE: 149
acctcagcct cccaaagt                                            18

<210> SEQ ID NO 150
<211> LENGTH: 20
<212> TYPE: DNA
<213> ORGANISM: Artificial Sequence
<220> FEATURE:
```

```
<223> OTHER INFORMATION: synthetic construct; CyclinA_human reverse
      primer

<400> SEQUENCE: 150
tagcagcatc caatagcaaa                                                  20

<210> SEQ ID NO 151
<211> LENGTH: 18
<212> TYPE: DNA
<213> ORGANISM: Artificial Sequence
<220> FEATURE:
<223> OTHER INFORMATION: synthetic construct; CyclinA_human forward
      primer

<400> SEQUENCE: 151
tagaccgctt tataggct                                                    18

<210> SEQ ID NO 152
<211> LENGTH: 19
<212> TYPE: DNA
<213> ORGANISM: Artificial Sequence
<220> FEATURE:
<223> OTHER INFORMATION: synthetic construct; CyclinA_human reverse
      primer

<400> SEQUENCE: 152
catacatagt aaccaggac                                                   19

<210> SEQ ID NO 153
<211> LENGTH: 18
<212> TYPE: DNA
<213> ORGANISM: Artificial Sequence
<220> FEATURE:
<223> OTHER INFORMATION: synthetic construct; CyclinA_human forward
      primer

<400> SEQUENCE: 153
cagtagttca aggtgcca                                                    18

<210> SEQ ID NO 154
<211> LENGTH: 20
<212> TYPE: DNA
<213> ORGANISM: Artificial Sequence
<220> FEATURE:
<223> OTHER INFORMATION: synthetic construct; CyclinA_human reverse
      primer

<400> SEQUENCE: 154
cttaacattt aggcgtttat                                                  20

<210> SEQ ID NO 155
<211> LENGTH: 20
<212> TYPE: DNA
<213> ORGANISM: Artificial Sequence
<220> FEATURE:
<223> OTHER INFORMATION: synthetic construct; CyclinA_human forward
      primer

<400> SEQUENCE: 155
cctgctcagt ttcctttggt                                                  20

<210> SEQ ID NO 156
<211> LENGTH: 20
<212> TYPE: DNA
<213> ORGANISM: Artificial Sequence
<220> FEATURE:
<223> OTHER INFORMATION: synthetic construct; CyclinA_human reverse
``` primer

<400> SEQUENCE: 156
atcccgcgac tattgaaatg                                              20

<210> SEQ ID NO 157
<211> LENGTH: 20
<212> TYPE: DNA
<213> ORGANISM: Artificial Sequence
<220> FEATURE:
<223> OTHER INFORMATION: synthetic construct; CyclinA_human forward
      primer

<400> SEQUENCE: 157
gttctcccat attagcatca                                              20

<210> SEQ ID NO 158
<211> LENGTH: 19
<212> TYPE: DNA
<213> ORGANISM: Artificial Sequence
<220> FEATURE:
<223> OTHER INFORMATION: synthetic construct; CyclinA_human reverse
      primer

<400> SEQUENCE: 158
gagctgagcg aagactaca                                               19

<210> SEQ ID NO 159
<211> LENGTH: 20
<212> TYPE: DNA
<213> ORGANISM: Artificial Sequence
<220> FEATURE:
<223> OTHER INFORMATION: synthetic construct; CyclinA_human forward
      primer

<400> SEQUENCE: 159
cctttgtggg aatgcctgtg                                              20

<210> SEQ ID NO 160
<211> LENGTH: 19
<212> TYPE: DNA
<213> ORGANISM: Artificial Sequence
<220> FEATURE:
<223> OTHER INFORMATION: synthetic construct; CyclinA_human reverse
      primer

<400> SEQUENCE: 160
rgggtgttgg cctttgctt                                               19

<210> SEQ ID NO 161
<211> LENGTH: 18
<212> TYPE: DNA
<213> ORGANISM: Artificial Sequence
<220> FEATURE:
<223> OTHER INFORMATION: synthetic construct; CyclinA_human forward
      primer

<400> SEQUENCE: 161
agccagacat cactaaca                                                18

<210> SEQ ID NO 162
<211> LENGTH: 19
<212> TYPE: DNA
<213> ORGANISM: Artificial Sequence
<220> FEATURE:
<223> OTHER INFORMATION: synthetic construct; CyclinA_human reverse
      primer

```
<400> SEQUENCE: 162
rtgtagttca cagccaaat                                                19

<210> SEQ ID NO 163
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 163
ccggttggag tgcagtag                                                 18

<210> SEQ ID NO 164
<211> LENGTH: 18
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 164
ctgggattgg tggtgtat                                                 18

<210> SEQ ID NO 165
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 165
tcaggagttt gaggttac                                                 18

<210> SEQ ID NO 166
<211> LENGTH: 18
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 166
tctgttcagg tattttgc                                                 18

<210> SEQ ID NO 167
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 167
gaaggcaggt gaaatgct                                                 18

<210> SEQ ID NO 168
<211> LENGTH: 18
<212> TYPE: DNA
<213> ORGANISM: Artificial Sequence
<220> FEATURE:
<223> OTHER INFORMATION: synthetic construct; CyclinB_human reverse
      primer
```

```
<400> SEQUENCE: 168
tgcgattaca ggcgtgag                                                  18

<210> SEQ ID NO 169
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 169
atctgagtaa agggcata                                                  18

<210> SEQ ID NO 170
<211> LENGTH: 20
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 170
gttttagctt tctatttgga                                                20

<210> SEQ ID NO 171
<211> LENGTH: 20
<212> TYPE: DNA
<213> ORGANISM: Artificial Sequence
<220> FEATURE:
<223> OTHER INFORMATION: synthetic construct; CyclinB_human forward
      primer

<400> SEQUENCE: 171
gagtgagtgc cacgaacagg                                                20

<210> SEQ ID NO 172
<211> LENGTH: 20
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 172
acccagcaga aaccaacagc                                                20

<210> SEQ ID NO 173
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 173
agaggtcggc ggaaactg                                                  18

<210> SEQ ID NO 174
<211> LENGTH: 18
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 174
```
aggtggggca caaggaga                                          18

<210> SEQ ID NO 175
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 175
aaatgcctat gaagaagg                                          18

<210> SEQ ID NO 176
<211> LENGTH: 18
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 176
ttttccagta gctgaagg                                          18

<210> SEQ ID NO 177
<211> LENGTH: 18
<212> TYPE: DNA
<213> ORGANISM: Artificial Sequence
<220> FEATURE:
<223> OTHER INFORMATION: synthetic construct; CyclinB_human forward
      primer

<400> SEQUENCE: 177
ggctggtctc gaactcct                                          18

<210> SEQ ID NO 178
<211> LENGTH: 18
<212> TYPE: DNA
<213> ORGANISM: Artificial Sequence
<220> FEATURE:
<223> OTHER INFORMATION: synthetic construct; CyclinB_human reverse
      primer

<400> SEQUENCE: 178
cttcatggca tcctcaaa                                          18

<210> SEQ ID NO 179
<211> LENGTH: 18
<212> TYPE: DNA
<213> ORGANISM: Artificial Sequence
<220> FEATURE:
<223> OTHER INFORMATION: synthetic construct; CyclinD_human forward
      primer

<400> SEQUENCE: 179
gcaagttccg gagtgggg                                          18

<210> SEQ ID NO 180
<211> LENGTH: 18
<212> TYPE: DNA
<213> ORGANISM: Artificial Sequence
<220> FEATURE:
<223> OTHER INFORMATION: synthetic construct; CyclinD_human reverse
      primer

<400> SEQUENCE: 180

```
gagacgcagg gcttcgct                                                      18
```

<210> SEQ ID NO 181
<211> LENGTH: 18
<212> TYPE: DNA
<213> ORGANISM: Artificial Sequence
<220> FEATURE:
<223> OTHER INFORMATION: synthetic construct; CyclinD_human forward
      primer

<400> SEQUENCE: 181

```
aacccaagcc ccgagccc                                                      18
```

<210> SEQ ID NO 182
<211> LENGTH: 18
<212> TYPE: DNA
<213> ORGANISM: Artificial Sequence
<220> FEATURE:
<223> OTHER INFORMATION: synthetic construct; CyclinD_human reverse
      primer

<400> SEQUENCE: 182

```
gcgtgttcgc caccgtcc                                                      18
```

<210> SEQ ID NO 183
<211> LENGTH: 19
<212> TYPE: DNA
<213> ORGANISM: Artificial Sequence
<220> FEATURE:
<223> OTHER INFORMATION: synthetic construct; CyclinD_human forward
      primer

<400> SEQUENCE: 183

```
tctgaggctt ggctatgcg                                                     19
```

<210> SEQ ID NO 184
<211> LENGTH: 18
<212> TYPE: DNA
<213> ORGANISM: Artificial Sequence
<220> FEATURE:
<223> OTHER INFORMATION: synthetic construct; CyclinD_human reverse
      primer

<400> SEQUENCE: 184

```
tggggagcga tgggttgc                                                      18
```

<210> SEQ ID NO 185
<211> LENGTH: 22
<212> TYPE: DNA
<213> ORGANISM: Artificial Sequence
<220> FEATURE:
<223> OTHER INFORMATION: synthetic construct; CyclinD_human forward
      primer

<400> SEQUENCE: 185

```
aggtaggaag gcagcccgaa ga                                                 22
```

<210> SEQ ID NO 186
<211> LENGTH: 18
<212> TYPE: DNA
<213> ORGANISM: Artificial Sequence
<220> FEATURE:
<223> OTHER INFORMATION: synthetic construct; CyclinD_human reverse
      primer

<400> SEQUENCE: 186

```
agcagcagcc caagatgg                                                      18
```

<210> SEQ ID NO 187
<211> LENGTH: 18
<212> TYPE: DNA
<213> ORGANISM: Artificial Sequence
<220> FEATURE:
<223> OTHER INFORMATION: synthetic construct; CyclinD_human forward primer

<400> SEQUENCE: 187
acccagccag gacccaca                                         18

<210> SEQ ID NO 188
<211> LENGTH: 19
<212> TYPE: DNA
<213> ORGANISM: Artificial Sequence
<220> FEATURE:
<223> OTHER INFORMATION: synthetic construct; CyclinD_human reverse primer

<400> SEQUENCE: 188
ggtttccact tcgcagcac                                        19

<210> SEQ ID NO 189
<211> LENGTH: 20
<212> TYPE: DNA
<213> ORGANISM: Artificial Sequence
<220> FEATURE:
<223> OTHER INFORMATION: synthetic construct; CyclinD_human forward primer

<400> SEQUENCE: 189
cgtttctttg ctactcaccc                                       20

<210> SEQ ID NO 190
<211> LENGTH: 18
<212> TYPE: DNA
<213> ORGANISM: Artificial Sequence
<220> FEATURE:
<223> OTHER INFORMATION: synthetic construct; CyclinD_human reverse primer

<400> SEQUENCE: 190
ccaccccttc ctccttca                                         18

<210> SEQ ID NO 191
<211> LENGTH: 18
<212> TYPE: DNA
<213> ORGANISM: Artificial Sequence
<220> FEATURE:
<223> OTHER INFORMATION: synthetic construct; CyclinD_human forward primer

<400> SEQUENCE: 191
tgaaagtgcg gcgtggtg                                         18

<210> SEQ ID NO 192
<211> LENGTH: 19
<212> TYPE: DNA
<213> ORGANISM: Artificial Sequence
<220> FEATURE:
<223> OTHER INFORMATION: synthetic construct; CyclinD_human reverse primer

<400> SEQUENCE: 192
rctcgggcga cccttttacc                                       19

<210> SEQ ID NO 193
<211> LENGTH: 19
<212> TYPE: DNA
<213> ORGANISM: Artificial Sequence
<220> FEATURE:
<223> OTHER INFORMATION: synthetic construct; CyclinD_human forward primer

<400> SEQUENCE: 193
ggatggaggg agatttgct				19

<210> SEQ ID NO 194
<211> LENGTH: 21
<212> TYPE: DNA
<213> ORGANISM: Artificial Sequence
<220> FEATURE:
<223> OTHER INFORMATION: synthetic construct; CyclinD_human reverse primer

<400> SEQUENCE: 194
rgaaggacga ggccagagta a				21

<210> SEQ ID NO 195
<211> LENGTH: 20
<212> TYPE: DNA
<213> ORGANISM: Artificial Sequence
<220> FEATURE:
<223> OTHER INFORMATION: synthetic construct; SAT2_human forward primer

<400> SEQUENCE: 195
aatcatcgaa tggtctcgat				20

<210> SEQ ID NO 196
<211> LENGTH: 20
<212> TYPE: DNA
<213> ORGANISM: Artificial Sequence
<220> FEATURE:
<223> OTHER INFORMATION: synthetic construct; SAT2_human reverse primer

<400> SEQUENCE: 196
ataattccat tcgattccac				20

<210> SEQ ID NO 197
<211> LENGTH: 19
<212> TYPE: DNA
<213> ORGANISM: Artificial Sequence
<220> FEATURE:
<223> OTHER INFORMATION: synthetic construct; GAPDH_human forward primer

<400> SEQUENCE: 197
accacagtcc atgccatca				19

<210> SEQ ID NO 198
<211> LENGTH: 20
<212> TYPE: DNA
<213> ORGANISM: Artificial Sequence
<220> FEATURE:
<223> OTHER INFORMATION: synthetic construct; GAPDH_human reverse primer

<400> SEQUENCE: 198
cagggatgat gttctggaga				20

<210> SEQ ID NO 199
<211> LENGTH: 20
<212> TYPE: DNA
<213> ORGANISM: Artificial Sequence

```
<220> FEATURE:
<223> OTHER INFORMATION: synthetic construct; SOX2 _human forward primer

<400> SEQUENCE: 199
gtgagcgccc tgcagtacaa                                              20

<210> SEQ ID NO 200
<211> LENGTH: 23
<212> TYPE: DNA
<213> ORGANISM: Artificial Sequence
<220> FEATURE:
<223> OTHER INFORMATION: synthetic construct; SOX2 _human reverse primer

<400> SEQUENCE: 200
gcgagtagga catgctgtag gtg                                          23

<210> SEQ ID NO 201
<211> LENGTH: 19
<212> TYPE: DNA
<213> ORGANISM: Artificial Sequence
<220> FEATURE:
<223> OTHER INFORMATION: synthetic construct; LSD1_human forward primer

<400> SEQUENCE: 201
agcgtcatgg tcttatcaa                                               19

<210> SEQ ID NO 202
<211> LENGTH: 18
<212> TYPE: DNA
<213> ORGANISM: Artificial Sequence
<220> FEATURE:
<223> OTHER INFORMATION: synthetic construct; LSD1_human reverse primer

<400> SEQUENCE: 202
gaaatgtggc aactcgtc                                                18

<210> SEQ ID NO 203
<211> LENGTH: 20
<212> TYPE: DNA
<213> ORGANISM: Artificial Sequence
<220> FEATURE:
<223> OTHER INFORMATION: synthetic construct; FOXA2_human forward primer

<400> SEQUENCE: 203
ccccaacaag atgctgacgc                                              20

<210> SEQ ID NO 204
<211> LENGTH: 19
<212> TYPE: DNA
<213> ORGANISM: Artificial Sequence
<220> FEATURE:
<223> OTHER INFORMATION: synthetic construct; FOXA2 _human reverse
      primer

<400> SEQUENCE: 204
gcgagtggcg gatggagtt                                               19

<210> SEQ ID NO 205
<211> LENGTH: 18
<212> TYPE: DNA
<213> ORGANISM: Artificial Sequence
<220> FEATURE:
<223> OTHER INFORMATION: synthetic construct; BMP2_human forward primer

<400> SEQUENCE: 205
acagcggaaa cgccttaa                                                18
```

<210> SEQ ID NO 206
<211> LENGTH: 18
<212> TYPE: DNA
<213> ORGANISM: Artificial Sequence
<220> FEATURE:
<223> OTHER INFORMATION: synthetic construct; BMP2 _human reverse primer

<400> SEQUENCE: 206
gggagccaca atccagtc                                                    18

<210> SEQ ID NO 207
<211> LENGTH: 18
<212> TYPE: DNA
<213> ORGANISM: Artificial Sequence
<220> FEATURE:
<223> OTHER INFORMATION: synthetic construct; EOMES_human forward primer

<400> SEQUENCE: 207
cccagaccca acctttcc                                                    18

<210> SEQ ID NO 208
<211> LENGTH: 22
<212> TYPE: DNA
<213> ORGANISM: Artificial Sequence
<220> FEATURE:
<223> OTHER INFORMATION: synthetic construct; EOMES _human reverse
      primer

<400> SEQUENCE: 208
gagccaattt cctctttcac tt                                               22

<210> SEQ ID NO 209
<211> LENGTH: 22
<212> TYPE: DNA
<213> ORGANISM: Artificial Sequence
<220> FEATURE:
<223> OTHER INFORMATION: synthetic construct; SOX17_human forward primer

<400> SEQUENCE: 209
ctgcaggcca gaagcagtgt ta                                               22

<210> SEQ ID NO 210
<211> LENGTH: 22
<212> TYPE: DNA
<213> ORGANISM: Artificial Sequence
<220> FEATURE:
<223> OTHER INFORMATION: synthetic construct; SOX17_human reverse primer

<400> SEQUENCE: 210
cccaaactgt tcaagtggca ga                                               22

<210> SEQ ID NO 211
<211> LENGTH: 23
<212> TYPE: DNA
<213> ORGANISM: Artificial Sequence
<220> FEATURE:
<223> OTHER INFORMATION: synthetic construct; HNF4A_human forward primer

<400> SEQUENCE: 211
agctgcagat cgatgacaat gag                                              23

<210> SEQ ID NO 212
<211> LENGTH: 23
<212> TYPE: DNA
<213> ORGANISM: Artificial Sequence

```
<220> FEATURE:
<223> OTHER INFORMATION: synthetic construct; HNF4A _human reverse
      primer

<400> SEQUENCE: 212
catactggcg gtcgttgatg tag                                              23

<210> SEQ ID NO 213
<211> LENGTH: 23
<212> TYPE: DNA
<213> ORGANISM: Artificial Sequence
<220> FEATURE:
<223> OTHER INFORMATION: synthetic construct; TP63_human forward primer

<400> SEQUENCE: 213
ccttactttg ctgagggttt gaa                                              23

<210> SEQ ID NO 214
<211> LENGTH: 25
<212> TYPE: DNA
<213> ORGANISM: Artificial Sequence
<220> FEATURE:
<223> OTHER INFORMATION: synthetic construct; TP63 _human reverse primer

<400> SEQUENCE: 214
caaggcccta gtgttacctg aatag                                            25

<210> SEQ ID NO 215
<211> LENGTH: 19
<212> TYPE: DNA
<213> ORGANISM: Artificial Sequence
<220> FEATURE:
<223> OTHER INFORMATION: synthetic construct; KRT6A_human forward primer

<400> SEQUENCE: 215
ggctgaggag cgtgaacag                                                   19

<210> SEQ ID NO 216
<211> LENGTH: 17
<212> TYPE: DNA
<213> ORGANISM: Artificial Sequence
<220> FEATURE:
<223> OTHER INFORMATION: synthetic construct; KRT6A _human reverse
      primer

<400> SEQUENCE: 216
caggaaccgc accttgt                                                     17

<210> SEQ ID NO 217
<211> LENGTH: 15
<212> TYPE: DNA
<213> ORGANISM: Artificial Sequence
<220> FEATURE:
<223> OTHER INFORMATION: synthetic construct; B-Actin _human forward
      primer

<400> SEQUENCE: 217
ggccacggct gcttc                                                       15

<210> SEQ ID NO 218
<211> LENGTH: 20
<212> TYPE: DNA
<213> ORGANISM: Artificial Sequence
<220> FEATURE:
<223> OTHER INFORMATION: synthetic construct; B-Actin_human reverse
      primer
```

```
<400> SEQUENCE: 218
gttggcgtac aggtctttgc                                              20

<210> SEQ ID NO 219
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 219
tcagtgccaa gtagacaaat                                              20

<210> SEQ ID NO 220
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 220
tacgaaatta acaggatgtg                                              20

<210> SEQ ID NO 221
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 221
ccaggtctcg ggtccgatta                                              20

<210> SEQ ID NO 222
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 222
ccctccctcc ttcttgaaat                                              20

<210> SEQ ID NO 223
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 223
ggtgtactcc cggcccatta                                              20

<210> SEQ ID NO 224
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 224
atttcttctc ccttgcgtct                                              20

<210> SEQ ID NO 225
<211> LENGTH: 20
```

```
<212> TYPE: DNA
<213> ORGANISM: Artificial Sequence
<220> FEATURE:
<223> OTHER INFORMATION: synthetic construct; Human FoxA2 forward primer

<400> SEQUENCE: 225
ccgcccactt ccaactaccg                                          20

<210> SEQ ID NO 226
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 226
gtcagccaaa gcaccgtccc                                          20

<210> SEQ ID NO 227
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 227
tttcaagtct gcggtcatcc                                          20

<210> SEQ ID NO 228
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 228
cagcaacatc agtgcccttt                                          20

<210> SEQ ID NO 229
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 229
caaccttcgg cacaacgatc                                          20

<210> SEQ ID NO 230
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 230
gaagccacca tacaaactga                                          20

<210> SEQ ID NO 231
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 231
```
caagcctcac atttgaaccc                                          20

<210> SEQ ID NO 232
<211> LENGTH: 20
<212> TYPE: DNA
<213> ORGANISM: Artificial Sequence
<220> FEATURE:
<223> OTHER INFORMATION: synthetic construct; Human FoxA2 reverse primer

<400> SEQUENCE: 232
ctgcggaacc actgaccacc                                          20

<210> SEQ ID NO 233
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 233
aacgctggcc gtctgtattg                                          20

<210> SEQ ID NO 234
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 234
gcctatggac tctgcccttc                                          20

<210> SEQ ID NO 235
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 235
aggctgagtg gagactttgg                                          20

<210> SEQ ID NO 236
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 236
atttccattc ccttccctat                                          20

<210> SEQ ID NO 237
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 237
ggacctcttc cctttctacc                                          20

<210> SEQ ID NO 238
<211> LENGTH: 20
<212> TYPE: DNA
<213> ORGANISM: Artificial Sequence

```
<220> FEATURE:
<223> OTHER INFORMATION: synthetic construct; Mouse FoxA2 reverse primer

<400> SEQUENCE: 238
gtcttcttgc ctccgctact                                               20

<210> SEQ ID NO 239
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 239
cccactccca gctacttccc                                               20

<210> SEQ ID NO 240
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 240
cagccacaac aaacgaccag                                               20

<210> SEQ ID NO 241
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 241
gctccaatgc ttactcctct                                               20

<210> SEQ ID NO 242
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 242
ttctcccaca aattcaaggt                                               20

<210> SEQ ID NO 243
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 243
ccccatagac aagtgtttcg                                               20

<210> SEQ ID NO 244
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 244
ttcttccagc cttccctaat                                               20
```

```
<210> SEQ ID NO 245
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 245
atggctttgc ctatttgtcc                                            20

<210> SEQ ID NO 246
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 246
ggtttcctgg ctgatgctta                                            20

<210> SEQ ID NO 247
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 247
ttctcctgcc tcagcctcct                                            20

<210> SEQ ID NO 248
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 248
gcctataatt ccagcacttt                                            20

<210> SEQ ID NO 249
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 249
tgcttcctcc ctactgtctg                                            20

<210> SEQ ID NO 250
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 250
ctcaccgcaa cctccatctc                                            20

<210> SEQ ID NO 251
<211> LENGTH: 20
<212> TYPE: DNA
<213> ORGANISM: Artificial Sequence
<220> FEATURE:
<223> OTHER INFORMATION: synthetic construct; Human Sox2 forward primer
```

<400> SEQUENCE: 251
catcacccac agcaaatgac                                                20

<210> SEQ ID NO 252
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 252
ttcctgcaaa gctcctaccg                                                20

<210> SEQ ID NO 253
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 253
caggagttgt caaggcagag                                                20

<210> SEQ ID NO 254
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 254
ggaaaatcag gcgaagaata                                                20

<210> SEQ ID NO 255
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 255
tttgggtctc ctaacttcta                                                20

<210> SEQ ID NO 256
<211> LENGTH: 20
<212> TYPE: DNA
<213> ORGANISM: Artificial Sequence
<220> FEATURE:
<223> OTHER INFORMATION: synthetic construct; Human Sox2 reverse
      construct

<400> SEQUENCE: 256
gtcattgttc tcccgctcat                                                20

<210> SEQ ID NO 257
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 257
gcattccgtt ggctattctc                                                20

```
<210> SEQ ID NO 258
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 258 gatgtgctttt gtttagtggg                                              20

<210> SEQ ID NO 259
<211> LENGTH: 20
<212> TYPE: DNA
<213> ORGANISM: Artificial Sequence
<220> FEATURE:
<223> OTHER INFORMATION: synthetic construct; Human Sox2 forward

<400> SEQUENCE: 259
aatactggtg gtcgtcaaac                                               20

<210> SEQ ID NO 260
<211> LENGTH: 20
<212> TYPE: DNA
<213> ORGANISM: Artificial Sequence
<220> FEATURE:
<223> OTHER INFORMATION: synthetic construct; Human Sox2 reverse primer

<400> SEQUENCE: 260
tgagaactag ccaagcatct                                               20

<210> SEQ ID NO 261
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 261
gggcatagac aaacagaacc                                               20

<210> SEQ ID NO 262
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 262
accacaacca tagcaggaat                                               20

<210> SEQ ID NO 263
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 263
tccaagtcgc tgcctttatt                                               20

<210> SEQ ID NO 264
<211> LENGTH: 20
<212> TYPE: DNA
<213> ORGANISM: Artificial Sequence
<220> FEATURE:
<223> OTHER INFORMATION: synthetic construct; Mouse Sox2 reverse primer
```

```
<400> SEQUENCE: 264
ttccgtttcc tccactctgt                                                 20

<210> SEQ ID NO 265
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 265
gtgctggcga caaggttgga                                                 20

<210> SEQ ID NO 266
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 266
atgggtggtt cagggcgact                                                 20

<210> SEQ ID NO 267
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 267
aagactaggg ctgggagaaa                                                 20

<210> SEQ ID NO 268
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 268
atctggcgga gaatagttgg                                                 20

<210> SEQ ID NO 269
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 269
ctggactgcg aactggagaa                                                 20

<210> SEQ ID NO 270
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 270
atttggatgg gattggtggt                                                 20

<210> SEQ ID NO 271
<211> LENGTH: 20
```

```
<212> TYPE: DNA
<213> ORGANISM: Artificial Sequence
<220> FEATURE:
<223> OTHER INFORMATION: synthetic construct; Mouse Sox2 forward primer

<400> SEQUENCE: 271
ggacatttgg ctacttagag                                          20

<210> SEQ ID NO 272
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 272
gaagatattg aaacagggac                                          20

<210> SEQ ID NO 273
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 273
tcccaacgag aagagtatga                                          20

<210> SEQ ID NO 274
<211> LENGTH: 20
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 274
agagcagtga cgggaacaga                                          20

<210> SEQ ID NO 275
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 275
tgtgcttatg gctgttgatg                                          20

<210> SEQ ID NO 276
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 276
ccactgtgcc ctgttagttt                                          20

<210> SEQ ID NO 277
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 277
```

```
gcattccgtt ggctattctc                                              20
```

<210> SEQ ID NO 278
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 278

```
gatgtgcttt gtttagtggg                                              20
```

<210> SEQ ID NO 279
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 279

```
ggatgtacgg cagcttgata                                              20
```

<210> SEQ ID NO 280
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 280

```
gctggacact ggaggataga                                              20
```

<210> SEQ ID NO 281
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 281

```
gccaccacca ttaggcaaac                                              20
```

<210> SEQ ID NO 282
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 282

```
gcgaagggac tactcaaccc                                              20
```

<210> SEQ ID NO 283
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 283

```
agaaagcgaa ccagtatcga                                              20
```

<210> SEQ ID NO 284
<211> LENGTH: 20
<212> TYPE: DNA
<213> ORGANISM: Artificial Sequence

```
<220> FEATURE:
<223> OTHER INFORMATION: synthetic construct; Human Oct4 reverse primer

<400> SEQUENCE: 284
gcgccggtta cagaaccaca                                               20

<210> SEQ ID NO 285
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 285
tgcttcctcc ctactgtctg                                               20

<210> SEQ ID NO 286
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 286
ctcaccgcaa cctccatctc                                               20

<210> SEQ ID NO 287
<211> LENGTH: 20
<212> TYPE: DNA
<213> ORGANISM: Artificial Sequence
<220> FEATURE:
<223> OTHER INFORMATION: synthetic construct; Human Oct4 forward primer

<400> SEQUENCE: 287
ttctcctgcc tcagcctcct                                               20

<210> SEQ ID NO 288
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 288
gcctataatt ccagcacttt                                               20

<210> SEQ ID NO 289
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 289
aggcactctg agggctattc                                               20

<210> SEQ ID NO 290
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 290
gacactaagg agacgggatt                                               20
```

```
<210> SEQ ID NO 291
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 291
tccaagtcgc tgcctttatt                                               20

<210> SEQ ID NO 292
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 292
ttccgtttcc tccactctgt                                               20

<210> SEQ ID NO 293
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 293
gcagaaggtc aggtccactc                                               20

<210> SEQ ID NO 294
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 294
cattcaagat aaccagccac                                               20

<210> SEQ ID NO 295
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 295
ggtcccgtcc taagggttgt                                               20

<210> SEQ ID NO 296
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 296
tgggtgggtg gaggagcaga                                               20

<210> SEQ ID NO 297
<211> LENGTH: 20
<212> TYPE: DNA
<213> ORGANISM: Artificial Sequence
<220> FEATURE:
<223> OTHER INFORMATION: synthetic construct; Mouse Oct4 forward primer
```

-continued

```
<400> SEQUENCE: 297
tcccaacgag aagagtatga                                          20

<210> SEQ ID NO 298
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 298
ccagagcagt gacgggaaca                                          20

<210> SEQ ID NO 299
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 299
ggacatttgg ctacttagag                                          20

<210> SEQ ID NO 300
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 300
gaagatattg aaacagggac                                          20

<210> SEQ ID NO 301
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 301
tcccaacgag aagagtatga                                          20

<210> SEQ ID NO 302
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 302
agagcagtga cgggaacaga                                          20

<210> SEQ ID NO 303
<211> LENGTH: 20
<212> TYPE: DNA
<213> ORGANISM: Artificial Sequence
<220> FEATURE:
<223> OTHER INFORMATION: synthetic construct; Mouse Sox2 forward primer

<400> SEQUENCE: 303
gtgagcgccc tgcagtacaa                                          20

<210> SEQ ID NO 304
```

```
<211> LENGTH: 23
<212> TYPE: DNA
<213> ORGANISM: Artificial Sequence
<220> FEATURE:
<223> OTHER INFORMATION: synthetic construct; Mouse Sox2 reverse primer

<400> SEQUENCE: 304
gcgagtagga catgctgtag gtg                                              23

<210> SEQ ID NO 305
<211> LENGTH: 20
<212> TYPE: DNA
<213> ORGANISM: Artificial Sequence
<220> FEATURE:
<223> OTHER INFORMATION: synthetic construct; Human Sox2 forward primer

<400> SEQUENCE: 305
gtgagcgccc tgcagtacaa                                                  20

<210> SEQ ID NO 306
<211> LENGTH: 23
<212> TYPE: DNA
<213> ORGANISM: Artificial Sequence
<220> FEATURE:
<223> OTHER INFORMATION: synthetic construct; Human Sox2 reverse primer

<400> SEQUENCE: 306
gcgagtagga catgctgtag gtg                                              23

<210> SEQ ID NO 307
<211> LENGTH: 20
<212> TYPE: DNA
<213> ORGANISM: Artificial Sequence
<220> FEATURE:
<223> OTHER INFORMATION: synthetic construct; Mouse Oct4 forward primer

<400> SEQUENCE: 307
gatcactcac atcgccaatc                                                  20

<210> SEQ ID NO 308
<211> LENGTH: 20
<212> TYPE: DNA
<213> ORGANISM: Artificial Sequence
<220> FEATURE:
<223> OTHER INFORMATION: synthetic construct; Mouse Oct4 reverse primer

<400> SEQUENCE: 308
ggtgtccctg tagcctcata                                                  20

<210> SEQ ID NO 309
<211> LENGTH: 23
<212> TYPE: DNA
<213> ORGANISM: Artificial Sequence
<220> FEATURE:
<223> OTHER INFORMATION: synthetic construct; Human Oct4 forward primer

<400> SEQUENCE: 309
tgaagctgga gaaggagaag ctg                                              23

<210> SEQ ID NO 310
<211> LENGTH: 20
<212> TYPE: DNA
<213> ORGANISM: Artificial Sequence
<220> FEATURE:
<223> OTHER INFORMATION: synthetic construct; Human Oct4 reverse primer

<400> SEQUENCE: 310
```
gcagatggtc gtttggctga					20

<210> SEQ ID NO 311
<211> LENGTH: 20
<212> TYPE: DNA
<213> ORGANISM: Artificial Sequence
<220> FEATURE:
<223> OTHER INFORMATION: synthetic construct; Mouse HDAC1 forward primer

<400> SEQUENCE: 311
ttgctcgctg ctggacttac					20

<210> SEQ ID NO 312
<211> LENGTH: 20
<212> TYPE: DNA
<213> ORGANISM: Artificial Sequence
<220> FEATURE:
<223> OTHER INFORMATION: synthetic construct; Mouse HDAC1 reverse primer

<400> SEQUENCE: 312
tggcttctcc tccttggttt					20

<210> SEQ ID NO 313
<211> LENGTH: 20
<212> TYPE: DNA
<213> ORGANISM: Artificial Sequence
<220> FEATURE:
<223> OTHER INFORMATION: synthetic construct; Human HDAC1 forward primer

<400> SEQUENCE: 313
gggatcggtt aggttgcttc					20

<210> SEQ ID NO 314
<211> LENGTH: 20
<212> TYPE: DNA
<213> ORGANISM: Artificial Sequence
<220> FEATURE:
<223> OTHER INFORMATION: synthetic construct; Human HDAC1 reverse primer

<400> SEQUENCE: 314
ttgtcagggt cgtcttcgtc					20

<210> SEQ ID NO 315
<211> LENGTH: 20
<212> TYPE: DNA
<213> ORGANISM: Artificial Sequence
<220> FEATURE:
<223> OTHER INFORMATION: synthetic construct; Mouse HDAC2 forward primer

<400> SEQUENCE: 315
ggacaggctt ggttgtttca					20

<210> SEQ ID NO 316
<211> LENGTH: 20
<212> TYPE: DNA
<213> ORGANISM: Artificial Sequence
<220> FEATURE:
<223> OTHER INFORMATION: synthetic construct; Mouse HDAC2 reverse primer

<400> SEQUENCE: 316
attcctacga cctccttcac					20

<210> SEQ ID NO 317
<211> LENGTH: 20
<212> TYPE: DNA

```
<213> ORGANISM: Artificial Sequence
<220> FEATURE:
<223> OTHER INFORMATION: synthetic construct; Human HDAC2 forward primer

<400> SEQUENCE: 317
aaggcaaata ctatgctgtc                                                20

<210> SEQ ID NO 318
<211> LENGTH: 20
<212> TYPE: DNA
<213> ORGANISM: Artificial Sequence
<220> FEATURE:
<223> OTHER INFORMATION: synthetic construct; Human HDAC2 reverse primer

<400> SEQUENCE: 318
ttgggaatct cacaatcaag                                                20

<210> SEQ ID NO 319
<211> LENGTH: 20
<212> TYPE: DNA
<213> ORGANISM: Artificial Sequence
<220> FEATURE:
<223> OTHER INFORMATION: synthetic construct; Mouse HDAC3 forward primer

<400> SEQUENCE: 319
ccgaaatgtt gcccggtgtt                                                20

<210> SEQ ID NO 320
<211> LENGTH: 20
<212> TYPE: DNA
<213> ORGANISM: Artificial Sequence
<220> FEATURE:
<223> OTHER INFORMATION: synthetic construct; Mouse HDAC3 reverse primer

<400> SEQUENCE: 320
gggtgcttct ggcctgctgt                                                20

<210> SEQ ID NO 321
<211> LENGTH: 20
<212> TYPE: DNA
<213> ORGANISM: Artificial Sequence
<220> FEATURE:
<223> OTHER INFORMATION: synthetic construct; Human HDAC3 forward primer

<400> SEQUENCE: 321
gcaccatgcc aagaagtttg                                                20

<210> SEQ ID NO 322
<211> LENGTH: 20
<212> TYPE: DNA
<213> ORGANISM: Artificial Sequence
<220> FEATURE:
<223> OTHER INFORMATION: synthetic construct; Human HDAC3 reverse primer

<400> SEQUENCE: 322
caccacccag cacgagtaga                                                20

<210> SEQ ID NO 323
<211> LENGTH: 20
<212> TYPE: DNA
<213> ORGANISM: Artificial Sequence
<220> FEATURE:
<223> OTHER INFORMATION: synthetic construct; Mouse HDAC6 forward primer

<400> SEQUENCE: 323
aaccgcactg ggctggtcta                                                20
```

<210> SEQ ID NO 324
<211> LENGTH: 20
<212> TYPE: DNA
<213> ORGANISM: Artificial Sequence
<220> FEATURE:
<223> OTHER INFORMATION: synthetic construct; Mouse HDAC6 reverse primer

<400> SEQUENCE: 324
tcaaagttgg caccttcacg                                              20

<210> SEQ ID NO 325
<211> LENGTH: 20
<212> TYPE: DNA
<213> ORGANISM: Artificial Sequence
<220> FEATURE:
<223> OTHER INFORMATION: synthetic construct; Human HDAC6 forward primer

<400> SEQUENCE: 325
cagcgaagaa gtaggcagaa                                              20

<210> SEQ ID NO 326
<211> LENGTH: 20
<212> TYPE: DNA
<213> ORGANISM: Artificial Sequence
<220> FEATURE:
<223> OTHER INFORMATION: synthetic construct; Human HDAC6 reverse primer

<400> SEQUENCE: 326
gctgtcatcc cagaggcaat                                              20

<210> SEQ ID NO 327
<211> LENGTH: 20
<212> TYPE: DNA
<213> ORGANISM: Artificial Sequence
<220> FEATURE:
<223> OTHER INFORMATION: synthetic construct; Mouse Sirt1 forward primer

<400> SEQUENCE: 327
gggaaccttt gcctcatcta                                              20

<210> SEQ ID NO 328
<211> LENGTH: 20
<212> TYPE: DNA
<213> ORGANISM: Artificial Sequence
<220> FEATURE:
<223> OTHER INFORMATION: synthetic construct; Mouse Sirt1 reverse primer

<400> SEQUENCE: 328
tactggaacc aacagcctta                                              20

<210> SEQ ID NO 329
<211> LENGTH: 20
<212> TYPE: DNA
<213> ORGANISM: Artificial Sequence
<220> FEATURE:
<223> OTHER INFORMATION: synthetic construct; Human Sirt1 forward primer

<400> SEQUENCE: 329
tcctcattgt tattgggtct                                              20

<210> SEQ ID NO 330
<211> LENGTH: 20
<212> TYPE: DNA
<213> ORGANISM: Artificial Sequence
<220> FEATURE:

<223> OTHER INFORMATION: synthetic construct; Human Sirt1 reverse primer

<400> SEQUENCE: 330
attactctta gctgcttggt                                          20

<210> SEQ ID NO 331
<211> LENGTH: 20
<212> TYPE: DNA
<213> ORGANISM: Artificial Sequence
<220> FEATURE:
<223> OTHER INFORMATION: synthetic construct; Mouse LSD1 forward primer

<400> SEQUENCE: 331
tcttatcaac ttcggcatct                                          20

<210> SEQ ID NO 332
<211> LENGTH: 20
<212> TYPE: DNA
<213> ORGANISM: Artificial Sequence
<220> FEATURE:
<223> OTHER INFORMATION: synthetic construct; Mouse LSD1 reverse primer

<400> SEQUENCE: 332
tagcaactcg tccacctact                                          20

<210> SEQ ID NO 333
<211> LENGTH: 19
<212> TYPE: DNA
<213> ORGANISM: Artificial Sequence
<220> FEATURE:
<223> OTHER INFORMATION: synthetic construct; Human LSD1 forward primer

<400> SEQUENCE: 333
agcgtcatgg tcttatcaa                                           19

<210> SEQ ID NO 334
<211> LENGTH: 18
<212> TYPE: DNA
<213> ORGANISM: Artificial Sequence
<220> FEATURE:
<223> OTHER INFORMATION: synthetic construct; Human LSD1 reverse primer

<400> SEQUENCE: 334
gaaatgtggc aactcgtc                                            18

<210> SEQ ID NO 335
<211> LENGTH: 20
<212> TYPE: DNA
<213> ORGANISM: Artificial Sequence
<220> FEATURE:
<223> OTHER INFORMATION: synthetic construct; Mouse HNF4A forward primer

<400> SEQUENCE: 335
gatgcttctc ggagggtctg                                          20

<210> SEQ ID NO 336
<211> LENGTH: 20
<212> TYPE: DNA
<213> ORGANISM: Artificial Sequence
<220> FEATURE:
<223> OTHER INFORMATION: synthetic construct; Mouse HNF4A reverse primer

<400> SEQUENCE: 336
gctgtggagt ctcgggagtg                                          20

```
<210> SEQ ID NO 337
<211> LENGTH: 23
<212> TYPE: DNA
<213> ORGANISM: Artificial Sequence
<220> FEATURE:
<223> OTHER INFORMATION: synthetic construct; Human HNF4A forward primer

<400> SEQUENCE: 337
agctgcagat cgatgacaat gag                                           23

<210> SEQ ID NO 338
<211> LENGTH: 23
<212> TYPE: DNA
<213> ORGANISM: Artificial Sequence
<220> FEATURE:
<223> OTHER INFORMATION: synthetic construct; Human HNF4A reverse primer

<400> SEQUENCE: 338
catactggcg gtcgttgatg tag                                           23

<210> SEQ ID NO 339
<211> LENGTH: 20
<212> TYPE: DNA
<213> ORGANISM: Artificial Sequence
<220> FEATURE:
<223> OTHER INFORMATION: synthetic construct; Mouse FoxA2 forward primer

<400> SEQUENCE: 339
agaactccat ccgccactct                                               20

<210> SEQ ID NO 340
<211> LENGTH: 20
<212> TYPE: DNA
<213> ORGANISM: Artificial Sequence
<220> FEATURE:
<223> OTHER INFORMATION: synthetic construct; Mouse FoxA2 reverse primer

<400> SEQUENCE: 340
ggtcttcttg cctccgctac                                               20

<210> SEQ ID NO 341
<211> LENGTH: 20
<212> TYPE: DNA
<213> ORGANISM: Artificial Sequence
<220> FEATURE:
<223> OTHER INFORMATION: synthetic construct; Human FoxA2 forward primer

<400> SEQUENCE: 341
ccccaacaag atgctgacgc                                               20

<210> SEQ ID NO 342
<211> LENGTH: 19
<212> TYPE: DNA
<213> ORGANISM: Artificial Sequence
<220> FEATURE:
<223> OTHER INFORMATION: synthetic construct; Human FoxA2 reverse primer

<400> SEQUENCE: 342
gcgagtggcg gatggagtt                                                19

<210> SEQ ID NO 343
<211> LENGTH: 20
<212> TYPE: DNA
<213> ORGANISM: Artificial Sequence
<220> FEATURE:
<223> OTHER INFORMATION: synthetic construct; Mouse Sox17 forward primer
```

```
<400> SEQUENCE: 343
gggatacgcc agtgacgacc                                              20

<210> SEQ ID NO 344
<211> LENGTH: 20
<212> TYPE: DNA
<213> ORGANISM: Artificial Sequence
<220> FEATURE:
<223> OTHER INFORMATION: synthetic construct; Mouse Sox17 reverse primer

<400> SEQUENCE: 344
ccacctcgcc tttcaccttt                                              20

<210> SEQ ID NO 345
<211> LENGTH: 22
<212> TYPE: DNA
<213> ORGANISM: Artificial Sequence
<220> FEATURE:
<223> OTHER INFORMATION: synthetic construct; Human Sox17 forward primer

<400> SEQUENCE: 345
ctgcaggcca gaagcagtgt ta                                           22

<210> SEQ ID NO 346
<211> LENGTH: 22
<212> TYPE: DNA
<213> ORGANISM: Artificial Sequence
<220> FEATURE:
<223> OTHER INFORMATION: synthetic construct; Human Sox17 reverse primer

<400> SEQUENCE: 346
cccaaactgt tcaagtggca ga                                           22

<210> SEQ ID NO 347
<211> LENGTH: 20
<212> TYPE: DNA
<213> ORGANISM: Artificial Sequence
<220> FEATURE:
<223> OTHER INFORMATION: synthetic construct; Mouse BMP2 forward primer

<400> SEQUENCE: 347
tgtgaggatt agcaggtctt                                              20

<210> SEQ ID NO 348
<211> LENGTH: 20
<212> TYPE: DNA
<213> ORGANISM: Artificial Sequence
<220> FEATURE:
<223> OTHER INFORMATION: synthetic construct; Mouse BMP2 reverse primer

<400> SEQUENCE: 348
gtccacatac aaagggtgtc                                              20

<210> SEQ ID NO 349
<211> LENGTH: 18
<212> TYPE: DNA
<213> ORGANISM: Artificial Sequence
<220> FEATURE:
<223> OTHER INFORMATION: synthetic construct; Human BMP2 forward primer

<400> SEQUENCE: 349
acagcggaaa cgccttaa                                                18

<210> SEQ ID NO 350
<211> LENGTH: 18
```

```
<212> TYPE: DNA
<213> ORGANISM: Artificial Sequence
<220> FEATURE:
<223> OTHER INFORMATION: synthetic construct; Human BMP2 reverse primer

<400> SEQUENCE: 350
gggagccaca atccagtc                                                 18

<210> SEQ ID NO 351
<211> LENGTH: 24
<212> TYPE: DNA
<213> ORGANISM: Artificial Sequence
<220> FEATURE:
<223> OTHER INFORMATION: synthetic construct; Human beta-Actin reverse
      primer

<400> SEQUENCE: 351
gaaggtggac agtgaggcca ggat                                          24

<210> SEQ ID NO 352
<211> LENGTH: 20
<212> TYPE: DNA
<213> ORGANISM: Artificial Sequence
<220> FEATURE:
<223> OTHER INFORMATION: synthetic construct; Mouse EOMES forward primer

<400> SEQUENCE: 352
cccaacagag cgaagaggtg                                               20

<210> SEQ ID NO 353
<211> LENGTH: 20
<212> TYPE: DNA
<213> ORGANISM: Artificial Sequence
<220> FEATURE:
<223> OTHER INFORMATION: synthetic construct; Mouse EOMES reverse primer

<400> SEQUENCE: 353
gaaggtcggg tcagggtaat                                               20

<210> SEQ ID NO 354
<211> LENGTH: 18
<212> TYPE: DNA
<213> ORGANISM: Artificial Sequence
<220> FEATURE:
<223> OTHER INFORMATION: synthetic construct; Human EOMES forward primer

<400> SEQUENCE: 354
cccagaccca acctttcc                                                 18

<210> SEQ ID NO 355
<211> LENGTH: 22
<212> TYPE: DNA
<213> ORGANISM: Artificial Sequence
<220> FEATURE:
<223> OTHER INFORMATION: synthetic construct; Human EOMES reverse primer

<400> SEQUENCE: 355
gagccaattt cctctttcac tt                                            22

<210> SEQ ID NO 356
<211> LENGTH: 23
<212> TYPE: DNA
<213> ORGANISM: Artificial Sequence
<220> FEATURE:
<223> OTHER INFORMATION: synthetic construct; Human beta-Actin forward
      primer
```

<400> SEQUENCE: 356
tccagccttc cttcttgggt atg                                    23

<210> SEQ ID NO 357
<211> LENGTH: 20
<212> TYPE: DNA
<213> ORGANISM: Artificial Sequence
<220> FEATURE:
<223> OTHER INFORMATION: synthetic construct; Mouse beta-Actin forward
      primer

<400> SEQUENCE: 357
tgcgtgacat caaagagaag                                        20

<210> SEQ ID NO 358
<211> LENGTH: 19
<212> TYPE: DNA
<213> ORGANISM: Artificial Sequence
<220> FEATURE:
<223> OTHER INFORMATION: synthetic construct; Mouse beta-Actin reverse
      primer

<400> SEQUENCE: 358
gatgccacag gattccata                                         19

<210> SEQ ID NO 359
<211> LENGTH: 20
<212> TYPE: DNA
<213> ORGANISM: Artificial Sequence
<220> FEATURE:
<223> OTHER INFORMATION: synthetic construct; Human Hes1 forward primer

<400> SEQUENCE: 359
atagctcgcg gcattccaag                                        20

<210> SEQ ID NO 360
<211> LENGTH: 20
<212> TYPE: DNA
<213> ORGANISM: Artificial Sequence
<220> FEATURE:
<223> OTHER INFORMATION: synthetic construct; Human Hes1 reverse primer

<400> SEQUENCE: 360
gaagcgggtc acctcgttca                                        20

<210> SEQ ID NO 361
<211> LENGTH: 20
<212> TYPE: DNA
<213> ORGANISM: Artificial Sequence
<220> FEATURE:
<223> OTHER INFORMATION: synthetic construct; Human DLL1 forward primer

<400> SEQUENCE: 361
acagcaagcg tgacaccaag                                        20

<210> SEQ ID NO 362
<211> LENGTH: 20
<212> TYPE: DNA
<213> ORGANISM: Artificial Sequence
<220> FEATURE:
<223> OTHER INFORMATION: synthetic construct; Human DLL1 reverse primer

<400> SEQUENCE: 362
tgaagttgaa cagcccgagt                                        20

```
<210> SEQ ID NO 363
<211> LENGTH: 20
<212> TYPE: DNA
<213> ORGANISM: Artificial Sequence
<220> FEATURE:
<223> OTHER INFORMATION: synthetic construct; Human Gadd45g forward
      primer

<400> SEQUENCE: 363
acgctgatcc aggctttctg                                               20

<210> SEQ ID NO 364
<211> LENGTH: 20
<212> TYPE: DNA
<213> ORGANISM: Artificial Sequence
<220> FEATURE:
<223> OTHER INFORMATION: synthetic construct; Human Gadd45g reverse
      primer

<400> SEQUENCE: 364
aacaggctga gcttctccaa                                               20

<210> SEQ ID NO 365
<211> LENGTH: 24
<212> TYPE: DNA
<213> ORGANISM: Artificial Sequence
<220> FEATURE:
<223> OTHER INFORMATION: synthetic construct; Mouse Hes1 forward primer

<400> SEQUENCE: 365
gacggccaat ttgcctttct catc                                          24

<210> SEQ ID NO 366
<211> LENGTH: 23
<212> TYPE: DNA
<213> ORGANISM: Artificial Sequence
<220> FEATURE:
<223> OTHER INFORMATION: synthetic construct; Mouse Hes1 reverse primer

<400> SEQUENCE: 366
tcagttccgc cacggtctcc aca                                           23

<210> SEQ ID NO 367
<211> LENGTH: 24
<212> TYPE: DNA
<213> ORGANISM: Artificial Sequence
<220> FEATURE:
<223> OTHER INFORMATION: synthetic construct; Mouse DLL1 forward primer

<400> SEQUENCE: 367
cagataaccc tgacggaggc taca                                          24

<210> SEQ ID NO 368
<211> LENGTH: 24
<212> TYPE: DNA
<213> ORGANISM: Artificial Sequence
<220> FEATURE:
<223> OTHER INFORMATION: synthetic construct; Mouse DLL1 reverse primer

<400> SEQUENCE: 368
ggaggaggca cagtcatcca catt                                          24

<210> SEQ ID NO 369
<211> LENGTH: 23
<212> TYPE: DNA
<213> ORGANISM: Artificial Sequence
<220> FEATURE:
```

```
<223> OTHER INFORMATION: synthetic construct; Mouse Gadd45g forward
      primer

<400> SEQUENCE: 369
cgtctacgag tccgccaaag tcc                                            23

<210> SEQ ID NO 370
<211> LENGTH: 25
<212> TYPE: DNA
<213> ORGANISM: Artificial Sequence
<220> FEATURE:
<223> OTHER INFORMATION: synthetic construct; Mouse Gadd45g reverse
      primer

<400> SEQUENCE: 370
cagaacgcct gaatcaacgt gaaat                                          25

<210> SEQ ID NO 371
<211> LENGTH: 20
<212> TYPE: DNA
<213> ORGANISM: Artificial Sequence
<220> FEATURE:
<223> OTHER INFORMATION: synthetic construct; Human Tip60 forward primer

<400> SEQUENCE: 371
gatggaatac cgtcagcacc                                                20

<210> SEQ ID NO 372
<211> LENGTH: 20
<212> TYPE: DNA
<213> ORGANISM: Artificial Sequence
<220> FEATURE:
<223> OTHER INFORMATION: synthetic construct; Human Tip60 reverse primer

<400> SEQUENCE: 372
tgaggcagaa ctcgcacagg                                                20

<210> SEQ ID NO 373
<211> LENGTH: 20
<212> TYPE: DNA
<213> ORGANISM: Artificial Sequence
<220> FEATURE:
<223> OTHER INFORMATION: synthetic construct; Mouse Tip60 forward primer

<400> SEQUENCE: 373
gtgaaacgga aggtggaggt                                                20

<210> SEQ ID NO 374
<211> LENGTH: 20
<212> TYPE: DNA
<213> ORGANISM: Artificial Sequence
<220> FEATURE:
<223> OTHER INFORMATION: synthetic construct; Mouse Tip60 reverse primer

<400> SEQUENCE: 374
ccagtcattc gtggtgctga                                                20
```

SUICIDAL LSD1 INHIBITORS TARGETING SOX2-EXPRESSING CANCER CELLS

CROSS-REFERENCE TO RELATED APPLICATIONS

This Application claims benefit of priority under 35 U.S.C. § 371 of PCT/US2014/040368, filed May 30, 2014, which claims the benefit under 35 U.S.C. § 119(e) of U.S. Provisional Application No. 61/828,749, filed on May 30, 2013, and U.S. Provisional Application No. 61/937,394, filed on Feb. 7, 2014, which are incorporated herein by reference in their entireties.

STATEMENT REGARDING FEDERALLY SPONSORED RESEARCH

This invention was made with government support under grant number RO1CA989559, awarded by the National Institutes of Health (NIH). The U.S. government has certain rights in the invention.

REFERENCE TO SEQUENCE LISTING

The Sequence Listing submitted Nov. 30, 2015 as a text file named "37474_0004U3_Sequence_Listing.txt", created on Nov. 30, 2015, and having a size of 82,955 bytes is hereby incorporated by reference pursuant to 37 C.F.R. § 1.52(e)(5).

BACKGROUND

The official name and symbol of the Sox2 gene are "SRY (sex determining region Y)-box 2" and SOX2, respectively. The SOX2 gene provides instructions for making a protein that plays a critical role in the formation of many different tissues and organs during embryonic development. This protein regulates the activity of other genes by attaching (binding) to specific regions of DNA in order to turn other genes on or off. On the basis of this action, the SOX2 protein is referred to as a transcription factor. The SOX2 protein is especially important for the development of the eyes. At least 33 mutations in the SOX2 gene have been found to cause the SOX2 anophthalmia syndrome or the anophthalmia-esophageal-genital (AEG) syndrome. Some of these mutations prevent the gene from making any SOX2 protein, while others result in the production of an abnormally short, nonfunctional version of the protein. A few mutations change single protein building blocks (amino acids) in the SOX2 protein. All of these mutations disrupt the protein's ability to regulate genes essential for normal development of the eyes and other parts of the body. Abnormal development of these structures causes the signs and symptoms of SOX2 anophthalmia syndrome or anophthalmia-esophageal-genital (AEG) syndrome.

In lung development, Sox2 controls the branching morphogenesis of the bronchial tree and differentiation of the epithelium of airways. Over-expression causes an increase in neuroendocrine, gastric/intestinal, and basal cells. Under normal conditions, Sox2 is critical for maintaining self-renewal and the appropriate proportion of basal cells in adult tracheal epithelium. However, its over-expression gives rise to extensive epithelial hyperplasia and eventually carcinoma in both developing and adult mouse lungs.

In squamous cell carcinoma, gene amplifications frequently target the 3q26.3 region. The gene for Sox2 lies within this region, which effectively characterizes Sox2 as an oncogene. Sox2 is a key upregulated factor in lung squamous cell carcinoma, directing many genes involved in tumor progression. Its over-expression also activates cellular migration and anchorage-independent growth. The ectopic expression of SOX2 may be related to abnormal differentiation of colorectal cancer cells.

Lung cancer is the most frequent cause of cancer death in the United States. Squamous cell carcinoma of the lung is a major form of frequent and aggressive lung cancer. Recent studies show that the gene amplification of Sox2 that encodes a high mobility group domain-containing transcription factor is the most frequent and common event in squamous cell carcinomas of the lung, esophagus, and oral cavity at 3q22.33 (Bass, A. J., et al. (2009) Nat. Genet. 41, 1238-1242). Sox2 is a master regulator of pluripotent embryonic stem cells (ESCs) and adult neural stem cells. It can reprogram somatic cells into the induced pluripotent stem cells (iPSCs) with Oct4, Klf4, and Myc, or with Oct4, Lin 28, and Nanog. Sox2 also plays an essential role in the morphogenesis and homeostasis of the esophageal, tracheobronchial and bronchiolar epithelia. Sox2 acts as a lineage-survival oncogene for the expression of pluripotent stem cell signatures and for the lineage-specific gene expression of squamous cells in lung squamous cell carcinomas. Ectopic expression of Sox2 causes the oncogenic transformation of normal tracheobronchial epithelial cells. The Sox2 gene is also amplified in a fraction of small-cell lung carcinomas (Rudin et al. (2012) Nat. Genet. 44, 1111-1116). Sox2 is expressed in lung adenocarcinomas whose expression is associated with poor prognosis. Sox2 is frequently expressed in other types of poorly differentiated and aggressive human cancers. Sox2 is expressed in a subpopulation of stem cell-like ovarian cancer cells with other pluripotent stem cell proteins such as Oct4 or Lin28. In breast carcinomas, expression of Sox2 is associated with basal-like phenotypes and is required for mammosphere formation in culture, which is considered as part of stem cell-like properties.

Histone methylation is a major covalent modification of histones that provides the structural and functional characteristics of chromatin to epigenetically define gene expression patterns in a cell. LSD1 (lysine-specific demethylase 1), also known as KDM1, AOF2, or BHC110, is a highly conserved flavin adenine dinucleotide (FAD)-dependent lysine-specific demethylase that belongs to the monoamine oxidase family and specifically removes monomethyl- and dimethyl-groups from histone H3 at lysine 4 (H3K4), and in certain cells lysine-9 (H3K9). LSD1 is highly expressed in undifferentiated ESCs but progressively downregulated during differentiation. Loss of LSD1 in the mouse causes early embryonic lethality. Recent studies indicate that LSD1 is an essential epigenetic regulator of pluripotency in ESCs. It has been previously shown that the levels of LSD1 are elevated in pluripotent teratocarcinoma, embryonic carcinoma, and seminoma cells (Wang, J. et al. (2011) Cancer Research 71, 7238-7249).

Elevated levels of Sox2 in cancers also correlate with the presence of lymphnode and distant metastases colon cancers (Neumann, J., et al. (2011) BMC Cancer 11, 518). The over-expression and gene amplification of Sox2 were also found in a fraction of glioblastoma multiforme (GBM) (Alonso, M. M., et al. (2011) PLoS One 6, e26740) the most aggressive primary brain tumor. Lengerke et al. discloses that SOX2 expression was detected in 28% of invasive breast carcinoma as well as in 44% of ductal carcinoma in situ (DCIS) lesions (see Lengerke, C., et al. (2011) BMC Cancer 11:42). A score of SOX2 expression (score 0 to 3)

was defined in order to distinguish SOX2 negative (score 0) from SOX2 positive samples (score 1-3) and among latter subgroup of SOX2 high expressors (score 3>50% positive cells). Overall, the incidence of SOX2 expression (score 1-3) was higher than previously reported in a cohort of lymph node negative patients (28% versus 16.7%). SOX2 expression was detected across different breast cancer subtypes and did not correlate with tumor grading. However, high SOX2 expression (score 3) was associated with larger tumor size (p=0.047) and positive lymph node status (0.018). Corresponding metastatic lymph nodes showed higher SOX2 expression and were significantly more often SOX2 positive than primary tumors (p=0.0432). It has further been shown that the embryonic stem cell factor SOX2 is expressed in a variety of early stage postmenopausal breast carcinomas and metastatic lymph nodes. These data suggest that SOX2 plays an early role in breast carcinogenesis and that high expression of SOX2 may promote metastatic potential. Further studies are needed to explore whether SOX2 can predict metastatic potential at an early tumor stage.

Histone acetylation is another post-transcription modification of histones controlled by two opposing enzymes: histone acetyltransferases (HATs) and histone deacetylases (HDACs) through adding and removing acetyl groups from lysine residues. In mammals, 18 HDACs have been identified, which catalyze deacetylation of histones and many other non-histone proteins. Histone deacetylase 1 (HDAC1) belongs to the Class I HDACs, which also include HDAC2, HDAC3, and HDAC8 and are mostly localized to the nucleus. HDAC1 and HDAC2 share substantial amino acid sequence homologies and are often found to co-exist in repressive transcriptional complexes. Both HDAC1 and HDAC2 can remove the acetyl group from the acetylated histone H3 at lysine 56 (H3K56) (Miller, K. M., et al. (2010) *Nature Struct. Mol. Biol.* 17, 1144-1151). However, HDAC1 and HDAC2 may have distinct functions because germ-line deletion of HDAC1 causes mouse embryo lethality before embryonic day 10.5 while HDAC2 specifically regulates synaptic plasticity and memory formation. HDAC1 is highly expressed in pancreatic ductal adenocarcinoma, colon cancer, ovarian cancer and lung cancer. A group of HDAC inhibitors are currently being tested in clinical applications. Most of these HDAC inhibitors, which usually belong to either aliphatic acids (i.e., butyrate and valproic acid), hydroxamates (i.e., tricostatin A and SAHA), benzamides (i.e., MS-275 and MGCD0103), cyclic peptides (i.e., FK228/resminostat), or electrophilic ketone hybrid molecules (i.e., trapoxin B or CHAP31) (Khan, O. and La Thangue, N. B. (2012) *Immunology and Cell Biology* 90, 85-94), interfere with the enzymatic activities of multiple members of class I HDACs or other HDACs. These HDAC inhibitors also usually induce histone H3 or H4 hyperacetylation, which correlate with broad cytotoxicities in different cancer cells.

Despite the knowledge that Sox2 is frequently overexpressed in variety of human cancers and acts as an oncogene to confer certain stem cell properties to carcinoma cells, compounds and compositions capable of selectively targeting Sox2-expressing cancer cells have remained elusive. Thus, there remains a need for selective inhibitors that target cancer cells that exhibit cancer stem cell properties and methods of making and using same.

SUMMARY

The present invention relates to the field of cancer treatments and especially the treatment of cancers in which Sox2 expression is involved in cancer propagation or metastasis. LSD1 was identified as a unique and selective epigenetic target for a wide variety of human carcinoma cells that express Sox2. In addition, one mechanism by which LSD1 suppresses the growth of cancer cells that express Sox2 is via modulation of the activity of histone deacetylase 1 (HDAC1) through the control of acetylation of histone H4 at lysine 16 (H4K16). LSD1 and HDAC1 form a protein complex in Sox2-expressing carcinoma cells to coordinately regulate histone methylation and acetylation. Indeed, the levels of both LSD1 and HDAC1 are elevated in these cells. The present technology employs the inactivation of LSD1 and/or HDAC1 to selectively suppress or inhibit growth of cells that express Sox2. The inhibition of these two enzymes selectively suppresses or inhibits the growth and/or replication of cancer cells that express Sox2.

In one aspect, the invention relates to compound having a structure represented by a formula:

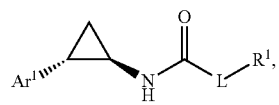

wherein L is a moiety selected from —O— and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —O—; or wherein R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$, when L is —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and monocyclic heteroaryl and wherein Ar$^1$ is substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

Also disclosed are compounds having a structure selected from:

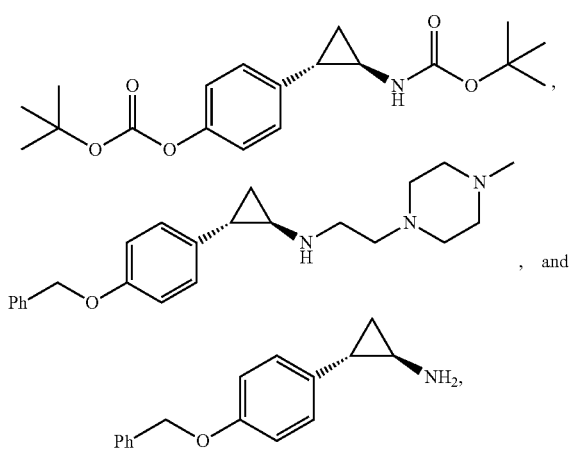

or a pharmaceutically acceptable salt thereof.

Also disclosed are pharmaceutical composition comprising a therapeutically effective amount of at least one disclosed compound, or a pharmaceutically acceptable salt, solvate, or polymorph thereof, and a pharmaceutically acceptable carrier.

Also disclosed are methods of modulating at least one histone methylation event in at least one cell, the method comprising contacting the cell with an effective amount of at least one compound having a structure represented by a formula:

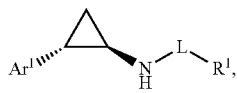

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{1b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

Also disclosed are methods of inhibiting LSD1 (lysine-specific demethylase I) in at least one cell, the method comprising the method comprising contacting the cell with an effective amount of at least one compound represented by a formula:

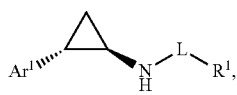

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^2$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

Also disclosed are methods of treating a cancer in a mammal, the method comprising administering to the mammal an effective amount of at least one LSD1 inhibitor.

Also disclosed are methods of treating a cancer in a mammal, the method comprising administering to the mammal an effective amount of at least one HDAC1 inhibitor.

Also disclosed are methods of inhibiting the proliferation of cancer cells in a mammal, the method comprising administering to the mammal an effective amount of at least one LSD1 inhibitor.

Also disclosed are methods of inhibiting the proliferation of cancer cells in a mammal, the method comprising administering to the mammal an effective amount of at least one HDAC1 inhibitor.

Also disclosed are methods of inhibiting the proliferation of at least one cancer cell, the method comprising contacting the at least one cell with an effective amount of at least one LSD1 inhibitor.

Also disclosed are methods of inhibiting the proliferation of at least one cancer cell, the method comprising contacting the at least one cell with an effective amount of at least one HDAC1 inhibitor.

Also disclosed are methods of inhibiting the survival of cancer cells in a mammal, the method comprising administering to the mammal an effective amount of at least one LSD1 inhibitor.

Also disclosed are methods of inhibiting the survival of cancer cells in a mammal, the method comprising administering to the mammal an effective amount of at least one HDAC1 inhibitor.

Also disclosed are methods of inhibiting the survival of at least one cancer cell, the method comprising contacting the at least one cell with an effective amount of at least one LSD1 inhibitor.

Also disclosed are methods of inhibiting the survival of at least one cancer cell, the method comprising contacting the at least one cell with an effective amount of at least one HDAC1 inhibitor.

Also disclosed are methods for the manufacture of a medicament for treatment of cancer in a mammal, the method comprising the step of combining an effective amount of at least one LSD1 inhibitor.

Also disclosed are methods for the manufacture of a medicament for treatment of cancer in a mammal, the method comprising the step of combining an effective amount of at least one HDAC1 inhibitor.

Also disclosed are kits comprising at least one disclosed compound or a pharmaceutically acceptable salt thereof, and one or more of: a) at least one agent known to inhibit LSD1; b) at least one agent known to inhibit HDAC1; c) at least one anticancer therapeutic agent; d) instructions for detecting cancer; and e) instructions for treating cancer.

BRIEF DESCRIPTION OF THE FIGURES

The accompanying figures, which are incorporated in and constitute a part of this specification, illustrate several aspects and together with the description serve to explain the principles of the invention.

FIG. 27A-F show representative data pertaining to the effects of inactivation of HDAC1 in ES/EC cells.

FIG. 28A-D show representative data demonstrating that inactivation of LSD1 or HDAC1 causes similar changes of histone methylation and acetylation in ES/EC cells.

FIG. 37A-C show representative data demonstrating that inactivation of MOF reverses the effects of LSD1 inactivation on increased acetylation of H4K16 and gene expression in ES/EC cells.

Figure 1A:
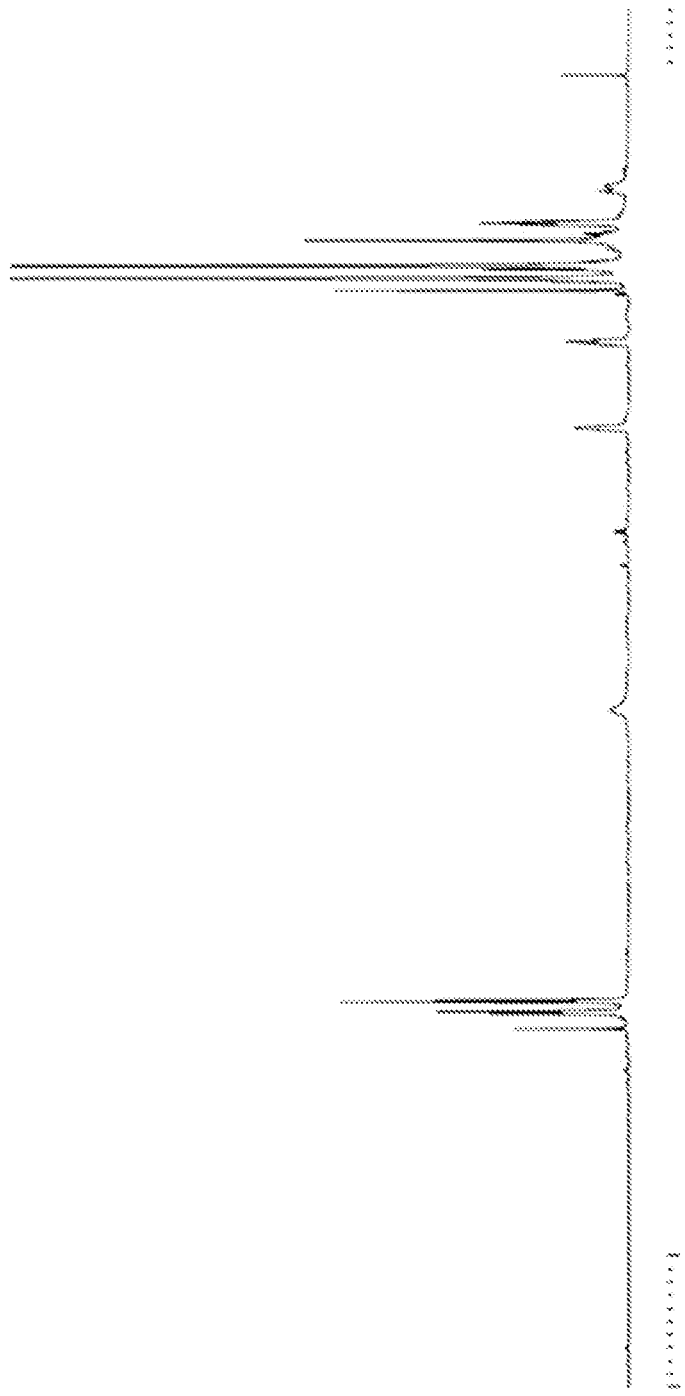
FIG. 1 shows representative spectral data for CBB3001 (Compound 10). Specifically, $^1$H NMR (1A), $^{13}$C NMR (1B), HRMS (1C), and HPLC (1D) spectra are shown.
Figure 1B:
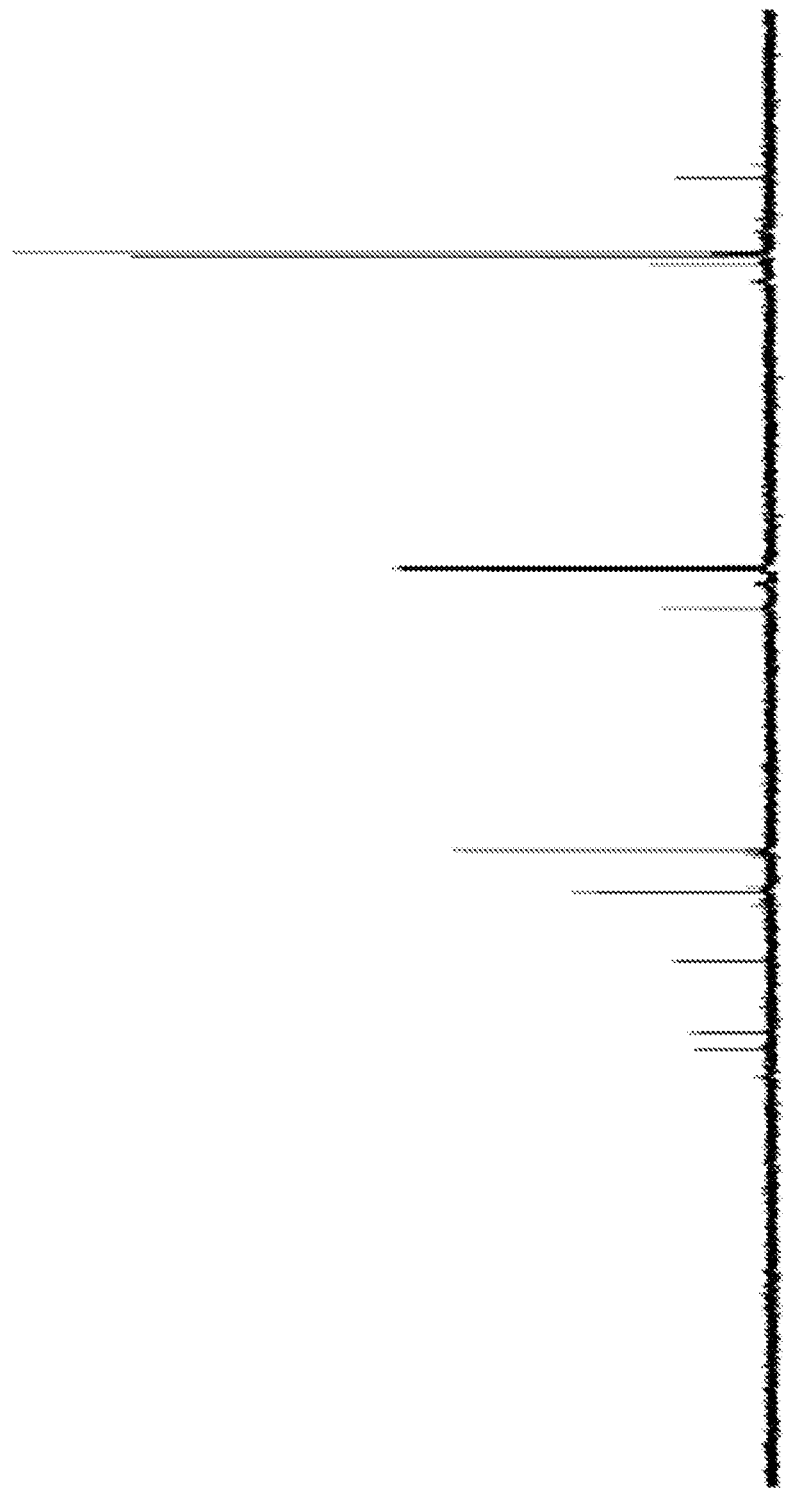
Figure 1C:
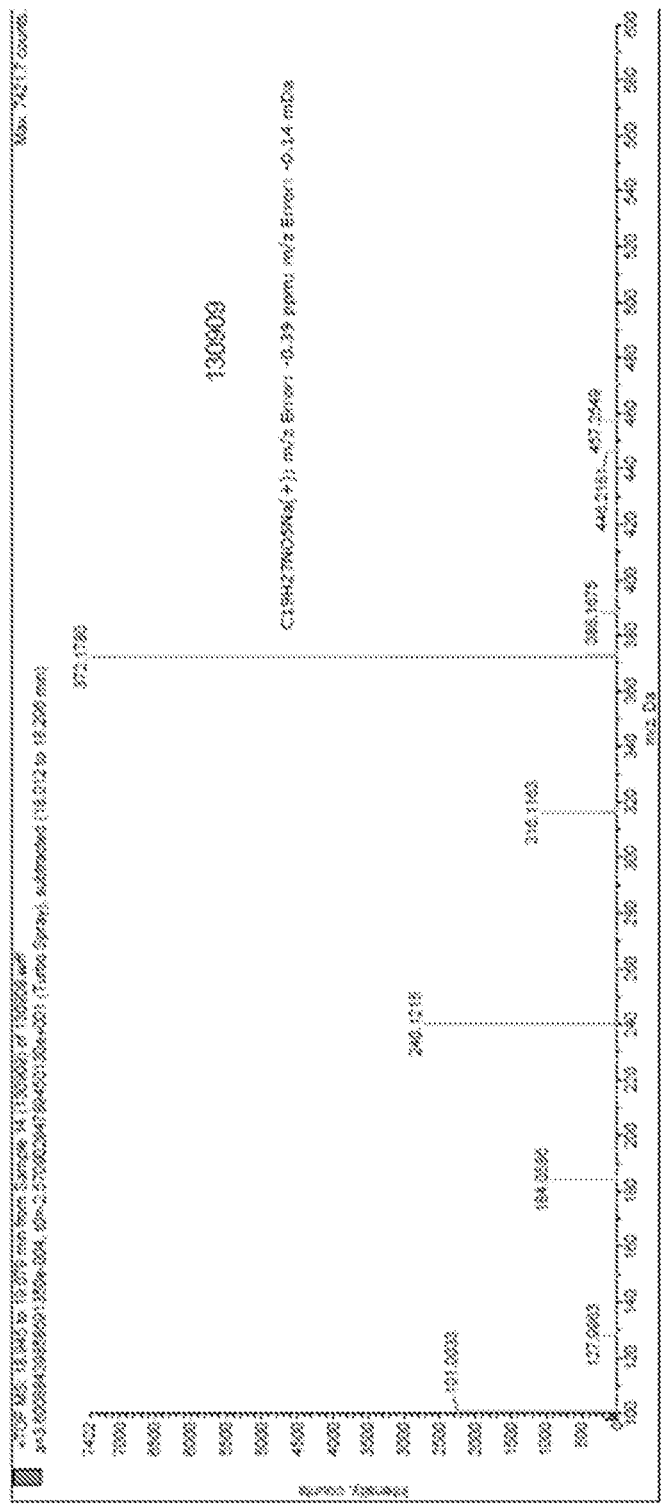
Figure 1D:
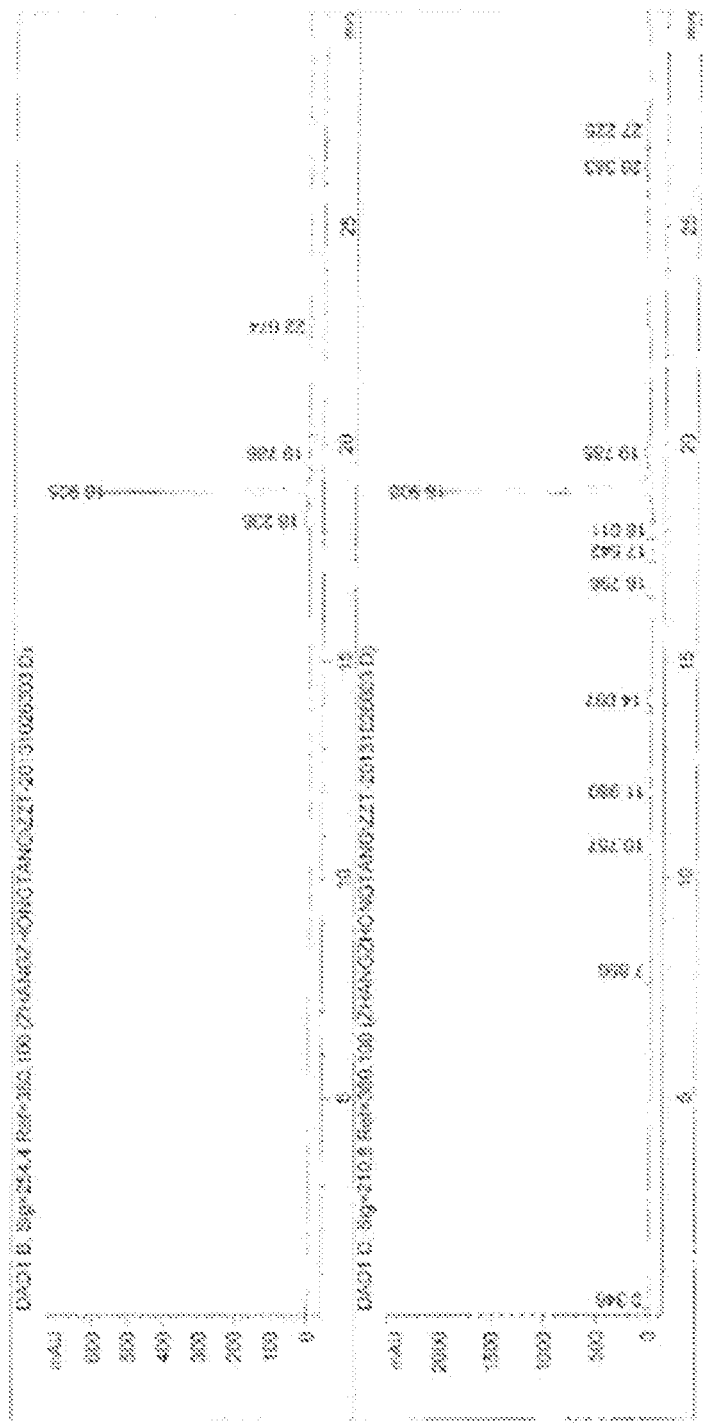

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are a disorder of cellular proliferation.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a disorder of cellular proliferation prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula (CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as OA$^1$ where A$^1$ is alkyl or cycloalkyl as defined above. "Alkoxy" also includes polymers of alkoxy groups as just described; that is, an alkoxy can be a polyether such as OA$^1$-OA$^2$ or OA$^1$(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^o$; —$(CH_2)_{0-4}OR^o$; —$O(CH_2)_{0-4}R^o$, O—$(CH_2)_{0-4}C(O)OR^o$; —$(CH_2)_{0-4}CH(OR^o)_2$; —$(CH_2)_{0-4}SR^o$; —$(CH_2)_{0-4}Ph$, which may be substituted with $R^o$; —$(CH_2)_{0-4}O(CH_2)_{0-1}Ph$ which may be substituted with $R^o$; CH=CHPh, which may be substituted with $R^o$; —$(CH_2)_{0-4}O(CH_2)_{0-1}$-pyridyl which may be substituted with $R^o$; —$NO_2$; —CN; —$N_3$; —$(CH_2)_{0-4}N(R^o)_2$; —$(CH_2)_{0-4}N(R^o)C(O)R^o$; —$N(R^o)C(S)R^o$; —$(CH_2)_{0-4}N(R^o)C(O)NR^o)_2$; —$N(R^o)C(S)NR^o)_2$; —$(CH_2)_{0-4}N(R^o)C(O)OR^o$; —$N(R^o)N(R^o)C(O)R^o$; —$N(R^o)N(R^o)C(O)NR^o)_2$; —$N(R^o)N(R^o)C(O)OR^o$; —$(CH_2)_{0-4}C(O)R^o$; —$C(S)R^o$; —$(CH_2)_{0-4}C(O)OR^o$; —$(CH_2)_{0-4}C(O)SR^o$; —$(CH_2)_{0-4}C(O)OSiR^o_3$; —$(CH_2)_{0-4}OC(O)R^o_2$; —$OC(O)(CH_2)_{0-4}SR^o$, SC(S)SR^o$; —$(CH_2)_{0-4}SC(O)R^o$; —$(CH_2)_{0-4}C(O)NR^o_2$; C(S)NR^o_2$; —C(S)SR^o$; SC(S)SR^o$, —$(CH_2)_{0-4}OC(O)NR^o_2$; —C(O)N(OR^o)R^o$; —C(O)C(O)R^o$; —C(O)CH_2C(O)R^o$; —C(NOR^o)R^o$; —$(CH_2)_{0-4}SSR^o$; —$(CH_2)_{0-4}S(O)_2R^o$; —$(CH_2)_{0-4}S(O)_2OR^o$; —$(CH_2)_{0-4}OS(O)_2R^o$; —S(O)_2NR^o_2$; —$(CH_2)_{0-4}S(O)R^o$; —N(R^o)S(O)_2NR^o_2$; —N(R^o)S(O)_2R^o$; —N(OR^o)R^o$; —C(NH)NR^o_2$; —P(O)_2R^o$; —P(O)R^o_2$; —OP(O)R^o_2$; —OP(O)(OR^o)_2$; SiR^o_3$; —$(C_{1-4}$ straight or branched)alkylene)O—$N(R^o)_2$; or —$(C_{1-4}$ straight or branched alkylene)C(O)O—$N(R^o)_2$, wherein each $R^o$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6 saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12 saturated, partially unsaturated, or aryl mono or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, (CH$_2$)$_{0-2}$NR$^\bullet_2$, —NO$_2$, SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^=$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, NR$^\bullet_2$, or NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono or bicyclic ring having 0-4 heteroatoms independently selected from nitrogen, oxygen, or sulfur.

Suitable substituents on the aliphatic group of R$^\dagger$ are independently halogen, —R$^\bullet$, -(halonR$^\bullet$), —OH, —OR$^\bullet$, —O(haloR$^\bullet$), —CN, —C(O)OH, —C(O)OR$^\bullet$, —NH$_2$, —NHR$^\bullet$, NR$^\bullet_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

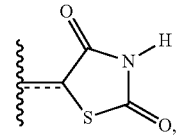

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. LSD1 INHIBITORS

In one aspect, the invention relates to inhibitors of lysine-specific demethylase I (LSD1) useful in the treatment of cancers. In various aspects, LSD1 inhibitors can be useful in the treatment or control of carcinomas, such as squamous cell carcinomas.

LSD1 is a gene which codes a flavin-dependent monoamine oxidase, which can demethylate mono- and di-methylated lysines, specifically histone 3, lysines 4 and 9 (H3K4 and H3K9). LSD1 is also involved in histone methylation. LSD1, also known as KDM1, is the first of several protein lysine demethylases discovered. Through a FAD-dependent oxidative reaction, LSD1 specifically removes histone H3K4me2 to H3K4me1 or H3K4me0. When forming a complex with androgen receptor (and possibly other nuclear hormone receptors), LSD1 changes its substrates to H3K9me2. It's now known that the LSD1 complex mediates a coordinated histone modification switch through enzymatic activities as well as histone modification readers in the complex.

LSD1 is co-expressed with Sox2 in lung squamous cell carcinomas with high frequency. Although the roles of Sox2 in carcinogenesis of many human cancers remains largely unclear, recent studies have shown that the gene amplification of Sox2 is the most frequent and common event in squamous cell carcinomas of lung, esophagus, and oral cavity at 3q22.33, as well as in a fraction of small cell lung carcinoma and glioblastoma multiforme. In lung squamous cell carcinomas, Sox2 acts as a lineage-survival oncogene for the expression of pluripotent stem cell signatures and genes for lineage-specific squamous cell differentiation.

Most LSD1 inhibitors bind to the active demethylation site to block LSD1 demethylase activity. Examples of LSD1 inhibitors include inhibitors of monoamine oxidases (i.e., derivatives of pamate (2-phenylcyclopropylamine/2-PCPA or derivatives of tranylcypromine) that form a covalent bond with FAD in LSD1, and derivatives of bisguanidine polyamine analogues, which may mimic the binding of the methylated H3K4 peptide substrate to LSD1 (Yang et al. (2007) *Biochemistry* 46, 8058-8065; Dawn, M. Z., et al. (2007) *Biochemistry* 46, 4408-4416; Harris, W. J., et al. (2012) *Cancer Cell* 21, 473-487); Huang, Y., et al. (2007) *PNAS* 104, 8023-8028). Recent studies also indicate that LSD1 is essential for maintaining the oncogenic potential of MLL-AF9 leukemia stem cells and acute myeloid leukemia. While LSD1 is essential for ESCs and related teratocarcinomas/embryonic carcinomas or leukemia cells, the mechanism by which LSD1 regulates the pluripotency of ESCs, teratocarcinomas/embryonic carcinomas, cancer stem cells or cancer cells has thus far remained unclear.

In a further aspect, the LSD1 inhibitor mimics the binding of methylated H3K4 peptide substrate to LSD1 in a non-covalent manner.

In a further aspect, the LSD1 inhibitor is a compound having a structure represented by a formula:

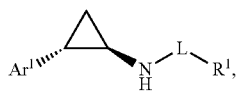

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is CO$_2$; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$R$^{10b}$, R$^{11a}$, and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is a compound having a structure represented by a formula:

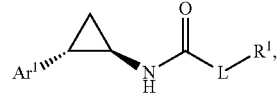

wherein L is a moiety selected from —O— and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —O—; or wherein R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$ when L is —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$, and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and monocyclic heteroaryl and wherein Ar$^1$ is substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof. In a further aspect, the LSD1 inhibitor is selected from:

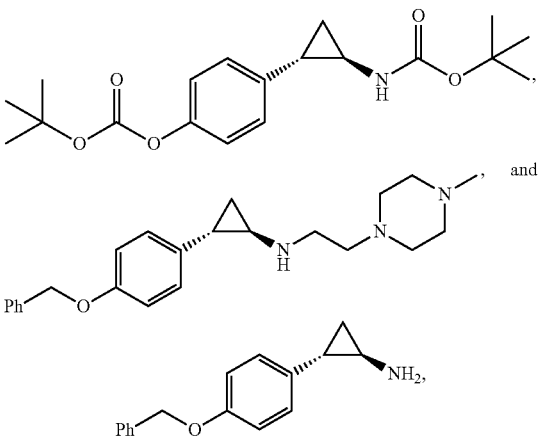

or a pharmaceutically acceptable salt thereof.

In a further aspect, the LSD1 inhibitor is selected from:

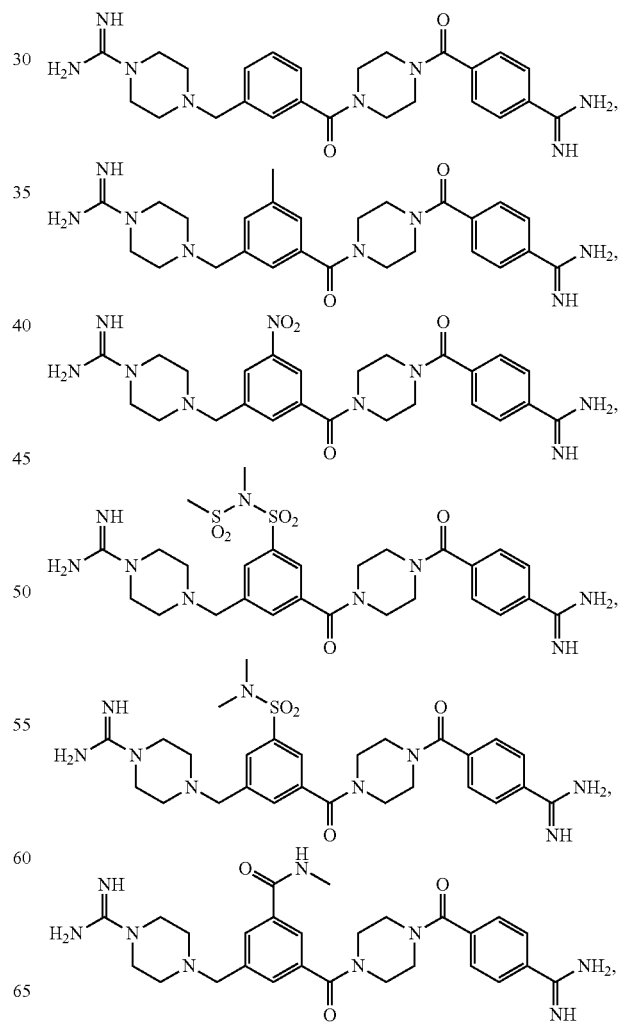

-continued

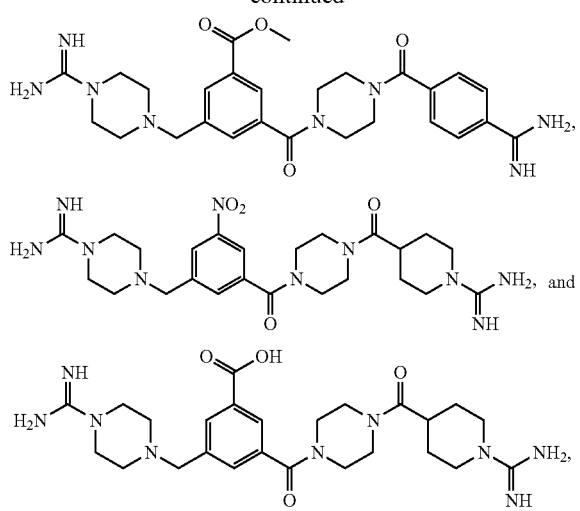

or a pharmaceutically acceptable salt thereof

In a further aspect, the LSD1 inhibitor is selected from:

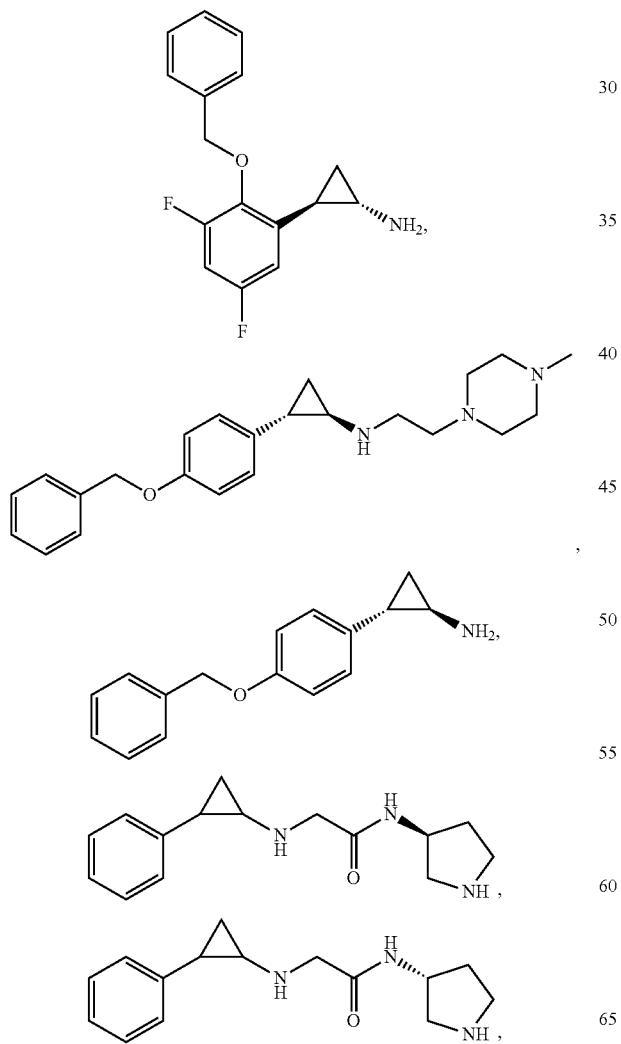

-continued or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

C. HDAC1 INHIBITORS

In one aspect, the invention relates to inhibitors of histone deacetylase I (HDAC1) useful in the treatment of cancers. In various aspects, HDAC1 inhibitors can be useful in the treatment or control of carcinomas, such as squamous cell carcinomas.

HDAC1 is an enzyme that in humans is encoded by the HDAC1 gene. Histone acetylation and deacetylation, catalyzed by multi-subunit complexes, play a key role in the regulation of eukaryotic gene expression. The protein encoded by this gene belongs to the histone deacetylase/acuc/apha family and is a component of the histone deacetylase complex. It also interacts with retinoblastoma tumor-suppressor protein and this complex is a key element in the control of cell proliferation and differentiation. In addition to histones, HDAC1 also deacetylates non-histone proteins. Together with metastasis-associated protein-2 MTA2, it deacetylates p53 and modulates its effect on cell growth and apoptosis.

Examples of HDAC inhibitors include, but are not limited to, aliphatic acids, hyroxamate, benzamide, cyclic peptide, and electrophilic ketone hybrid molecules. Additional examples can include butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOCPAC, PTACH, and PP.

In various aspects, HDAC1 forms a unique complex with LSD1 and CoREST in stem cells or Sox2-expressing cancer cells. In the LSD1-CoREST-HDAC1 complex, the LSD1 activity is dependent on the presence of an active HDAC1. So in Sox2-expressing cancer cells, HDAC1 inhibitors, such as MS-275, not only inhibited the activity of HDAC1, but also reduced the activity of LSD1, thereby producing the same growth inhibitory effects on Sox2-expressing cancer cells or cancer stem cells as that of LSD1 inhibitors.

D. COMPOUNDS

In one aspect, the invention relates to compounds useful in treating or controlling oncological disorders, such as cancer. The compounds and pharmaceutical compositions containing the compounds can be useful in the treatment or control of carcinomas, such as squamous cell carcinomas.

In one aspect, the disclosed compounds exhibit inhibition of LSD1.

In one aspect, the compounds of the invention are useful in the treatment of cancers characterized by the presence of Sox2, as described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds having a structure represented by a formula:

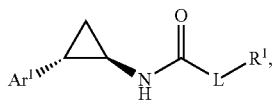

wherein L is a moiety selected from —O— and —$(CR^{2a}R^{2b})_n$—; wherein n is an integer selected from 1, and 2; wherein each of $R^{2a}$ and $R^{2b}$, when present, is independently selected from hydrogen, halogen, —OH, —$NH_2$, —$NO_2$, —CN, and —$N_3$; wherein $R^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, $Ar^2$, and $Cy^1$ when L is —O—; or wherein $R^1$ is selected from —$NO_2$, —CN, —$N_3$, —$OR^3$, —$SR^4$, —$NR^{5a}R^{5b}$, —$P(R^6)_3$—, —$CO_2R^7$, —$C(O)SR^8$, —$SO_2R^9$, —$CONR^{10a}R^{10b}$, and —$SO_2NR^{11a}R^{11b}$, when L is —$(CR^{2a}R^{2b})_n$—; wherein each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, C1-C4 alkyl, C1-C4 monohaloalkyl, C1-C4 polyhaloalkyl, $Ar^3$, and $Cy^2$; wherein $Ar^3$, when present, is selected from aryl and heteroaryl and wherein $Ar^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^2$, when present, is selected from C3-C6 cycloalkyl and C2-C5 heterocycloalkyl and wherein $Cy^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^2$, when present, is selected from aryl and heteroaryl and wherein $Ar^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^1$ is selected from phenyl and monocyclic heteroaryl and wherein $Ar^1$ is substituted with 0, 1, 2, or 3 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$; wherein $R^{12}$, when present, is selected from hydrogen, C1-C4 alkyl, C1-C4 monohaloalkyl, C1-C4 polyhaloalkyl, and —$CO_2R^{21}$; wherein $R^{21}$, when present, is selected from hydrogen and C1-C4 alkyl; wherein each of $R^{13}$, $R^{14a}$, $R^{14b}$, $R^{15}$, $R^{16}$, $R^{17}$, $R^{18}$, $R^{19}$, $R^{20a}$, and $R^{20b}$, when present, is independently selected from hydrogen, C1-C4 alkyl, C1-C4 monohaloalkyl, and C1-C4 polyhaloalkyl; wherein $Ar^4$, when present, is selected from aryl and heteroaryl and wherein $Ar^2$, when present, is substituted with 0, 1, 2, or 3 groups independently selected from halogen, —$NH_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In one aspect, the invention relates to compounds having a structure selected from:

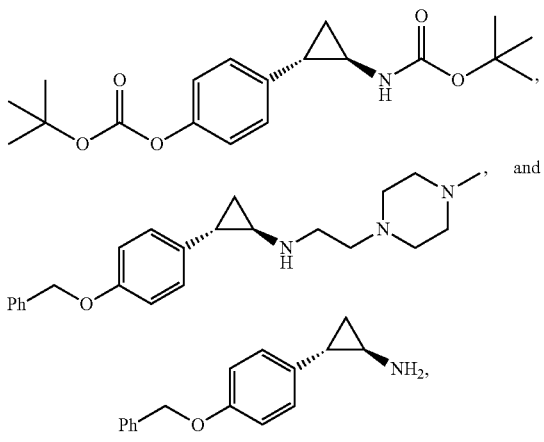

or a pharmaceutically acceptable salt thereof

In a further aspect, the compound has a structure represented by a formula:

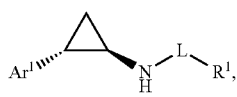

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the compound has a structure represented by a formula:

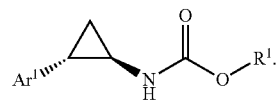

In a still further aspect, the compound has a structure represented by a formula:

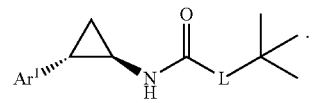

In yet a further aspect, the compound has a structure represented by a formula:

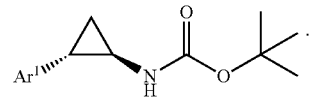

In a further aspect, the compound has a structure represented by a formula:

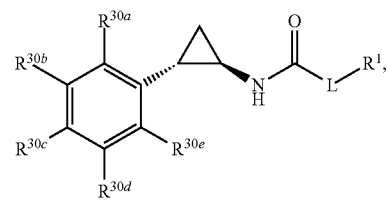

wherein each of R$^{30a}$, R$^{30b}$, R$^{30c}$, R$^{30d}$, and R$^{30e}$ is independently selected from hydrogen, halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a still further aspect, the compound has a structure represented by a formula:

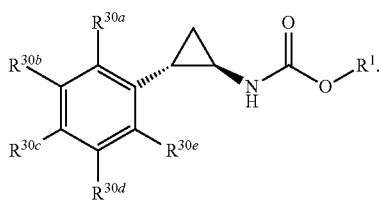

In yet a further aspect, the compound has a structure represented by a formula:

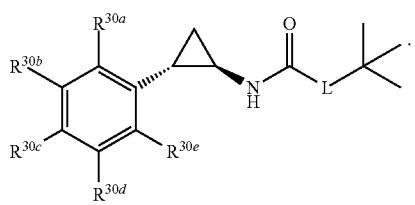

In an even further aspect, the compound has a structure represented by a formula:

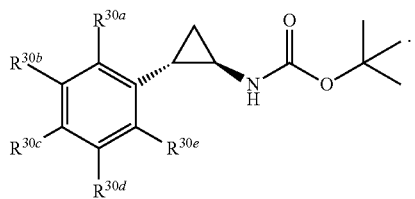

In a still further aspect, the compound has a structure represented by a formula selected from:

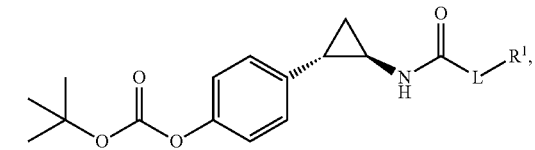

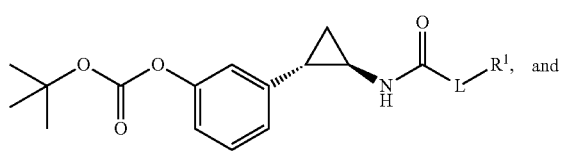

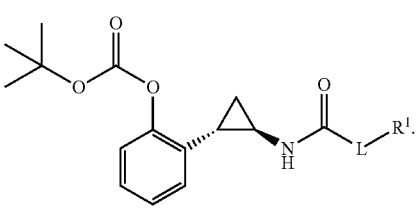

In yet a further aspect, the compound has a structure represented by a formula:

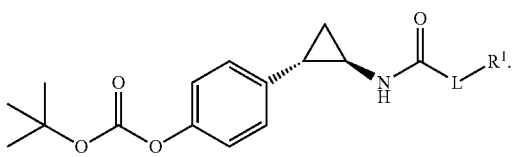

In a further aspect, the compound has a structure represented by a formula selected from:

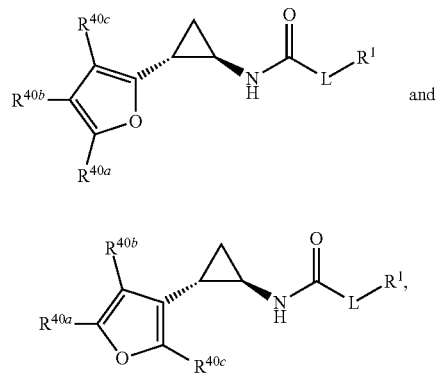

wherein each of $R^{40a}$, $R^{40b}$, and $R^{40c}$ is independently selected from hydrogen, halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a still further aspect, the compound has a structure represented by a formula selected from:

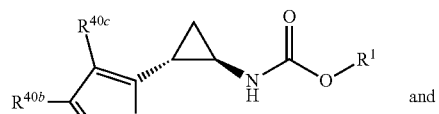

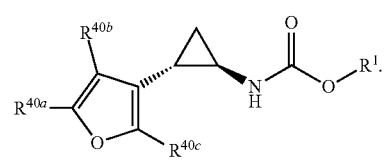

In yet a further aspect, the compound has a structure represented by a formula selected from:

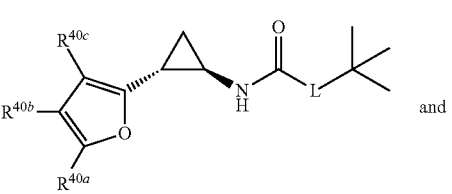

-continued

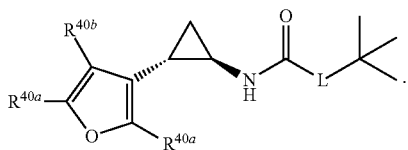

In an even further aspect, the compound has a structure represented by a formula selected from:

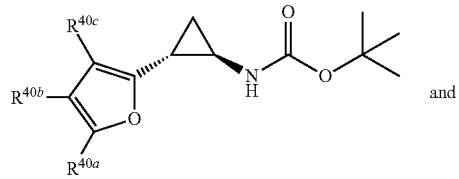

and

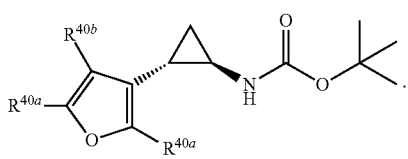

In a still further aspect, the compound has a structure represented by a formula selected from:

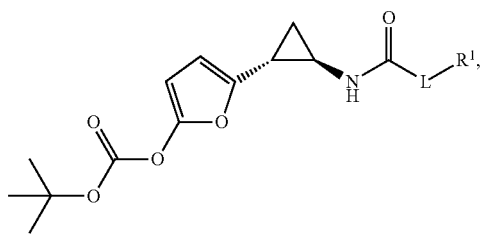

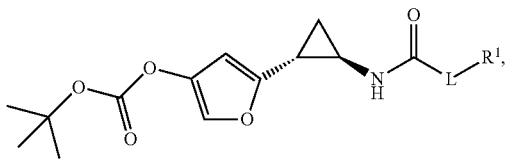

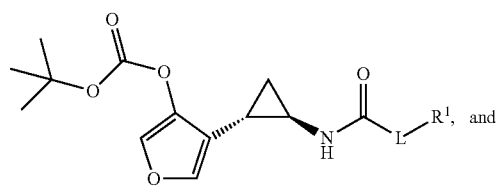

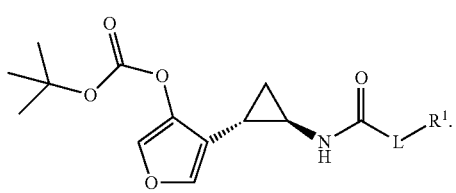

In a further aspect, the compound is selected from:

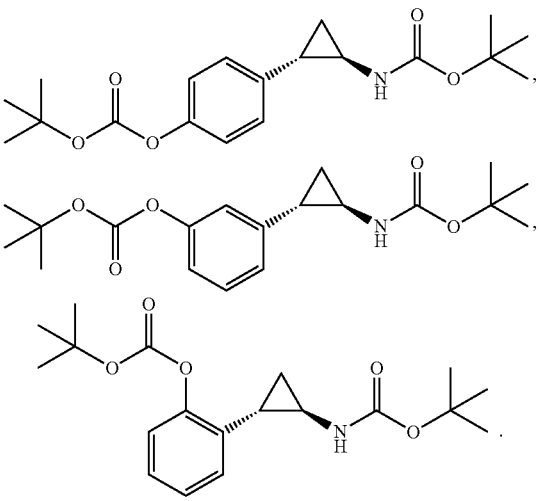

In a further aspect, the compound is:

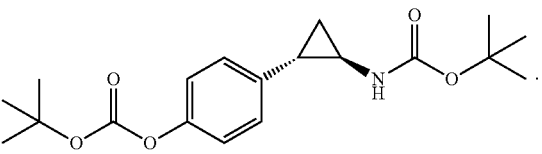 [SMILES: CC(C)(C)OC(=O)N[C@@H]1C[C@H]1c1ccc(OC(=O)OC(C)(C)C)cc1]

In a further aspect, n is an integer selected from 1 and 2. In a still further aspect, n is 1. In yet a further aspect, n is 2.

a. L Groups

In one aspect, L is a moiety selected from —O— and $(CR^{2a}R^{2b})_n$—. In a further aspect, L is —O—. In a still further aspect, L is —$(CR^{2a}R^{2b})_n$—.

In one aspect, L is a moiety selected from —C(O)—, —CO$_2$—, and —$(CR^{2a}R^{2b})_n$—. In a further aspect, L is a moiety selected from —C(O)— and —CO$_2$—. In a still further aspect, L is —C(O)—. In yet a further aspect, L is —CO$_2$—. In an even further aspect, L is —$(CR^{2a}R^{2b})_n$—.

b. $R^1$ Groups

In one aspect, $R^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, $Ar^2$, and $Cy^1$ when L is —O—; or wherein $R^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$ when L is —$(CR^{2a}R^{2b})_n$—. In a further aspect, $R^1$ is selected from hydrogen, C1-C4 alkyl, C1-C4 alkenyl, C1-C4 alkynyl, C1-C4 monohaloalkyl, C1-C4 polyhaloalkyl, C1-C4 hydroxyalkyl, $Ar^2$, and $Cy^1$ when L is —O—; or wherein $R^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$ when L is —$(CR^{2a}R^{2b})_n$—.

In one aspect, $R^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, $Ar^2$, and $Cy^1$ when L is —CO$_2$—; or wherein $R^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—. In a further aspect, R$^1$ is selected from hydrogen, C1-C4 alkyl, C1-C4 alkenyl, C1-C4 alkynyl, C1-C4 monohaloalkyl, C1-C4 polyhaloalkyl, C1-C4 hydroxyalkyl, Ar$^2$, and Cy$^1$ when L is —CO$_2$—; or wherein R$^1$ is selected from C1-C4 alkyl, C1-C4 alkenyl, C1-C4 alkynyl, C1-C4 monohaloalkyl, C1-C4 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^2$)$_n$—.

In a further aspect, R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ and L is —O—. In a still further aspect, R$^1$ is selected from hydrogen, C1-C4 alkyl, C1-C4 alkenyl, C1-C4 alkynyl, C1-C4 monohaloalkyl, C1-C4 polyhaloalkyl, C1-C4 hydroxyalkyl, Ar$^2$, and Cy$^1$ and L is —O—. In yet a further aspect, R$^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, but-2-yne, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, Ar$^2$, and Cy$^1$ and L is —O—. In an even further aspect, R$^1$ is selected from hydrogen, methyl, ethyl, i-propyl, n-propyl, ethene, propene, ethyne, prop-1-yne, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —OCH$_2$CH$_3$, Ar$^2$, and Cy$^1$ and L is —O—. In a still further aspect, R$^1$ is selected from hydrogen, methyl, ethyl, ethene, ethyne, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, Ar$^2$, and Cy$^1$ and L is —O—. In yet a further aspect, R$^1$ is selected from hydrogen, methyl, —CH$_2$F, —CHF$_2$, —CF$_3$, —CH$_2$Cl, —CHCl$_2$, —CCl$_3$, —OCH$_3$, Ar$^2$, and Cy$^1$ and L is —O—.

In a further aspect, R$^1$ is selected from hydrogen, C1-C8 alkyl, C1-C8 alkenyl, and C1-C8 alkynyl and L is —O—. In a still further aspect, R$^1$ is selected from hydrogen, C1-C4 alkyl, C1-C4 alkenyl, and C1-C4 alkynyl and L is —O—. In yet a further aspect, R$^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, and but-2-yne and L is —O—. In an even further aspect, R$^1$ is selected from hydrogen, methyl, ethyl, i-propyl, n-propyl, ethene, propene, ethyne, and prop-1-yne and L is —O—. In a still further aspect, R$^1$ is selected from hydrogen, methyl, ethyl, ethene, and ethyne and L is —O—. In yet a further aspect, R$^1$ is selected from hydrogen and methyl and L is —O—. In an even further aspect, R$^1$ is hydrogen and L is —O—. In In a further aspect, R$^1$ is C1-C8 alkyl and L is —O—. In a still further aspect, R$^1$ is C1-C4 alkyl and L is —O—. In yet a further aspect, R$^1$ is selected from methyl, ethyl, i-propyl, n-propyl, i-butyl, n-butyl, s-butyl, and t-butyl and L is —O—. In an even further aspect, R$^1$ is selected from methyl, ethyl, i-propyl, and n-propyl and L is —O—. In a still further aspect, R$^1$ is selected from methyl and ethyl and L is —O—. In yet a further aspect, R$^1$ is methyl and L is —O—. In an even further aspect, R$^1$ is ethyl and L is —O—. In a still further aspect, R$^1$ is i-propyl and L is —O—. In yet a further aspect, R$^1$ is n-propyl and L is —O—. In an even further aspect, R$^1$ is i-butyl and L is —O—. In a still further aspect, R$^1$ is n-butyl and L is —O—. In yet a further aspect, R$^1$ is s-butyl and L is —O—. In an even further aspect, R$^1$ is t-butyl and L is —O—.

In a further aspect, R$^1$ is selected from hydrogen, C1-C8 monohaloalkyl, C1-C8 polyhaloalkyl, and C1-C8 hydroxyalkyl and L is —O—. In a still further aspect, R$^1$ is selected from hydrogen, C1-C4 monohaloalkyl, C1-C4 polyhaloalkyl, and C1-C4 hydroxyalkyl and L is —O—. In yet a further aspect, R$^1$ is selected from hydrogen, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, and —O—CH$_2$CH$_3$ and L is —O—. In an even further aspect, R$^1$ is selected from hydrogen, —CH$_2$F, —CHF$_2$, —CF$_3$, —CH$_2$Cl, —CHCl$_2$, —CCl$_3$, and OCH$_3$ and L is —O—.

In a further aspect, R$^1$ is selected from hydrogen, Ar$^2$, and Cy$^1$ and L is —O—. In a still further aspect, R$^1$ is selected from hydrogen and Ar$^2$ and L is —O—. In yet a further aspect, R$^1$ is Ar$^2$ and L is —O—. In an even further aspect, R$^1$ is Cy$^1$ and L is —O—.

In a further aspect, R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$, when L is —(CR$^{2a}$R$^{2b}$)$_n$—. In a still further aspect, R$^1$ is selected from —NO$_2$, —CN, —N$_3$, —OR$^3$, —SR$^4$, —NR$^{5a}$R$^{5b}$, —CO$_2$R$^7$, —C(O)SR$^8$, —SO$_2$R$^9$, —CONR$^{10a}$R$^{10b}$, and —SO$_2$NR$^{11a}$R$^{11b}$ and L is —(CR$^{2a}$R$^{2b}$)$_n$—. In yet a further aspect, R$^1$ is selected from —OR$^3$, —SR$^4$, —NR$^{5a}$R$^{5b}$, —CO$_2$R$^7$, —C(O)SR$^8$, —SO$_2$R$^9$, —CONR$^{10a}$R$^{10b}$, and —SO$_2$NR$^{11a}$R$^{11b}$ and L is —(CR$^{2a}$R$^{2b}$)$_n$—. In an even further aspect, R$^1$ is selected from —OH, —SH, —NH$_2$, —CO$_2$H, —C(O)SH, —SO$_2$H, —CONH$_2$, and —SO$_2$NH$_2$ and L is —(CR$^{2a}$R$^{2b}$)$_n$—.

In a further aspect, R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$, when L is —(CR$^{2a}$R$^{2b}$)$_n$—. In a still further aspect, R$^1$ is selected from —NO$_2$, —CN, —N$_3$, —OR$^3$, —SR$^4$, —NR$^{5a}$R$^{5b}$, —CO$_2$R$^7$, —C(O)SR$^8$, —SO$_2$R$^9$, —CONR$^{10a}$R$^{10b}$, and —SO$_2$NR$^{11a}$R$^{11b}$ and L is —(CR$^{2a}$R$^{2b}$)$_n$—. In yet a further aspect, R$^1$ is selected from —OR$^3$, —SR$^4$, —NR$^{5a}$R$^{5b}$, —CO$_2$R$^7$, —C(O)SR$^8$, —SO$_2$R$^9$, —CONR$^{10a}$R$^{10b}$, and —SO$_2$NR$^{11a}$R$^{11b}$ and L is —(CR$^{2a}$R$^{2b}$)$_n$—. In an even further aspect, R$^1$ is selected from —OH, —SH, —NH$_2$, —CO$_2$H, —C(O)SH, —SO$_2$H, —CONH$_2$, and —SO$_2$NH$_2$ and L is —(CR$^{2a}$R$^{2b}$)$_n$—.

In a further aspect, R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ and L is —CO$_2$—. In a still further aspect, R$^1$ is selected from hydrogen, C1-C4 alkyl, C1-C4 alkenyl, C1-C4 alkynyl, C1-C4 monohaloalkyl, C1-C4 polyhaloalkyl, C1-C4 hydroxyalkyl, Ar$^2$, and Cy$^1$ and L is —CO$_2$—. In yet a further aspect, R$^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, and but-2-yne and L is —CO$_2$—. In an even further aspect, R$^1$ is selected from hydrogen, methyl, ethyl, i-propyl, n-propyl, ethene, propene, ethyne, and prop-1-yne and L is —CO$_2$—. In a still further aspect, R$^1$ is selected from hydrogen, methyl, ethyl, ethene, and ethyne and L is —CO$_2$—. In yet a further aspect, R$^1$ is selected from hydrogen and methyl and L is —CO$_2$—. In an even further aspect, R$^1$ is hydrogen and L is —CO$_2$—.

In a further aspect, $R^1$ is C1-C8 alkyl and L is —$CO_2$—. In a still further aspect, $R^1$ is C1-C4 alkyl and L is —$CO_2$—. In yet a further aspect, $R^1$ is selected from methyl, ethyl, i-propyl, n-propyl, i-butyl, n-butyl, s-butyl, and t-butyl and L is —$CO_2$—. In an even further aspect, $R^1$ is selected from methyl, ethyl, i-propyl, and n-propyl and L is —$CO_2$—. In a still further aspect, $R^1$ is selected from methyl and ethyl and L is —$CO_2$—. In yet a further aspect, $R^1$ is methyl and L is —$CO_2$—. In an even further aspect, $R^1$ is ethyl and L is —$CO_2$—. In a still further aspect, $R^1$ is i-propyl and L is —$CO_2$—. In yet a further aspect, $R^1$ is n-propyl and L is —$CO_2$—. In an even further aspect, $R^1$ is i-butyl and L is —$CO_2$—. In a still further aspect, $R^1$ is n-butyl and L is —$CO_2$—. In yet a further aspect, $R^1$ is s-butyl and L is —$CO_2$—. In an even further aspect, $R^1$ is t-butyl and L is —$CO_2$—.

In a further aspect, $R^1$ is selected from hydrogen, C1-C8 monohaloalkyl, C1-C8 polyhaloalkyl, and C1-C8 hydroxyalkyl and L is —$CO_2$—. In a still further aspect, $R^1$ is selected from hydrogen, C1-C4 monohaloalkyl, C1-C4 polyhaloalkyl, and C1-C4 hydroxyalkyl and L is —$CO_2$—. In yet a further aspect, $R^1$ is selected from hydrogen, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, and —O—$CH_2CH_3$ and L is —$CO_2$—. In an even further aspect, $R^1$ is selected from hydrogen, —$CH_2F$, —$CHF_2$, —$CF_3$, —$CH_2Cl$, —$CHCl_2$, —$CCl_3$, and —$OCH_3$ and L is —$CO_2$—.

In a further aspect, $R^1$ is selected from hydrogen, $Ar^2$, and $Cy^1$ and L is —$CO_2$—. In a still further aspect, $R^1$ is selected from hydrogen and $Ar^2$ and L is —$CO_2$—. In yet a further aspect, $R^1$ is $Ar^2$ and L is —$CO_2$—. In an even further aspect, $R^1$ is $Cy^1$ and L is —$CO_2$—.

In a further aspect, $R^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is selected from —C(O)— and —$(CR^{2a}R^{2b})_n$—. In a still further aspect, $R^1$ is selected from C1-C4 alkyl, C1-C4 alkenyl, C1-C4 alkynyl, C1-C4 monohaloalkyl, C1-C4 polyhaloalkyl, C1-C4 hydroxyalkyl, —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is selected from —C(O)— and —$(CR^{2a}R^{2b})_n$—.

In a further aspect, $R^1$ is selected from C1-C8 alkyl, C1-C8 alkenyl, C1-C8 alkynyl, C1-C8 monohaloalkyl, C1-C8 polyhaloalkyl, and C1-C8 hydroxyalkyl and L is selected from —C(O)— and —$(CR^{2a}R^{2b})_n$—. In a still further aspect, $R^1$ is selected from C1-C4 alkyl, C1-C4 alkenyl, C1-C4 alkynyl, C1-C4 monohaloalkyl, C1-C4 polyhaloalkyl, and C1-C8 hydroxyalkyl and L is selected from —C(O)— and —$(CR^{2a}R^{2b})_n$—. In yet a further aspect, $R^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, and but-2-yne and L is selected from —C(O)— and —$(CR^{2a}R^{2b})_n$—. In an even further aspect, $R^1$ is selected from hydrogen, methyl, ethyl, i-propyl, n-propyl, ethene, propene, ethyne, and prop-1-yne and L is selected from —C(O)— and —$(CR^{2a}R^{2b})_n$—. In a still further aspect, $R^1$ is selected from hydrogen, methyl, ethyl, ethene, and ethyne and L is selected from —C(O)— and —$(CR^{2a}R^{2b})_n$—. In yet a further aspect, $R^1$ is selected from hydrogen and methyl and L is selected from —C(O)— and —$(CR^{2a}R^{2b})_n$—. In an even further aspect, $R^1$ is hydrogen and L is selected from —C(O)— and —$(CR^{2a}R^{2b})_n$—.

In a further aspect, $R^1$ is selected from —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is selected from —C(O)— and —$(CR^{2a}R^{2b})_n$—. In a still further aspect, $R^1$ is selected from —$NO_2$, —CN, —$N_3$, —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is selected from —C(O)— and —$(CR^{2a}R^{2b})_n$—. In yet a further aspect, $R^1$ is selected from —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is selected from —C(O)— and —$(CR^{2a}R^{2b})_n$—.

In a further aspect, $R^1$ is selected from C1-C8 alkyl, C1-C8 alkenyl, C1-C8 alkynyl, C1-C8 monohaloalkyl, C1-C8 polyhaloalkyl, and C1-C8 hydroxyalkyl and L is —C(O)—. In a still further aspect, $R^1$ is selected from C1-C4 alkyl, C1-C4 alkenyl, C1-C4 alkynyl, C1-C4 monohaloalkyl, C1-C4 polyhaloalkyl, and C1-C8 hydroxyalkyl and L is —C(O)—. In yet a further aspect, $R^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, and but-2-yne and L is —C(O)—. In an even further aspect, $R^1$ is selected from hydrogen, methyl, ethyl, i-propyl, n-propyl, ethene, propene, ethyne, and prop-1-yne and L is —C(O)—. In a still further aspect, $R^1$ is selected from hydrogen, methyl, ethyl, ethene, and ethyne and L is —C(O)—. In yet a further aspect, $R^1$ is selected from hydrogen and methyl and L is —$CO_2$—. In an even further aspect, $R^1$ is hydrogen and L is —C(O)—.

In a further aspect, $R^1$ is selected from —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is —C(O)—. In a still further aspect, $R^1$ is selected from —$NO_2$, —CN, —$N_3$, —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is —C(O)—. In yet a further aspect, $R^1$ is selected from —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is —C(O)—.

In a further aspect, $R^1$ is selected from C1-C8 alkyl, C1-C8 alkenyl, C1-C8 alkynyl, C1-C8 monohaloalkyl, C1-C8 polyhaloalkyl, and C1-C8 hydroxyalkyl and —$NO_2$, —CN, —$N_3$, —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is —$(CR^{2a}R^{2b})_n$—. In a still further aspect, $R^1$ is selected from C1-C4 alkyl, C1-C4 alkenyl, C1-C4 alkynyl, C1-C4 monohaloalkyl, C1-C4 polyhaloalkyl, C1-C4 hydroxyalkyl, —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is —$(CR^{2a}R^{2b})_n$—.

In a further aspect, $R^1$ is selected from C1-C8 alkyl, C1-C8 alkenyl, C1-C8 alkynyl, C1-C8 monohaloalkyl, C1-C8 polyhaloalkyl, and C1-C8 hydroxyalkyl and L is —$(CR^{2a}R^{2b})_n$—. In a still further aspect, $R^1$ is selected from C1-C4 alkyl, C1-C4 alkenyl, C1-C4 alkynyl, C1-C4 monohaloalkyl, C1-C4 polyhaloalkyl, and C1-C4 hydroxyalkyl and L is —$(CR^{2a}R^{2b})_n$—. In yet a further aspect, $R^1$ is selected from hydrogen, methyl, ethyl, i-propyl, n-propyl, i-butyl, n-butyl, s-butyl, t-butyl, ethene, propene, but-2-ene, but-1-ene, ethyne, prop-1-yne, but-1-yne, and but-2-yne and L is —$(CR^{2a}R^{2b})_n$—. In an even further aspect, $R^1$ is selected from hydrogen, methyl, ethyl, i-propyl, n-propyl, ethene, propene, ethyne, and prop-1-yne and L is —$(CR^{2a}R^{2b})_n$—. In a still further aspect, $R^1$ is selected from hydrogen, methyl, ethyl, ethene, and ethyne and L is —$(CR^{2a}R^{2b})_n$—. In yet a further aspect, $R^1$ is selected from hydrogen and methyl and L is —$(CR^{2a}R^{2b})_n$—. In an even further aspect, $R^1$ is hydrogen and L is —$(CR^{2a}R^{2b})_n$—.

In a further aspect, $R^1$ is selected from —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, —$SO_2NR^{11a}R^{11b}$, $Ar^2$ and $Cy^1$ and L is —$(CR^{2a}R^{2b})_n$—. In a still further aspect, $R^1$ is selected from —$NO_2$, —CN, —$N_3$, —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is —$(CR^{2a}R^{2b})_n$—.

In a further aspect, $R^1$ is selected from —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, $Ar^2$, and $Cy^1$ and L is —$(CH_2)_n$—. In a still further aspect, $R^1$ is selected from —$NO_2$, —CN, —$N_3$, —$OR^3$, —$SR^4$, —$NR^{5a}R^{5b}$, —$CO_2R^7$, —$C(O)SR^8$, —$SO_2R^9$, —$CONR^{10a}R^{10b}$, $Ar^2$, and $Cy^1$ and L is —$(CH_2)_n$—. In yet a further aspect, $R^1$ is selected from —$OR^3$, —$SR^4$, —$NR^{5a}R^{5b}$, —$CO_2R^7$, —$C(O)SR^8$, —$SO_2R^9$, —$CONR^{10a}R^{10b}$, —$SO_2NR^{11a}R^{11b}$, $Ar^2$, and $Cy^1$ and L is —$(CH_2)_n$—.

c. $R^{2A}$ AND $R^{2B}$ Groups

In one aspect, each of $R^{2a}$ and $R^{2b}$, when present, is independently selected from hydrogen, halogen, —OH, —$NH_2$, —$NO_2$, —CN, and —$N_3$. In a further aspect, each of $R^{2a}$ and $R^{2b}$, when present, is hydrogen.

In a further aspect, each of $R^{2a}$ and $R^{2b}$, when present, is independently selected from hydrogen, —OH, —$NH_2$, —$NO_2$, —CN, and —$N_3$. In a still further aspect, each of $R^{2a}$ and $R^{2b}$, when present, is independently selected from hydrogen, —OH, —$NH_2$, —$NO_2$, and —CN. In yet a further aspect, each of $R^{2a}$ and $R^{2b}$, when present, is independently selected from hydrogen, —OH, —$NH_2$, and —$NO_2$. In an even further aspect, each of $R^{2a}$ and $R^{2b}$, when present, is independently selected from hydrogen, —OH, and —$NH_2$. In a still further aspect, each of $R^{2a}$ and $R^{2b}$, when present, is independently selected from hydrogen and —OH. In yet a further aspect, each of $R^{2a}$ and $R^{2b}$, when present, is independently selected from hydrogen and —$NH_2$. In an even further aspect, each of $R^{2a}$ and $R^{2b}$, when present, is independently selected from hydrogen and —$NO_2$. In a still further aspect, each of $R^{2a}$ and $R^{2b}$, when present, is independently selected from hydrogen and —CN. In yet a further aspect, each of $R^{2a}$ and $R^{2b}$, when present, is independently selected from hydrogen and —$N_3$.

In a further aspect, each of $R^{2a}$ and $R^{2b}$, when present, is independently selected from hydrogen and halogen. In a still further aspect, each of $R^{2a}$ and $R^{2b}$, when present, is independently selected from hydrogen, —F, —Cl, and —Br. In yet a further aspect, each of $R^{2a}$ and $R^{2b}$, when present, is independently selected from hydrogen, —F, and —Cl. In an even further aspect, each of $R^{2a}$ and $R^{2b}$, when present, is independently selected from hydrogen and —F. In a still further aspect, each of $R^{2a}$ and $R^{2b}$, when present, is independently selected from hydrogen and —Cl.

d. $R^3$, $R^4$, $R^{5A}$, $R^{5B}$, $R^6$, $R^7$, $R^8$, $R^9$, $R^{10A}$, $R^{10B}$, $R^{11A}$, and $R^{11B}$ Groups In one aspect each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, C1-C4 alkyl, C1-C4 monohaloalkyl, C1-C4 polyhaloalkyl, $Ar^3$, and $Cy^2$. In a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is hydrogen.

In a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen and C1-C4 alkyl. In a still further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, methyl, ethyl, i-propyl, and n-propyl. In yet a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, methyl, and ethyl. In an even further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen and methyl. In a still further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen and ethyl.

In a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, C1-C4 monohaloalkyl, and C1-C4 polyhaloalkyl. In a still further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, and —$CH_2CCl_3$. In yet a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, —$CH_2F$, —$CHF_2$, —$CF_3$, —$CH_2Cl$, —$CHCl_2$, and —$CCl_3$. In an even further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, —$CH_2F$, —$CHF_2$, and —$CF_3$.

In a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, $Ar^3$, and $Cy^2$. In a still further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen and $Ar^3$. In yet a further aspect, each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen and $Cy^2$.

e. $R^{12}$ Groups

In one aspect, $R^{12}$, when present, is selected from hydrogen, C1-C4 alkyl, C1-C4 monohaloalkyl, C1-C4 polyhaloalkyl, and —$CO_2R^{21}$. In a further aspect, $R^{12}$, when present, is hydrogen.

In a further aspect, $R^{12}$, when present, is selected from hydrogen and —$CO_2R^{21}$. In a still further aspect, $R^{12}$, when present, is —$CO_2R^{21}$.

In a further aspect, $R^{12}$, when present, is selected from hydrogen, C1-C4 monohaloalkyl, and C1-C4 polyhaloalkyl. In a still further aspect, $R^{12}$, when present, is selected from hydrogen, —$CH_2F$, —$CHF_2$, —$CF_3$, —$CH_2Cl$, —$CHCl_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In yet a further aspect, R$^{12}$, when present, is selected from hydrogen, —CH$_2$F, —CHF$_2$, —CF$_3$, —CH$_2$Cl, —CHCl$_2$, and —CCl$_3$. In an even further aspect, R$^{12}$, when present, is selected from hydrogen, —CH$_2$F, —CHF$_2$, and —CF$_3$.

In a further aspect, R$^{12}$, when present, is selected from hydrogen and C1-C4 alkyl. In a still further aspect, R$^{12}$, when present, is selected from hydrogen, methyl, ethyl, i-propyl, and n-propyl. In yet a further aspect, R$^{12}$, when present, is selected from hydrogen, methyl, and ethyl. In an even further aspect, R$^{12}$, when present, is selected from hydrogen and methyl. In a still further aspect, R$^{12}$, when present, is selected from hydrogen and ethyl.

f. R$^{13}$, R$^{14A}$, R$^{14B}$, R$^{15}$, R$^{16}$, R$^{17}$, R$^{18}$, R$^{19}$, R$^{20A}$, and R$^{20B}$ Groups In one aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl. In a further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is hydrogen.

In a further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen and C1-C4 alkyl. In a still further aspect each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, methyl, ethyl, i-propyl, and n-propyl. In yet a further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, methyl, and ethyl. In an even further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen and methyl. In a still further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen and ethyl.

In a further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 monohaloalkyl, and C1-C4 polyhaloalkyl. In a still further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, and —CH$_2$CCl$_3$. In yet a further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, —CH$_2$F, —CHF$_2$, —CF$_3$, —CH$_2$Cl, —CHCl$_2$, and —CCl$_3$. In an even further aspect, each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, —CH$_2$F, —CHF$_2$, and —CF$_3$.

g. R$^{21}$ Groups

In one aspect, R$^{21}$, when present, is selected from hydrogen and C1-C4 alkyl. In a further aspect, R$^{21}$, when present, is hydrogen.

In a further aspect, R$^{21}$, when present, is selected from hydrogen, methyl, ethyl, i-propyl, n-propyl, i-butyl, n-butyl, t-butyl, and s-butyl. In a still further aspect, R$^{21}$, when present, is selected from methyl, ethyl, i-propyl, n-propyl, i-butyl, n-butyl, t-butyl, and s-butyl. In yet a further aspect, R$^{21}$, when present, is selected from ethyl, i-propyl, n-propyl, i-butyl, n-butyl, t-butyl, and s-butyl. In an even further aspect, R$^{21}$, when present, is selected from i-propyl, n-propyl, i-butyl, n-butyl, t-butyl, and s-butyl. In a still further aspect, R$^{21}$, when present, is selected from i-butyl, n-butyl, t-butyl, and s-butyl. In yet a further aspect, R$^{21}$, when present, is selected from i-butyl, n-butyl, and t-butyl. In an even further aspect, R$^{21}$, when present, is selected from i-butyl and t-butyl. In a still further aspect, R$^{21}$, when present, is methyl. In yet a further aspect, R$^{21}$, when present, is ethyl. In an even further aspect, R$^{21}$, when present, is i-propyl. In a still further aspect, R$^{21}$, when present, is n-propyl. In yet a further aspect, R$^{21}$, when present, is i-butyl. In an even further aspect, R$^{21}$, when present, is n-butyl. In a still further aspect, R$^{21}$, when present, is s-butyl. In yet a further aspect, R$^{21}$, when present, is t-butyl.

h. R$^{30A}$, R$^{30B}$, R$^{30C}$, R$^{30D}$, and R$^{30E}$ Groups

In one aspect, each of R$^{30a}$, R$^{30b}$, R$^{30c}$, R$^{30d}$, and R$^{30e}$ independently selected from hydrogen, halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a further aspect, each of R$^{30a}$, R$^{30b}$, R$^{30c}$, R$^{30d}$, and R$^{30e}$ is hydrogen.

In a further aspect, each of R$^{30a}$, R$^{30b}$, R$^{30c}$, R$^{30d}$, and R$^{30e}$ is independently selected from hydrogen, —F, —Cl, —CN, —N$_3$, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —CH$_2$OH, —CH$_2$CH$_2$OH, OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a still further aspect, each of R$^{30a}$, R$^{30b}$, R$^{30c}$, R$^{30d}$, and R$^{30e}$ is independently selected from hydrogen, —F, —Cl, —CN, —N$_3$, —CH$_3$, —CH$_2$F, —CHF$_2$, —CF$_3$, —CH$_2$Cl, —CHCl$_2$, —CCl$_3$, —CH$_2$OH, OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a further aspect, each of R$^{30a}$, R$^{30b}$, R$^{30c}$, R$^{30d}$, and R$^{30e}$ is independently selected from hydrogen and halogen. In a still further aspect, each of R$^{30a}$, R$^{30b}$, R$^{30c}$, R$^{30d}$, and R$^{30e}$ is independently selected from hydrogen, —F, —Cl, and —Br. In yet a further aspect, each of R$^{30a}$, R$^{30b}$, R$^{30c}$, R$^{30d}$, and R$^{30e}$ is independently selected from hydrogen, —F and —Cl. In an even further aspect, each of R$^{30a}$, R$^{30b}$, R$^{30c}$, R$^{30d}$, and R$^{30e}$ is independently selected from hydrogen and —F. In a still further aspect, each of R$^{30a}$, R$^{30b}$, R$^{30c}$, R$^{30d}$, and R$^{30e}$ is independently selected from hydrogen and —Cl.

In a further aspect, each of R$^{30a}$, R$^{30b}$, R$^{30c}$, R$^{30d}$, and R$^{30e}$ is independently selected from hydrogen and C1-C4 alkyl. In a still further aspect, each of R$^{30a}$, R$^{30b}$, R$^{30c}$, R$^{30d}$, and R$^{30e}$ is independently selected from hydrogen, methyl, ethyl, i-propyl, and n-propyl. In yet a further aspect, each of R$^{30a}$, R$^{30b}$, R$^{30c}$, R$^{30d}$, and R$^{30e}$ is independently selected from hydrogen, methyl, and ethyl. In an even further aspect, each of R$^{30a}$, R$^{30b}$, R$^{30c}$, R$^{30d}$, and R$^{30e}$ is independently selected from hydrogen and methyl. In a still further aspect, each of R$^{30a}$, R$^{30b}$, R$^{30c}$, R$^{30d}$, and R$^{30e}$ is independently selected from hydrogen and ethyl.

In a further aspect, each of R$^{30a}$, R$^{30b}$, R$^{30c}$, R$^{30d}$, and R$^{30e}$ is independently selected from hydrogen, C1-C4 monohaloalkyl, C1-C4 polyhaloalkyl, and C1-C4 hydroxyalkyl. In a still further aspect, each of R$^{30a}$, R$^{30b}$, R$^{30c}$, R$^{30d}$, and R$^{30e}$ is independently selected from hydrogen, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —CH$_2$OH, and —CH$_2$CH$_2$OH. In yet a further aspect, each of $R^{30a}$, $R^{30b}$, $R^{30c}$, $R^{30d}$, and $R^{30e}$ is independently selected from hydrogen, —CH$_2$F, —CHF$_2$, —CF$_3$, —CH$_2$Cl, —CHCl$_2$, —CCl$_3$, and —CH$_2$OH.

In a further aspect, each of $R^{30a}$, $R^{30b}$, $R^{30c}$, $R^{30d}$, and $R^{30e}$ is independently selected from hydrogen, —CN, —N$_3$, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a still further aspect, each of $R^{30a}$, $R^{30b}$, $R^{30c}$, $R^{30d}$, and $R^{30e}$ is independently selected from hydrogen, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In yet a further aspect, each of $R^{30a}$, $R^{30b}$, $R^{30c}$, $R^{30d}$, and $R^{30e}$ is independently selected from hydrogen, —OR$^{12}$, —SR$^{13}$, —NR$^{14a}$R$^{14b}$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In an even further aspect, each of $R^{30a}$, $R^{30b}$, $R^{30c}$, $R^{30d}$, and $R^{30e}$ is independently selected from hydrogen, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a further aspect, each of $R^{30a}$, $R^{30b}$, $R^{30c}$, $R^{30d}$, and $R^{30e}$ is independently selected from hydrogen, OR$^{12}$, —SR$^{13}$, —NR$^{14a}$R$^{14b}$. In a still further aspect, each of $R^{30a}$, $R^{30b}$, $R^{30c}$, $R^{30d}$, and $R^{30e}$ is independently selected from hydrogen, —OR$^{12}$ and —SR$^{13}$. In yet a further aspect, each of $R^{30a}$, $R^{30b}$, $R^{30c}$, $R^{30d}$, and $R^{30e}$ is independently selected from hydrogen and —NR$^{14a}$R$^{14b}$. In an even further aspect, each of $R^{30a}$, $R^{30b}$, $R^{30c}$, $R^{30d}$, and $R^{30e}$ is independently selected from hydrogen and —SR$^{13}$. In a still further aspect, each of $R^{30a}$, $R^{30b}$, $R^{30c}$, $R^{30d}$, and $R^{30e}$ is independently selected from hydrogen and —OR$^{12}$.

i. $R^{40A}$, $R^{40B}$, and $R^{40C}$ Groups

In one aspect, each of $R^{40a}$, $R^{40b}$, and $R^{40c}$ is independently selected from hydrogen, halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a further aspect, each of $R^{40a}$, $R^{40b}$, and $R^{40c}$ is hydrogen.

In a further aspect, each of $R^{40a}$, $R^{40b}$, and $R^{40c}$ is independently selected from hydrogen, —F, —Cl, —CN, —N$_3$, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —CH$_2$OH, —CH$_2$CH$_2$OH, OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a still further aspect, each of $R^{40a}$, $R^{40b}$, and $R^{40c}$ is independently selected from hydrogen, —F, —Cl, —CN, —N$_3$, —CH$_3$, —CH$_2$F, —CHF$_2$, —CF$_3$, —CH$_2$Cl, —CHCl$_2$, —CCl$_3$, —CH$_2$OH, OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a further aspect, each of $R^{40a}$, $R^{40b}$, and $R^{40c}$ is independently selected from hydrogen and halogen. In a still further aspect, each of $R^{40a}$, $R^{40b}$, and $R^{40c}$ is independently selected from hydrogen, —F, —Cl, and —Br. In yet a further aspect, each of $R^{40a}$, $R^{40b}$, and $R^{40c}$ is independently selected from hydrogen, —F and —Cl. In an even further aspect, each of each of $R^{40a}$, $R^{40b}$, and $R^{40c}$ is independently selected from hydrogen and —F. In a still further aspect, each of $R^{40a}$, $R^{40b}$, and $R^{40c}$ is independently selected from hydrogen and —Cl.

In a further aspect, each of $R^{40a}$, $R^{40b}$, and $R^{40c}$ is independently selected from hydrogen and C1-C4 alkyl. In a still further aspect, each of $R^{40a}$, $R^{40b}$, and $R^{40c}$ is independently selected from hydrogen, methyl, ethyl, i-propyl, and n-propyl. In yet a further aspect, each of each of $R^{40a}$, $R^{40b}$, and $R^{40c}$ is independently selected from hydrogen, methyl, and ethyl. In an even further aspect, each of $R^{40a}$, $R^{40b}$, and $R^{40c}$ is independently selected from hydrogen and methyl. In a still further aspect, each of $R^{40a}$, $R^{40b}$, and $R^{40c}$ is independently selected from hydrogen and ethyl.

In a further aspect, each of $R^{40a}$, $R^{40b}$, and $R^{40c}$ is independently selected from hydrogen, C1-C4 monohaloalkyl, C1-C4 polyhaloalkyl, and C1-C4 hydroxyalkyl. In a still further aspect, each of $R^{40a}$, $R^{40b}$, and $R^{40c}$ is independently selected from hydrogen, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —CH$_2$OH, and —CH$_2$CH$_2$OH. In yet a further aspect, each of each of $R^{40a}$, $R^{40b}$, and $R^{40c}$ is independently selected from hydrogen, —CH$_2$F, —CHF$_2$, —CF$_3$, —CH$_2$Cl, —CHCl$_2$, —CCl$_3$, and —CH$_2$OH.

In a further aspect, each of $R^{40a}$, $R^{40b}$, and $R^{40c}$ is independently selected from hydrogen, —CN, —N$_3$, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In a still further aspect, each of $R^{40a}$, $R^{40b}$, and $R^{40c}$ is independently selected from hydrogen, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In yet a further aspect, each of $R^{40a}$, $R^{40b}$, and $R^{40c}$ is independently selected from hydrogen, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$. In an even further aspect, each of $R^{40a}$, $R^{40b}$, and $R^{40c}$ is independently selected from hydrogen, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a further aspect, each of $R^{40a}$, $R^{40b}$, and $R^{40c}$ is independently selected from hydrogen, —OR$^{12}$, —SR$^{13}$, —NR$^{14a}$R$^{14b}$. In a still further aspect, each of $R^{40a}$, $R^{40b}$, and $R^{40c}$ is independently selected from hydrogen, —OR$^{12}$ and —SR$^{13}$. In yet a further aspect, each of $R^{40a}$, $R^{40b}$, and $R^{40c}$ is independently selected from hydrogen and —NR$^{14a}$R$^{14b}$. In an even further aspect, each of $R^{40a}$, $R^{40b}$, and $R^{40c}$ is independently selected from hydrogen and —SR$^{13}$. In a still further aspect, each of $R^{40a}$, $R^{40b}$, and $R^{40c}$ is independently selected from hydrogen and —OR$^{12}$.

j. Ar$^1$ Groups

In one aspect, Ar$^1$ is selected from phenyl and monocyclic heteroaryl and wherein Ar$^1$ is substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In one aspect, Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$.

In a further aspect, Ar$^1$ is phenyl substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is phenyl with 0, 1, or 2 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is phenyl with 0 or 1 group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is phenyl monosubstituted with a group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is unsubstituted phenyl.

In a further aspect, $Ar^1$ is phenyl substituted with 0, 1, 2, or 3 groups independently selected from —F, —CN, —$N_3$, —$CH_3$, —$CH_2CH_3$, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, —$CH_2CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is phenyl substituted with 0, 1, 2, or 3 groups independently selected from —F, —CN, —$N_3$, —$CH_3$, —$CH_2F$, —$CHF_2$, —$CF_3$, —$CH_2Cl$, —$CHCl_2$, —$CCl_3$, —$CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$.

In a further aspect, $Ar^1$ is phenyl substituted with 0, 1, 2, or 3 halogen groups. In a still further aspect, $Ar^1$ is phenyl substituted with 0, 1, 2, or 3 groups independently selected from —F, —Cl, and —Br. In yet a further aspect, $Ar^1$ is phenyl substituted with 0, 1, 2, or 3 groups independently selected from —F and —Cl. In an even further aspect, $Ar^1$ is phenyl substituted with 0, 1, 2, or 3 fluoro groups. In a still further aspect, $Ar^1$ is phenyl substituted with 0, 1, 2, or 3 chloro groups.

In a further aspect, $Ar^1$ is phenyl substituted with 0, 1, 2, or 3 C1-C4 alkyl groups. In a still further aspect, $Ar^1$ is phenyl substituted with 0, 1, 2, or 3 groups independently selected from methyl, ethyl, i-propyl, and n-propyl. In yet a further aspect, $Ar^1$ is phenyl substituted with 0, 1, 2, or 3 groups independently selected from methyl, and ethyl. In an even further aspect, $Ar^1$ is phenyl substituted with 0, 1, 2, or 3 methyl groups. In a still further aspect, $Ar^1$ is phenyl substituted with 0, 1, 2, or 3 ethyl groups.

In a further aspect, $Ar^1$ is phenyl substituted with 0, 1, 2, or 3 groups independently selected from C1-C4 monohaloalkyl, C1-C4 polyhaloalkyl, and C1-C4 hydroxyalkyl. In a still further aspect, $Ar^1$ is phenyl substituted with 0, 1, 2, or 3 groups independently selected from —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, and —$CH_2CH_2OH$. In yet a further aspect, $Ar^1$ is phenyl substituted with 0, 1, 2, or 3 groups independently selected from —$CH_2F$, —$CHF_2$, —$CF_3$, —$CH_2Cl$, —$CHCl_2$, —$CCl_3$, and —$CH_2OH$.

In a further aspect, $Ar^1$ is phenyl substituted with 0, 1, 2, or 3 groups independently selected from —CN, —$N_3$, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is phenyl substituted with 0, 1, 2, or 3 groups independently selected from —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is phenyl substituted with 0, 1, 2, or 3 groups independently selected from —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is phenyl substituted with 0, 1, 2, or 3 groups independently selected from —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$.

In a further aspect, $Ar^1$ is phenyl substituted with 0, 1, 2, or 3 groups independently selected from —$OR^{12}$, —$SR^{13}$, —$NR^{14a}R^{14b}$. In a still further aspect, $Ar^1$ is phenyl substituted with 0, 1, 2, or 3 groups independently selected from —$OR^{12}$ and —$SR^{13}$. In yet a further aspect, $Ar^1$ is phenyl substituted with 0, 1, 2, or 3 —$NR^{14a}R^{14b}$ groups. In an even further aspect, $Ar^1$ is phenyl substituted with 0, 1, 2, or 3 —$SR^{13}$ groups. In a still further aspect, $Ar^1$ is phenyl substituted with 0, 1, 2, or 3 —$OR^{12}$ groups.

In a further aspect, $Ar^1$ is heteroaryl with 0, 1, 2, or 3 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is heteroaryl with 0, 1, or 2 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is heteroaryl with 0 or 1 group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is heteroaryl monosubstituted with a group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is unsubstituted heteroaryl.

In a further aspect, $Ar^1$ is heteroaryl substituted with 0, 1, 2, or 3 groups independently selected from —F, —CN, —$N_3$, —$CH_3$, —$CH_2CH_3$, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, —$CH_2CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is heteroaryl substituted with 0, 1, 2, or 3 groups independently selected from —F, —CN, —$N_3$, —$CH_3$, —$CH_2F$, —$CHF_2$, —$CF_3$, —$CH_2Cl$, —$CHCl_2$, —$CCl_3$, —$CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$.

In a further aspect, $Ar^1$ is heteroaryl substituted with 0, 1, 2, or 3 halogen groups. In a still further aspect, $Ar^1$ is heteroaryl substituted with 0, 1, 2, or 3 groups independently selected from —F, —Cl, and —Br. In yet a further aspect, $Ar^1$ is heteroaryl substituted with 0, 1, 2, or 3 groups independently selected from —F and —Cl. In an even further aspect, $Ar^1$ is heteroaryl substituted with 0, 1, 2, or 3 fluoro groups. In a still further aspect, $Ar^1$ is heteroaryl substituted with 0, 1, 2, or 3 chloro groups.

In a further aspect, $Ar^1$ is heteroaryl substituted with 0, 1, 2, or 3 C1-C4 alkyl groups. In a still further aspect, $Ar^1$ is heteroaryl substituted with 0, 1, 2, or 3 groups independently selected from methyl, ethyl, i-propyl, and n-propyl. In yet a further aspect, $Ar^1$ is heteroaryl substituted with 0, 1, 2, or 3 groups independently selected from methyl, and ethyl. In an even further aspect, $Ar^1$ is heteroaryl substituted with 0, 1, 2, or 3 methyl groups. In a still further aspect, $Ar^1$ is heteroaryl substituted with 0, 1, 2, or 3 ethyl groups.

In a further aspect, $Ar^1$ is heteroaryl substituted with 0, 1, 2, or 3 groups independently selected from C1-C4 monohaloalkyl, C1-C4 polyhaloalkyl, and C1-C4 hydroxyalkyl. In a still further aspect, $Ar^1$ is heteroaryl substituted with 0, 1, 2, or 3 groups independently selected from —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, and —$CH_2CH_2OH$. In yet a further aspect, $Ar^1$ is heteroaryl substituted with 0, 1, 2, or 3 groups independently selected from —$CH_2F$, —$CHF_2$, —$CF_3$, —$CH_2Cl$, —$CHCl_2$, —$CCl_3$, and —$CH_2OH$.

In a further aspect, $Ar^1$ is heteroaryl substituted with 0, 1, 2, or 3 groups independently selected from —CN, —$N_3$, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is heteroaryl substituted with 0, 1, 2, or 3 groups independently selected from —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is heteroaryl substituted with 0, 1, 2, or 3 groups independently selected from —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is heteroaryl substituted with 0, 1, 2, or 3 groups independently selected from —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$.

In a further aspect, $Ar^1$ is heteroaryl substituted with 0, 1, 2, or 3 groups independently selected from —$OR^{12}$, —$SR^{13}$, and —$NR^{14a}R^{14b}$. In a still further aspect, $Ar^1$ is heteroaryl substituted with 0, 1, 2, or 3 groups independently selected from —$OR^{12}$ and —$SR^{13}$. In yet a further aspect, $Ar^1$ is heteroaryl substituted with 0, 1, 2, or 3 —$NR^{14a}R^{14b}$ groups. In an even further aspect, $Ar^1$ is heteroaryl substituted with 0, 1, 2, or 3 —$SR^{13}$ groups. In a still further aspect, $Ar^1$ is heteroaryl substituted with 0, 1, 2, or 3 —$OR^{12}$ groups.

In a further aspect, $Ar^1$ is selected from phenyl, furan, thiophene, pyrrole, pyrazole, imidazole, thiazole, isothiazole, oxazole, isoxazole, pyridine, pyridazine, and pyrazine.

In a further aspect, $Ar^1$ is furan with 0, 1, 2, or 3 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is furan with 0, 1, or 2 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is furan with 0 or 1 group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is furan monosubstituted with a group selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is unsubstituted furan.

In a further aspect, $Ar^1$ is furan substituted with 0, 1, 2, or 3 groups independently selected from —F, —CN, —$N_3$, —$CH_3$, —$CH_2CH_3$, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, —$CH_2CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is furan substituted with 0, 1, 2, or 3 groups independently selected from —F, —CN, —$N_3$, —$CH_3$, —$CH_2F$, —$CHF_2$, —$CF_3$, —$CH_2Cl$, —$CHCl_2$, —$CCl_3$, —$CH_2OH$, $OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$.

In a further aspect, $Ar^1$ is furan substituted with 0, 1, 2, or 3 halogen groups. In a still further aspect, $Ar^1$ is furan substituted with 0, 1, 2, or 3 groups independently selected from —F, —Cl, and —Br. In yet a further aspect, $Ar^1$ is furan substituted with 0, 1, 2, or 3 groups independently selected from —F and —Cl. In an even further aspect, $Ar^1$ is furan substituted with 0, 1, 2, or 3 fluoro groups. In a still further aspect, $Ar^1$ is furan substituted with 0, 1, 2, or 3 chloro groups.

In a further aspect, $Ar^1$ is furan substituted with 0, 1, 2, or 3 C1-C4 alkyl groups. In a still further aspect, $Ar^1$ is furan substituted with 0, 1, 2, or 3 groups independently selected from methyl, ethyl, i-propyl, and n-propyl. In yet a further aspect, $Ar^1$ is furan substituted with 0, 1, 2, or 3 groups independently selected from methyl, and ethyl. In an even further aspect, $Ar^1$ is furan substituted with 0, 1, 2, or 3 methyl groups. In a still further aspect, $Ar^1$ is furan substituted with 0, 1, 2, or 3 ethyl groups.

In a further aspect, $Ar^1$ is furan substituted with 0, 1, 2, or 3 groups independently selected from C1-C4 monohaloalkyl, C1-C4 polyhaloalkyl, and C1-C4 hydroxyalkyl. In a still further aspect, $Ar^1$ is furan substituted with 0, 1, 2, or 3 groups independently selected from —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2OH$, and —$CH_2CH_2OH$. In yet a further aspect, $Ar^1$ is furan substituted with 0, 1, 2, or 3 groups independently selected from —$CH_2F$, —$CHF_2$, —$CF_3$, —$CH_2Cl$, —$CHCl_2$, —$CCl_3$, and —$CH_2OH$.

In a further aspect, $Ar^1$ is furan substituted with 0, 1, 2, or 3 groups independently selected from —CN, —$N_3$, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In a still further aspect, $Ar^1$ is furan substituted with 0, 1, 2, or 3 groups independently selected from —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In yet a further aspect, $Ar^1$ is furan substituted with 0, 1, 2, or 3 groups independently selected from —$OR^{12}$, —$SR^{13}$, —$NR^{14a}R^{14b}$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$. In an even further aspect, $Ar^1$ is furan substituted with 0, 1, 2, or 3 groups independently selected from —$CO_2R^{16}$, —$C(O)SR^{17}$, —$SO_2R^{18}$, —$CONR^{19a}R^{19b}$, —$Cy^3$, and $Ar^4$.

In a further aspect, $Ar^1$ is furan substituted with 0, 1, 2, or 3 groups independently selected from —$OR^{12}$, —$SR^{13}$, and —$NR^{14a}R^{14b}$. In a still further aspect, $Ar^1$ is furan substituted with 0, 1, 2, or 3 groups independently selected from —OR$^{12}$ and —SR$^{13}$. In yet a further aspect, Ar$^1$ is furan substituted with 0, 1, 2, or 3 —NR$^{14a}$R$^{14b}$ groups. In an even further aspect, Ar$^1$ is furan substituted with 0, 1, 2, or 3 —SR$^{13}$ groups. In a still further aspect, Ar$^1$ is furan substituted with 0, 1, 2, or 3 —OR$^{12}$ groups.

k. Ar$^2$ Groups

In one aspect, Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a further aspect, Ar$^2$, when present, is selected from aryl and heteroaryl and wherein Ar$^2$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is selected from aryl and heteroaryl and wherein Ar$^2$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^2$, when present, is selected from aryl and heteroaryl and wherein Ar$^2$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^2$, when present, is selected from aryl and heteroaryl and wherein Ar$^2$, when present, is unsubstituted.

In a further aspect, Ar$^2$, when present, is selected from aryl and heteroaryl and wherein Ar$^2$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^2$, when present, is selected from aryl and heteroaryl and wherein Ar$^2$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^2$, when present, is aryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is aryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^2$, when present, is aryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^2$, when present, is aryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is unsubstituted aryl.

In a further aspect, Ar$^2$, when present, is aryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^2$, when present, is aryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^2$, when present, is phenyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is phenyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^2$, when present, is phenyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^2$, when present, is phenyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is unsubstituted phenyl.

In a further aspect, Ar$^2$, when present, is phenyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^2$, when present, is phenyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^2$, when present, is heteroaryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is heteroaryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^2$, when present, is heteroaryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^2$, when present, is heteroaryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is unsubstituted heteroaryl.

In a further aspect, Ar$^2$, when present, is heteroaryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^2$, when present, is heteroaryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^2$, when present is selected from furan, thiophene, pyrrole, pyrazole, imidazole, thiazole, oxazole, pyridine, pyridazine, pyrazine, indole, quinoline, and isoquinoline and wherein Ar$^2$, when present, is unsubstituted.

In a further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^2$, when present, is selected from furan, thiophene, pyrrole, pyrazole, imidazole, thiazole, oxazole, pyridine, pyridazine, pyrazine, indole, quinoline, and isoquinoline and wherein Ar$^2$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

l. Ar$^3$ Groups

In one aspect, Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a further aspect, Ar$^3$, when present, is selected from aryl and heteroaryl and wherein Ar$^3$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^3$, when present, is selected from aryl and heteroaryl and wherein Ar$^3$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^3$, when present, is selected from aryl and heteroaryl and wherein Ar$^3$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^3$, when present, is selected from aryl and heteroaryl and wherein Ar$^3$, when present, is unsubstituted.

In a further aspect, Ar$^3$, when present, is selected from aryl and heteroaryl and wherein Ar$^3$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^3$, when present, is selected from aryl and heteroaryl and wherein Ar$^3$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^3$, when present, is aryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is aryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^3$, when present, is aryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^3$, when present, is aryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is unsubstituted aryl.

In a further aspect, $Ar^3$, when present, is aryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^3$, when present, is aryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Ar^3$, when present, is phenyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is phenyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^3$, when present, is phenyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^3$, when present, is phenyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is unsubstituted phenyl.

In a further aspect, $Ar^3$, when present, is phenyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^3$, when present, is phenyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Ar^3$, when present, is heteroaryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is heteroaryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^3$, when present, is heteroaryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^3$, when present, is heteroaryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is unsubstituted heteroaryl.

In a further aspect, $Ar^3$, when present, is heteroaryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^3$, when present, is heteroaryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^3$, when present is selected from furan, thiophene, pyrrole, pyrazole, imidazole, thiazole, oxazole, pyridine, pyridazine, pyrazine, indole, quinoline, and isoquinoline and wherein $Ar^3$, when present, is unsubstituted.

In a further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^3$, when present, is selected from furan, thiophene, pyrrole, pyrazole, imidazole, thiazole, oxazole, pyridine, pyridazine, pyrazine, indole, quinoline, and isoquinoline and wherein $Ar^3$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

m. $Ar^4$ Groups

In one aspect, $Ar^4$, when present, is selected from aryl and heteroaryl and wherein $Ar^4$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a further aspect, $Ar^4$, when present, is selected from aryl and heteroaryl and wherein $Ar^4$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^4$, when present, is selected from aryl and heteroaryl and wherein $Ar^4$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^4$, when present, is selected from aryl and heteroaryl and wherein $Ar^4$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^4$, when present, is selected from aryl and heteroaryl and wherein $Ar^4$, when present, is unsubstituted.

In a further aspect, $Ar^4$, when present, is selected from aryl and heteroaryl and wherein $Ar^4$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^4$, when present, is aryl and heteroaryl and wherein $Ar^4$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Ar^4$, when present, is aryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^4$, when present, is aryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^4$, when present, is aryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^4$, when present, is aryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^4$, when present, is unsubstituted aryl.

In a further aspect, $Ar^4$, when present, is aryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Ar^4$, when present, is aryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Ar^4$, when present, is phenyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^4$, when present, is phenyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Ar^4$, when present, is phenyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Ar^4$, when present, is phenyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Ar^4$, when present, is unsubstituted phenyl.

In a further aspect, $Ar^4$, when present, is phenyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^4$, when present, is phenyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^4$, when present, is heteroaryl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^4$, when present, is heteroaryl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^4$, when present, is heteroaryl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^4$, when present, is heteroaryl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^4$, when present, is unsubstituted heteroaryl.

In a further aspect, Ar$^4$, when present, is heteroaryl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^4$, when present, is heteroaryl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Ar$^4$, when present is selected from furan, thiophene, pyrrole, pyrazole, imidazole, thiazole, oxazole, pyridine, pyridazine, pyrazine, indole, quinoline, and isoquinoline and wherein Ar$^4$, when present, is unsubstituted.

In a further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Ar$^4$, when present, is selected from furan, thiophene, pyrrole, pyrazole, imidazole, thiazole, oxazole, pyridine, pyridazine, pyrazine, indole, quinoline, and isoquinoline and wherein Ar$^4$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

n. Cy$^1$ Groups

In one aspect, Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino.

In a further aspect, Cy$^1$, when present, is C3-C6 cycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^1$, when present, is C3-C6 cycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Cy$^1$, when present, is C3-C6 cycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Cy$^1$, when present, is C3-C6 cycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is unsubstituted C3-C6 cycloalkyl.

In a further aspect, $Cy^1$, when present, is C3-C6 cycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Cy^1$, when present, is C3-C6 cycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^1$, when present, is selected from cyclopropyl, cyclobutyl, and cyclopentyl and wherein $Cy^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is selected from cyclopropyl, cyclobutyl, and cyclopentyl and wherein $Cy^1$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^1$, when present, is selected from cyclopropyl, cyclobutyl, and cyclopentyl and wherein $Cy^1$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^1$, when present, is selected from cyclopropyl, cyclobutyl, and cyclopentyl and wherein $Cy^1$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is selected from cyclopropyl, cyclobutyl, and cyclopentyl and wherein $Cy^1$, when present, is unsubstituted.

In a further aspect, $Cy^1$, when present, is selected from cyclopropyl, cyclobutyl, and cyclopentyl and wherein $Cy^1$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Cy^1$, when present, is selected from cyclopropyl, cyclobutyl, and cyclopentyl and wherein $Cy^1$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^1$, when present, is C2-C5 heterocycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is C2-C5 heterocycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^1$, when present, is C2-C5 heterocycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^1$, when present, is C2-C5 heterocycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is unsubstituted C2-C5 heterocycloalkyl.

In a further aspect, $Cy^1$, when present, is C2-C5 heterocycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Cy^1$, when present, is C2-C5 heterocycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is unsubstituted.

In a further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Cy^1$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^1$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

o. $Cy^2$ Groups

In one aspect, $Cy^2$, when present, is selected from C3-C6 cycloalkyl and C2-C5 heterocycloalkyl and wherein $Cy^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino.

In a further aspect, $Cy^2$, when present, is C3-C6 cycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^2$, when present, is C3-C6 cycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^2$, when present, is C3-C6 cycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^2$, when present, is C3-C6 cycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^2$, when present, is unsubstituted C3-C6 cycloalkyl.

In a further aspect, $Cy^2$, when present, is C3-C6 cycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$) (CH$_3$)$_2$. In a still further aspect, $Cy^2$, when present, is C3-C6 cycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^2$, when present, is selected from cyclopropyl, cyclobutyl, and cyclopentyl and wherein $Cy^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^2$, when present, is selected from cyclopropyl, cyclobutyl, and cyclopentyl and wherein $Cy^2$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^2$, when present, is selected from cyclopropyl, cyclobutyl, and cyclopentyl and wherein $Cy^2$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^2$, when present, is selected from cyclopropyl, cyclobutyl, and cyclopentyl and wherein $Cy^2$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^2$, when present, is selected from cyclopropyl, cyclobutyl, and cyclopentyl and wherein $Cy^2$, when present, is unsubstituted.

In a further aspect, $Cy^2$, when present, is selected from cyclopropyl, cyclobutyl, and cyclopentyl and wherein $Cy^2$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH (CH$_3$)$_2$, —N(CH$_3$)$_2$, —N(CH$_3$)—CH$_2$CH$_3$, and —N(CH$_3$) CH(CH$_3$)$_2$. In a still further aspect, $Cy^2$, when present, is selected from cyclopropyl, cyclobutyl, and cyclopentyl and wherein $Cy^2$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH (CH$_3$)$_2$, and —N(CH$_3$)$_2$.

In a further aspect, $Cy^2$, when present, is C2-C5 heterocycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^2$, when present, is C2-C5 heterocycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^2$, when present, is C2-C5 heterocycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Cy$^2$, when present, is C2-C5 heterocycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^2$, when present, is unsubstituted C2-C5 heterocycloalkyl.

In a further aspect, Cy$^2$, when present, is C2-C5 heterocycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Cy$^2$, when present, is C2-C5 heterocycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is unsubstituted.

In a further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, Cy$^2$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^2$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

p. Cy$^3$ Groups

In one aspect, Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino.

In a further aspect, Cy$^3$, when present, is C3-C6 cycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^3$, when present, is C3-C6 cycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, Cy$^3$, when present, is C3-C6 cycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, Cy$^3$, when present, is C3-C6 cycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, Cy$^3$, when present, is unsubstituted C3-C6 cycloalkyl.

In a further aspect, Cy$^3$, when present, is C3-C6 cycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, N(CH$_3$)$_2$, —N(CH$_3$)—CH$_2$CH$_3$, and —N(CH$_3$)CH(CH$_3$)$_2$. In a still further aspect, Cy$^3$, when present, is C3-C6 cycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^3$, when present, is selected from cyclopropyl, cyclobutyl, and cyclopentyl and wherein $Cy^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is selected from cyclopropyl, cyclobutyl, and cyclopentyl and wherein $Cy^3$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^3$, when present, is selected from cyclopropyl, cyclobutyl, and cyclopentyl and wherein $Cy^3$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^3$, when present, is selected from cyclopropyl, cyclobutyl, and cyclopentyl and wherein $Cy^3$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is selected from cyclopropyl, cyclobutyl, and cyclopentyl and wherein $Cy^3$, when present, is unsubstituted.

In a further aspect, $Cy^3$, when present, is selected from cyclopropyl, cyclobutyl, and cyclopentyl and wherein $Cy^3$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, N(CH$_3$)$_2$, —N(CH$_3$)—CH$_2$CH$_3$, and —N(CH$_3$)CH(CH$_3$)$_2$. In a still further aspect, $Cy^3$, when present, is selected from cyclopropyl, cyclobutyl, and cyclopentyl and wherein $Cy^3$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH (CH$_3$)$_2$, and —N(CH$_3$)$_2$.

In a further aspect, $Cy^3$, when present, is C2-C5 heterocycloalkyl substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is C2-C5 heterocycloalkyl substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^3$, when present, is C2-C5 heterocycloalkyl substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^3$, when present, is C2-C5 heterocycloalkyl monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is unsubstituted C2-C5 heterocycloalkyl.

In a further aspect, $Cy^3$, when present, is C2-C5 heterocycloalkyl substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, —N(CH$_3$)$_2$, —N(CH$_3$)—CH$_2$CH$_3$, and —N(CH$_3$)CH(CH$_3$)$_2$. In a still further aspect, $Cy^3$, when present, is C2-C5 heterocycloalkyl substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

In a further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is substituted with 0, 1, or 2 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In yet a further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is substituted with 0 or 1 group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In an even further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is monosubstituted with a group selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino. In a still further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is unsubstituted.

In a further aspect, $Cy^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein $Cy^3$, when present, is substituted with 0, 1, 2, or 3 groups independently selected from —F, —Cl, —OH, —NH$_2$, —CN, —CH$_3$, —CH$_2$CH$_3$, —CH$_2$F, —CHF$_2$, —CF$_3$, —CH$_2$Cl, —CHCl$_2$, —CCl$_3$, —CH$_2$CH$_2$F, —CH$_2$CHF$_2$, —CH$_2$CF$_3$, —CH$_2$CH$_2$Cl, —CH$_2$CHCl$_2$, —CH$_2$CCl$_3$, —OCH$_3$, —O—CH$_2$CH$_3$, —CH$_2$OH, —CH$_2$CH$_2$OH, —CH(CH$_3$)$_2$, —NHCH$_3$, —NH—CH$_2$CH$_3$, —NHCH(CH$_3$)$_2$, N(CH$_3$)$_2$, —N(CH$_3$)—CH$_2$CH$_3$, and —N(CH$_3$)CH(CH$_3$)$_2$. In a still further aspect, Cy$^3$, when present, is selected from aziridine, oxirane, thiirane, azetidine, oxetane, thietane, tetrahydrofuran, tetrahydrothiophene, pyrrolidine, tetrahydro-2H-pyran, tetrahydro-2H-thiopyran, and piperidine and wherein Cy$^3$, when present, is substituted with 0, 1, 2, or 3 groups independently selected from —F, —Cl, —OH, —NH$_2$, —CN, —CH$_3$, —CF$_3$, —CCl$_3$, —OCH$_3$, —O—CH$_2$CH$_3$, —CH$_2$OCH$_3$, —OCF$_3$, —O—CH$_2$CF$_3$, —CH$_2$OCF$_3$, —NHCH$_3$, —NH—CH$_2$CH$_3$, —NHCH(CH$_3$)$_2$, and —N(CH$_3$)$_2$.

2. Example Compounds

In one aspect, a compound can be present as the following structure:

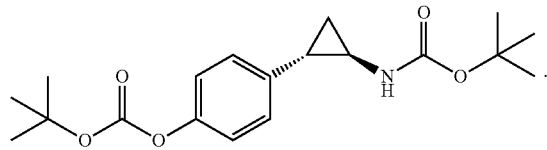 [SMILES: CC(C)(C)OC(=O)N[C@@H]1C[C@H]1c1ccc(OC(=O)OC(C)(C)C)cc1]

In one aspect, the invention relates to compounds having a structure selected from:

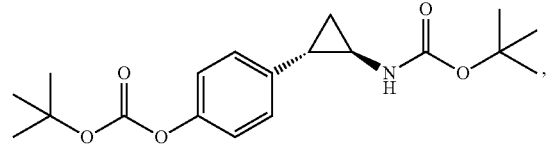

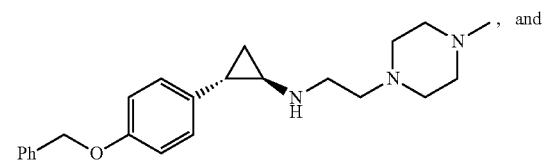

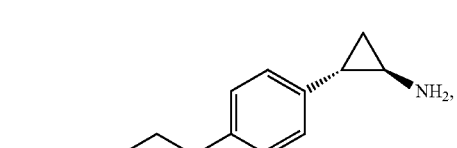

or a pharmaceutically acceptable salt thereof

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of LSD1, and such activity can be determined using the assay methods described herein.

In one aspect, a compound can be selected from:

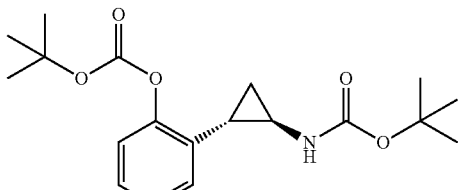

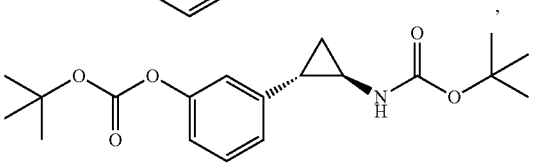

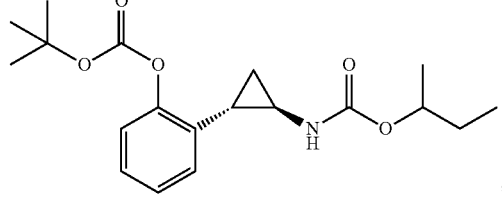

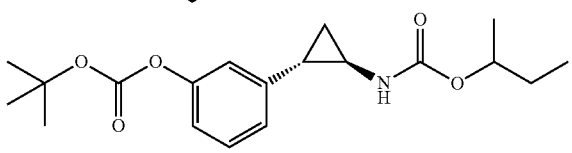

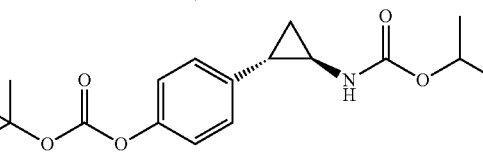

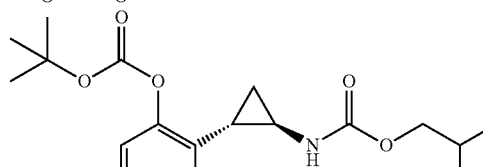

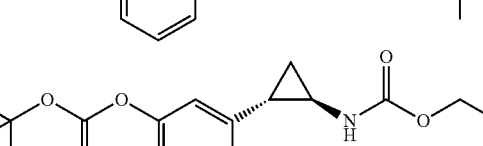

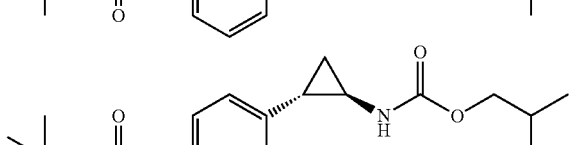

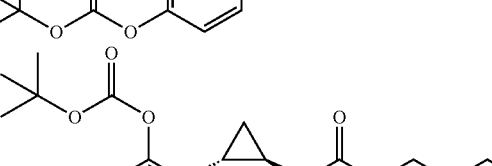

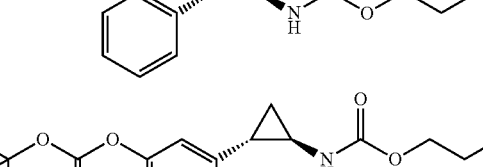

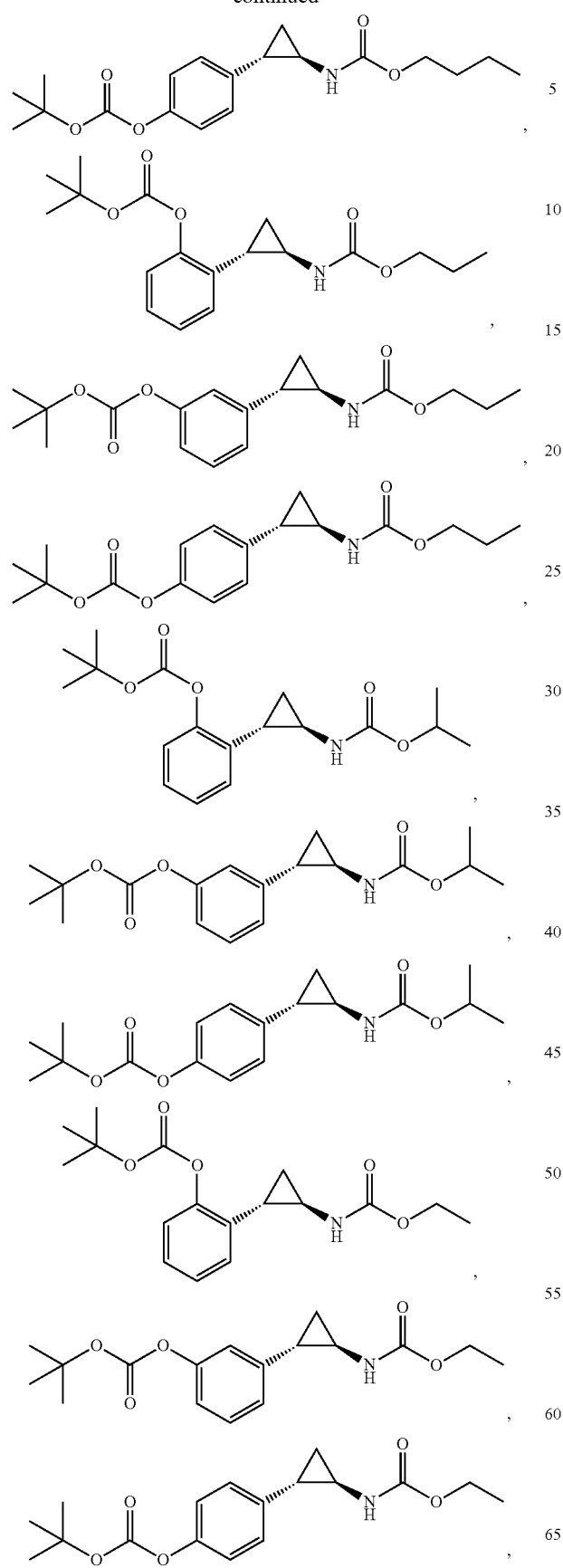
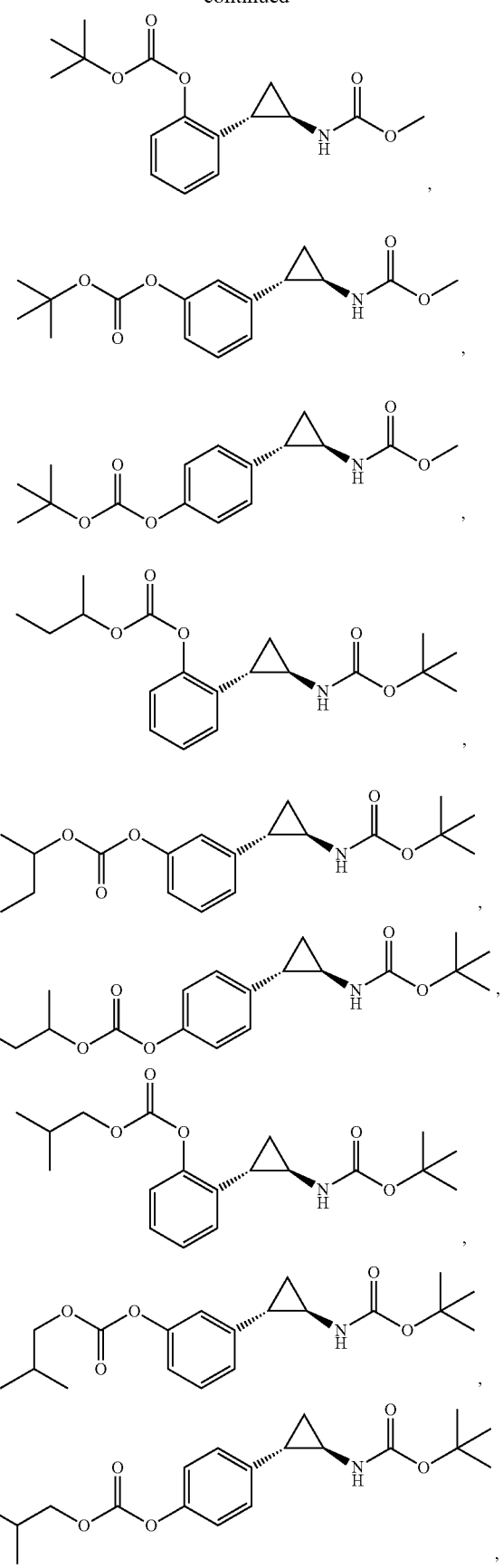

-continued

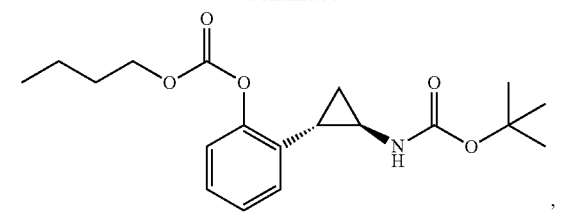,

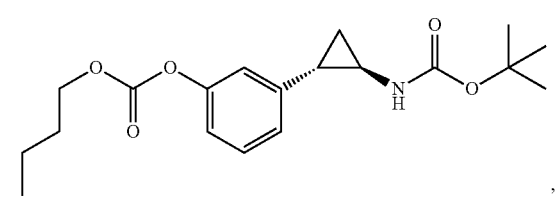,

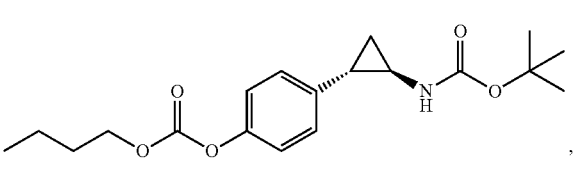,

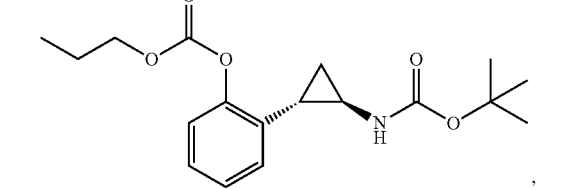,

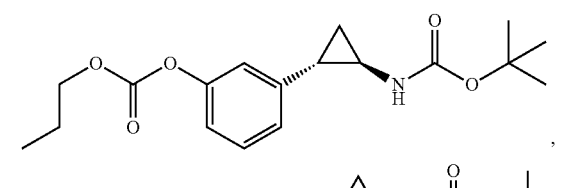,

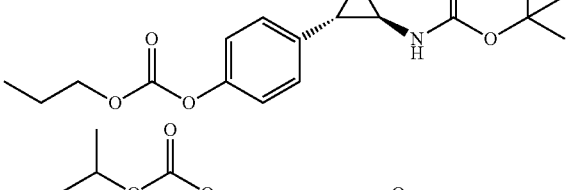,

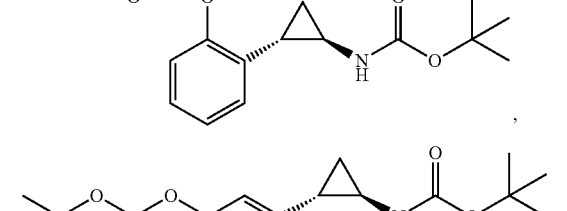,

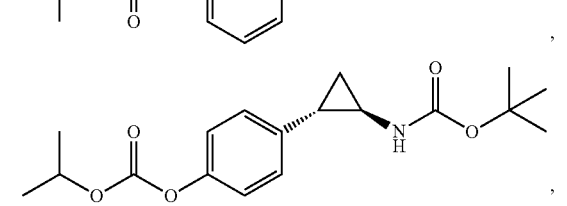,

-continued

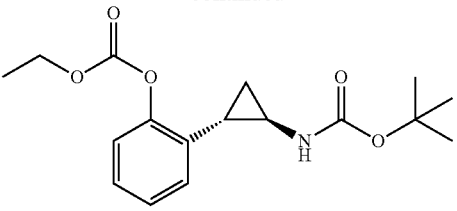,

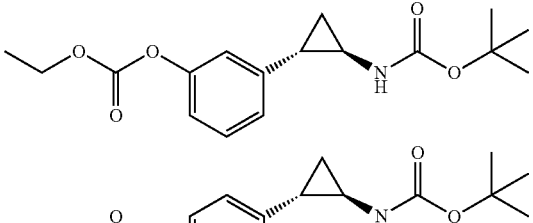,

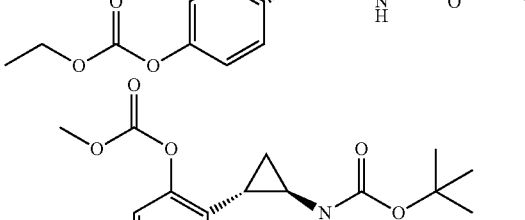,

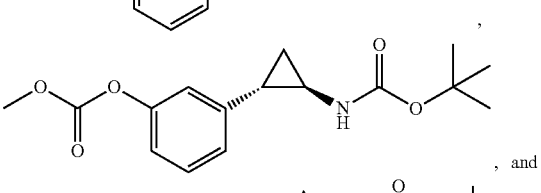,

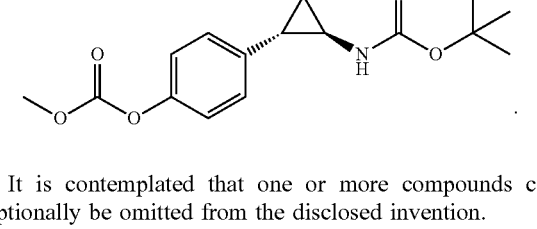, and

It is contemplated that one or more compounds can optionally be omitted from the disclosed invention.

It is understood that the disclosed compounds can be used in connection with the disclosed methods, compositions, kits, and uses.

It is understood that pharmaceutically acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

E. PHARMACEUTICAL COMPOSITIONS

In one aspect, the invention relates to pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

In one aspect, the invention relates to pharmaceutical compositions comprising a therapeutically effective amount of at least one disclosed compound, or a pharmaceutically acceptable salt, solvate, or polymorph thereof; and a pharmaceutically acceptable carrier.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of a cancer. In a still further aspect, the mammal has been diagnosed with a need for treatment of a cancer prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the composition further comprises at least one agent anticancer therapeutic agent. In a still further aspect, the anticancer therapeutic agent is selected from: a) a hormone therapy therapeutic agent, or a pharmaceutically acceptable prodrug, salt, solvate, or polymorph thereof; b) an alkylating therapeutic agent, or a pharmaceutically acceptable prodrug, salt, solvate, or polymorph thereof; c) an antineoplastic antimetabolite therapeutic agent, or a pharmaceutically acceptable prodrug, salt, solvate, or polymorph thereof; d) a mitotic inhibitor therapeutic agent, or a pharmaceutically acceptable prodrug, salt, solvate, or polymorph thereof; e) an antineoplastic antibiotic therapeutic agent, or a pharmaceutically acceptable prodrug, salt, solvate, or polymorph thereof; or f) other chemotherapeutic agent, or a pharmaceutically acceptable prodrug, salt, solvate, or polymorph thereof.

In a further aspect, the composition further comprises at least one agent known to have a side effect of increasing the risk of cancer.

It is understood that the disclosed compositions can be prepared from the disclosed compounds. It is also understood that the disclosed compositions can be employed in the disclosed methods of using.

F. METHODS OF MAKING THE COMPOUNDS

In various aspects, the invention relates to methods of making compounds useful to treat cancer. Thus, in one aspect, the invention relates to methods of making a compound having a structure represented by a formula:

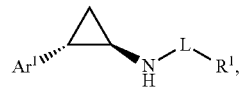

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof, the method comprising the steps of:

(a) providing a compound having a structure represented by a formula:

and (b) reacting with a compound having a structure represented by a formula:

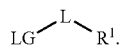

In a further aspect, providing comprises the steps of:
(a) providing a compound having a structure represented by a formula:

and (b) reacting with a reducing agent.
In a further aspect, the reducing agent is Zn/HCl.
In a further aspect, providing comprises the steps of:
(a) providing a compound having a structure represented by a formula:

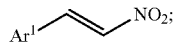

and (b) reacting with a cyclizing agent.

In a further aspect, the cyclizing agent comprises trimethylsulfoxonium iodide and potassium tert-butoxide.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted trans-cyclopropanes can be prepared as shown below.

Compounds are represented in generic form, with substituents as noted in compound descriptions elsewhere herein. A more specific example is set forth below.

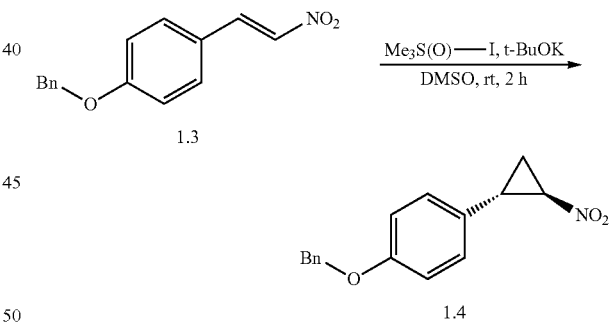

In one aspect, compounds of type 1.2, and similar compounds, can be prepared according to reaction Scheme 1B above. Thus, compounds of type 1.4 can be prepared by cyclization of an appropriate alkene, e.g., 1.3 as shown above. Appropriate alkenes are commercially available or prepared by methods known to one skilled in the art. The cyclization is carried out in the presence of an appropriate cyclizing agent, e.g., trimethylsulfoxonium iodide and potassium tert-butoxide, in an appropriate solvent, e.g., dimethylsulfoxide (DMSO), at an appropriate temperature, e.g., room temperature, for a sufficient period of time, e.g., 2 hours. As can be appreciated by one skilled in the art, the above reaction provides an example of a generalized approach wherein compounds similar in structure to the specific reactants above (compounds similar to compounds of type 1.1), can be substituted in the reaction to provide substituted trans-cyclopropanes similar to Formula 1.2.

2. Route II

In one aspect, substituted trans-cyclopropanes can be prepared as shown below.

SCHEME 2A.

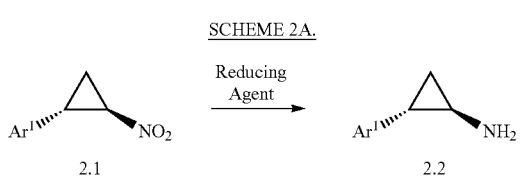

Compounds are represented in generic form, with substituents as noted in compound descriptions elsewhere herein. A more specific example is set forth below.

SCHEME 2B.

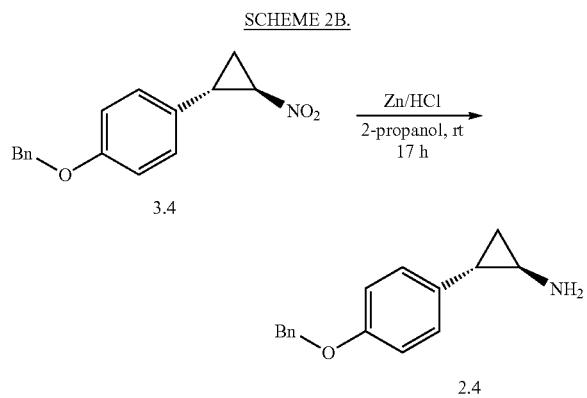

In one aspect, compounds of type 2.2, and similar compounds, can be prepared according to reaction Scheme 2B above. Thus, compounds of type 2.4 can be prepared by reduction of an appropriate nitrocycloalkane, e.g., 2.3 as shown above. Appropriate nitrocycloalkanes are commercially available or prepared by methods known to one skilled in the art. The reduction is carried out in the presence of an appropriate reducing agent, e.g., Zn/HCl, in an appropriate solvent, e.g., 2-propanol, at an appropriate temperature, e.g., room temperature, for a sufficient period of time, e.g., 17 hours. As can be appreciated by one skilled in the art, the above reaction provides an example of a generalized approach wherein compounds similar in structure to the specific reactants above (compounds similar to compounds of type 2.1), can be substituted in the reaction to provide substituted trans-cyclopropanes similar to Formula 2.2.

3. Route III

In one aspect, substituted trans-cyclopropanes can be prepared as shown below.

SCHEME 3A.

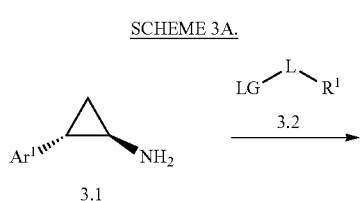

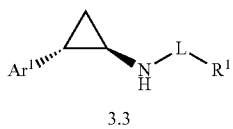

Compounds are represented in generic form, with substituents as noted in compound descriptions elsewhere herein. A more specific example is set forth below.

SCHEME 3B.

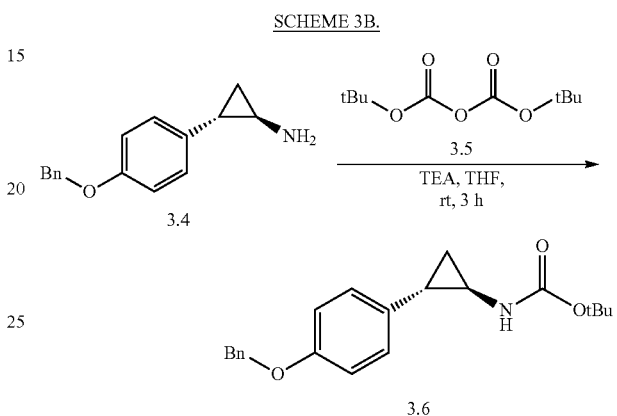

In one aspect, compounds of type 3.3, and similar compounds, can be prepared according to reaction Scheme 3B above. Thus, compounds of type 3.6 can be prepared by acylation (or alkylation) of an appropriate amine, e.g., 3.4 as shown above. Appropriate amines are commercially available or prepared by methods known to one skilled in the art. The reduction is carried out in the presence of an appropriate acylating agent (or alkylating agent), e.g., di-tert-butyl dicarbonate, in the presence of an appropriate base, e.g., triethylamine (TEA), at an appropriate temperature, e.g., room temperature, for a sufficient period of time, e.g., 3 hours. As can be appreciated by one skilled in the art, the above reaction provides an example of a generalized approach wherein compounds similar in structure to the specific reactants above (compounds similar to compounds of type 3.1 and 3.2), can be substituted in the reaction to provide substituted trans-cyclopropanes similar to Formula 3.3.

4. Route IV

In one aspect, substituted trans-cyclopropanes can be prepared as shown below.

SCHEME 4A.

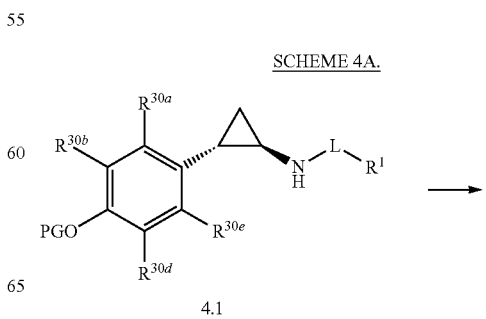

-continued

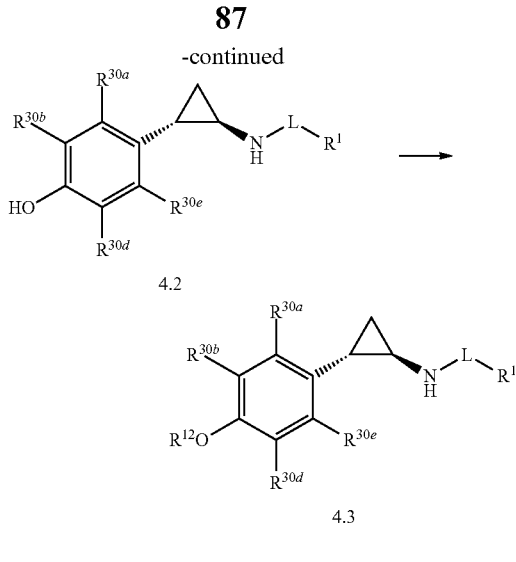

4.2

4.3

Compounds are represented in generic form, with substituents as noted in compound descriptions elsewhere herein. A more specific example is set forth below.

SCHEME 4B.

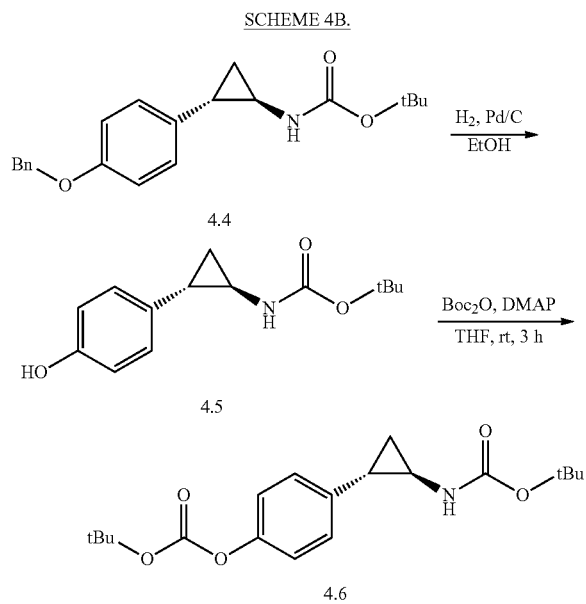

4.4

4.5

4.6

In one aspect, compounds of type 4.3, and similar compounds, can be prepared according to reaction Scheme 4B above. Thus, compounds of type 4.5 can be prepared by deprotection of an appropriate cyclopropane, e.g., 4.4 as shown above. The deprotection is carried out in the presence of an appropriate deprotecting agent, e.g., hydrogen gas and palladium on carbon, and an appropriate solvent, e.g., ethanol (EtOH). Compounds of type 4.6 can be prepared by acylation (or alkylation) of an appropriate phenol, e.g., 4.5 as shown above. The acylation (or alkylation) is carried out in the presence of an appropriate acylating agent (or alkylating agent), e.g., di-tert-butyl dicarbonate, in the presence of an appropriate activating agent, e.g., 4-dimethylaminopyridine (DMAP), in an appropriate solvent, e.g., tetrahydrofuran (THF), at an appropriate temperature, e.g., room temperature, for a sufficient period of time, e.g., 3 hours. As can be appreciated by one skilled in the art, the above reaction provides an example of a generalized approach wherein compounds similar in structure to the specific reactants above (compounds similar to compounds of type 4.1 and 4.2), can be substituted in the reaction to provide substituted trans-cyclopropanes similar to Formula 4.3.

G. METHODS OF MODULATING A HISTONE METHYLATION EVENT IN CELLS

In one aspect, the invention relates to a method of modulating at least one histone methylation event in at least one cell, the method comprising contacting the cell with an effective amount of at least one compound having a structure represented by a formula:

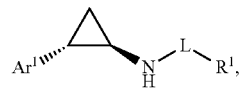

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is CO$_2$; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from C(O) and (CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In one aspect, the invention relates to a method of modulating a histone methylation event in at least one cell, the method comprising contacting the cell with an effective amount of at least one compound selected from:

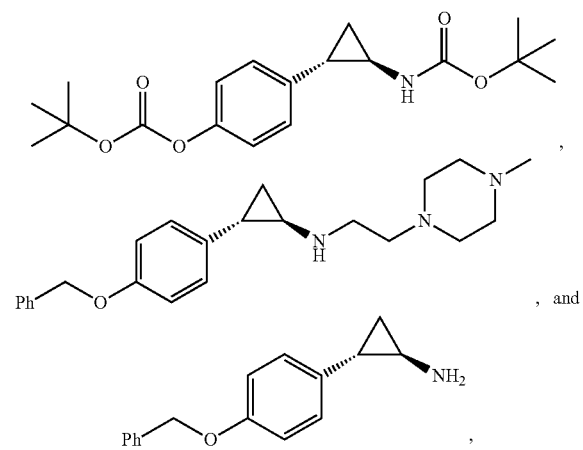

or a pharmaceutically acceptable salt thereof

In a further aspect, modulating is inhibiting.

In a further aspect, the histone methylation event occurs on histone H3.

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an IC$_{50}$ of less than about 100 mM. In a still further aspect, the compound exhibits an IC$_{50}$ of less than about 90 mM. In yet a further aspect, the compound exhibits an IC$_{50}$ of less than about 80 mM. In an even further aspect, the compound exhibits an IC$_{50}$ of less than about 70 mM. In a still further aspect, the compound exhibits an IC$_{50}$ of less than about 60 mM. In yet a further aspect, the compound exhibits an IC$_{50}$ of less than about 50 mM. In an even further aspect, the compound exhibits an IC$_{50}$ of less than about 40 mM. In a still further aspect, the compound exhibits an IC$_{50}$ of less than about 30 mM. In yet a further aspect, the compound exhibits an IC$_{50}$ of less than about 20 mM. In an even further aspect, the compound exhibits an IC$_{50}$ of less than about 10 mM.

H. METHODS OF INHIBITING LSD1 IN CELLS

In one aspect, the invention relates to a method of inhibiting LSD1 (lysine-specific demethylase I) in at least one cell, the method comprising the method comprising contacting the cell with an effective amount of at least one compound having a structure represented by a formula:

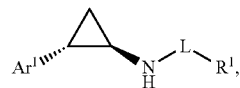

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar¹ is selected from phenyl and heteroaryl and wherein Ar¹ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In one aspect, the invention relates to a method of inhibiting LSD1 in at least one cell, the method comprising contacting the at least one cell with an effective amount of at least one compound selected from:

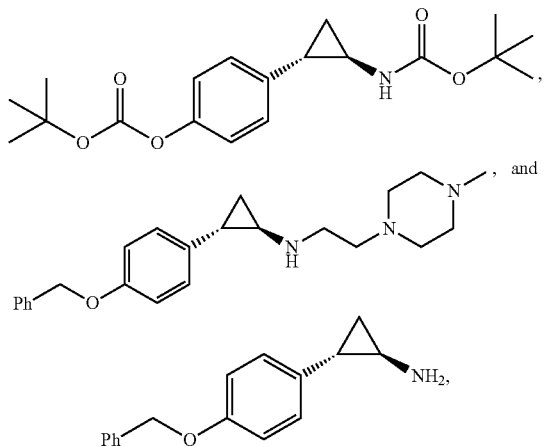

or a pharmaceutically acceptable salt thereof

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an IC$_{50}$ of less than about 100 mM. In a still further aspect, the compound exhibits an IC$_{50}$ of less than about 90 mM. In yet a further aspect, the compound exhibits an IC$_{50}$ of less than about 80 mM. In an even further aspect, the compound exhibits an IC$_{50}$ of less than about 70 mM. In a still further aspect, the compound exhibits an IC$_{50}$ of less than about 60 mM. In yet a further aspect, the compound exhibits an IC$_{50}$ of less than about 50 mM. In an even further aspect, the compound exhibits an IC$_{50}$ of less than about 40 mM. In a still further aspect, the compound exhibits an IC$_{50}$ of less than about 30 mM. In yet a further aspect, the compound exhibits an IC$_{50}$ of less than about 20 mM. In an even further aspect, the compound exhibits an IC$_{50}$ of less than about 10 mM.

I. METHODS OF INHIBITING CANCER CELL PROLIFERATION

1. Via Administration of a LSD1 Inhibitor

In one aspect, the invention relates to a method of inhibiting the proliferation of cancer cells in a mammal, the method comprising administering to the mammal an effective amount of at least one LSD1 inhibitor.

In a further aspect, the LSD1 inhibitor is a compound having a structure represented by a formula:

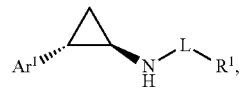

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy¹, when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar¹ is selected from phenyl and heteroaryl and wherein Ar¹ is substituted with 0, 1, 2, or 3 groups independently selected from halogen, —NO₂, —CN, —N₃, C1-C4 alkyl, C1-C4 monohaloalkyl, C1-C4 polyhaloalkyl, C1-C4 hydroxyalkyl, —OR¹², —SR¹³, —NR¹⁴ᵃR¹⁴ᵇ, —P(R¹⁵)₃, —CO₂R¹⁶, —C(O)SR¹⁷, —SO₂R¹⁸, —CONR¹⁹ᵃR¹⁹ᵇ, —SO₂NR²⁰ᵃR²⁰ᵇ, Cy³, and Ar⁴; wherein R¹², when present, is selected from hydrogen, C1-C4 alkyl, C1-C4 monohaloalkyl, C1-C4 polyhaloalkyl, and —CO₂R²¹; wherein R²¹, when present, is selected from hydrogen and C1-C4 alkyl; wherein each of R¹³, R¹⁴ᵃ, R¹⁴ᵇ, R¹⁵, R¹⁶, R¹⁷, R¹⁸, R¹⁹, R²⁰ᵃ, and R²⁰ᵇ, when present, is independently selected from hydrogen, C1-C4 alkyl, C1-C4 monohaloalkyl, and C1-C4 polyhaloalkyl; wherein Ar⁴, when present, is selected from aryl and heteroaryl and wherein Ar², when present, is substituted with 0, 1, 2, or 3 groups independently selected from halogen, —NH₂, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy³, when present, is selected from C3-C6 cycloalkyl and C2-C5 heterocycloalkyl and wherein Cy³, when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

the LSD1 inhibitor is a compound having a structure represented by a formula:

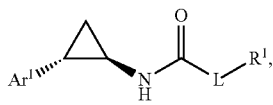

wherein L is a moiety selected from —O— and —(CR²ᵃR²ᵇ)ₙ—; wherein n is an integer selected from 1, and 2; wherein each of R²ᵃ and R²ᵇ, when present, is independently selected from hydrogen, halogen, —OH, —NH₂, —NO₂, —CN, and —N₃; wherein R¹ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar², and Cy¹ when L is —O—; or wherein R¹ is selected from —NO₂, —CN, —N₃, —OR³, —SR⁴, —NR⁵ᵃR⁵ᵇ, —P(R⁶)₃, —CO₂R⁷, —C(O)SR⁸, —SO₂R⁹, —CONR¹⁰ᵃR¹⁰ᵇ, and —SO₂NR¹¹ᵃR¹¹ᵇ when L is —(CR²ᵃR²ᵇ)ₙ—; wherein each of R³, R⁴, R⁵ᵃ, R⁵ᵇ, R⁶, R⁷, R⁸, R⁹, R¹⁰ᵃ, R¹⁰ᵇ, R¹¹ᵃ and R¹¹ᵇ, when present, is independently selected from hydrogen, C1-C4 alkyl, C1-C4 monohaloalkyl, C1-C4 polyhaloalkyl, Ar³, and Cy²; wherein Ar³, when present, is selected from aryl and heteroaryl and wherein Arᵃ, when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy², when present, is selected from C3-C6 cycloalkyl and C2-C5 heterocycloalkyl and wherein Cy², when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar², when present, is selected from aryl and heteroaryl and wherein Ar², when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy¹, when present, is selected from C3-C6 cycloalkyl and C2-C5 heterocycloalkyl and wherein Cy¹, when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar¹ is selected from phenyl and monocyclic heteroaryl and wherein Ar¹ is substituted with 0, 1, 2, or 3 groups independently selected from halogen, —CN, —N₃, C1-C4 alkyl, C1-C4 monohaloalkyl, C1-C4 polyhaloalkyl, C1-C4 hydroxyalkyl, —OR¹², —SR¹³, —NR¹⁴ᵃR¹⁴ᵇ, —P(R¹⁵)₃, —CO₂R¹⁶, —C(O)SR¹⁷, —SO₂R¹⁸, —CONR¹⁹ᵃR¹⁹ᵇ, —SO₂NR²⁰ᵃR²⁰ᵇ, Cy³, and Ar⁴; wherein R¹², when present, is selected from hydrogen, C1-C4 alkyl, C1-C4 monohaloalkyl, C1-C4 polyhaloalkyl, and —CO₂R²¹; wherein R²¹, when present, is selected from hydrogen and C1-C4 alkyl; wherein each of R¹³, R¹⁴ᵃ, R¹⁴ᵇ, R¹⁵, R¹⁶, R¹⁷, R¹⁸, R¹⁹, R²⁰ᵃ, and R²⁰ᵇ, when present, is independently selected from hydrogen, C1-C4 alkyl, C1-C4 monohaloalkyl, and C1-C4 polyhaloalkyl; wherein Ar⁴, when present, is selected from aryl and heteroaryl and wherein Ar², when present, is substituted with 0, 1, 2, or 3 groups independently selected from halogen, —NH₂, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy³, when present, is selected from C3-C6 cycloalkyl and C2-C5 heterocycloalkyl and wherein Cy³, when present, is substituted with 0, 1, 2, or 3 groups independently selected from halogen, —OH, —NH₂, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is selected from:

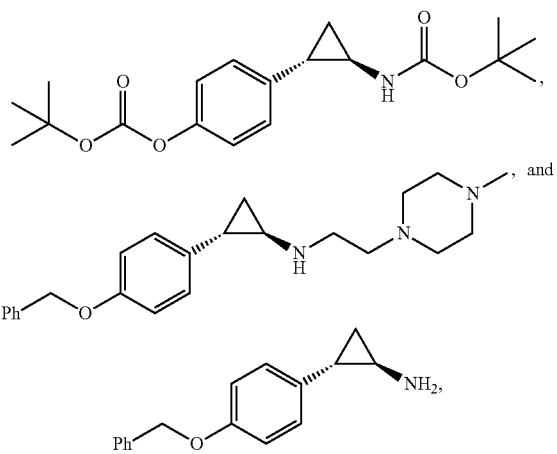

or a pharmaceutically acceptable salt thereof

In a further aspect, the LSD1 inhibitor is selected from:
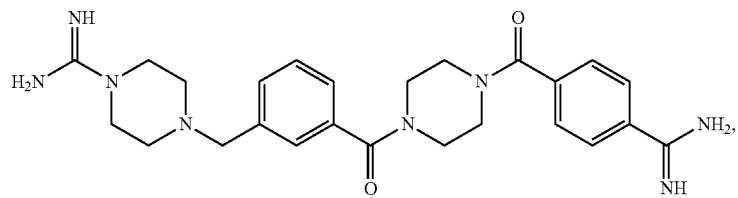
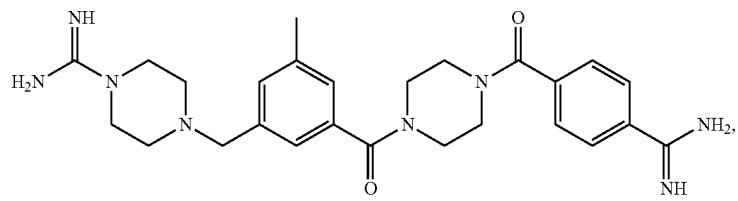
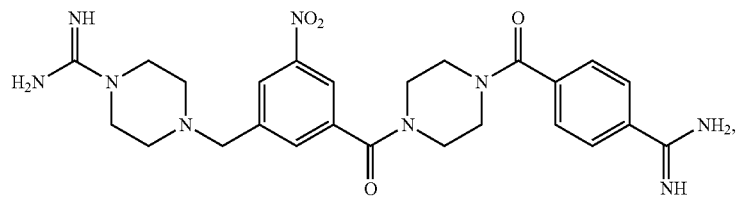
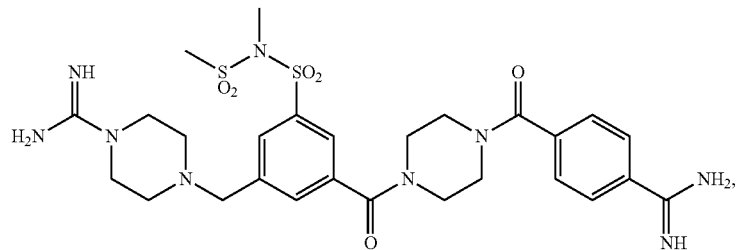
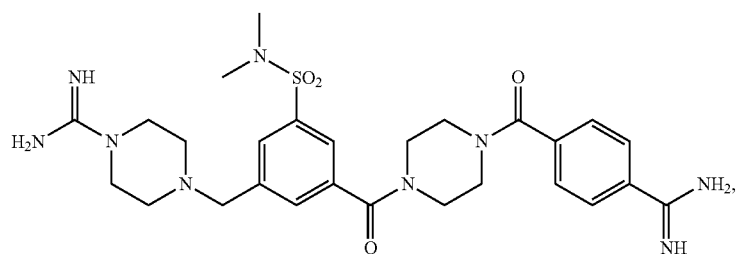
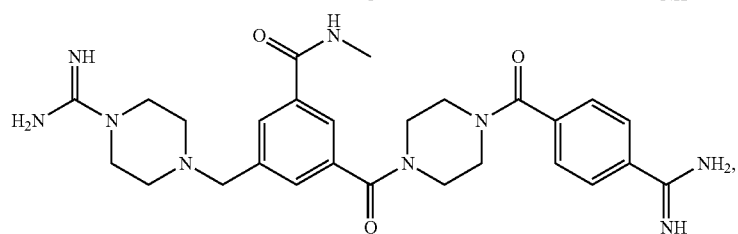
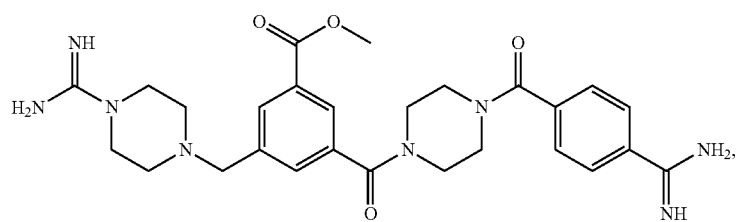

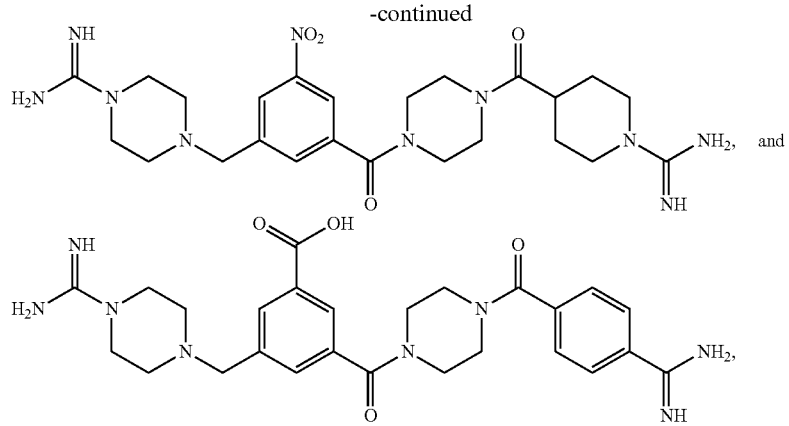

or a pharmaceutically acceptable salt thereof

In a further aspect, the LSD1 inhibitor is selected from:

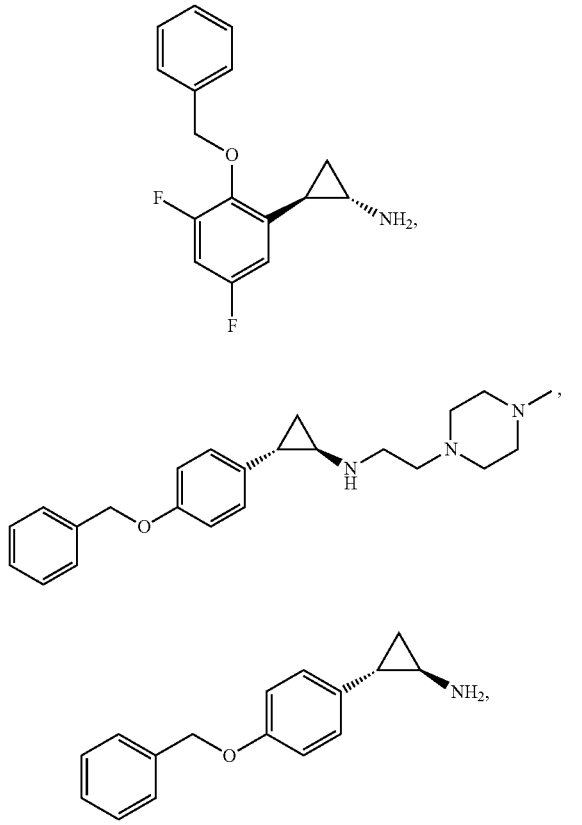

-continued

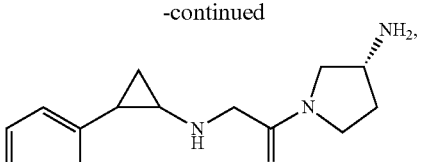

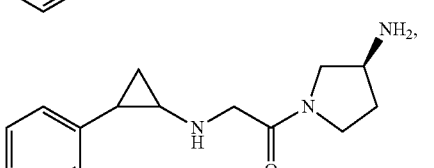

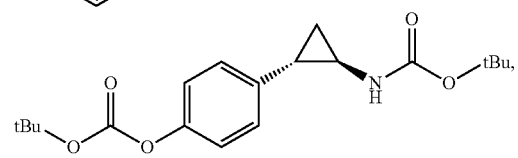

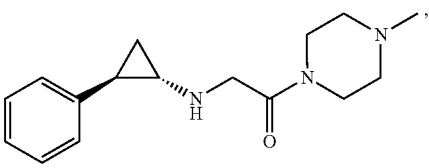

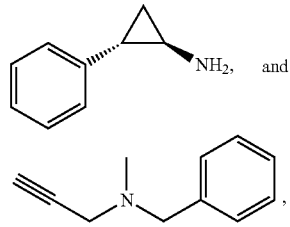

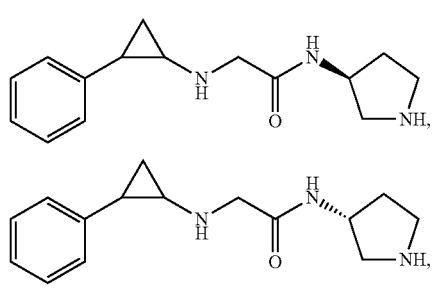

or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

In a further aspect, the cancer comprises cells expressing at least one Sox2 stem cell marker.

In a further aspect, the mammal is a human. In a still further aspect, the mammal has been diagnosed with a need for treatment of a cancer prior to the administering step. In yet a further aspect, the method further comprises the step of identifying a mammal in need of treatment of a cancer.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

2. Via Administration of an HDAC1 Inhibitor

In one aspect, the invention relates to a method of inhibiting the proliferation of cancer cells in a mammal, the method comprising administering to the mammal an effective amount of at least one HDAC1 inhibitor.

In a further aspect, the HDAC1 inhibitor is selected from aliphatic acids, hyroxamate, benzamide, cyclic peptide, and electrophilic ketone hybrid molecules. In a still further aspect, the HDAC1 inhibitor is selected from butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOCPAC, PTACH, and PP.

In a further aspect, the cancer comprises cells expressing at least one Sox2 stem cell marker.

In a further aspect, the mammal is a human. In a still further aspect, the mammal has been diagnosed with a need for treatment of a cancer prior to the administering step. In yet a further aspect, the method further comprises the step of identifying a mammal in need of treatment of a cancer.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

3. Via Contacting at Least One Cell with a LSD1 Inhibitor

In one aspect, the invention relates to a method of inhibiting the survival of cancer cells in a mammal, the method comprising administering to the mammal an effective amount of at least one LSD1 inhibitor.

In a further aspect, the LSD1 inhibitor is a compound having a structure represented by a formula:

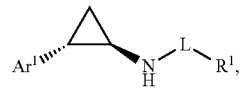

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is a compound having a structure represented by a formula:

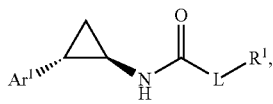

wherein L is a moiety selected from —O— and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —O—; or wherein R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$ when L is —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and monocyclic heteroaryl and wherein Ar$^1$ is substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is selected from:

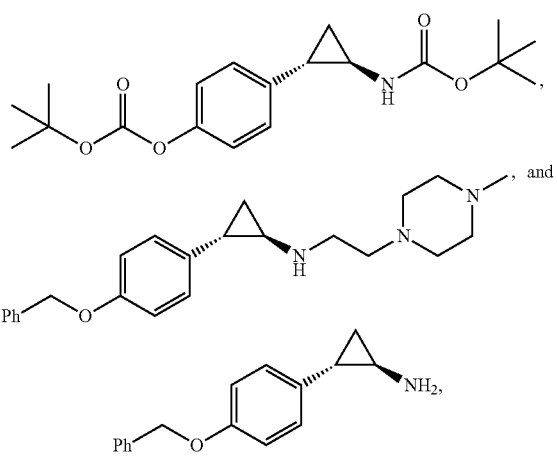

or a pharmaceutically acceptable salt thereof

In a further aspect, the LSD1 inhibitor is selected from:
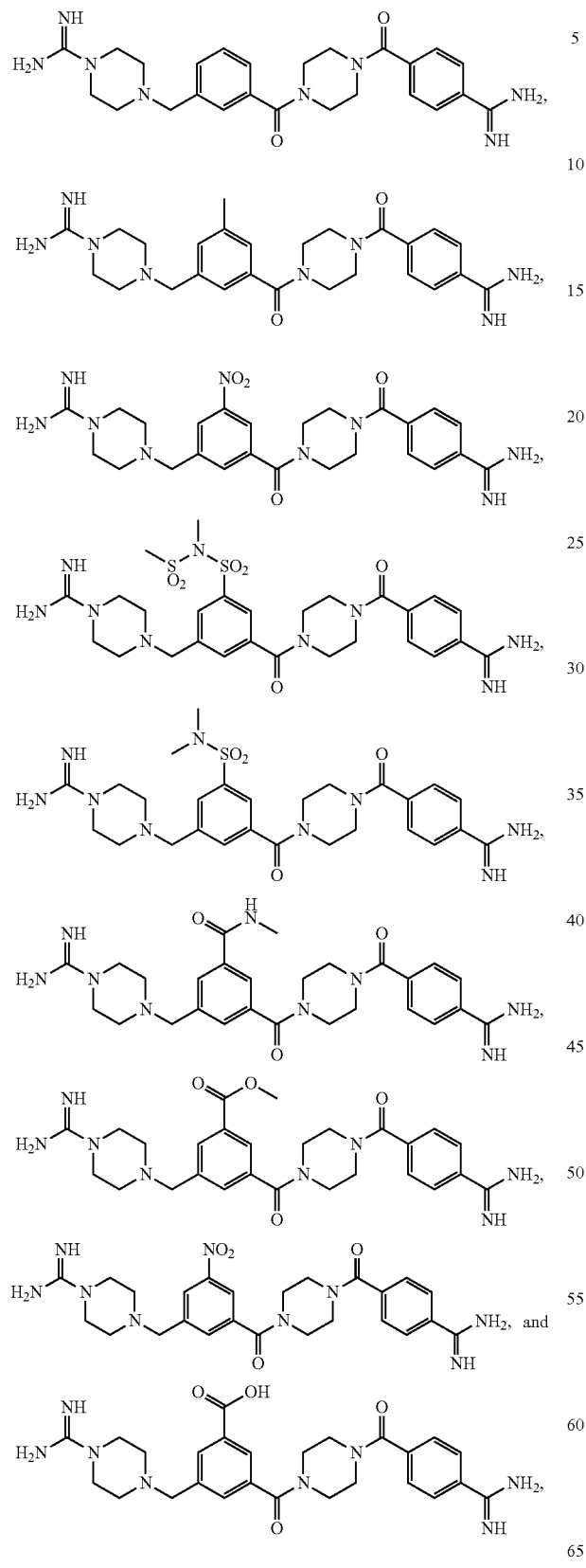
or a pharmaceutically acceptable salt thereof
In a further aspect, the LSD1 inhibitor is selected from:
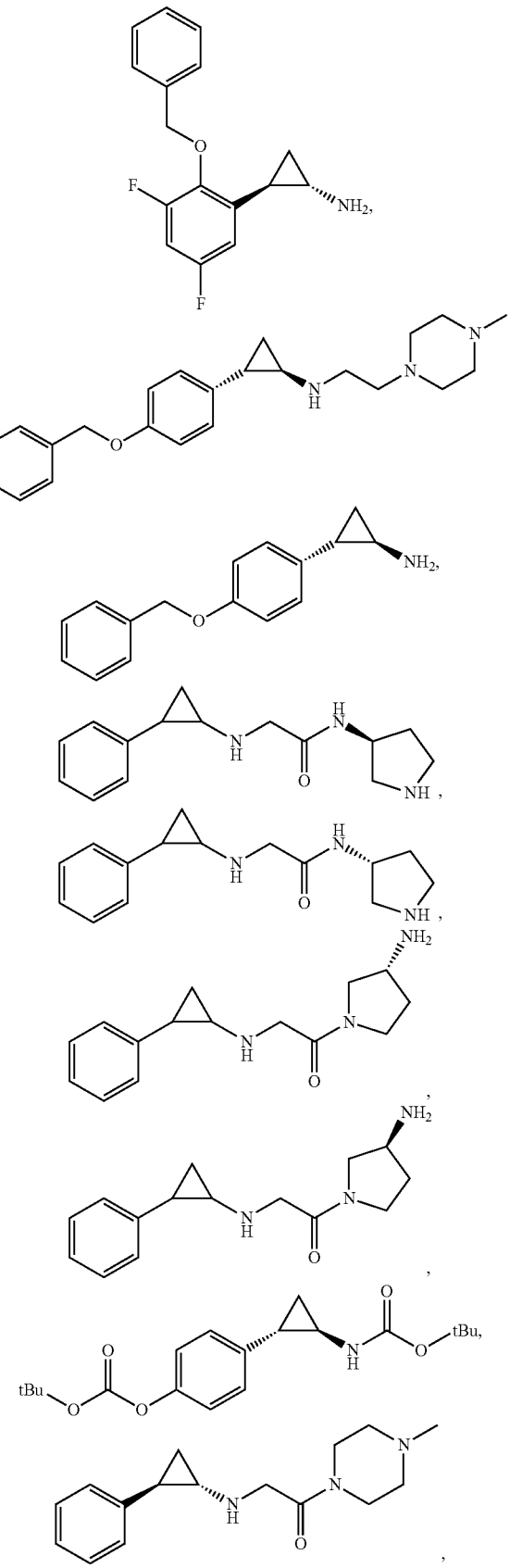

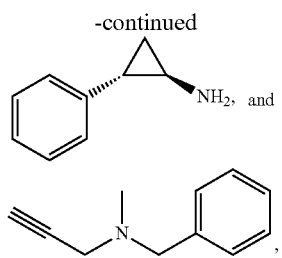

or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an $IC_{50}$ of less than about 100 mM. In a still further aspect, the compound exhibits an $IC_{50}$ of less than about 90 mM. In yet a further aspect, the compound exhibits an $IC_{50}$ of less than about 80 mM. In an even further aspect, the compound exhibits an $IC_{50}$ of less than about 70 mM. In a still further aspect, the compound exhibits an $IC_{50}$ of less than about 60 mM. In yet a further aspect, the compound exhibits an $IC_{50}$ of less than about 50 mM. In an even further aspect, the compound exhibits an $IC_{50}$ of less than about 40 mM. In a still further aspect, the compound exhibits an $IC_{50}$ of less than about 30 mM. In yet a further aspect, the compound exhibits an $IC_{50}$ of less than about 20 mM. In an even further aspect, the compound exhibits an $IC_{50}$ of less than about 10 mM.

4. Via Contacting at Least One Cell with a HDAC1 Inhibitor

In one aspect, the invention relates to a method of inhibiting the survival of cancer cells in a mammal, the method comprising administering to the mammal an effective amount of at least one HDAC1 inhibitor.

In a further aspect, the HDAC1 inhibitor is selected from aliphatic acids, hyroxamate, benzamide, cyclic peptide, and electrophilic ketone hybrid molecules. In a still further aspect, the HDAC1 inhibitor is selected from butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOC-PAC, PTACH, and PP.

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an $IC_{50}$ of less than about 100 mM. In a still further aspect, the compound exhibits an $IC_{50}$ of less than about 90 mM. In yet a further aspect, the compound exhibits an $IC_{50}$ of less than about 80 mM. In an even further aspect, the compound exhibits an $IC_{50}$ of less than about 70 mM. In a still further aspect, the compound exhibits an $IC_{50}$ of less than about 60 mM. In yet a further aspect, the compound exhibits an $IC_{50}$ of less than about 50 mM. In an even further aspect, the compound exhibits an $IC_{50}$ of less than about 40 mM. In a still further aspect, the compound exhibits an $IC_{50}$ of less than about 30 mM. In yet a further aspect, the compound exhibits an $IC_{50}$ of less than about 20 mM. In an even further aspect, the compound exhibits an $IC_{50}$ of less than about 10 mM.

J. METHODS OF INHIBITING SURVIVAL OF CANCER CELLS

1. Via Contacting at Least One Cell with a LSD1 Inhibitor

In one aspect, the invention relates to a method of inhibiting the survival of at least one cancer cell, the method comprising contacting the at least one cell with an effective amount of at least one LSD1 inhibitor.

In a further aspect, the LSD1 inhibitor is a compound having a structure represented by a formula:

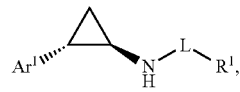

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^2$, when present, is selected from aryl and heteroaryl and wherein $Ar^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^1$ is selected from phenyl and heteroaryl and wherein $Ar^1$ is substituted with 0, 1, 2, or 3 groups independently selected from halogen, —$NO_2$, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$; wherein $R^{12}$, when present, is selected from hydrogen, C1-C4 alkyl, C1-C4 monohaloalkyl, C1-C4 polyhaloalkyl, and —$CO_2R^{21}$; wherein $R^{21}$, when present, is selected from hydrogen and C1-C4 alkyl; wherein each of $R^{13}$, $R^{14a}$, $R^{14b}$, $R^{15}$, $R^{16}$, $R^{17}$, $R^{18}$, $R^{19}$, $R^{20a}$, and $R^{20b}$, when present, is independently selected from hydrogen, C1-C4 alkyl, C1-C4 monohaloalkyl, and C1-C4 polyhaloalkyl; wherein $Ar^4$, when present, is selected from aryl and heteroaryl and wherein $Ar^2$, when present, is substituted with 0, 1, 2, or 3 groups independently selected from halogen, —$NH_2$, —OH, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

the LSD1 inhibitor is a compound having a structure represented by a formula:

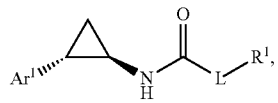

wherein L is a moiety selected from —O— and —$(CR^{2a}R^{2b})_n$—; wherein n is an integer selected from 1, and 2; wherein each of $R^{2a}$ and $R^{2b}$, when present, is independently selected from hydrogen, halogen, —OH, —$NH_2$, —$NO_2$, —CN, and —$N_3$; wherein $R^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, $Ar^2$, and $Cy^1$ when L is —O—; or wherein $R^1$ is selected from $NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, and —$SO_2NR^{11a}R^{11b}$ when L is —$(CR^{2a}R^{2b})_n$—; wherein each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, C1-C4 alkyl, C1-C4 monohaloalkyl, C1-C4 polyhaloalkyl, $Ar^3$, and $Cy^2$; wherein $Ar^3$, when present, is selected from aryl and heteroaryl and wherein $Ar^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^2$, when present, is selected from C3-C6 cycloalkyl and C2-C5 heterocycloalkyl and wherein $Cy^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^2$, when present, is selected from aryl and heteroaryl and wherein $Ar^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^1$ is selected from phenyl and monocyclic heteroaryl and wherein $Ar^1$ is substituted with 0, 1, 2, or 3 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$; wherein $R^{12}$, when present, is selected from hydrogen, C1-C4 alkyl, C1-C4 monohaloalkyl, C1-C4 polyhaloalkyl, and —$CO_2R^{21}$; wherein $R^{21}$, when present, is selected from hydrogen and C1-C4 alkyl; wherein each of $R^{13}$, $R^{14a}$, $R^{14b}$, $R^{15}$, $R^{16}$, $R^{17}$, $R^{18}$, $R^{19}$, $R^{20a}$, and $R^{20b}$, when present, is independently selected from hydrogen, C1-C4 alkyl, C1-C4 monohaloalkyl, and C1-C4 polyhaloalkyl; wherein $Ar^4$, when present, is selected from aryl and heteroaryl and wherein $Ar^2$, when present, is substituted with 0, 1, 2, or 3 groups independently selected from halogen, —$NH_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is selected from:

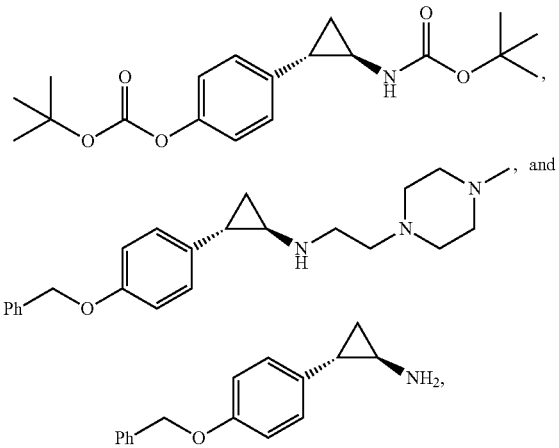

or a pharmaceutically acceptable salt thereof

In a further aspect, the LSD1 inhibitor is selected from:
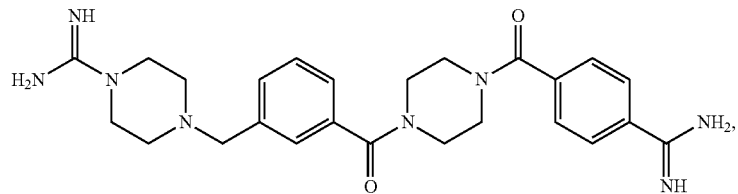
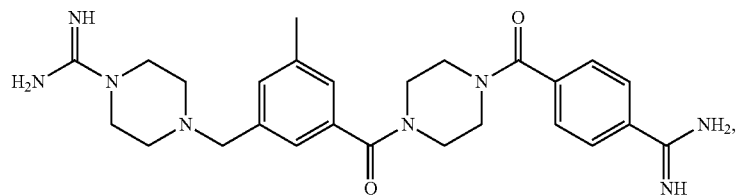
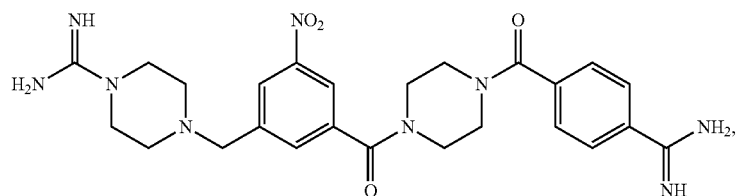
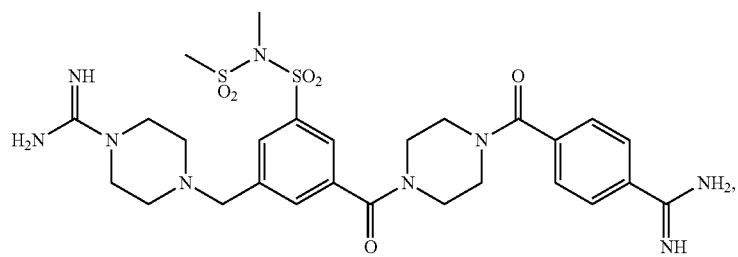
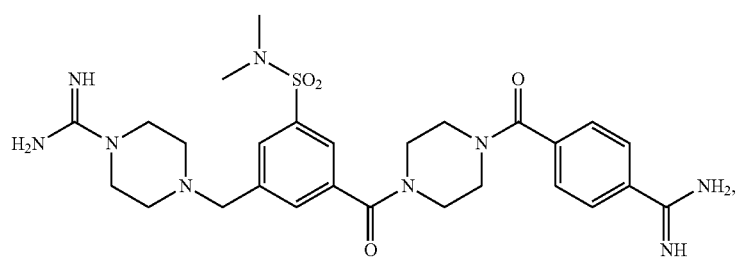
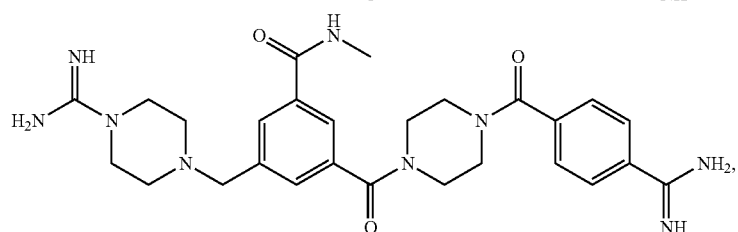
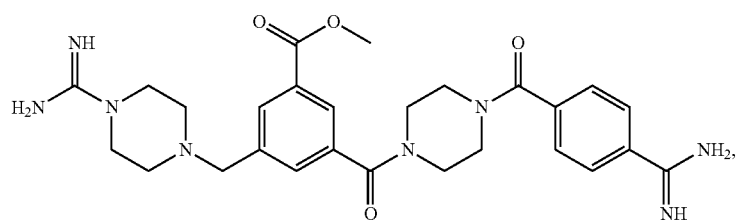

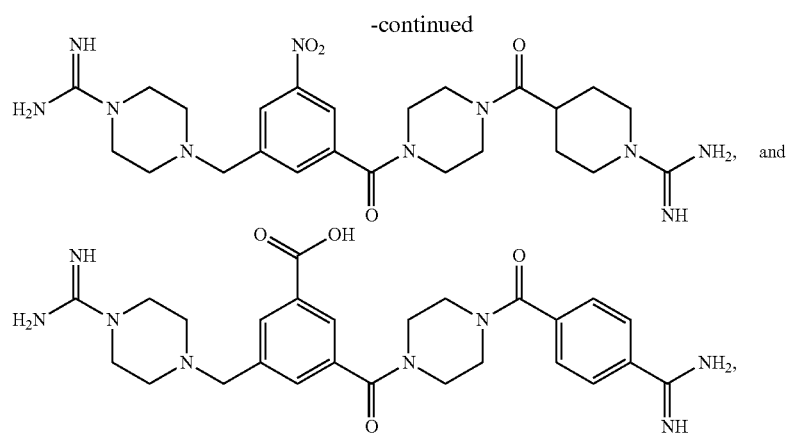

or a pharmaceutically acceptable salt thereof

In a further aspect, the LSD1 inhibitor is selected from:

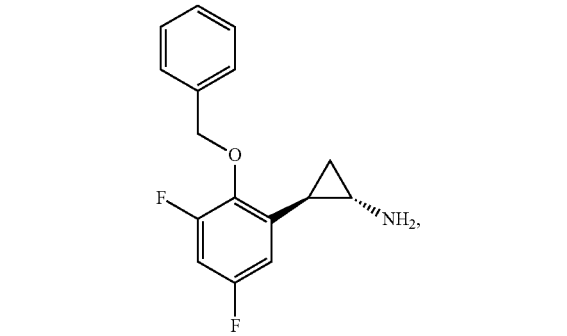

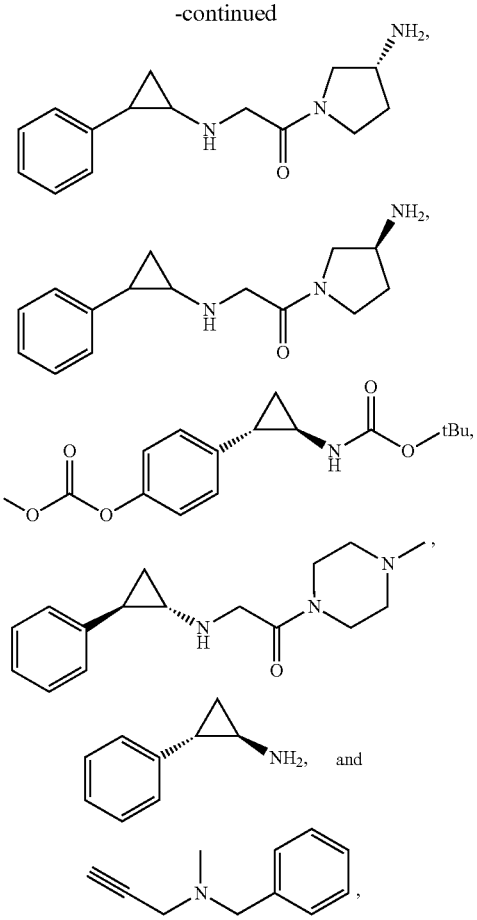

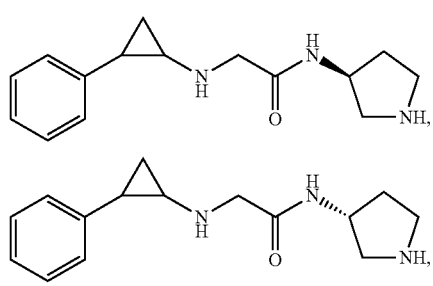

or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an $IC_{50}$ of less than about 100 mM. In a still further aspect, the compound exhibits an $IC_{50}$ of less than about 90 mM. In yet a further aspect, the compound exhibits an $IC_{50}$ of less than about 80 mM. In an even further aspect, the compound exhibits an $IC_{50}$ of less than about 70 mM. In a still further aspect, the compound exhibits an $IC_{50}$ of less than about 60 mM. In yet a further aspect, the compound exhibits an $IC_{50}$ of less than about 50 mM. In an even further aspect, the compound exhibits an $IC_{50}$ of less than about 40 mM. In a still further aspect, the compound exhibits an $IC_{50}$ of less than about 30 mM. In yet a further aspect, the compound exhibits an $IC_{50}$ of less than about 20 mM. In an even further aspect, the compound exhibits an $IC_{50}$ of less than about 10 mM.

2. Via Contacting at Least One Cell with a HDAC1 Inhibitor

In one aspect, the invention relates to a method of inhibiting the survival of at least one cancer cell, the method comprising contacting the at least one cell with an effective amount of at least one HDAC1 inhibitor.

In a further aspect, the HDAC1 inhibitor is selected from aliphatic acids, hyroxamate, benzamide, cyclic peptide, and electrophilic ketone hybrid molecules. In a still further aspect, the HDAC1 inhibitor is selected from butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOC-PAC, PTACH, and PP.

In a further aspect, the cell is selected from a cancer stem cell and a cancer-initiating cell. In a still further aspect, the cell expresses at least one Sox2 stem cell marker. In yet a further aspect, the cancer stem cell is an embryonic cancer stem cell with germ tumor cell properties.

In a further aspect, contacting is via administration to a mammal. In a still further aspect, the mammal has been diagnosed with a need for treatment of a cancer prior to the administering step. In yet a further aspect, the method further comprises the step of identifying a mammal in need of treatment of a cancer.

In a further aspect, the compound exhibits an $IC_{50}$ of less than about 100 mM. In a still further aspect, the compound exhibits an $IC_{50}$ of less than about 90 mM. In yet a further aspect, the compound exhibits an $IC_{50}$ of less than about 80 mM. In an even further aspect, the compound exhibits an $IC_{50}$ of less than about 70 mM. In a still further aspect, the compound exhibits an $IC_{50}$ of less than about 60 mM. In yet a further aspect, the compound exhibits an $IC_{50}$ of less than about 50 mM. In an even further aspect, the compound exhibits an $IC_{50}$ of less than about 40 mM. In a still further aspect, the compound exhibits an $IC_{50}$ of less than about 30 mM. In yet a further aspect, the compound exhibits an $IC_{50}$ of less than about 20 mM. In an even further aspect, the compound exhibits an $IC_{50}$ of less than about 10 mM.

K. METHODS OF USING THE COMPOUNDS

The compounds and pharmaceutical compositions of the invention are useful in treating or controlling oncological disorders, such as cancer. The compounds and pharmaceutical compositions containing the compounds can be useful in the treatment or control of squamous cell carcinomas by action of inhibiting LSD1 and/or HDAC.

Examples of cancers for which the compounds and compositions can be useful in treating, include, but are not limited to, glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

To treat or control the oncological disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of an oncological disorder, such as cancer.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition, such as cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or preventing an oncological disorder, such as cancer. Thus, provided are methods comprising administering a therapeutically effective amount of at least one LSD1 inhibitor and/or HDAC1 inhibitor. In one aspect, the method can be a method for treating an oncological disorder. In yet another aspect, the method can be a method for treating a cancer. In a still further aspect, the method can be a method for inhibiting LSD1 and/or HDAC1.

a. Treating a Cancer Via Administration of a LSD1 Inhibitor

The present invention relates to methods and compositions and procedures for the treatment of a cancer, at least by suppression of cancer cell growth. A method for treating a cancer in which Sox2 stem cell markers are present in the expression of cancer cells may include steps such as: a) identifying the existence of Sox2 stem cell markers in the cancer within a patient; and b) introducing LSD1 inhibitors or reagents that interfere with LSD1 activity into or onto the patient to suppress gene expression by the cancer cells having Sox2 stem cell markers.

Thus, in one aspect, the invention relates to a method of treating a cancer in a mammal, the method comprising administering to the mammal an effective amount of at least one LSD1 inhibitor.

The LSD1 inhibitor may be introduced into the patient by infusion, perfusion, transdermal application, implanted delivery system, ingestion or intravenous introduction. One method includes the LSD1 inhibitors being introduced onto the patient by application of a liquid or gel. The term "onto" includes either conventional transdermal application on the outer layers of the skin, or direct application of the liquid or gel to an organ or tissue. In one embodiment, the liquid or gel further contains a transdermal carrier.

The rate of delivery and final amount of delivery of the various inhibitors will depend upon the treatment parameters defined by the condition of the patient, the extent and location of the cancer and the aggressiveness of the treatment desired. The rate of delivery is generally lowest with transdermal delivery, as is the amount delivered during any transdermal treatment. In general, a useful range requires at least 0.1 milligrams during a 24 hour period and other treatments may use 500 milligrams or more in a 24 hour treatment period. So one range would be 0.1 to 500 milligrams inhibitor/24 hour period. Other useful ranges of treatment could include least 20 grams in 24 hours and at least 50 grams in 24 hour, a rate selected from the group consisting of at least 5 grams in 24 hours and at least 10 grams in 24 hours, a rate selected from the group consisting of at least 200 milligrams in 24 hours, at least 0.5 grams in 24 hours and at least 1 gram in 24 hours, a rate selected from the group consisting of between 50 milligrams in 24 hours and 5 grams in 24 hours, a rate selected from the group consisting of between 5 milligrams in 24 hours and 1 gram in 24 hours.

Particularly in transdermal or gel/liquid applications, the range of concentration of the inhibitors as compared to the total weight of the liquid or gel composition (including the inhibitor) might be about 0.1 milligrams inhibitor to 200 milligrams to milliliter of liquid or gel. Ranges for compositions might include any minimum amount of 0.1, 0.5, 1.0, 2.5, 5, 10, 50, 100 or 200 milligrams inhibitor to each milliliter of total volume with the liquid or gel.

In a further aspect, the LSD1 inhibitor is a compound having a structure represented by a formula:

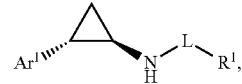

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is a compound having a structure represented by a formula:

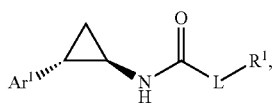

wherein L is a moiety selected from —O— and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —O—; or wherein R$^1$ is selected from —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, and —SO$_2$NR$^{11a}$R$^{11b}$, when L is —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and monocyclic heteroaryl and wherein Ar$^1$ is substituted with 0, 1, 2, or 3 groups independently selected from halogen, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and —CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^3$, when present, is selected from C3-C6 cycloalkyl and C2-C5 heterocycloalkyl and wherein Cy$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is selected from:

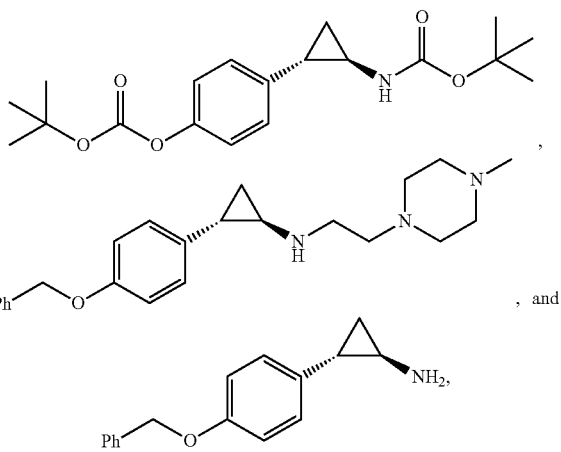

or a pharmaceutically acceptable salt thereof

In a further aspect, the LSD1 inhibitor is selected from:
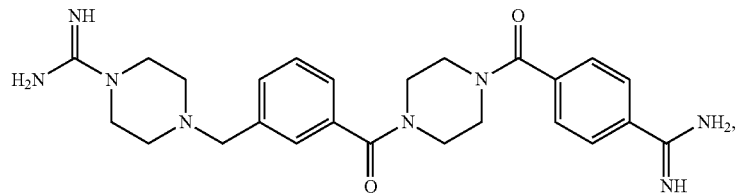
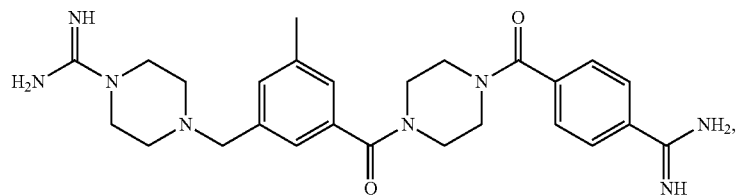
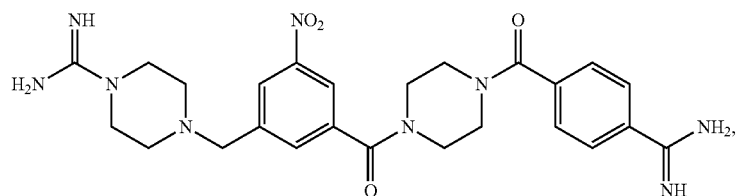
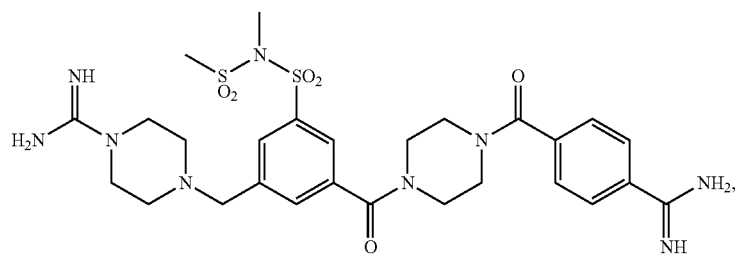
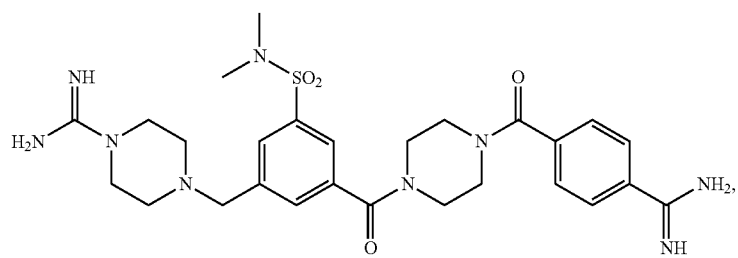
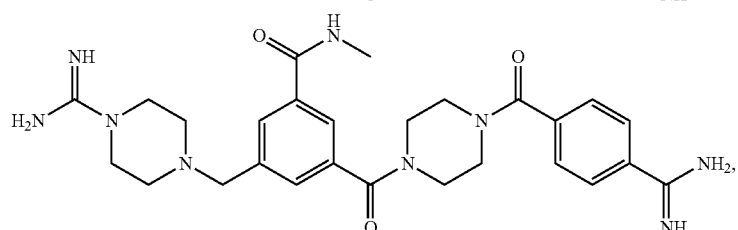
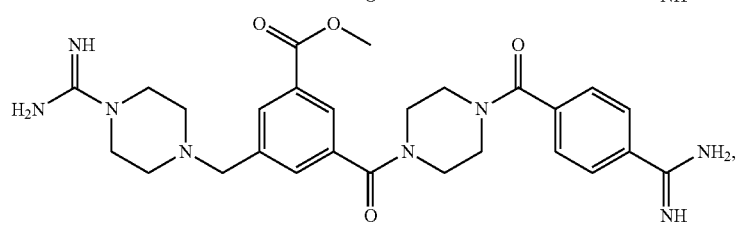

-continued

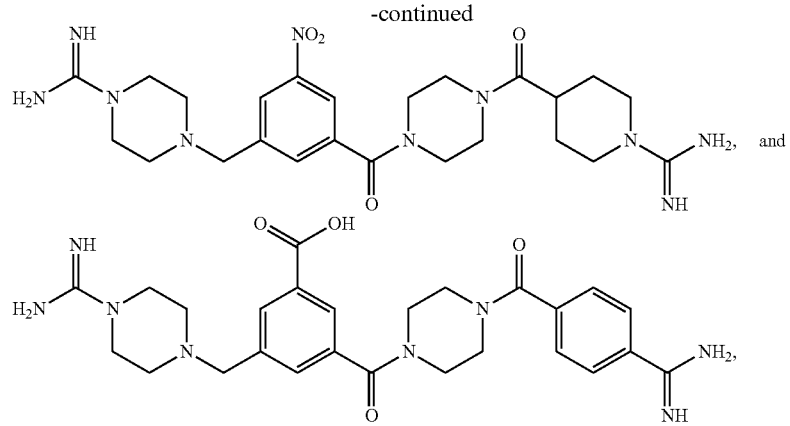

or a pharmaceutically acceptable salt thereof

In a further aspect, the LSD1 inhibitor is selected from:

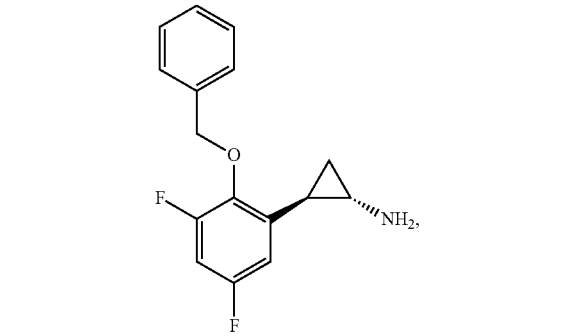

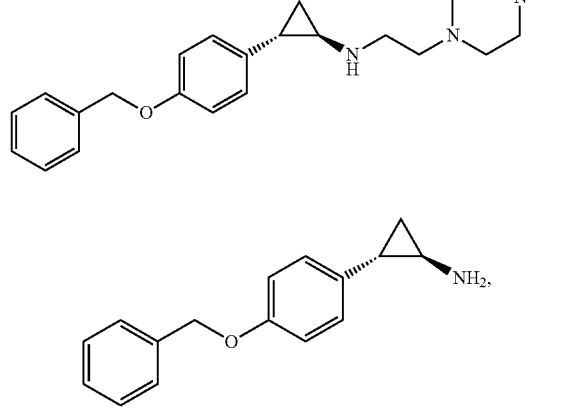

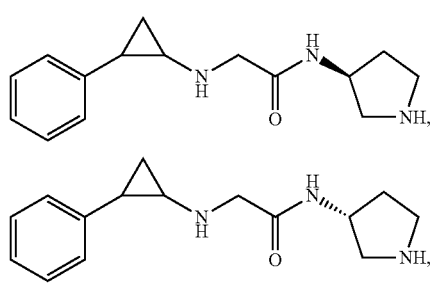

-continued

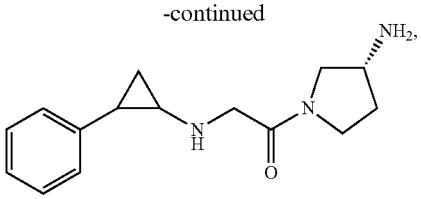

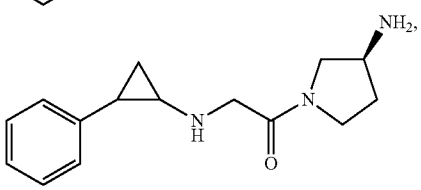

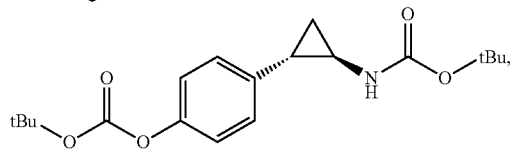

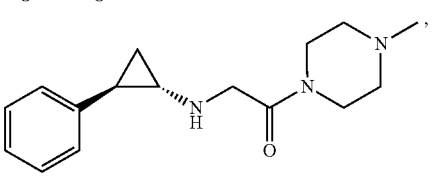

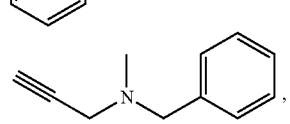

or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

In a further aspect, the cancer comprises cells expressing at least one Sox2 stem cell marker.

In a further aspect, the mammal is a human. In a still further aspect, the mammal has been diagnosed with a need for treatment of a cancer prior to the administering step. In yet a further aspect, the method further comprises the step of identifying a mammal in need of treatment of a cancer.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

b. Treating a Cancer Via Administration of an HDAC1 Inhibitor

The present invention relates to methods and compositions and procedures for the treatment of a cancer, at least by suppression of cancer cell growth. A method for treating a cancer in which Sox2 stem cell markers are present in the expression of cancer cells may include steps such as: a) identifying the existence of Sox2 stem cell markers in the cancer within a patient; and b) introducing HDAC1 inhibitors or reagents that interfere with HDAC1 activity to suppress gene expression by the cancer cells having Sox2 stem cell markers.

Thus, in one aspect, the invention relates to a method of treating a cancer in a mammal, the method comprising administering to the mammal an effective amount of at least one HDAC1 inhibitor.

The HDAC1 inhibitors may be introduced into the patient by infusion, perfusion, transdermal application, implanted delivery system, ingestion or intravenous introduction. One method includes the HDAC1 inhibitors being introduced onto the patient by application of a liquid or gel. The term "onto" includes either conventional transdermal application on the outer layers of the skin, or direct application of the liquid or gel to an organ or tissue. In one embodiment, the liquid or gel further contains a transdermal carrier.

The rate of delivery and final amount of delivery of the various inhibitors will depend upon the treatment parameters defined by the condition of the patient, the extent and location of the cancer and the aggressiveness of the treatment desired. The rate of delivery is generally lowest with transdermal delivery, as is the amount delivered during any transdermal treatment. In general, a useful range requires at least 0.1 milligrams during a 24 hour period and other treatments may use 500 milligrams or more in a 24 hour treatment period. So one range would be 0.1 to 500 milligrams inhibitor/24 hour period. Other useful ranges of treatment could include least 20 grams in 24 hours and at least 50 grams in 24 hour, a rate selected from the group consisting of at least 5 grams in 24 hours and at least 10 grams in 24 hours, a rate selected from the group consisting of at least 200 milligrams in 24 hours, at least 0.5 grams in 24 hours and at least 1 gram in 24 hours, a rate selected from the group consisting of between 50 milligrams in 24 hours and 5 grams in 24 hours, a rate selected from the group consisting of between 5 milligrams in 24 hours and 1 gram in 24 hours.

Particularly in transdermal or gel/liquid applications, the range of concentration of the inhibitors as compared to the total weight of the liquid or gel composition (including the inhibitor) might be about 0.1 milligrams inhibitor to 200 milligrams to milliliter of liquid or gel. Ranges for compositions might include any minimum amount of 0.1, 0.5, 1.0, 2.5, 5, 10, 50, 100 or 200 milligrams inhibitor to each milliliter of total volume with the liquid or gel.

In a further aspect, the HDAC1 inhibitor is selected from aliphatic acids, hyroxamate, benzamide, cyclic peptide, and electrophilic ketone hybrid molecules. In a still further aspect, the HDAC1 inhibitor is selected from butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOCPAC, PTACH, and PP.

In a further aspect, the cancer comprises cells expressing at least one Sox2 stem cell marker.

In a further aspect, the mammal is a human. In a still further aspect, the mammal has been diagnosed with a need for treatment of a cancer prior to the administering step. In yet a further aspect, the method further comprises the step of identifying a mammal in need of treatment of a cancer.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

2. Use of Compounds

In one aspect, the invention relates to the use of a disclosed compound or a product of a disclosed method. In a further aspect, a use relates to the manufacture of a medicament for the treatment of a cancer in a mammal. In a further aspect, a use relates to treatment of a cancer in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a cancer in a mammal. Also disclosed is the use of a compound for inhibition of LSD1 and/or HDAC1. In one aspect, the use is characterized in that the mammal is a human. In one aspect, the use is characterized in that the disorder is a cancer characterized by the presence of Sox2. In one aspect, the cancer characterized by the presence of Sox2 is treated by inhibition of LSD1 and/or HDAC1 activity in a mammal.

In a further aspect, the use relates to the manufacture of a medicament for the treatment of a cancer characterized by the presence of Sox2 in a mammal. In a further aspect, the medicament is used in the treatment of a cancer characterized by the presence of Sox2 in a mammal.

In a further aspect, the use relates to inhibition of LSD1 and/or HDAC1 activity in a mammal. In a further aspect, the use relates to modulating LSD1 and/or HDAC1 activity in a mammal. In a still further aspect, the use relates to modulating LSD1 and/or HDAC1 activity in a cell. In yet a further aspect, the mammal is a human.

In one aspect, the use is associated with the treatment of a cancer characterized by the presence of Sox2. In a further aspect, the use is associated with a cancer selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a cancer associated with gene amplification of Sox2. In a still further aspect, the gene amplification occurs at 3q22.33.

3. Manufacture of a Medicament

In one aspect, the invention relates to a method for the manufacture of a medicament for treatment of cancer in a mammal, the method comprising the step of combining an effective amount of at least one LSD1 inhibitor.

In one aspect, the invention relates to a method for the manufacture of a medicament for treatment of cancer in a mammal, the method comprising the step of combining an effective amount of at least one HDAC1 inhibitor.

In a further aspect, the HDAC1 inhibitor is selected from aliphatic acids, hyroxamate, benzamide, cyclic peptide, and electrophilic ketone hybrid molecules. In a still further aspect, the HDAC1 inhibitor is selected from butyrate acid, Valproate (valproic acid), Tricostatin A (TSA), Vorinostat (SAHA), Entinostat (MS-275, SNDX-275), MGCD-0103, Romidepsin (FK-228/resminostate), trapoxin B, CHAP31, Panobinostate (Belinostat, PXD101), M344 (PCI-34051), CI994 (Tacedinaline), Tubastatin A hydrochloride, AR-42 (HDAC-42), SB939 (Pracinostat), ITF2357, Givinostat, CUDC-101, LAQ824 (NVP-LAQ824, Dacinostat), PCI-24781 (CRA-024781), APHA compound 8, BATCP, MOC-PAC, PTACH, and PP.

In a further aspect, the LSD1 inhibitor is a compound having a structure represented by a formula:

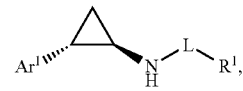

wherein L is a moiety selected from —C(O)—, —CO$_2$, and (CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is CO$_2$; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^2$, when present, is selected from aryl and heteroaryl and wherein $Ar^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^1$ is selected from phenyl and heteroaryl and wherein $Ar^1$ is substituted with 0, 1, 2, or 3 groups independently selected from halogen, —$NO_2$, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$; wherein $R^{12}$, when present, is selected from hydrogen, C1-C4 alkyl, C1-C4 monohaloalkyl, C1-C4 polyhaloalkyl, and —$CO_2R^{21}$; wherein $R^{21}$, when present, is selected from hydrogen and C1-C4 alkyl; wherein each of $R^{13}$, $R^{14a}$, $R^{14b}$, $R^{15}$, $R^{16}$, $R^{17}$, $R^{18}$, $R^{19}$, $R^{20a}$, and $R^{20b}$, when present, is independently selected from hydrogen, C1-C4 alkyl, C1-C4 monohaloalkyl, and C1-C4 polyhaloalkyl; wherein $Ar^4$, when present, is selected from aryl and heteroaryl and wherein $Ar^2$, when present, is substituted with 0, 1, 2, or 3 groups independently selected from halogen, —$NH_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

the LSD1 inhibitor is a compound having a structure represented by a formula:

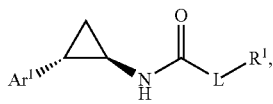

wherein L is a moiety selected from —O— and —$(CR^{2a}R^{2b})_n$—; wherein n is an integer selected from 1, and 2; wherein each of $R^{2a}$ and $R^{2b}$, when present, is independently selected from hydrogen, halogen, —OH, —$NH_2$, —$NO_2$, —CN, and —$N_3$; wherein $R^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, $Ar^2$, and $Cy^1$ when L is —O—; or wherein $R^1$ is selected from —$NO_2$, —CN, —$N_3$, —$OR^3$, —$SR^4$, —$NR^{5a}R^{5b}$, —$P(R^6)_3$, —$CO_2R^7$, —$C(O)SR^8$, —$SO_2R^9$, —$CONR^{10a}R^{10b}$, and —$SO_2NR^{11a}R^{11b}$, when L is —$(CR^{2a}R^{2b})_n$—; wherein each of $R^3$, $R^4$, $R^{5a}$, $R^{5b}$, $R^6$, $R^7$, $R^8$, $R^9$, $R^{10a}$, $R^{10b}$, $R^{11a}$ and $R^{11b}$, when present, is independently selected from hydrogen, C1-C4 alkyl, C1-C4 monohaloalkyl, C1-C4 polyhaloalkyl, $Ar^3$, and $Cy^2$; wherein $Ar^3$, when present, is selected from aryl and heteroaryl and wherein $Ar^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^2$, when present, is selected from C3-C6 cycloalkyl and C2-C5 heterocycloalkyl and wherein $Cy^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^2$, when present, is selected from aryl and heteroaryl and wherein $Ar^2$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Ar^1$ is selected from phenyl and monocyclic heteroaryl and wherein $Ar^1$ is substituted with 0, 1, 2, or 3 groups independently selected from halogen, —CN, —$N_3$, C1-C4 alkyl, C1-C4 monohaloalkyl, C1-C4 polyhaloalkyl, C1-C4 hydroxyalkyl, —$OR^{12}$, —$SR^{13}$, —$NR^{14a}R^{14b}$, —$P(R^{15})_3$, —$CO_2R^{16}$, —$C(O)SR^{17}$, —$SO_2R^{18}$, —$CONR^{19a}R^{19b}$, —$SO_2NR^{20a}R^{20b}$, $Cy^3$, and $Ar^4$; wherein $R^{12}$, when present, is selected from hydrogen, C1-C4 alkyl, C1-C4 monohaloalkyl, C1-C4 polyhaloalkyl, and $CO_2R^{21}$; wherein $R^{21}$, when present, is selected from hydrogen and C1-C4 alkyl; wherein each of $R^{13}$, $R^{14a}$, $R^{14b}$, $R^{15}$, $R^{16}$, $R^{17}$, $R^{18}$, $R^{19}$, $R^{20a}$, and $R^{20b}$, when present, is independently selected from hydrogen, C1-C4 alkyl, C1-C4 monohaloalkyl, and C1-C4 polyhaloalkyl; wherein $Ar^4$, when present, is selected from aryl and heteroaryl and wherein $Ar^2$, when present, is substituted with 0, 1, 2, or 3 groups independently selected from halogen, —$NH_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof.

In a further aspect, the LSD1 inhibitor is selected from:

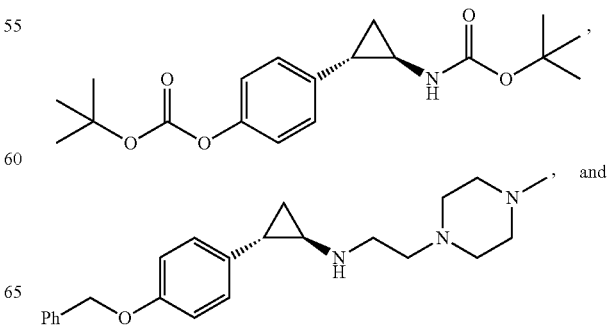

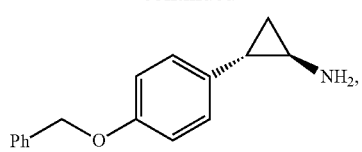
or a pharmaceutically acceptable salt thereof
In a further aspect, the LSD1 inhibitor is selected from:
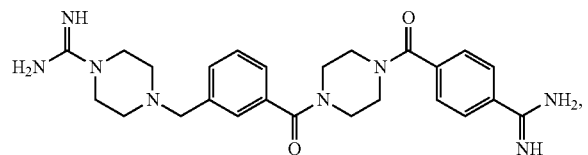
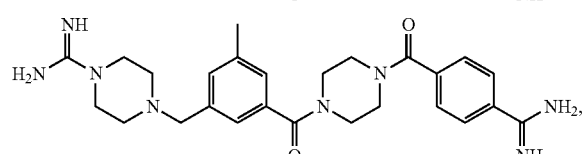
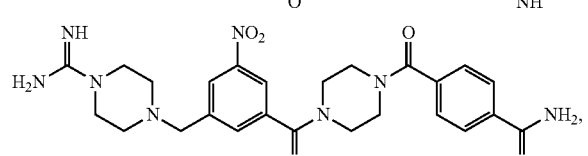
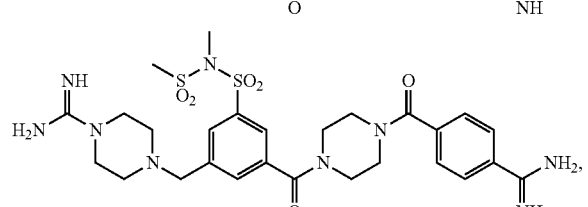
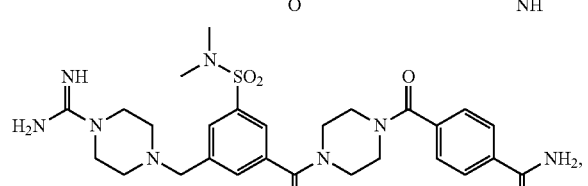
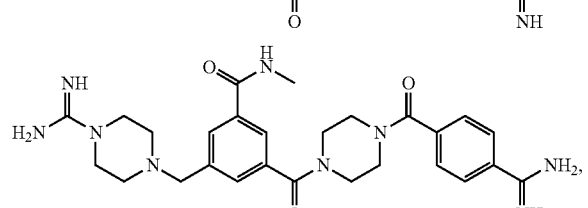
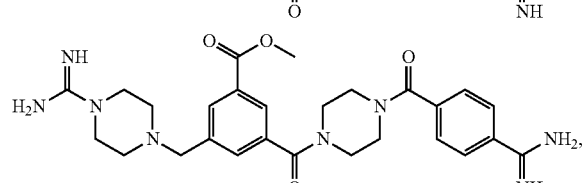
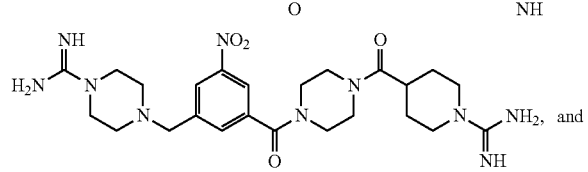
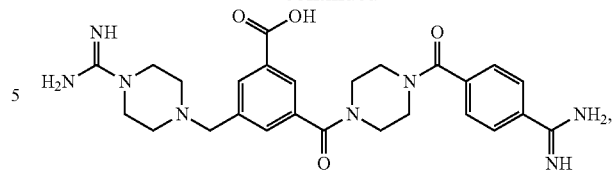
or a pharmaceutically acceptable salt thereof
In a further aspect, the LSD1 inhibitor is selected from:
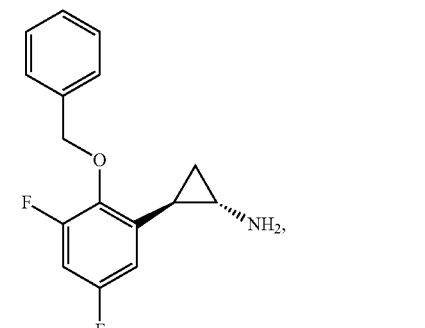
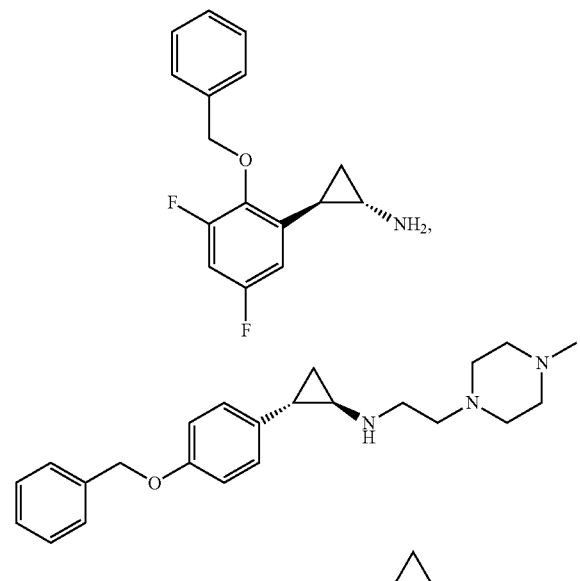
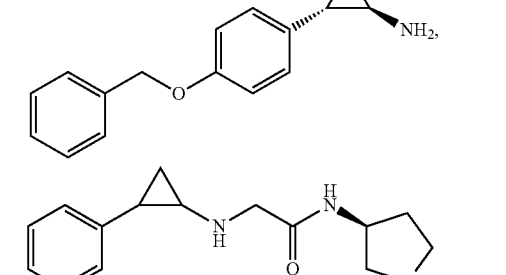
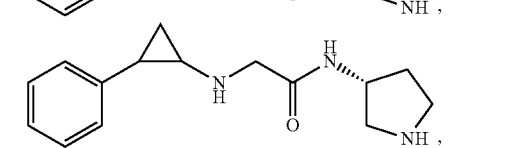
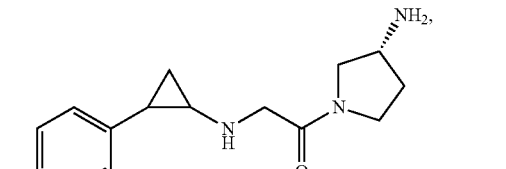
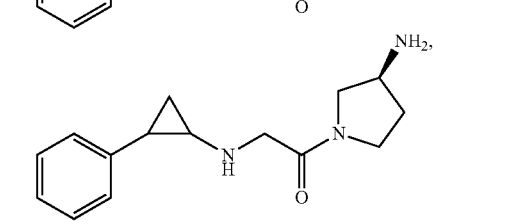

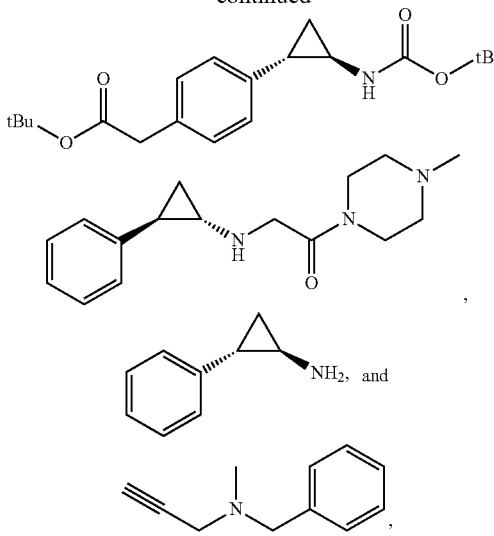

or a pharmaceutically acceptable salt thereof

In a further aspect, the LSD1 inhibitor is selected from parnate 2-phenylcyclopropylamine (2-PCPA), tranylcypromine, and derivatives thereof. In a still further aspect, the LSD1 inhibitor is a bisguanidine polyamine.

In a further aspect, the cancer comprises cells expressing at least one Sox2 stem cell marker.

In a further aspect, the mammal is a human. In a still further aspect, the mammal has been diagnosed with a need for treatment of a cancer prior to the administering step. In yet a further aspect, the method further comprises the step of identifying a mammal in need of treatment of a cancer.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

4. Kits

In one aspect, the invention relates to kits comprising at least one compound having a structure represented by a formula:

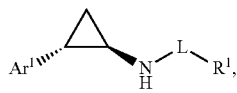

wherein L is a moiety selected from —C(O)—, —CO$_2$—, and —(CR$^{2a}$R$^{2b}$)$_n$—; wherein n is an integer selected from 1, and 2; wherein each of R$^{2a}$ and R$^{2b}$, when present, is independently selected from hydrogen, halogen, —OH, —NH$_2$, —NO$_2$, —CN, and —N$_3$; wherein R$^1$ is selected from hydrogen, C1-C8 alkyl, C1-C8 alkenyl, C1-C8 alkynyl, C1-C8 monohaloalkyl, C1-C8 polyhaloalkyl, C1-C8 hydroxyalkyl, Ar$^2$, and Cy$^1$ when L is —CO$_2$—; or wherein R$^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, —NO$_2$, —CN, —N$_3$, —OR$^3$, —SR$^4$, —NR$^{5a}$R$^{5b}$, —P(R$^6$)$_3$, —CO$_2$R$^7$, —C(O)SR$^8$, —SO$_2$R$^9$, —CONR$^{10a}$R$^{10b}$, —SO$_2$NR$^{11a}$R$^{11b}$, Ar$^2$, and Cy$^1$ when L is selected from —C(O)— and —(CR$^{2a}$R$^{2b}$)$_n$—; wherein each of R$^3$, R$^4$, R$^{5a}$, R$^{5b}$, R$^6$, R$^7$, R$^8$, R$^9$, R$^{10a}$, R$^{10b}$, R$^{11a}$ and R$^{11b}$, when present, is independently selected from hydrogen, C1-C4 alkyl, C1-C4 monohaloalkyl, C1-C4 polyhaloalkyl, Ar$^3$, and Cy$^2$; wherein Ar$^3$, when present, is selected from aryl and heteroaryl and wherein Ar$^3$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^2$, when present, is selected from C3-C6 cycloalkyl and C2-C5 heterocycloalkyl and wherein Cy$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^2$, when present, is selected from aryl and heteroaryl and wherein Ar$^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Cy$^1$, when present, is selected from C3-C6 cycloalkyl and C2-C5 heterocycloalkyl and wherein Cy$^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein Ar$^1$ is selected from phenyl and heteroaryl and wherein Ar$^1$ is substituted with 0, 1, 2, or 3 groups independently selected from halogen, —NO$_2$, —CN, —N$_3$, C1-C4 alkyl, C1-C4 monohaloalkyl, C1-C4 polyhaloalkyl, C1-C4 hydroxyalkyl, —OR$^{12}$, —SR$^{13}$, —NR$^{14a}$R$^{14b}$, —P(R$^{15}$)$_3$, —CO$_2$R$^{16}$, —C(O)SR$^{17}$, —SO$_2$R$^{18}$, —CONR$^{19a}$R$^{19b}$, —SO$_2$NR$^{20a}$R$^{20b}$, Cy$^3$, and Ar$^4$; wherein R$^{12}$, when present, is selected from hydrogen, C1-C4 alkyl, C1-C4 monohaloalkyl, C1-C4 polyhaloalkyl, and CO$_2$R$^{21}$; wherein R$^{21}$, when present, is selected from hydrogen and C1-C4 alkyl; wherein each of R$^{13}$, R$^{14a}$, R$^{14b}$, R$^{15}$, R$^{16}$, R$^{17}$, R$^{18}$, R$^{19}$, R$^{20a}$, and R$^{20b}$, when present, is independently selected from hydrogen, C1-C4 alkyl, C1-C4 monohaloalkyl, and C1-C4 polyhaloalkyl; wherein Ar$^4$, when present, is selected from aryl and heteroaryl and wherein Ar$^2$, when present, is substituted with 0, 1, 2, or 3 groups independently selected from halogen, —NH$_2$, —OH, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; wherein $Cy^3$, when present, is selected from C3-C6 cycloalkyl and C2-C5 heterocycloalkyl and wherein $Cy^3$, when present, is substituted with 0, 1, 2, or 3 groups independently selected from halogen, —OH, —$NH_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino; or a pharmaceutically acceptable salt thereof, and one or more of: a) at least one agent known to inhibit LSD1; b) at least one agent known to inhibit HDAC1; c) at least one anticancer therapeutic agent; d) instructions for detecting a cancer; and e) instructions for treating a cancer.

In one aspect, the invention relates to a kit comprising at least one compound selected from:

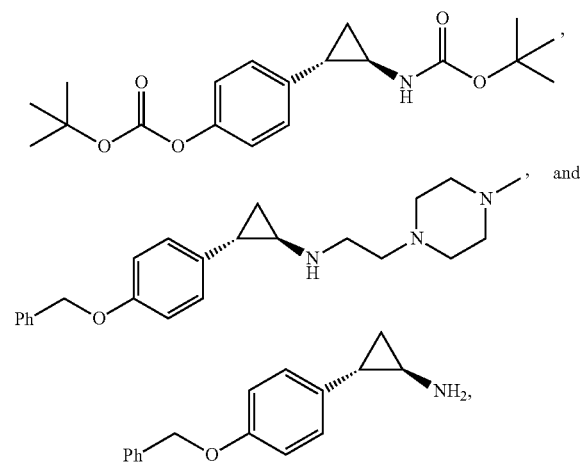

or a pharmaceutically acceptable salt thereof, and one or more of: a) at least one agent known to inhibit LSD1; b) at least one agent known to inhibit HDAC1; c) at least one agent know to treat a cancer; d) instructions for detecting a cancer; and e) instructions for treating a cancer.

In a further aspect, the compound and the agent are co-formulated. In a still further aspect, the compound and the agent are co-packaged.

In a further aspect, the kit further comprises a plurality of dosage forms, the plurality comprising one or more doses; wherein each dose comprises an effective amount of the compound and the agent known to inhibit LSD1. In a still further aspect, the effective amount is a therapeutically effective amount. In yet a further aspect, the effective amount is a prophylactically effective amount.

In a further aspect, each dose of the compound and the agent known to inhibit LSD1 are co-formulated. In a still further aspect, each dose of the compound and the agent known to inhibit LSD1 are co-packaged.

In a further aspect, the dosage form for the compound is formulated for oral administration and the dosage form for the agent known to inhibit LSD1 is formulated for intravenous administration. In a still further aspect, the dosage form for the compound is formulated for intravenous administration and the dosage form for the agent known to inhibit LSD1 is formulated for oral administration.

In a further aspect, the kit further comprises a plurality of dosage forms, the plurality comprising one or more doses; wherein each dose comprises an effective amount of the compound and the agent known to inhibit HDAC1. In a still further aspect, the effective amount is a therapeutically effective amount. In yet a further aspect, the effective amount is a prophylactically effective amount.

In a further aspect, each dose of the compound and the agent known to inhibit HDAC1 are co-formulated. In a still further aspect, each dose of the compound and the agent known to inhibit HDAC1 are co-packaged.

In a further aspect, the dosage form for the compound is formulated for oral administration and the dosage form for the agent known to inhibit HDAC1 is formulated for intravenous administration. In a still further aspect, the dosage form for the compound is formulated for intravenous administration and the dosage form for the agent known to inhibit HDAC1 is formulated for oral administration.

In a further aspect, the kit further comprises a plurality of dosage forms, the plurality comprising one or more doses; wherein each dose comprises an effective amount of the compound and the anticancer therapeutic agent. In a still further aspect, the effective amount is a therapeutically effective amount. In yet a further aspect, the effective amount is a prophylactically effective amount.

In a further aspect, each dose of the compound and the anticancer therapeutic are co-formulated. In a still further aspect, each dose of the compound and the anticancer therapeutic agent are co-packaged.

In a further aspect, the dosage form for the compound is formulated for oral administration and the dosage form for the anticancer therapeutic agent is formulated for intravenous administration. In a still further aspect, the dosage form for the compound is formulated for intravenous administration and the dosage form for the anticancer therapeutic agent is formulated for oral administration.

In a further aspect, the dosage forms are formulated for oral and/or intravenous administration. In a still further aspect, the dosage forms are formulated for oral administration. In yet a further aspect, the dosage forms are formulated for intravenous administration.

In a further aspect, the agent known to inhibit LSD1 is a monoamine oxidase inhibitor. In a still further aspect, the monoamine oxidase inhibitor is selected from a MAO-A inhibitor and a MOA-B inhibitor. In yet a further aspect, the monoamine oxidase inhibitor is selected from pargyline and phenelzine. In an even further aspect, the monoamine oxidase is a trans-2-phenylcyclopropylamine. In a still further aspect, the trans-2-phenylcyclopropylamine is selected from tranylcypromine, 2-PCPA, parnate, tranylcypromine (TCP), S2101, and RN-1.

In a further aspect, the anticancer therapeutic agent is selected from: a) a hormone therapy therapeutic agent, or a pharmaceutically acceptable prodrug, salt, solvate, or polymorph thereof; b) an alkylating therapeutic agent, or a pharmaceutically acceptable prodrug, salt, solvate, or polymorph thereof; c) an antineoplastic antimetabolite therapeutic agent, or a pharmaceutically acceptable prodrug, salt, solvate, or polymorph thereof; d) a mitotic inhibitor therapeutic agent, or a pharmaceutically acceptable prodrug, salt, solvate, or polymorph thereof; e) an antineoplastic antibiotic therapeutic agent, or a pharmaceutically acceptable prodrug, salt, solvate, or polymorph thereof; or f) other chemotherapeutic agent, or a pharmaceutically acceptable prodrug, salt, solvate, or polymorph thereof.

In a further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the antineoplastic antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the cancer is selected from a lymphoma, sarcoma, and a carcinoma. In a still further aspect, the carcinoma is a squamous cell carcinoma.

In a further aspect, the cancer is characterized by the presence of Sox2. In a still further aspect, the cancer is selected from glioblastoma multiforme, breast cancer, lung cancer, skin cancer, neuroblastoma, leukemia, lymphoma, prostate cancer, glioma, bladder cancer, colon and rectal cancer, gastric cancer, liver cancer, germ cell tumor, endometrial cancer, cervical cancer, retinoblastoma, medulloblastoma, medulloepithelioma, bronchial cancer, brain cancer, mesothelioma, kidney cancer, pancreatic cancer, lip and oral cancer, laryngeal and pharyngeal cancer, melanoma, pituitary cancer, penile cancer, parathyroid cancer, thyroid cancer, pheochromocytoma and paraganglioma, thymoma and thymic carcinoma, plasma cell neoplasms, myeloproliferative disorders, islet cell tumor, small intestine cancer, transitional cell cancer, pleuropulmonary blastoma, gestational trophoblastic cancer, esophageal cancer, central nervous system cancer, head and neck cancer, endocrine cancer, cardiovascular cancer, rhabdomyosarcoma, soft tissue carcinomas, carcinomas of bone, cartilage, fat, vascular, neural, and hematopoietic tissues and AIDS-related cancers, and ovarian cancer.

In a further aspect, the cancer is associated with gene amplification of Sox2. In a still further aspect, the gene amplification occurs at 3q22.33.

L. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. Experimental Procedures a. Cell Lines and Cell Culture

Lung, breast, ovarian, and other carcinoma cells were either obtained from American Type Culture Collection (ATCC) or from the DTP and DCTD Tumor Repository of National Cancer Institute (the NCI-60 cancer cell line panel), operated by Charles River Laboratory, Inc., as listed in Table 1. They were cultured according to instructions and treated with various concentrations of LSD1 inhibitors for 30-36 hours for mRNA analysis by quantitative real time RT-PCR or for 30-48 hours for protein analysis and the cell viability assays using Western blotting or microscopy and MTT assays as described previously (Wang, J., et al. (2011) *Cancer Research* 71, 7238-7249).

TABLE 1

| Cell Lines | Sources | Cancer Types | Oct4 | Lin28 | Sox2 | Sensitivity to LSD1 inhibitors |
|---|---|---|---|---|---|---|
| F9* | ATCC | Murine teratocarcinoma | Yes | Yes | Yes | Yes |
| PA-1** | ATCC | Ovarian teratocarcinoma | Yes | Yes | Yes | Yes |
| NTERA-2** | ATCC | Embryonal carcinoma | Yes | Yes | Yes | Yes |
| HS38.T | ATCC | Ovarian teratoma (fibroblast-like) | No | No | No | No |
| HeLa | ATCC | Cervical adenocarcinoma | No | No | No | No |
| IGROV-1 | NCI-60 | Ovarian adenocarcinoma | Yes | Yes | Yes | Yes |
| A2780** | NCI-60 | Ovarian carcinoma | No | Yes | Yes | Yes |
| SKOV-3 | NCI-60 | Ovarian adenocarcinoma | No | No | Yes | Yes |
| OVCAR-3 | NCI-60 | Ovarian adenocarcinoma | No | No | Yes | Yes |
| OVCAR-8 | NCI-60 | Ovarian carcinoma | No | No | No | No |
| ES-2 | ATCC | Ovarian carcinoma | No | No | No | No |
| MCF7 | NCI-60 | Breast adenocarcinoma | No | No | Yes | Yes |
| T47D | NCI-60 | Breast ductal carcinoma | No | Yes | Yes | Yes |

TABLE 1-continued

| Cell Lines | Sources | Cancer Types | Oct4 | Lin28 | Sox2 | Sensitivity to LSD1 inhibitors |
|---|---|---|---|---|---|---|
| MDA-MB-453 | ATCC | Breast carcinoma | No | No | Yes | Yes |
| MDA-MB-468 | NCI-60 | Breast adenocarcinoma | No | No | Yes | Yes |
| MDA-MB-231 | NCI-60 | Breast adenocarcinoma | No | No | No | No |
| MDA-MB-361 | ATCC | Breast adenocarcinoma | No | No | Yes | Yes |
| SK-BR-3 | ATCC | Breast adenocarcinoma | No | No | No | No |
| BT-549 | ATCC | Breast ductal carcinoma | No | No | No | No |
| NCI-H520 | ATCC | Lung squamous cell carcinoma | No | No | Yes | Yes |
| NCI-H1437 | ATCC | Lung adenocarcinoma | No | No | No | No |
| A549 | NCI-60 | Lung carcinoma | No | No | Yes | Yes |
| H1299 | ATCC | Lung carcinoma | No | No | No | No |
| G401** | ATCC | Kidney rhabdoid tumor | No | Yes | Yes | Yes |
| MDA-MB-435s | NCI-60 | Melanoma | No | No | No | No |
| K562 | NCI-60 | Myelogenous leukemia | No | No | Yes | Yes |

*Also expresses Nanog and Sall4;
**Also express Sall4

Cell culture was conducted as described earlier (Wang, J., et al. (2011) Cancer Research 71, 7238-7249). PA-1 and MCF7 were maintained in Eagle's Minimum Essential Medium; Hs38.T, F9, HeLa and 293 cells were in Dulbecco's Modified Eagle's Medium; IGROV-1 cells were in RPMI Medium 1640 without folic acid; SKOV-3, ES-2, SK-BR-3 and G401 cells were in McCoy's 5a Medium; A2780, OVCAR-3, OVCAR-8, T47D, BT-549, and H1299 cells were in RPMI-1640 Medium; MDA-MB-231, MDA-MB-468, MDA-MB-453, MDAMB-435s and MDA-MB-361 cells were in Leibovitz's L-15 Medium; A549 cells were maintained in F-12K Medium and K562 cells were maintained in Iscove's Modified Dulbecco's Medium. All media were supplemented with 10% FBS, whereas OVCAR-3 cells were cultured with 20% FBS. The media for OVCAR-3 and MCF7 cells were supplemented with 0.01 mg/mL bovine insulin, while the medium for BT-549 cells was with 0.023 IU/mL insulin.

Mouse ES cells, F9 teratocarcinoma cells, immortalized NIH 3T3 cells, and PA-1 human ovarian teratocarcinoma, HeLa cervical carcinoma, and HCT116 colorectal carcinoma cells were purchased from the American Type Culture Collection (ATCC). The mouse normal liver cell line NCTC1469 was from the Cell Center of Shanghai Institutes for Biological Sciences, Chinese Academy of Sciences. The cells were cultured as previously described (Wang, J., et al. (2011) Cancer Research 71, 7238-7249). For mouse ES cells, they were cultured in knockout Dulbecco modified Eagle medium supplemented with 15% knockout serum replacement, 0.1 mM 2-mercaptoethanol, 200 mM L-glutamine, 1/100 (vol/vol) nonessential amino acids, and 1/100 (vol/vol) penicillin-streptomycin (all from Gibco) and 1/1,000 (vol/vol) leukemia inhibitory factor (Millipore). The ES cells were maintained on a feeder layer of mitomycin C-treated primary mouse embryonic fibroblasts (MEFs).

b. Western Blot, Immunohistochemistry, and Antibodies

Log-phase growing cancer cells were directly lysed in a buffer containing 0.5% SDS. Proteins in the lysates were equalized and analyzed by Western blotting using antibodies against Sox2, LSD1, H3K4Me1, H3K4Me2, Oct4, and other proteins as described previously or in the figure descriptions (Wang, J., et al. (2011) Cancer Research 71, 7238-7249). For immunohistochemical staining, rabbit monoclonal anti-LSD1 (clone C69G12, cat. #2184) and anti-Sox2 (clone D6D9, cat. #3579) antibodies were obtained from Cell Signaling. Rabbit anti-Sox2 polyclonal antibodies were raised using the purified GST-Sox2 fusion protein as the antigen.

Immunohistochemical staining was performed as described previously (Wang, J., et al. (2011) Cancer Research 71, 7238-7249). Briefly, tumor tissues from clinic patients were fixed in 10% neutral buffered formalin and then embedded in paraffin. Serial section was carried out to produce 5 microns slices. Slides were deparaffinized, rehydrated, and immersed in 3% $H_2O_2$ to inactivate the endogenous peroxidase. Antigens were retrieved and immunostained with anti-LSD1 and anti-Sox2 antibodies. The slides were then incubated with the Rabbit-Probe Streptavidin-Peroxidase polymer detection system, developed with 3,3'-diaminobenzidine (DAB) substrate, counterstained with hematoxylin, dehydrated, and then mounted with Neutral balsam. Images were captured on a Zeiss fluorescence microscope (Axio Observer) coupled with a cooled charge-coupled device camera (AxioCam MRM, Zeiss) and processed by using AxioVision program.

Protein detection using Western blotting was conducted as previously described (Wang, J., et al. (2011) Cancer Research 71, 7238-7249). The rabbit polyclonal anti-LSD1, Sal14, Nanog, H3K4Me1, H3K4Me2, and Histone 3 antibodies were purchased from Abcam; anti-Lin28 and anti-Klf4 antibodies were from Proteintech Group; anti-H3K4Me3 antibody was from Millipore; anti-FoxA2 antibodies were from Sigma; and anti-Sox2 antibodies were from Bethyl Laboratory. The goat anti-mouse IgG-HRP and goat anti-rabbit IgG-HRP and mouse monoclonal anti-Oct4 antibodies were purchased from Santa Cruz Biotechnologies.

Antibodies against HDAC1, HDAC2, HDAC3, HDAC6, Sox2, and CoREST were obtained from Bethyl Laboratories; anti-histone H4 peptide with acetylated lysine 16 (anti-H4K16ac; catalog no. 07-329), anti-histone H4 peptide with acetylated lysine 12 (anti-H4K12ac; catalog no. 04719), and histone H3 peptide with trimethylated lysine 4 (anti-H3K4me3) antibodies were from Millipore; anti-histone H3 peptide with acetylated lysine 56 (H3K56ac) antibodies (catalog no. 39281) were from Active Motif; anti-histone H3 peptide with dimethylated lysine 4 (H3K4me2; ab32356), histone H3 peptide with methylated lysine 4 (H3K4me1; ab8895), histone H3 (ab1791), histone H3 peptide with acetylated lysine 14 (H3K14ac; ab52946), histone H3 peptide with acetylated lysine 9 (H3K9ac; ab4441), histone H3 peptide with acetylated lysine 27 (H3K27ac; ab4279), Sal14, Nanog, and LSD1 (ab17721) antibodies were from Abcam; and Lin28 and Klf4 antibodies were from Proteintech Group. Goat anti-mouse IgGhorseradish peroxidase (HRP), goat anti-rabbit IgGHRP, and mouse monoclonal anti-Oct4 antibodies were from Santa Cruz Biotechnologies. MS-275, valproic acid (VPA), all-trans-retinoic acid (RA), and trichostatin A (TSA) were from Sigma. CBB1003 and CBB1007 were synthesized as described previously (Wang, J., et al. (2011) *Cancer Research* 71, 7238-7249).

For immunoaffinity purification, cells were lysed in ice-cold lysis buffer (50 mM Tris-HCl, pH 7.5, 120 mM NaCl, 0.5% Nonidet P-40, 10% glycerol, protease inhibitors) and centrifuged at 13,000 rpm for 15 min, and the supernatant was incubated with anti-LSD1 or anti-HDAC1 antibodies and rabbit IgG (normal rabbit serum [NRS]) overnight at 4° C. The immunocomplexes were captured by protein A-Sepharose. Isolated LSD1-protein A or HDAC1-protein A complexes were verified by Western blotting with LSD1 and HDAC1 antibodies. For purification of the 3_Flag-3_ hemagglutinin (HA)-LSD1 complexes, human LSD1 cDNA was cloned into the 3_ Flag-3_ HA-pMSCV retroviral vector. The recombinant virus was packaged in 293 cells and used to transfect F9 cells (Jin, J., et a. (2006) *Mol. Cell* 23, 709-721). Stable 3_Flag-3_HA-LSD1-expressing F9 cells were selected under puromycin selection, and the expression of tagged LSD1 was confirmed by Western blotting. For the isolation of 3_ Flag-3_ HA-LSD1 complexes, 30 dishes (15 cm) of F9 cells were harvested and the tagged LSD1 complexes were first immunoprecipitated using anti-Flag M2 affinity gel (Sigma) and eluted with the 3_ Flag peptide. The eluted complex was further purified by anti-HA affinity Sepharose (Roche). The proteins in the 3_ Flag-3_ HA-LSD1 complexes were separated on an SDS-polyacrylamide gel, excised, trypsinized, and identified using an ESI LTQ Orbitrap XL mass spectrometer (Thermo Scientific) coupled with an Eksigent nano-liquid chromatograph. The presence of CoREST and HDAC1 in the LSD1 complex was confirmed independently by immunoprecipitation and Western blotting.

c. Small RNA Interference

Cells were transfected with 50-100 nM siRNAs using the DharmaFECT reagent 1 (Dharmacon) for 30-36 hours for mRNA analysis using quantitative real-time RT-PCR or for 48-60 hours for Western blotting as described previously (Wang, J., et al. (2011) *Cancer Research* 71, 7238-7249). The siRNA sequences are: human LSD1: GGAAGAAGAUAGUGAAAAC (SEQ ID NO:1) and human Sox2: CGCUCAUGAAGAAGGAUAA (SEQ ID NO:2).

For the small interfering RNA (siRNA) assay, cells were seeded at a density of 30% confluence at 20 h before transfection and transfected with 50 nM the indicated siRNAs using the DharmaFECT transfection reagent (Thermo Scientific) for F9, NCTC1469, PA-1, and HCT116 cells, while Oligofectamine (Invitrogen) was used for HeLa and NIH 3T3 cells. Cells were harvested at 48 h after transfection. To optimize transfection efficiency in mouse ES (mES) cells, mES cells were passaged twice on plates coated with 0.1% gelatin and supplemented with ES cell complete medium recovered from MEFs. Mouse ES cells were cultured for 24 h prior to transfection and were transfected with 50 nM the indicated siRNAs using the DharmaFECT transfection reagent. The medium was replaced with fresh ES complete medium at 24 h after transfection, and samples were harvested 48 h later. The siRNAs used are listed in Table 2. To prevent potential off-target effects of siRNAs, at least two independent siRNAs against each target were designed and used. All of the siRNA experiments were repeated at least three times to ensure consistent results.

TABLE 2

| siRNA Name | Sequence (5'-3') | SEQ. ID NO. |
|---|---|---|
| Mouse-HDAC1 | GCAAGCAGATGCAGAGATT | 3 |
| Human-HDAC1 | GCAAGCAGATGCAGAGATT | 4 |
| Mouse-HDAC2 | CCAGAACACTCCAGAATAT | 5 |
| Human-HDAC2 | AGACTGATATGGCTGTTAA | 6 |
| Mouse-HDAC3 | GCATTGATGACCAGAGTTA | 7 |
| Human-HDAC3 | AAAGCGATGTGGAGATTTA | 8 |
| Mouse-HDAC6 | GGATGTTCATCATGGTAAT | 9 |
| Human-HDAC6 | TGACCAAAATATGATGAAT | 10 |
| Mouse-Sirt1 | CCATGAAGTATGACAAAGA | 11 |
| Human-Sirt1 | CCTCAAAGTAAGACCAGTA | 12 |
| Mouse-LSD1 | AAGGAAAGCUAGAAGAAAA | 13 |
| Human-LSD1 | AAGGAAAGCUAGAAGAAAA | 14 |
| Mouse-MOF | GATCCAGTCTCGAGTGAAC | 15 |
| Human-MOF | GATCCAGTCTCGAGTGAAC | 16 |
| Mouse-HDAC1 5'-UTR | GCAAGAUGGCGCAGACUCA | 17 |
| Human-HDAC1 3'-UTR | AAGACAAACUCCUGAAAUG | 18 |
| Mouse-LSD1 3'-UTR | AAGCAAGUGGUGUGAGAUA | 19 |
| Human-LSD1 3'-UTR | GGGAGGAACUUGUCCAUUA | 20 |
| Mouse-MOF 3'-UTR | TCTGGGTTTCCTGGCCTCT | 21 |
| Human-MOF 3'-UTR | GGGAAGGGGAGGCCAAGAA | 22 |
| Mouse-Tip60 | GACGGAGUAUGACUGCAAA | 23 |
| Human-Tip60 | CUCCAGGCAAUGAGAUUUA | 24 | d. Chromatin Immunoprecipitation (ChIP) Assays

The ChIP assays were carried out according to the Abcam protocol and other published protocols (Whyte, W. A., et al. (2012) *Nature* 482, 221-225). After cross-linking the chromatin proteins, chromatin DNA was sonicated to average 500-1,000 base pairs and used for immunoprecipitation by specific antibodies. DNA was isolated for quantitative real time PCR after reversing the cross-linking on immunoprecipitated chromatin fragments. The real-time PCR primers are shown in Tables 3 and 4. The ChIP grade anti-H3K4Me2 (Ab32356), anti-H3K4Me1 (Ab8895), and anti-LSD1 (Ab17721) antibodies were from Abcam.

TABLE 3

Chromatin Immunoprecipitation (ChIP) qPCR Analysis

| Gene | Primer sequence (5'-3') | SEQ. ID NO. |
|---|---|---|
| SOX2_human (-4000)-F | AATACTGGTGGTCGTCAAAC | 25 |
| SOX2_human (-4000)-R | TGAGAACTAGCCAAGCATCT | 26 |
| SOX2_human (-3000)-F | TGCTGGATTGAAATAGAGTG | 27 |
| SOX2_human (-3000)-R | TAAGCCTGCTGTACTTATCG | 28 |
| SOX2_human (-2000)-F | CTTAGACGAGGCTTTGTTTG | 29 |
| SOX2_human (-2000)-R | GGGTTAGAGGAGGATGAGAT | 30 |
| SOX2_human (-1000)-F | TTTGGGTCTCCTAACTTCTA | 31 |
| SOX2_human (-1000)-R | GTCATTGTTCTCCCGCTCAT | 32 |
| SOX2_human (0)-F | CAGGAGTTGTCAAGGCAGAG | 33 |
| SOX2_human (0)-R | GGAAAATCAGGCGAAGAATA | 34 |
| SOX2_human (+1000)-F | CATCACCCACAGCAAATGAC | 35 |
| SOX2_human (+1000)-R | TTCCTGCAAAGCTCCTACCG | 36 |
| SOX2_human (+2000)-F | TACTGTGCTCAGCCAAGAAA | 37 |
| SOX2_human (+2000)-R | GCAACAAGTGGCATAAATCA | 38 |
| SOX2_human (+4000)-F | TCCCGGAATTTGAGGCAGTC | 39 |
| SOX2_human (+4000)-R | TTGGCTCGGCGATATGAAGG | 40 |
| FOXA2_human (-4000)-F | CAACCTTCGGCACAACGATC | 41 |
| FOXA2_human (-4000)-R | GAAGCCACCATACAAACTGA | 42 |
| FOXA2_human (-2500)-F | AATAGTGCTGTGGTGGAGGT | 43 |
| FOXA2_human (-2500)-R | TTTGTGAGCTTATGTGGGTG | 44 |
| FOXA2_human (-1500)-F | CCTGTGCCTACTGCTACCTC | 45 |
| FOXA2_human (-1500)-R | GTTAGCCTGTGAGCCCAGAT | 46 |
| FOXA2_human (-1000)-F | GCTTCTCCCGAGGCCGTTCC | 47 |
| FOXA2_human (-1000)-R | ACTCGCCCGCTGCTGCTCCT | 48 |
| FOXA2_human (0)-F | CCGCCCACTTCCAACTACCG | 49 |
| FOXA2_human (0)-R | GTCAGCCAAAGCACCGTCCC | 50 |
| FOXA2_human (+1000)-F | GGTGTACTCCCGGCCCATTA | 51 |
| FOXA2_human (+1000)-R | ATTTCTTCTCCCTTGCGTCT | 52 |
| FOXA2_human (+2000)-F | CCAGGTCTCGGGTCCGATTA | 53 |
| FOXA2_human (+2000)-R | CCCTCCCTCCTTCTTGAAAT | 54 |
| Lin28A_human (-4000)-F | GGGTGGATCACGAGGTCA | 55 |
| Lin28A_human (-4000)-R | CCAGGTTCAAGCCATTCT | 56 |
| Lin28A_human (-3000)-F | TTGCAGCGAGCCAAGATC | 57 |
| Lin28A_human (-3000)-R | TGTAAAGGGTTAGGAAAGAA | 58 |
| Lin28A_human (-1500)-F | TAAATGGGTTGTAGTGGTGG | 59 |
| Lin28A_human (-1500)-R | TACTGCCCTGGTCGGAGA | 60 |
| Lin28A_human (-1000)-F | AGGCAGACATTCAGATGTAGT | 61 |
| Lin28A_human (-1000)-R | GTGCTTAGATAGACCTGGAGT( | 62 |
| Lin28A_human (0)-F | AAAGGGAGGGAAAGGAGA | 63 |
| Lin28A_human (0)-R | GCACAATAGCGGTGGGAG | 64 |
| Lin28A_human (+500)-F | TGCGCCAAGGCGGCAGAAGA | 65 |
| Lin28A_human (+500)-R | TGGACAGGAAGCCGAACCC | 66 |
| Lin28A_human (+1000)-F | GGGGCGTAAAGCCGAGAA | 67 |
| Lin28A_human (+1000)-R | ACGGGAACTGGACAGCAAAG | 68 |
| Lin28A_human (+3000)-F | ATGGCATGATCTCCACTCA | 69 |
| Lin28A_human (+3000)-R | CCTGTAATCCCAGCACTTT | 70 |
| KLF4_human (-4000)-F | GAGCCAAGATCACGCCACT | 71 |
| KLF4_human (-4000)-R | TGCCGCAGGACTCAAGAA | 72 |
| KLF4_human (-2500)-F | GATCTTAGAGGGATTCCTGG | 73 |
| KLF4_human (-2500)-R | TGTTTGAACCCTGCGATT | 74 |
| KLF4_human (-1500)-F | TGGCGCACGCCTGTAATC | 75 |
| KLF4_human (-1500)-R | CATCTCGAAGCCCTTTCC | 76 |
| KLF4_human (-1000)-F | GGAGATGGAGGGCTGGATG | 77 |
| KLF4_human (-1000)-R | GCGAAGACTGGTGGGGTCA | 78 |
| KLF4_human (0)-F | ACGCTGCTGAGTGGAAGA | 79 |
| KLF4 human (0)-R | AATTGGCCGAGATCCTTC | 80 |
| KLF4_human (+500)-F | TGTATGCCCGTGGTGCGA | 81 |
| KLF4_human (+500)-R | TCTGGCCCAGCCAGTGTC | 82 |
| KLF4 human (+1000)-F | GAGACCGAGGAGTTCAACGA | 83 |
| KLF4 human (+1000)-R | GCGACGACGAAGAGGAGG | 84 |
| KLF4 human (+3000)-F | GGTGTAGGTGGTGGTTGT | 85 |
| KLF4 human (+3000)-R | TGACCCTATCCTAAAGAAAT | 86 |
| BMP2_human (-2500)-F | CCCAGCGGGGAAATAAGAGG | 87 |
| BMP2_human (-2500)-R | CGCCTCCACTCCCTGCTC | 88 |
| BMP2_human (-1500)-F | TCCTAAGGAGGACGACAGCA | 89 |
| BMP2_human (-1500)-R | TCGGAGATGGCGAAGCAG | 90 |
| BMP2_human (-1000)-F | TCTTCCACCCCTCTTTCT | 91 |
| BMP2_human (-1000)-R | AGGGATTTCTTTGACCCA | 92 |
| BMP2_human (0)-F | GAGGGCAAATCCCAAATC | 93 |
| BMP2_human (0)-R | GGTAAGACCGACCGAAGC | 94 |
| BMP2_human (+500)-F | AGTAACTCCGCACCCTCT | 95 |
| BMP2_human (+500)-R | TTGCACGTTTAGCTGACTAG | 96 |
| BMP2_human (+1800)-F | ATAAAAGCGTTTGTAGCA | 97 |
| BMP2_human (+1800)-R | CAAGCAGAAATATCCCAC | 98 |

TABLE 3-continued

Chromatin Immunoprecipitation (ChIP) qPCR Analysis

| Gene | Primer sequence (5'-3') | SEQ. ID NO. |
|---|---|---|
| BMP2_human (+3000)-F | CCAGGTGCTTCTTGTTCT | 99 |
| BMP2_human (+3000)-R | TTTGTGGAAAGAGGGTTA | 100 |
| TP63_human (-4000)-F | AGTGGCTACCACATCAGA | 101 |
| TP63_human (-4000)-R | CACATTAGACACCGAGTA | 102 |
| TP63_human (-2500)-F | GCTCATGCCTGTAATCCC | 103 |
| TP63_human (-2500)-R | TCTGCCTCAGCTTCCTGT | 104 |
| TP63_human (-1500)-F | TCTCGGGCTAAGTAAAGG | 105 |
| TP63_human (-1500)-R | AGTTCACATCTTCCCTTC | 106 |
| TP63_human (-1000)-F | TAAAGAATAGAGTGGAGCCG | 107 |
| TP63_human (-1000)-R | TTTGCCTGACCCGAATAA | 108 |
| TP63_human (0)-F | AAAATCAAGAAACGCTCCG | 109 |
| TP63_human (0)-R | GCAATAGGGTCAAATGCT | 110 |
| TP63_human (+500)-F | CAGCACCTACTCACTCAA | 111 |
| TP63_human (+500)-R | AATGACAAGCCACAATCT | 112 |
| TP63_human (+1000)-F | GGGGTCTCCAAGGTTTCA | 113 |
| TP63_human (+1000)-R | AACCCAATCCTCAACTGC | 114 |
| TP63_human (+3000)-F | GGGACTTCATCCTCTGTT | 115 |
| TP63_human (+3000)-R | GGTAATGTGATTTTATCCAACT | 116 |
| KRT6A_human (-4000)-F | CCTTCGTGCTTCTGTCTA | 117 |
| KRT6A_human (-4000)-R | TTCAGTGCCTAATCTTGC | 118 |
| KRT6A_human (-2500)-F | ACCACCTTTCCTTCCAAT | 119 |
| KRT6A_human (-2500)-R | CAGGCTTGTGCCACATTA | 120 |
| KRT6A_human (-1500)-F | CTTGCCAGACGCTGAGTT | 121 |
| KRT6A_human (-1500)-R | AGCAGTCCATTTCTCCA | 122 |
| KRT6A_human (-1000)-F | TGGCAGAAGTCAGGTCTC | 123 |
| KRT6A_human (-1000)-R | CTTTACACTGTAGGAGCAAC | 124 |
| KRT6A_human (0)-F | GCTGGAAGGCAGGAGAAT | 125 |
| KRT6A_human (0)-R | GGTGAGCTTGCAGGTTGG | 126 |
| KRT6A_human (+500)-F | GAGGTCACCGTCAACCAG | 127 |
| KRT6A_human (+500)-R | CGATGAAGGAGGCAAACT | 128 |
| KRT6A_human (+1500)-F | TGTTCGAGCAGTACATCAA | 129 |
| KRT6A_human (+1500)-R | CCTGGTCACCCAATAGTC | 130 |
| KRT6A_human (+3000)-F | GAACTTATGCCCAAGTCAA | 131 |
| KRT6A_human (+3000)-R | CCTCATTATGGCACCACT | 132 |
| Sox17_human (-4000)-F | ACGCTGCTGATAAGGCTGTC | 133 |
| Sox17_human (-4000)-R | TGGGCTGTGGAACCTCATAC | 134 |
| Sox17_human (-3000)-F | CCAAGAACAAGGGCAAATAA | 135 |
| Sox17_human (-3000)-R | TCAAGCGATTCTCCTGTCTC | 136 |
| Sox17_human (-2000)-F | GGAGGCTGAGACAGGAGAAT | 137 |
| Sox17_human (-2000)-R | GGAGCCAAGAAGGTGGAGAA | 138 |
| Sox17_human (-1000)-F | TCTTTGCTAATGCTGGAGGG | 139 |
| Sox17_human (-1000)-R | AAATGTCCGAGTTTGTTTGG | 140 |
| Sox17_human (0)-F | CAGTGCCTCACTCCCCACCC | 141 |
| Sox17_human (0)-R | GCCTCGCCCTTCACCTTCAT | 142 |
| Sox17_human (+2000)-F | TTCCCATAGTTGGATTGTCA | 143 |
| Sox17_human (+2000)-R | GCATTTATGTTCACCCTTTT | 144 |
| Sox17_human (+4000)-F | TGTCCCAAGAGTTCCCAGTA | 145 |
| Sox17_human (+4000)-R | AACACCAATCCCTCCATCCA | 146 |
| CyclinA_human (-4000)-F | AGGGAAAGAAGGAGTGAG | 147 |
| CyclinA_human (-4000)-R | ACCTTGCAGAGCTATTGT | 148 |
| CyclinA_human (-3000)-F | ACCTCAGCCTCCCAAAGT | 149 |
| CyclinA_human (-3000)-R | TAGCAGCATCCAATAGCAAA | 150 |
| CyclinA_human (-2000)-F | TAGACCGCTTTATAGGCT | 151 |
| CyclinA_human (-2000)-R | CATACATAGTAACCAGGAC | 152 |
| CyclinA_human (-1000)-F | CAGTAGTTCAAGGTGCCA | 153 |
| CyclinA_human (-1000)-R | CTTAACATTTAGGCGTTTAT | 154 |
| CyclinA_human (0)-F | CCTGCTCAGTTTCCTTTGGT | 155 |
| CyclinA_human (0)-R | ATCCCGCGACTATTGAAATG | 156 |
| CyclinA_human (+500)-F | GTTCTCCCATATTAGCATCA | 157 |
| CyclinA_human (+500)-R | GAGCTGAGCGAAGACTACA | 158 |
| CyclinA_human (+1000)-F | CCTTTGTGGGAATGCCTGTG | 159 |
| CyclinA_human (+1000)-R | GGGTGTTGGCCTTTGCTT | 160 |
| CyclinA_human (+3000)-F | AGCCAGACATCACTAACA | 161 |
| CyclinA_human (+3000)-R | TGTAGTTCACAGCCAAAT | 162 |
| CyclinB_human (-4000)-F | CCGGTTGGAGTGCAGTAG | 163 |
| CyclinB_human (-4000)-R | CTGGGATTGGTGGTGTAT | 164 |
| CyclinB_human (-3000)-F | TCAGGAGTTTGAGGTTAC | 165 |
| CyclinB_human (-3000)-R | TCTGTTCAGGTATTTTGC | 166 |
| CyclinB_human (-2000)-F | GAAGGCAGGTGAAATGCT | 167 |
| CyclinB_human (-2000)-R | TGCGATTACAGGCGTGAG | 168 |
| CyclinB_human (-1000)-F | ATCTGAGTAAAGGGCATA | 169 |
| CyclinB_human (-1000)-R | GTTTTAGCTTTCTATTTGGA | 170 |
| CyclinB_human (0)-F | GAGTGAGTGCCACGAACAGG | 171 |
| CyclinB_human (0)-R | ACCCAGCAGAAACCAACAGC | 172 |

TABLE 3-continued

Chromatin Immunoprecipitation (ChIP) qPCR Analysis

| Gene | Primer sequence (5'-3') | SEQ. ID NO. |
|---|---|---|
| CyclinB_human (+500)-F | AGAGGTCGGCGGAAACTG | 173 |
| CyclinB_human (+500)-R | AGGTGGGGCACAAGGAGA | 174 |
| CyclinB_human (+1000)-F | AAATGCCTATGAAGAAGG | 175 |
| CyclinB_human (+1000)-R | TTTTCCAGTAGCTGAAGG | 176 |
| CyclinB_human (+3000)-F | GGCTGGTCTCGAACTCCT | 177 |
| CyclinB_human (+3000)-R | CTTCATGGCATCCTCAAA | 178 |
| CyclinD_human (-4000)-F | GCAAGTTCCGGAGTGGGG | 179 |
| CyclinD_human (-4000)-R | GAGACGCAGGGCTTCGCT | 180 |
| CyclinD_human (-3000)-F | AACCCAAGCCCCGAGCCC | 181 |
| CyclinD_human (-3000)-R | GCGTGTTCGCCACCGTCC | 182 |
| CyclinD_human (-2000)-F | TCTGAGGCTTGGCTATGCG | 183 |
| CyclinD_human (-2000)-R | TGGGGAGCGATGGGTTGC | 184 |
| CyclinD_human (-1000)-F | AGGTAGGAAGGCAGCCCGAAGA | 185 |
| CyclinD_human (-1000)-R | AGCAGCAGCCCAAGATGG | 186 |
| CyclinD_human (0)-F | ACCCAGCCAGGACCCACA | 187 |
| CyclinD_human (0)-R | GGTTTCCACTTCGCAGCAC | 188 |
| CyclinD_human (+500)-F | CGTTTCTTTGCTACTCACCC | 189 |
| CyclinD_human (+500)-R | CCACCCCTTCCTCCTTCA | 190 |
| CyclinD_human (+1000)-F | TGAAAGTGCGGCGTGGTG | 191 |
| CyclinD_human (+1000)-R | CTCGGGCGACCCTTTACC | 192 |
| CyclinD_human (+3000)-F | GGATGGAGGGAGATTTGCT | 193 |
| CyclinD_human (+3000)-R | GAAGGACGAGGCCAGAGTAA | 194 |
| SAT2_human-F | AATCATCGAATGGTCTCGAT | 195 |
| SAT2_human-R | ATAATTCCATTCGATTCCAC | 196 |
| GAPDH_human-F | ACCACAGTCCATGCCATCA | 197 |
| GAPDH_human-R | CAGGGATGATGTTCTGGAGA | 198 |

TABLE 4 mRNA qPCR Analysis

| Gene | Primer Sequence (5'-3') | SEQ. ID NO. |
|---|---|---|
| SOX2_human-F | GTGAGCGCCCTGCAGTACAA | 199 |
| SOX2_human-R | GCGAGTAGGACATGCTGTAGGTG | 200 |
| LSD1_human-F | AGCGTCATGGTCTTATCAA | 201 |
| LSD1_human-R | GAAATGTGGCAACTCGTC | 202 |
| FOXA2_human-F | CCCCAACAAGATGCTGACGC | 203 |
| FOXA2_human-R | GCGAGTGGCGGATGGAGTT | 204 |
| BMP2_human-F | ACAGCGGAAACGCCTTAA | 205 |
| BMP2_human-R | GGGAGCCACAATCCAGTC | 206 |
| EOMES_human-F | CCCAGACCCAACCTTTCC | 207 |
| EOMES_human-R | GAGCCAATTTCCTCTTTCACTT | 208 |
| SOX17_human-F | CTGCAGGCCAGAAGCAGTGTTA | 209 |
| SOX17_human-R | CCCAAACTGTTCAAGTGGCAGA | 210 |
| HNF4A_human-F | AGCTGCAGATCGATGACAATGAG | 211 |
| HNF4A_human-R | CATACTGGCGGTCGTTGATGTAG | 212 |
| TP63_human-F | CCTTACTTTGCTGAGGGTTTGAA | 213 |
| TP63_human-R | CAAGGCCCTAGTGTTACCTGAATAG | 214 |
| KRT6A_human-F | GGCTGAGGAGCGTGAACAG | 215 |
| KRT6A_human-R | CAGGAACCGCACCTTGT | 216 |
| β-Actin_human-F | GGCCACGGCTGCTTC | 217 |
| β-Actin_human-R | GTTGGCGTACAGGTCTTTGC | 218 |

Alternatively, $1 \times 10^7$ human A2780 cells were used for each immunoprecipitation. Cells were fixed in 0.75% formaldehyde, collected, resuspended in the FA lysis buffer (0.1% SDS, 0.1% sodium deoxycholate, 1 mM EDTA, 1% Triton X-100, 140 mM NaCl and 50 mM HEPES-KOH, pH 7.5) and sonicated to generate DNA fragments of 500-1000 base pairs (bp). The sonicated chromatin was cleared and incubated with specific primary antibodies or normal rabbit IgG overnight followed by incubation with protein A Sepharose beads (pre-adsorbed with sonicated single-stranded herring sperm DNA and BSA) for 1 hour. After incubation, the immunocomplexes were washed sequentially with wash buffer (0.1% SDS, 1% Triton X-100, 2 mM EDTA, 20 mM Tris-HCl, at pH 8.0 and 150 mM NaCl), final wash buffer (0.1% SDS, 1% Triton X-100, 2 mM EDTA, 20 mM Tris-HCl, at pH 8.0, and 500 mM NaCl). Immunocomplexes were eluted in elution buffer (0.1% SDS and 0.1M NaHCO3) and the crosslinking was reversed overnight at 65° C. DNA was extracted with phenol/chloroform and precipitated with ethanol. Purified DNA was quantified by real-time PCR.

Alternatively, chromatin immunoprecipitation (ChIP) assays were carried out according to previously described procedures (8, 9). Briefly, $1 \times 10^7$ to $5 \times 10^7$ cells were used for each sample. Proteins were cross-linked to DNA by addition of formaldehyde to a final concentration of 0.75%. After incubating with 125 mM glycine for 5 min, cells were harvested, resuspended in FA lysis buffer (50 mM HEPES-$K^+$, pH 7.5, 140 mM NaCl, 1 mM EDTA pH 8.0, 1% Triton X-100, 0.1% sodium deoxycholate, 0.1% SDS, protease inhibitors), and sonicated to generate DNA fragments of 500 to 1,000 by in average length. Soluble chromatin fragments were diluted (1:8) in radioimmunoprecipitation assay buffer (50 mM Tris-HCl, pH 8.0, 150 mM NaCl, 2 mM EDTA, 1% NP-40, 0.5% sodium deoxycholate, 0.1% SDS, protease inhibitors) and incubated with primary antibodies overnight. The immunocomplexes were incubated with protein A-Sep harose resins for 2 h, briefly centrifuged, and washed sequentially with the wash buffer (0.1% SDS, 1% Triton X-100, 2 mM EDTA, 150 mM NaCl, 20 mM Tris-HCl, pH 8.0) and the final wash buffer (0.1% SDS, 1% Triton X-100, 2 mM EDTA, pH 8.0, 500 mM NaCl, 20 mM Tris-HCl, pH 8.0). Immunocomplexes were eluted, and the crosslinks were reversed in the elution buffer (1% SDS, 0.1 M NaHCO3) at 65° C. Purified DNA was quantified by real-time qPCR using beta-actin as a control. The sequences of the primers used for ChIP assays are listed in Table 5.

TABLE 5

| Primer | Orientation | Position Relative to ATG | Sequence (5'-3') | SEQ. ID NO. |
|---|---|---|---|---|
| Human FoxA2 | Forward | +4000 | TCAGTGCCAAGTAGACAAAT | 219 |
| Human FoxA2 | Reverse | +4000 | TACGAAATTAACAGGATGTG | 220 |
| Human FoxA2 | Forward | +2000 | CCAGGTCTCGGGTCCGATTA | 221 |
| Human FoxA2 | Reverse | +2000 | CCCTCCCTCCTTCTTGAAAT | 222 |
| Human FoxA2 | Forward | +1500 | GGTGTACTCCCGGCCCATTA | 223 |
| Human FoxA2 | Reverse | +1500 | ATTTCTTCTCCCTTGCGTCT | 224 |
| Human FoxA2 | Forward | 0(-1000) | CCGCCCACTTCCAACTACCG | 225 |
| Human FoxA2 | Reverse | 0(-890) | GTCAGCCAAAGCACCGTCCC | 226 |
| Human FoxA2 | Forward | -2000 | TTTCAAGTCTGCGGTCATCC | 227 |
| Human FoxA2 | Reverse | -2000 | CAGCAACATCAGTGCCCTTT | 228 |
| Human FoxA2 | Forward | -4000 | CAACCTTCGGCACAACGATC | 229 |
| Human FoxA2 | Reverse | -4000 | GAAGCCACCATACAAACTGA | 230 |
| Human FoxA2 | Forward | -6000 | CAAGCCTCACATTTGAACCC | 231 |
| Human FoxA2 | Reverse | -6000 | CTGCGGAACCACTGACCACC | 232 |
| Mouse FoxA2 | Forward | +4000 | AACGCTGGCCGTCTGTATTG | 233 |
| Mouse FoxA2 | Reverse | +4000 | GCCTATGGACTCTGCCCTTC | 234 |
| Mouse FoxA2 | Forward | +2000 | AGGCTGAGTGGAGACTTTGG | 235 |
| Mouse FoxA2 | Reverse | +2000 | ATTTCCATTCCCTTCCCTAT | 236 |
| Mouse FoxA2 | Forward | +1500 | GGACCTCTTCCCTTTCTACC | 237 |
| Mouse FoxA2 | Reverse | +1500 | GTCTTCTTGCCTCCGCTACT | 238 |
| Mouse FoxA2 | Forward | 0(-900) | CCCACTCCCAGCTACTTCCC | 239 |
| Mouse FoxA2 | Reverse | 0(-650) | CAGCCACAACAAACGACCAG | 240 |
| Mouse FoxA2 | Forward | -2000 | GCTCCAATGCTTACTCCTCT | 241 |
| Mouse FoxA2 | Reverse | -2000 | TTCTCCCACAAATTCAAGGT | 242 |
| Mouse FoxA2 | Forward | -4000 | CCCCATAGACAAGTGTTTCG | 243 |
| Mouse FoxA2 | Reverse | -4000 | TTCTTCCAGCCTTCCCTAAT | 244 |
| Mouse FoxA2 | Forward | -6000 | ATGGCTTTGCCTATTTGTCC | 245 |
| Mouse FoxA2 | Reverse | -6000 | GGTTTCCTGGCTGATGCTTA | 246 |
| Human Sox2 | Forward | +4000 | TTCTCCTGCCTCAGCCTCCT | 247 |
| Human Sox2 | Reverse | +4000 | GCCTATAATTCCAGCACTTT | 248 |
| Human Sox2 | Forward | +2000 | TGCTTCCTCCCTACTGTCTG | 249 |
| Human Sox2 | Reverse | +2000 | CTCACCGCAACCTCCATCTC | 250 |
| Human Sox2 | Forward | +1000 | CATCACCCACAGCAAATGAC | 251 |
| Human Sox2 | Reverse | +1000 | TTCCTGCAAAGCTCCTACCG | 252 |

TABLE 5-continued

| Primer | Orientation | Position Relative to ATG | Sequence (5'-3') | SEQ. ID NO. |
|---|---|---|---|---|
| Human Sox2 | Forward | 0(-400) | CAGGAGTTGTCAAGGCAGAG | 253 |
| Human Sox2 | Reverse | 0(-400) | GGAAAATCAGGCGAAGAATA | 254 |
| Human Sox2 | Forward | -1000 | TTTGGGTCTCCTAACTTCTA | 255 |
| Human Sox2 | Reverse | -1000 | GTCATTGTTCTCCCGCTCAT | 256 |
| Human Sox2 | Forward | -2000 | GCATTCCGTTGGCTATTCTC | 257 |
| Human Sox2 | Reverse | -2000 | GATGTGCTTTGTTTAGTGGG | 258 |
| Human Sox2 | Forward | -4000 | AATACTGGTGGTCGTCAAAC | 259 |
| Human Sox2 | Reverse | -4000 | TGAGAACTAGCCAAGCATCT | 260 |
| Mouse Sox2 | Forward | -4000 | GGGCATAGACAAACAGAACC | 261 |
| Mouse Sox2 | Reverse | -4000 | ACCACAACCATAGCAGGAAT | 262 |
| Mouse Sox2 | Forward | -2000 | TCCAAGTCGCTGCCTTTATT | 263 |
| Mouse Sox2 | Reverse | -2000 | TTCCGTTTCCTCCACTCTGT | 264 |
| Mouse Sox2 | Forward | -1000 | GTGCTGGCGACAAGGTTGGA | 265 |
| Mouse Sox2 | Reverse | -1000 | ATGGGTGGTTCAGGGCGACT | 266 |
| Mouse Sox2 | Forward | 0(-300) | AAGACTAGGGCTGGGAGAAA | 267 |
| Mouse Sox2 | Reverse | 0(-300) | ATCTGGCGGAGAATAGTTGG | 268 |
| Mouse Sox2 | Forward | +1000 | CTGGACTGCGAACTGGAGAA | 269 |
| Mouse Sox2 | Reverse | +1000 | ATTTGGATGGGATTGGTGGT | 270 |
| Mouse Sox2 | Forward | +2000 | GGACATTTGGCTACTTAGAG | 271 |
| Mouse Sox2 | Reverse | +2000 | GAAGATATTGAAACAGGGAC | 272 |
| Mouse Sox2 | Forward | +4000 | TCCCAACGAGAAGAGTATGA | 273 |
| Mouse Sox2 | Reverse | +4000 | AGAGCAGTGACGGGAACAGA | 274 |
| Human Oct4 | Forward | -1000 | TGTGCTTATGGCTGTTGATG | 275 |
| Human Oct4 | Reverse | -1000 | CCACTGTGCCCTGTTAGTTT | 276 |
| Human Oct4 | Forward | -2000 | GCATTCCGTTGGCTATTCTC | 277 |
| Human Oct4 | Reverse | -2000 | GATGTGCTTTGTTTAGTGGG | 278 |
| Human Oct4 | Forward | -4000 | GGATGTACGGCAGCTTGATA | 279 |
| Human Oct4 | Reverse | -4000 | GCTGGACACTGGAGGATAGA | 280 |
| Human Oct4 | Forward | 0(-100) | GCCACCACCATTAGGCAAAC | 281 |
| Human Oct4 | Reverse | 0(-100) | GCGAAGGGACTACTCAACCC | 282 |
| Human Oct4 | Forward | +1000 | AGAAAGCGAACCAGTATCGA | 283 |
| Human Oct4 | Reverse | +1000 | GCGCCGGTTACAGAACCACA | 284 |
| Human Oct4 | Forward | +2000 | TGCTTCCTCCCTACTGTCTG | 285 |
| Human Oct4 | Reverse | +2000 | CTCACCGCAACCTCCATCTC | 286 |
| Human Oct4 | Forward | +4000 | TTCTCCTGCCTCAGCCTCCT | 287 |
| Human Oct4 | Reverse | +4000 | GCCTATAATTCCAGCACTTT | 288 |
| Mouse Oct4 | Forward | -1000 | AGGCACTCTGAGGGCTATTC | 289 |
| Mouse Oct4 | Reverse | -1000 | GACACTAAGGAGACGGGATT | 290 |

TABLE 5-continued

| Primer | Orientation | Position Relative to ATG | Sequence (5'-3') | SEQ. ID NO. |
|---|---|---|---|---|
| Mouse Oct4 | Forward | −2000 | TCCAAGTCGCTGCCTTTATT | 291 |
| Mouse Oct4 | Reverse | −2000 | TTCCGTTTCCTCCACTCTGT | 292 |
| Mouse Oct4 | Forward | −4000 | GCAGAAGGTCAGGTCCACTC | 293 |
| Mouse Oct4 | Reverse | −4000 | CATTCAAGATAACCAGCCAC | 294 |
| Mouse Oct4 | Forward | 0(−100) | GGTCCCGTCCTAAGGGTTGT | 295 |
| Mouse Oct4 | Reverse | 0(−100) | TGGGTGGGTGGAGGAGCAGA | 296 |
| Mouse Oct4 | Forward | +1000 | TCCCAACGAGAAGAGTATGA | 297 |
| Mouse Oct4 | Reverse | +1000 | CCAGAGCAGTGACGGGAACA | 298 |
| Mouse Oct4 | Forward | +2000 | GGACATTTGGCTACTTAGAG | 299 |
| Mouse Oct4 | Reverse | +2000 | GAAGATATTGAAACAGGGAC | 300 |
| Mouse Oct4 | Forward | +4000 | TCCCAACGAGAAGAGTATGA | 301 |
| Mouse Oct4 | Reverse | +4000 | AGAGCAGTGACGGGAACAGA | 302 | e. Statistical Analyses

Statistical analysis was performed using the GraphPad Prism v4.0 software as described previously (Wang, J., et al. (2011) *Cancer Research* 71, 7238-7249). Data are presented as mean±SD. One-way ANOVA was used for comparisons.

f. RNA Extraction, Reverse Transcription, and Quantitative Real-Time RT-PCR/PCR

Total RNA was extracted using TRIZOL reagent (TaKaRa) and complementary DNA was generated according to instructions in the PrimeScript 1st strand cDNA Synthesis Kit (TaKaRa) as described previously (Wang, J., et al. (2011) *Cancer Research* 71, 7238-7249). The cDNAs were diluted to 1/20 and 1 μL of each diluted sample was used as template for each sample. Real-time quantitative PCR was performed on an ABI Prism 7300 sequence detection system (Applied Biosystems) using SYBR Green (TaKaRa) according to the manufacturer's instructions. PCR amplification of the housekeeping gene β-Actin was performed as a control. Experiments for specific silencing or induction of gene expression were repeated at least three times. The real-time PCR primers of human genes are described in Table 3 above.

Alternatively, total RNA was extracted with the TRIzol reagent (Invitrogen), and cDNA was generated using a cloned avian myeloblastosis virus first-strand cDNA synthesis kit (TaKaRa). The mRNA levels of the target genes were quantified by realtime PCR using SYBR green (TaKaRa) in an ABI Prism 7300 real-time PCR system (Applied Biosystems). The sequences of the oligonucleotide primers used for quantitative PCR (qPCR) are listed in Table 6.

TABLE 6

| Primer Name | Orientation | Sequence (5'-3') | SEQ. ID NO. |
|---|---|---|---|
| Mouse Sox2 | Forward | GTGAGCGCCCTGCAGTACAA | 303 |
| Mouse Sox2 | Reverse | GCGAGTAGGACATGCTGTAGGTG | 304 |
| Human Sox2 | Forward | GTGAGCGCCCTGCAGTACAA | 305 |
| Human Sox2 | Reverse | GCGAGTAGGACATGCTGTAGGTG | 306 |
| Mouse Oct4 | Forward | GATCACTCACATCGCCAATC | 307 |
| Mouse Oct4 | Reverse | GGTGTCCCTGTAGCCTCATA | 308 |
| Human Oct4 | Forward | TGAAGCTGGAGAAGGAGAAGCTG | 309 |
| Human Oct4 | Reverse | GCAGATGGTCGTTTGGCTGA | 310 |
| Mouse HDAC1 | Forward | TTGCTCGCTGCTGGACTTAC | 311 |
| Mouse HDAC1 | Reverse | TGGCTTCTCCTCCTTGGTTT | 312 |

TABLE 6-continued

| Primer Name | Orientation | Sequence (5'-3') | SEQ. ID NO. |
|---|---|---|---|
| Human HDAC1 | Forward | GGGATCGGTTAGGTTGCTTC | 313 |
| Human HDAC1 | Reverse | TTGTCAGGGTCGTCTTCGTC | 314 |
| Mouse HDAC2 | Forward | GGACAGGCTTGGTTGTTTCA | 315 |
| Mouse HDAC2 | Reverse | ATTCCTACGACCTCCTTCAC | 316 |
| Human HDAC2 | Forward | AAGGCAAATACTATGCTGTC | 317 |
| Human HDAC2 | Reverse | TTGGGAATCTCACAATCAAG | 318 |
| Mouse HDAC3 | Forward | CCGAAATGTTGCCCGGTGTT | 319 |
| Mouse HDAC3 | Reverse | GGGTGCTTCTGGCCTGCTGT | 320 |
| Human HDAC3 | Forward | GCACCATGCCAAGAAGTTTG | 321 |
| Human HDAC3 | Reverse | CACCACCCAGCACGAGTAGA | 322 |
| Mouse HDAC6 | Forward | AACCGCACTGGGCTGGTCTA | 323 |
| Mouse HDAC6 | Reverse | TCAAAGTTGGCACCTTCACG | 324 |
| Human HDAC6 | Forward | CAGCGAAGAAGTAGGCAGAA | 325 |
| Human HDAC6 | Reverse | GCTGTCATCCCAGAGGCAAT | 326 |
| Mouse Sirt1 | Forward | GGGAACCTTTGCCTCATCTA | 327 |
| Mouse Sirt1 | Reverse | TACTGGAACCAACAGCCTTA | 328 |
| Human Sirt1 | Forward | TCCTCATTGTTATTGGGTCT | 329 |
| Human Sirt1 | Reverse | ATTACTCTTAGCTGCTTGGT | 330 |
| Mouse LSD1 | Forward | TCTTATCAACTTCGGCATCT | 331 |
| Mouse LSD1 | Reverse | TAGCAACTCGTCCACCTACT | 332 |
| Human LSD1 | Forward | AGCGTCATGGTCTTATCAA | 333 |
| Human LSD1 | Reverse | GAAATGTGGCAACTCGTC | 334 |
| Mouse HNF4A | Forward | GATGCTTCTCGGAGGGTCTG | 335 |
| Mouse HNF4A | Reverse | GCTGTGGAGTCTCGGGAGTG | 336 |
| Human HNF4A | Forward | AGCTGCAGATCGATGACAATGAG | 337 |
| Human HNF4A | Reverse | CATACTGGCGGTCGTTGATGTAG | 338 |
| Mouse FoxA2 | Forward | AGAACTCCATCCGCCACTCT | 339 |
| Mouse FoxA2 | Reverse | GGTCTTCTTGCCTCCGCTAC | 340 |

TABLE 6-continued

| Primer Name | Orientation | Sequence (5'-3') | SEQ. ID NO. |
|---|---|---|---|
| Human FoxA2 | Forward | CCCCAACAAGATGCTGACGC | 341 |
| Human FoxA2 | Reverse | GCGAGTGGCGGATGGAGTT | 342 |
| Mouse Sox17 | Forward | GGGATACGCCAGTGACGACC | 343 |
| Mouse Sox17 | Reverse | CCACCTCGCCTTTCACCTTT | 344 |
| Human Sox17 | Forward | CTGCAGGCCAGAAGCAGTGTTA | 345 |
| Human Sox17 | Reverse | CCCAAACTGTTCAAGTGGCAGA | 346 |
| Mouse BMP2 | Forward | TGTGAGGATTAGCAGGTCTT | 347 |
| Mouse BMP2 | Reverse | GTCCACATACAAAGGGTGTC | 348 |
| Human BMP2 | Forward | ACAGCGGAAACGCCTTAA | 349 |
| Human BMP2 | Reverse | GGGAGCCACAATCCAGTC | 350 |
| Human beta-Actin | Reverse | GAAGGTGGACAGTGAGGCCAGGAT | 351 |
| Mouse EOMES | Forward | CCCAACAGAGCGAAGAGGTG | 352 |
| Mouse EOMES | Reverse | GAAGGTCGGGTCAGGGTAAT | 353 |
| Human EOMES | Forward | CCCAGACCCAACCTTTCC | 354 |
| Human EOMES | Reverse | GAGCCAATTTCCTCTTTCACTT | 355 |
| Human beta-Actin | Forward | TCCAGCCTTCCTTCTTGGGTATG | 356 |
| Mouse beta-Actin | Forward | TGCGTGACATCAAAGAGAAG | 357 |
| Mouse beta-Actin | Reverse | GATGCCACAGGATTCCATA | 358 |
| Human Hes1 | Forward | ATAGCTCGCGGCATTCCAAG | 359 |
| Human Hes1 | Reverse | GAAGCGGGTCACCTCGTTCA | 360 |
| Human DLL1 | Forward | ACAGCAAGCGTGACACCAAG | 361 |
| Human DLL1 | Reverse | TGAAGTTGAACAGCCCGAGT | 362 |
| Human Gadd45g | Forward | ACGCTGATCCAGGCTTTCTG | 363 |
| Human Gadd45g | Reverse | AACAGGCTGAGCTTCTCCAA | 364 |
| Mouse Hes1 | Forward | GACGGCCAATTTGCCTTTCTCATC | 365 |
| Mouse Hes1 | Reverse | TCAGTTCCGCCACGGTCTCCACA | 366 |
| Mouse DLL1 | Forward | CAGATAACCCTGACGGAGGCTACA | 367 |
| Mouse DLL1 | Reverse | GGAGGAGGCACAGTCATCCACATT | 368 |
| Mouse Gadd45g | Forward | CGTCTACGAGTCCGCCAAAGTCC | 369 |
| Mouse Gadd45g | Reverse | CAGAACGCCTGAATCAACGTGAAAT | 370 |

TABLE 6-continued

| Primer Name | Orientation | Sequence (5'-3') | SEQ. ID NO. |
|---|---|---|---|
| Human Tip60 | Forward | GATGGAATACCGTCAGCACC | 371 |
| Human Tip60 | Reverse | TGAGGCAGAACTCGCACAGG | 372 |
| Mouse Tip60 | Forward | GTGAAACGGAAGGTGGAGGT | 373 |
| Mouse Tip60 | Reverse | CCAGTCATTCGTGGTGCTGA | 374 | g. Cell Cycle Analysis, Viability, Synchronization, and Differentiation

The fluorescence-activated cell sorting (FACS) and 3-(4,5-dimethyl-2-thiazolyl)-2,5-diphenyl-2H-tetrazolium bromide (MTT) assays were conducted as described previously (Lan, R., et al. (2012) Lab. Invest. 92, 1503-1514). To synchronize PA-1 and F9 cells at the $G_1$/S phase transition, cells were treated with 2.5 mM thymidine for 12 h, released into fresh medium for 6 h, and blocked again with 2.5 mM thymidine for an additional 12 h. The cell cycle arrest was analyzed by FACS. For differentiation, F9 and PA-1 cells were seeded in 6-well plates at a density of $1\times10^4$ cells per well and supplemented with 5 µM RA for 3 days. Cells were then recultured in fresh medium without RA for another 2 days, and the cell cycle was analyzed on a BD FACSCalibur cell sorter using the CellQuest program (Becton, Dickinson, Mountain View, Calif.). The percentages of cells in $G_1$, S, and $G_2$/M phases were determined by the use of ModFit LT software.

Alternatively, cell viability assays were conducted as previously described (Wang, J., et al. (2011) Cancer Research 71, 7238-7249). For the MTT assay, cells were seeded onto 96-well culture plates with a density of 2000-5000 cells/well, and incubated with CBB1003 or CBB1007 at various concentrations from 1 to 100 µM for 30-48 hours, depending cell growth rate. Dimethylsulfoxide (DMSO) was used as a solvent control. MTT was added to a final concentration of 0.5 mg/mL and cells were re-incubated for 4 hours. After removing the medium, 200 µL DMSO was added to dissolve formazan, followed by incubation for 10 minutes, and absorbance was measured at 490 nm by a Bio Red microplate reader. All assays were performed in triplicates for each concentration. The cell viability rate was calculated as the relative percentage of MTT absorption as follows: % cell viability=(mean experimental absorbance/mean control absorbance)×100.

h. Peptide and Recombinant Proteins

H3K4me2 and H4K16ac were purchased from AnaSpec and Shanghai Science Peptide Biological Technology Co., Ltd., respectively. Human LSD1 and HDAC1 full-length cDNAs were obtained from Open Biosystems. Human CoREST cDNA was amplified by reverse transcription-PCR (RT-PCR) using mRNA isolated from HeLa cells. These cDNAs were fully sequenced and cloned into the pGEX-KG or pET28a vector and expressed as the glutathione S-transferase (GST)- or His-tagged fusion proteins in the Escherichia coli BL21 strain and affinity purified with glutathione or Ni-Sepharose (GE Healthcare, United Kingdom) resin. The GST tag of purified protein GSTHDAC1 or GST-LSD1 was removed by the use of PreScission protease at 4° C. for 16 h in the digestion buffer (20 mM Tris-HCl, pH 7.4, 200 mM NaCl, 1 mM dithiothreitol [DTT], protease and phosphatase inhibitors). The GST tag and uncut GST-HDAC1/GST-LSD1 proteins were depleted by glutathione-Sepharose. For the reconstitution reaction, recombinant GST-CoREST, His-LSD1, and recombinant HDAC1 (rHDAC1) (GST was removed by the use of PreScission protease) (10 µg) were assembled into the LSD1-CoREST-HDAC1 complex and then pulled down by GSTSepharose resins. Protein A-Sepharose was used as a negative-control resin.

i. Preparation of Nucleosomes

Nucleosomes were purified according to previously described procedures (Shi, Y. J., et al. (2005) Mol. Cell 19, 857-864). Briefly, cells ($1\times10^6$) were washed twice with ice-cold hypotonic buffer (20 mM potassium-HEPES, pH 7.8, 5 mM potassium acetate, 0.5 mM $MgCl_2$, 0.5 mM DTT), swelled, and disrupted with 25 strokes in a Dounce homogenizer using a tightfitting pestle. Nuclei were pelleted at 4,000 rpm for 5 min and resuspended in buffer A (20 mM HEPES, pH 7.9, 1.5 mM magnesium acetate, 50 mM potassium acetate, 10% glycerol, 0.5 mM DTT, 150 mM NaCl, protease and phosphatase inhibitors). After incubation on ice for 15 min, the nuclei were centrifuged for 10 min at 10,000 rpm. The chromatin pellet was resuspended in 0.5 mL buffer B (0.32 M sucrose, 50 mM Tris-HCl, pH 7.5, 4 mM MgCl2, 1 mM $CaCl_2$, 0.1 mM phenylmethylsulfonyl fluoride) and incubated with 30 units of micrococcal nuclease for 10 min at 37° C. The digested samples were centrifuged at 8,000×g for 10 min, and the supernatant, which contained oligonucleosomes, was recovered.

j. In Vitro Deacetylation and Demethylation Assays

For a typical deacetylation assay, 1 µg rHDAC1 or 1 µg immunoprecipitated endogenous HDAC1-protein A complexes (from two 10-cm dishes) was incubated with 0.4 µg H4K16ac peptide in the presence or absence of 50 µM CBB1007 or 2 µM MS-275 at 30° C. for 1 h. The percentages of deacetylated products were analyzed by mass spectrometry, and the data were analyzed by GraphPad Prism (version 5) software. The reaction products were analyzed by mass spectrometry to separate the peptide substrate (H4K16ac) and the product (H4K16), as previously described (Wang, J., et al. (2011) Cancer Research 71, 7238-7249). For a typical demethylation assay, 0.4 µg H3K4me2 substrate peptide was incubated individually with 1 µg recombinant LSD1 (rLSD1) or 1 µg immunoprecipitated LSD1-protein A complex in the presence or absence of 50 µM CBB1007 or 2 µM MS-275 at 30° C. for 1 h. The reaction products were analyzed by mass spectrometry to separate the products (H3K4me1 and H3K4) from the substrate (H3K4me2), as previously described (Wang, J., et al. (2011) Cancer Research 71, 7238-7249).

For reactions with nucleosomes, 2 µg nucleosomes was incubated with 1 µg rLSD1, rHDAC1, or the recombinant CoREST-LSD1-HDAC1 complex in the presence or absence of 50 µM CBB1007 or 2 µM MS-275 at 30° C. for 45 min. The reaction products (demethylated or deacetylated histones) were analyzed by Western blotting.

k. Reexpression and siRNA Rescues

Wild-type pCMV10-3Flag-LSD1, pCMV10-3Flag-HDAC1, and pCMV10-3 Flag-MOF plasmids were constructed by fusing the full-length cDNAs of human LSD1, HDAC1, or MOF with the Flag tag in the pCMV10-3Flag vector (Clontech). F9 and PA-1 cells were transfected with LSD1, HDAC1, and MOF siRNAs for the untranslated regions (UTRs) first by use of the DharmaFECT transfection reagent to silence the endogenous LSD1, HDAC1, and MOF proteins. Twenty-four hours later, these cells were transfected with 5 µg of each recombinant plasmid by use of Lipofectamine LTX and PLUS reagent (Invitrogen) for 24 to 36 h, and cells were harvested and analyzed. The green fluorescent protein (GFP) expression control vector was used in parallel to estimate the transfection efficiency in each experiment, which was about 50 to 60% of total cells. The efficacy of siRNAs and the expression of exogenous proteins were further confirmed by Western blotting or qPCR.

l. Immunoblotting and Quantification

To quantify and compare the protein band densities in the Western blots shown in the figures, a titration by serial dilution of the siRNA protein samples for mES cell lysates was used as a reference. The concentration of titration samples was measured by use of a NanoDrop 2000 apparatus, and the protein concentration of all titration samples was adjusted to 1 µg/µL. The protein samples were loaded onto an SDS-polyacrylamide gel at levels ranging from 1 µg to 13 µg at 2-µg intervals and immune blotted with each antibody, including anti-LSD1, anti-HDAC1, and anti-histone H3 antibodies, with three independent loadings. The Western blots were developed with exposure times ranging from 30 s to 1 min. The exposure density of each band was scanned by Adobe Photoshop Elements (version 4.0) software using a CanonScan 8600F scanner (Canon, Calif.) and was subsequently quantified by use of the area density tool of Gel-Pro Analyzer (version 4.0) software (Media Cybernetics, Inc.) and plotted. The regression analysis of each signal was performed by use of the Microsoft Excel program's Analysis Tool Pak regression option. The titration data showed that the association between the amount of proteins loaded and protein band intensities after Western blotting was statistically significant and all of the values used for quantification fell within the linear range. Using the titration plots as references, all of the samples for the Western blots shown in the figures were loaded with 5 µg to 7 µg total proteins, and the exposure time was from 30 s to 3 min. The amount of the protein band in the Western blot shown in the figures was quantified by scanning, as described for the reference titration. The band density of each protein in various samples was internally corrected by the use of loading controls, such as histone H3, which is assumed to be constant in each sample. The quantity of protein band densities between two protein samples was externally corrected by use of the reference plots. The internally and externally corrected protein band intensities were compared between duplicate or triplicate samples tested in parallel or independently and plotted. The statistical differences between the experimental and control groups were analyzed by one-way analysis of variance (ANOVA). All Western blotting results are representative of those from at least three independent experiments.

2. Preparation of Tert-Butyl ((1R,2S)-2-(4-((Tert-Butoxycarbonyl)Oxy)Phenyl)Cyclopropyl)Carbamate (CBB3001; Compound 10)

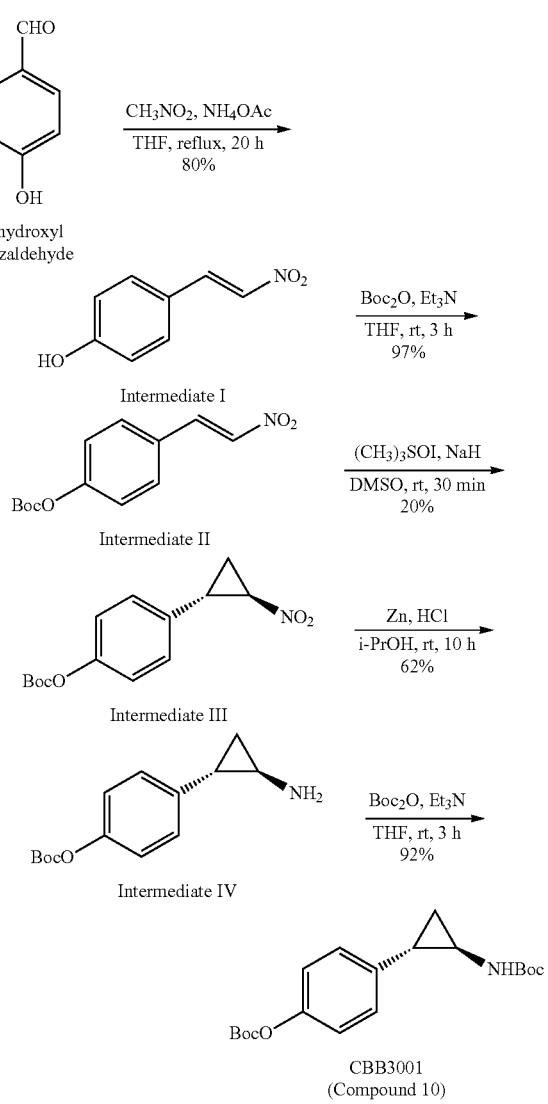

a. Synthesis of (E)-1-Hydroxy-4-(2-Nitrovinyl)Benzene

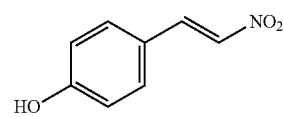 [SMILES: O=[N+]([O-])/C=C/c1ccc(O)cc1]

A mixture of p-hydroxyl benzaldehyde (2.5 g, 20 mmol) and NH$_4$OAc (2.0 g, 26 mmol) in dry THF (30 mL) and CH₃NO₂ was refluxed for 20 h, and the solvent was removed. Then the resulting was pour into water (30 mL), and extracted with EtOAc (25 mL×3), the organic layers were washed with brine (20 mL), dried over anhydrous Na₂SO₄ and concentrated. The residue was purified by column chromatography on silica gel (hexanes/EtOAc 3/1) affording (E)-1-hydroxy-4-(2-nitrovinyl)benzene as a yellow solid (2.10 g, 80%).

b. Synthesis of (E)-Tert-Butyl (4-(2-Nitrovinyl)Phenyl) Carbonate

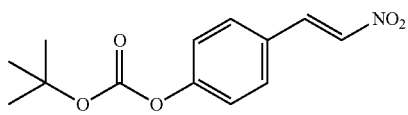 [SMILES: CC(C)(C)OC(=O)Oc1ccc(/C=C/[N+](=O)[O-])cc1]

Boc₂O (3 mL, 20.2 mmol) was added to a solution of (E)-1-hydroxy-4-(2-nitrovinyl)benzene (1.7 g, 10.1 mmol) and NEt₃ (3 mL, 20.1 mmol) in THF (50 mL) and stirred for 3 h at rt. After removal of the solvent, the residue was purified by column chromatography on silica gel (hexanes/EtOAc 5/1) affording (E)-tert-butyl (4-(2-nitrovinyl)phenyl) carbonate as a yellow solid (2.68 g, 97%).

c. Synthesis of Tert-Butyl (4-((Trans)-2-Nitrocyclopropyl)Phenyl) Carbonate

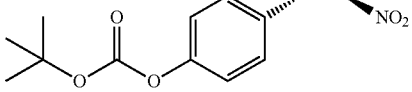

Trimethylsulfoxonium iodide (297 mg, 1.61 mmol) was added in small portions to a suspension of NaH (0.07 g, 1.61 mmol) in dry DMSO (5 mL). The mixture was stirred until gas evolution ceased and a clear solution was formed (45 min) Then a solution of (E)-tert-butyl (4-(2-nitrovinyl)phenyl) carbonate (312 mg, 1.52 mmol) in DMSO (2 mL) was transferred via cannula and the reaction was stirred for 30 min in an ice-bath. The mixture was poured into water (15 mL), and extracted with Et₂O (20 mL×3). The organic layers were washed with brine (20 mL), dried and concentration. Then the residue was purified by column chromatography on silica gel (hexanes/EtOAc 10/1) affording tert-butyl (4-((trans)-2-nitrocyclopropyl)phenyl) carbonate as a white solid (62 mg, 20%).

d. Synthesis of 4-((Trans)-2-Aminocyclopropyl)Phenyl Tert-Butyl Carbonate

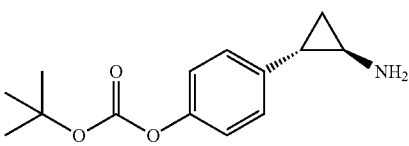 [SMILES: CC(C)(C)OC(=O)Oc1ccc([C@@H]2C[C@H]2N)cc1]

Zn dust (260 mg, 4 mmol) was added in small portions, over a period of 20 min, to a vigorously stirred solution of tert-butyl (4-((trans)-2-nitrocyclopropyl)phenyl) carbonate (110 mg, 0.4 mmol) in i-PrOH (10 mL) and HCl (2 mL of 2 N aqueous solution, 4 mmol). After 10 h, the mixture was basified with NaOH (10% aqueous solution, 15 mL) and filtered through a pad of Celite. The mixture was extracted with EtOAc (20 mL×3), the organic layers were dried and concentrated. Then the residue was purified by column chromatography on silica gel (CH₂Cl₂/MeOH 50:1) affording 4-((trans)-2-aminocyclopropyl)phenyl tert-butyl carbonate as a white solid (70 mg, 62%).

e. Synthesis of Tert-Butyl ((1R,2S)-2-(4-((Tert-Butoxycarbonyl)Oxy)Phenyl)Cyclopropyl)Carbamate (CBB3001)

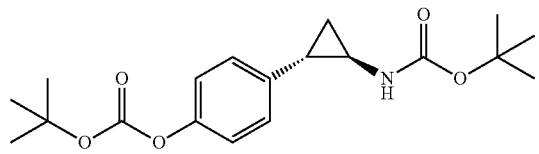 [SMILES: CC(C)(C)OC(=O)N[C@@H]1C[C@H]1c1ccc(OC(=O)OC(C)(C)C)cc1]

Boc₂O (0.15 mL, 1 mmol) was added to a solution of (E)-1-hydroxy-4-(2-nitrovinyl)benzene (125 mg, 0.5 mmol) and Et₃N (0.15 mL, 1 mmol) in THF (20 mL) and stirred for 3 h at rt. After removal of the solvent, the residue was purified by column chromatography on silica gel (hexanes/EtOAc 15/1) affording a white solid (165 mg, 92%). ¹H-NMR (CDCl₃) δ (ppm) 7.14 (d, 2H), 7.05 (d, 2H), 4.84 (br, 1H), 2.69 (br, 1H), 2.01-2.05 (m, 1H), 1.55 (s, 9H), 1.45 (s, 9H), 1.13-1.26 (m, 2H). ¹³C-NMR (CDCl₃) δ (ppm) 155.6 (s), 151.9 (s), 149.3 (s), 138.2 (s), 127.5 (d×2), 121.0 (d×2), 83.3 (s), 29.6 (d), 28.3 (q), 28.0 (d), 27.6 (q), 16.1 (t). HR-MS [M+Na]⁺ 372.1780. (See FIG. 1A-1D).

3. Evaluation of Exemplary Compounds

Figure 2A:
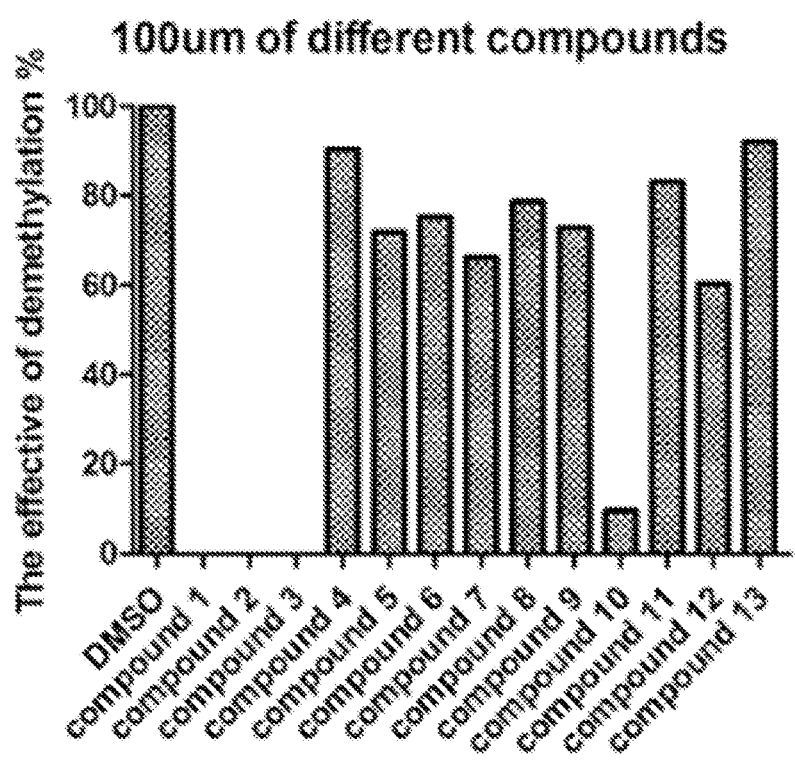
FIG. 2 shows representative data pertaining to the potency of representative compounds 1-10. Specifically, FIG. 2A quantifies the enzyme activity in the presence of 100 µM compound.
FIG. 2B shows concentration effect curves for compounds 1, 2 (CBB3002), 3 (CBB3003), and 10 (CBB3001).
Figure 2B:
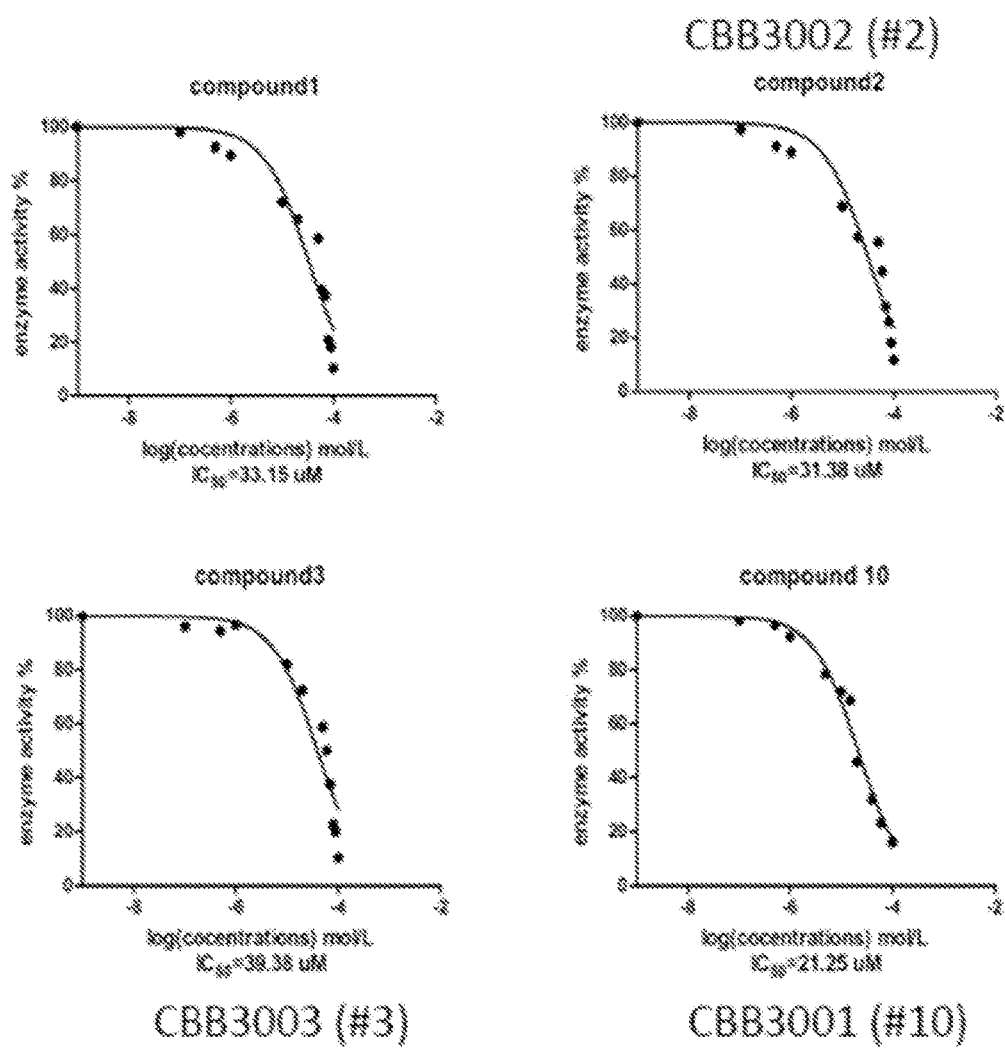

Table 7 below lists specific compounds and LSD1 activity determined in a cell-based assay as described herein (see also FIGS. 2A and 2B).

TABLE 7
| Compound No. | UNLV No. | Structure | LSD1 IC$_{50}$ (μM) |
|---|---|---|---|
| 1 | — | | 33.15 |
| 2 | CBB3002 | 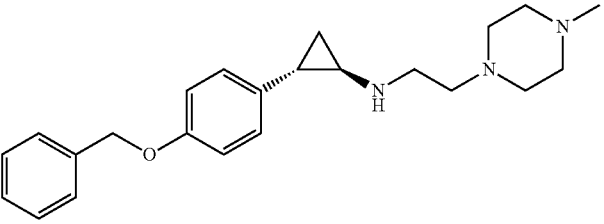 [SMILES: CN1CCN(CCN[C@@H]2C[C@H]2c2ccc(OCc3ccccc3)cc2)CC1] | 31.38 |
| 3 | CBB3003 | 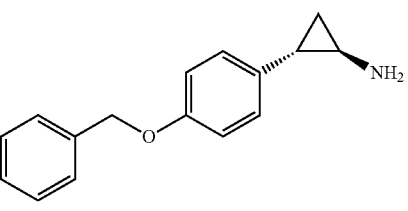 [SMILES: N[C@@H]1C[C@H]1c1ccc(OCc2ccccc2)cc1] | 39.38 |
| 4 | — | 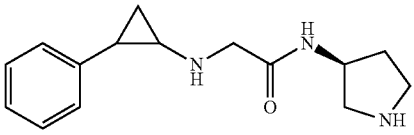 [SMILES: O=C(CNC1CC1c1ccccc1)N[C@H]1CCNC1] | |
| 5 | — | 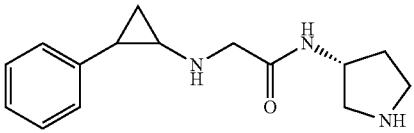 [SMILES: O=C(CNC1CC1c1ccccc1)N[C@@H]1CCNC1] | |
| 6 | — | 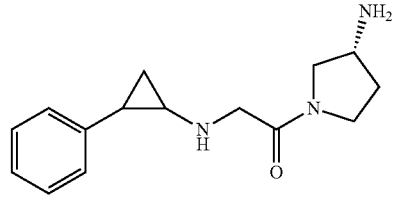 [SMILES: N[C@@H]1CCN(C(=O)CNC2CC2c2ccccc2)C1] | |
| 7 | — | 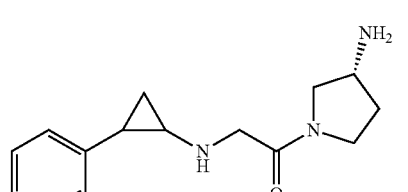 | |
| 8 | — | 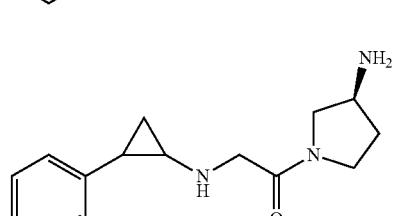 | |

TABLE 7-continued

| Compound No. | UNLV No. | Structure | LSD1 IC$_{50}$ (μM) |
|---|---|---|---|
| 9 | — | [structure: phenyl-cyclopropyl-NH-CH2-C(O)-N-pyrrolidinyl-NH2] | |
| 10 | CBB3001 | | 21.25 |
| 11 | — | | |
| 12 | — | | |
| 13 | — | | |

Figures 3A, 3B, 3C:
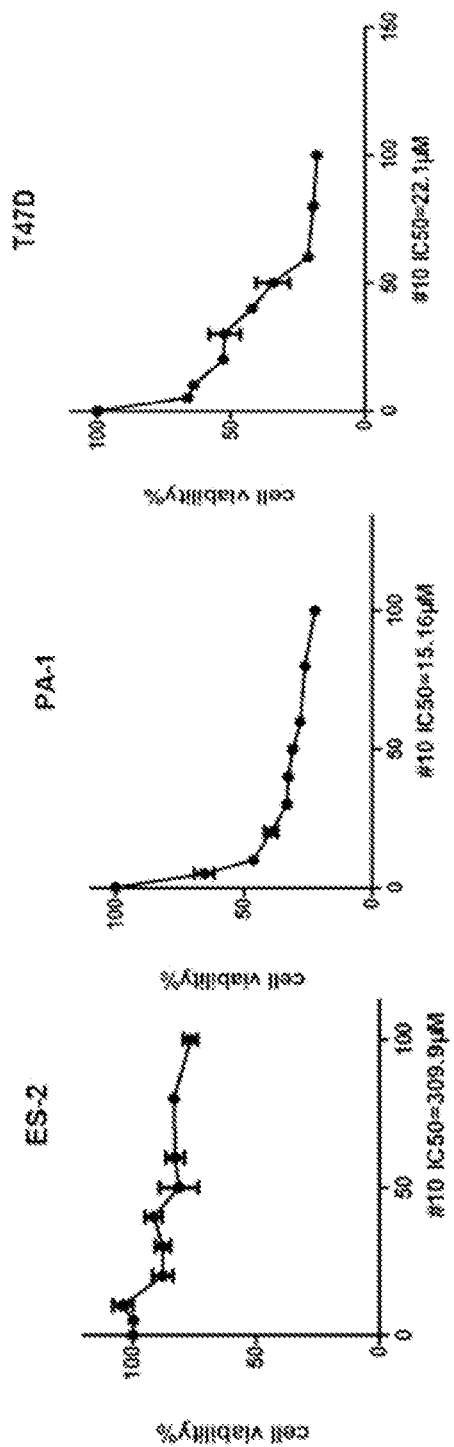
FIG. 3 shows representative data pertaining to the potency of compound 10 (CBB3001) in ES-2 (3A), PA-1 (3B), and T47D (3C) cells.

Table 8 below lists activity of CBB3001 (compound 10) in Sox2-negative (ES-2) and Sox2-expressing (PA-1 and T47D) cancer cells determined in a cell-based assay as described herein (see also FIG. 3A-C).

TABLE 8

| Compound No. | Cell Type | IC$_{50}$ (μM) |
|---|---|---|
| 10 | ES-2 | 309.9 |
| 10 | PA-1 | 15.16 |
| 10 | T47D | 22.1 |

4. LSD1 Expression is Elevated in Human Lung SCCs that Overexpress Sox2

Figure 4A:
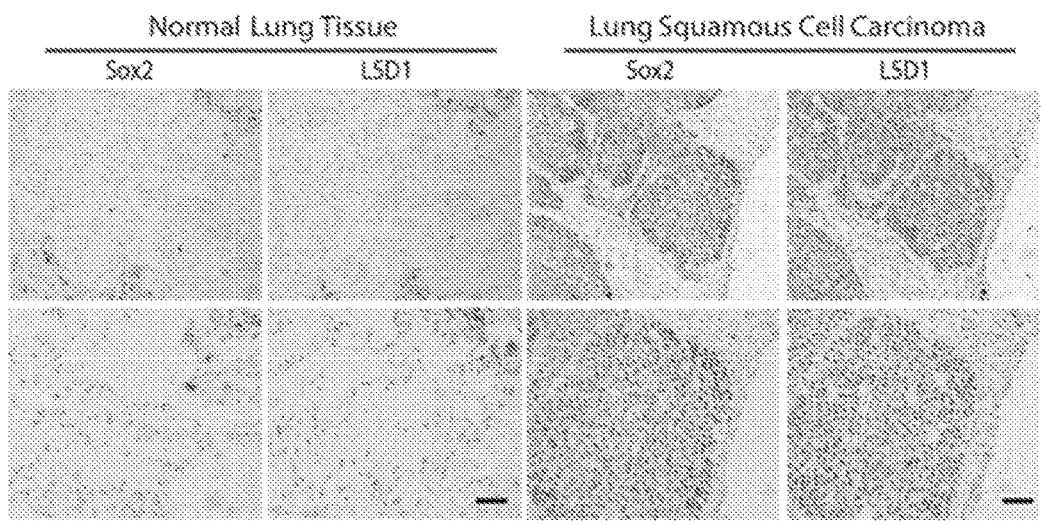
FIG. 4A-C show representative data pertaining to the expression of Sox2 in lung SCCs.
Figure 4B:
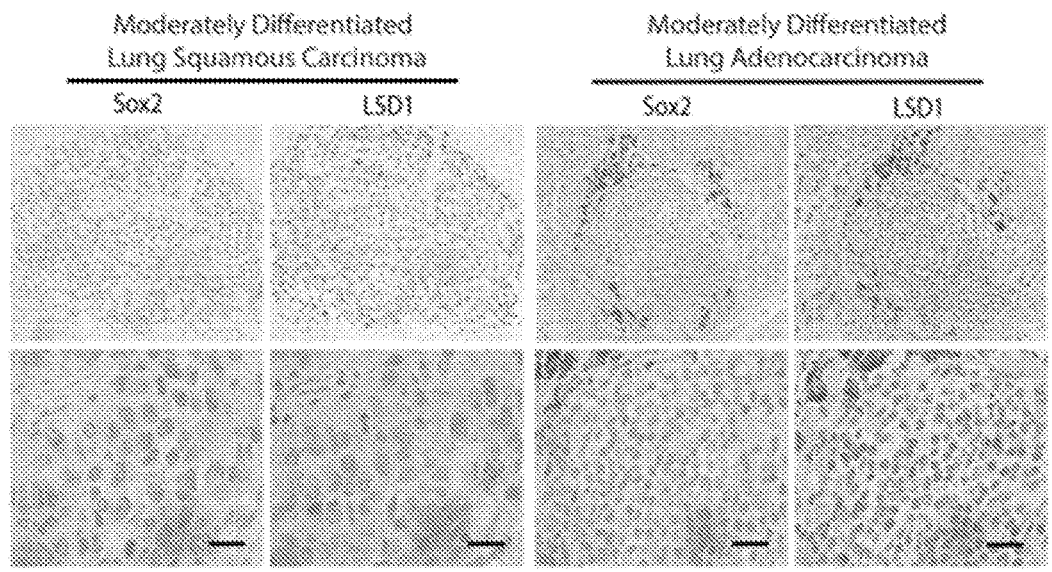

Previous studies indicated that germ cell tumors such as teratocarcinomas and embryonic carcinoma cells expressed elevated levels of LSD1. They were also highly sensitive to the LSD1-specific inhibitors that noncovalently interact with LSD1 (Wang, J., et al. (2011) *Cancer Research* 71, 7238-7249). Given that these cells usually express the PSC proteins Oct4, Sox2, and Lin28, which are also expressed in other human cancers (Leis, O., et al. (2012) *Oncogene* 31, 1354-1365; Peng, S., et al. (2008) *Oncogene* 29, 2153-2159; Zhong, X., et al. (2010) *J. Biol. Chem.* 285, 41961-41971), LSD1 was examined in various human cancer tissues that also co-express some of the PSC markers (only de-identified samples were used, which were acquired with the approval of the Ethics Committee of the First Affiliated Hospital, Shihezi University School of Medicine). In 13 independent cases of human lung SCC, highly elevated levels of Sox2 and LSD1 were observed in five poorly differentiated cases, moderate Sox2 and LSD1 increases in seven moderately differentiated cancer cases, and low LSD1 expression in a single Sox2-negative and moderately differentiated cancer (FIGS. 4A and 4B; and Table 9). Statistical analysis revealed a significant correlation between Sox2 and LSD1 expression (Pearson's correlations: $R^2$=0.4372 and p=0.014). In contrast, Sox2 expression was low or non-detectable in all 17 cases of lung adenocarcinoma carcinomas. In the lung adenocarcinoma samples, only two cases of poorly differentiated cancers had moderately increased levels of LSD1, and LSD1 was low in the remaining 15 moderately differentiated cancers. As a control, the surrounding normal lung tissues expressed undetectable levels of LSD1 and Sox2 proteins (FIG. 4A).

TABLE 9

| Type | Differentiation Degree | LSD1 expression | Sox2 expression | total |
|---|---|---|---|---|
| Lung Squamous Carcinomas (13 cases) | Poorly differentiated (5/13) | +++ | +++ | 5 |
| | Moderately differentiated (8/13) | +++ | +++ | 1 |
| | | ++ | +++ | 3 |
| | | + | ++ | 3 |
| | | + | − | 1 |
| Lung Adenocarcinoma Carcinomas (17 cases) | Poorly differentiated (2/1) | ++/+++ | − | 2 |
| | Moderately differentiated (15/17) | +/++ | − | 15 |

Referring to FIG. 4A, LSD1 and Sox2 expression are illustrated in lung SCCs. One example of serial tissue sections from clinical lung SCC patients (n=13) immunostained with Sox2 or LSD1 antibodies. LSD1 and Sox2 were strongly stained in pathological tissues (right), but weakly stained or nondetectable in normal lung tissue (left) surrounding the pathological areas (scale bar=100 μM; lower panels represent magnified images, 4× of upper panels, total magnification=400×).

Referring to FIG. 4B, LSD1 and Sox2 expression are illustrated in human lung SCC (left panels, N=13) and lung adenocarcinoma (right panel, N=17) tissues. Serial tissue sections from clinical patient samples were immunostained with anti-Sox2 or LSD1 antibodies. LSD1 and Sox2 were elevated in squamous cell carcinoma pathological tissues. Sox2 is non-detectable in all 17 adenocarcinoma cases and LSD1 is lower in lung adenocarcinoma cases (scale bar=100 microns; lower panels represent magnified images, 4×).

Figure 4C:
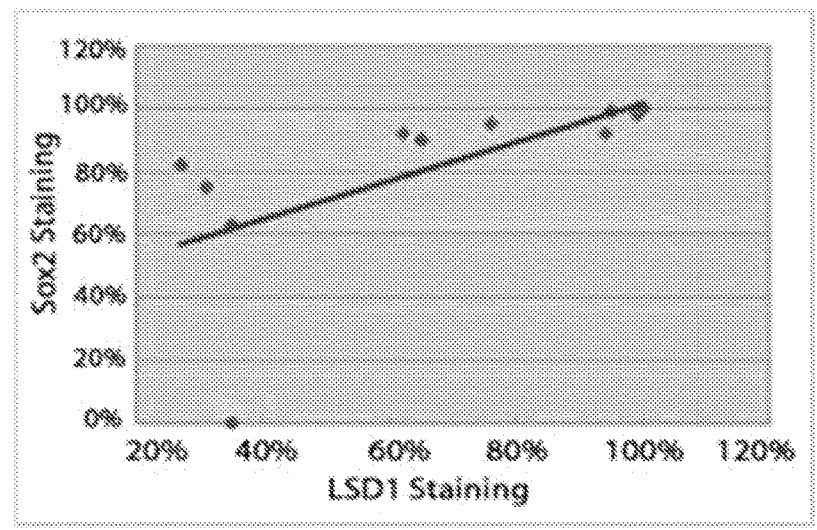

Referring to FIG. 4C, statistical analysis of the correlation (Pearson's) between Sox2 an LSD1 expression in lung squamous cell carcinomas are shown.

The finding that the levels of LSD1 are significantly elevated in Sox2-expressing SCCs is consistent with previously reported studies. For example, in a search of publicly reported tumor microarray data from Oncomine (http://www.oncome.org), it was discovered that in 21 SCC cases reported by Bhattacharjee et al. (2001), Sox2 was overexpressed in 18 cases, whereas LSD1 was co-overexpressed in 16 cases. In another six small cell lung carcinoma cases with elevated LSD1, Sox2 was also over-expressed in four of them. In 17 cases of esophagus carcinomas (Hu, N., et al. (2010) *BMC Genomics* 11, 576) with high LSD1 levels, Sox2 was overexpressed in 14 cases. The overexpression of Sox2 and LSD1 was also found in other cancers. For example, in 19 cases of large cell lung carcinomas (Hu, N., et al. (2010) BMC Genomics 11, 576), 16 cases overexpressed LSD1 and 15 overexpressed Sox2. In a study of cervical SCCS (Scotto, L., et al. (2008) Genes Chromosomes Cancer 47, 755-765), Sox2 was overexpressed in 50% of 84 cases and LSD1 was co-elevated in 48% of all cases. In 122 cases of ductal breast carcinomas (Sortie, T., et al. (2003) Proc. Natl. Acad. Sci. USA 100, 8418-8423), Sox2 was overexpressed in 52% of them and LSD1 was co-overexpressed with Sox2 in 49% of all cases. In a single undifferentiated breast carcinoma case, both Sox2 and LSD1 were overexpressed. Without wishing to be bound by theory, these data suggest that there is a significant correlation between Sox2 and LSD1 expression in a wide array of human cancers.

Figure 5A:
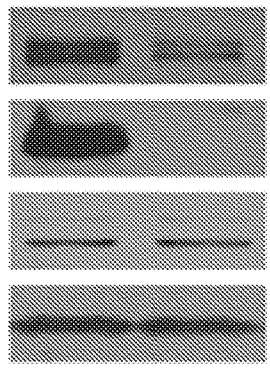
FIG. 5A-C show representative data illustrating that lung carcinoma cells expressing Sox2 are selectively sensitive to LSD1 inactivation.
Figure 5A:
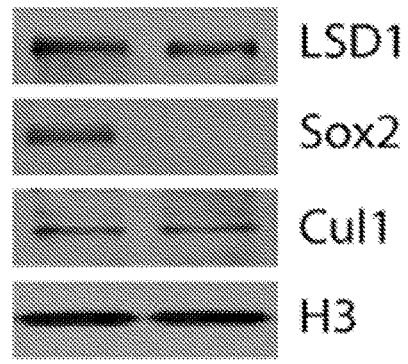

5. Lung SCC Cells that Contain Amplified Sox2 Gene or Other Lung Carcinoma Cells that Express Sox2 are Particularly Sensitive to LSD1 Inactivation The observation that LSD1 levels are elevated in Sox2-expressing lung SCCs prompted an investigation of the functional relationship between Sox2 and LSD1 in lung carcinomas. For this purpose, human SCC NCI-H520 cells that contain the Sox2 gene amplification at 3q26.33, and human lung adenocarcinoma NCI-H1437 cells that do not express Sox2 were used (Bass, A. J., et al. (2009) Nat. Genet. 41, 1238-1242; FIG. 5A). H520 and H1437 cells were treated with LSD1 inhibitors for 24-30 hr, and cell growth was analyzed. The LSD1 inhibitor CBB1007 was found to selectively and specifically inhibit the growth of H520 cells, but had no detectable effects on H1437 (FIGS. 5B and 5C).

Referring to FIG. 5A, Sox2 and LSD1 expression are illustrated in human lung SCC NCI-H520, lung adenocarcinoma A549, and lung carcinoma NCI-H1437 and H1299 cells (CUL1 and histone H3=loading control).

Figure 5B:
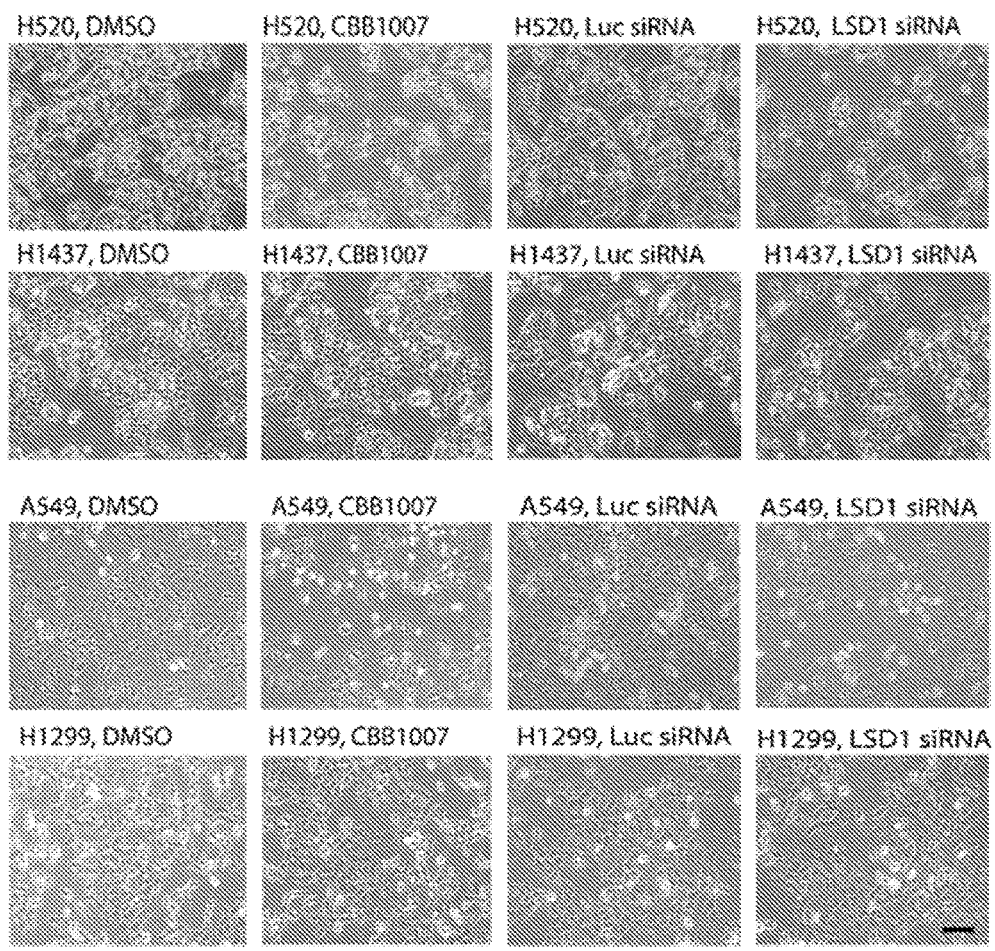

Referring to FIG. 5B, LSD1 inactivation specifically inhibited the growth of H520 and A549 cells, but not that of H1437 or H1299 cells. Actively growing lung cancer cells were treated with 50 μM LSD1 inhibitor CBB1007 for 30 hr or were transfected with 50 nM control luciferase (Luc) or LSD1 siRNAs for 60 hr. Cell growth was examined by microscopy.

Figure 5C:
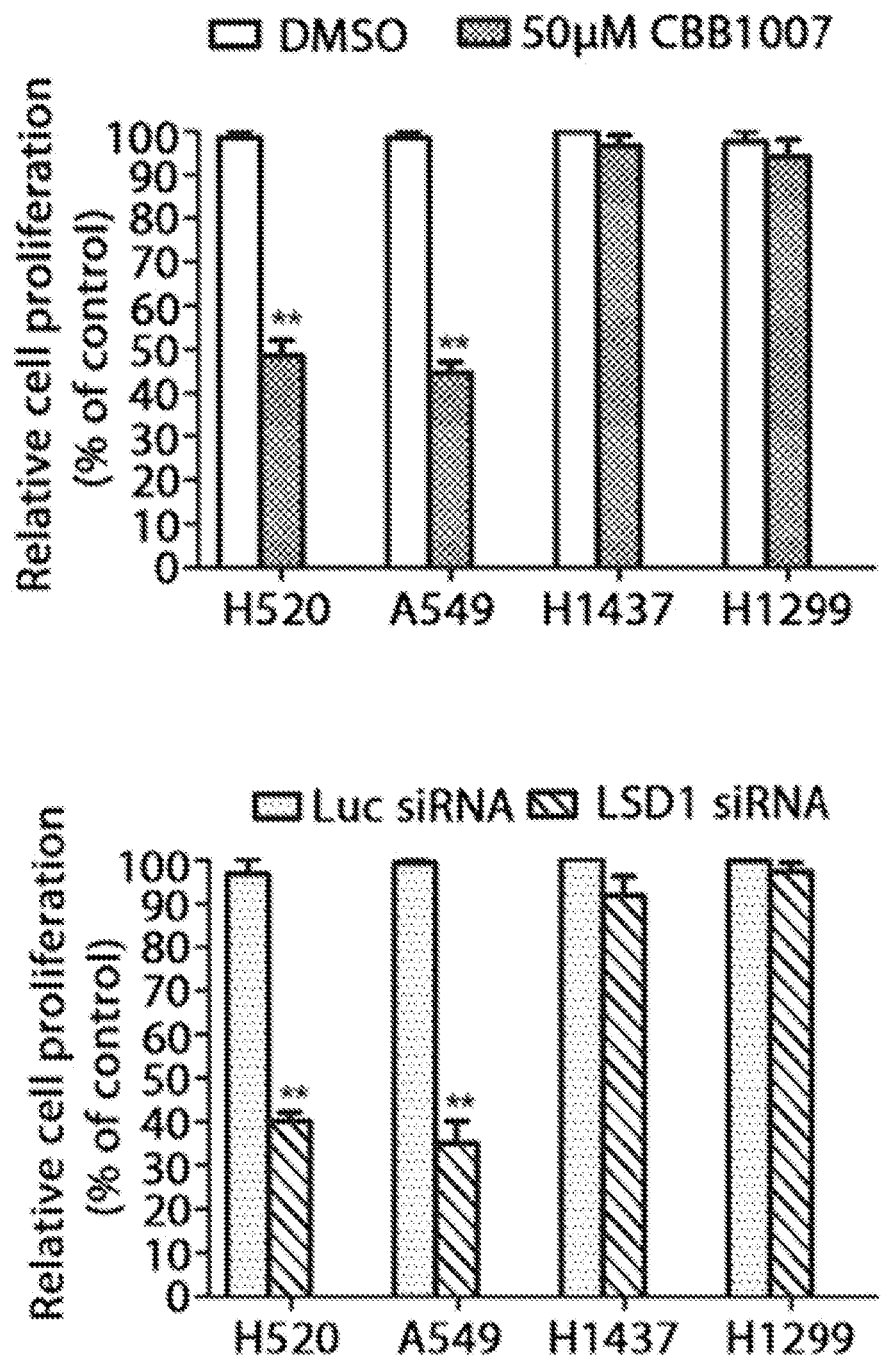

Referring to FIG. 5C, the percent viability of cells treated with LSD1 inhibitors or siRNAs compared with control cells, as determined by 3-(4,5-dimethylthiazol-2-yl)-2,5-diphenyltetrazolium bromide (MTT) assay is shown. Data are presented as mean±SD. The statistical differences between inhibitor-treated and control groups were analyzed by one-way ANOVA (scale bar=100 μM; **$p<0.01$).

To identify additional Sox2 or other PSC-specific gene-expression signatures in carcinoma cells, the microarray mRNA data of the Cancer Genome Anatomy Project database (http://cgap.nci.nih.gov/Microarray/GeneList) was search in 60 cancer cell lines collected by the National Cancer Institute. Using this approach, it was discovered that approximately one-third of these cancer cells express Sox2 or other PSC proteins. Treatment of A549, a Sox2-expressing human lung adenocarcinoma cell derived from adenocarcinomic alveolar basal epithelial cells, and H1299, a Sox2-negative human non-small cell lung carcinoma cell (FIG. 5A), with LSD1 inhibitors revealed that A549 cells are highly sensitive to LSD1 inhibitors, whereas H1299 cells are not (FIGS. 5B and 5C). The expression of LSD1 was also ablated using specific siRNAs in both H520, H1437, A549, and H1299 cells, and these studies showed that ablation of LSD1 phenocopied the selective growth-inhibitory effects of LSD1 inhibitors on H520 and A549 cells, but not on H1437 and H1299 cells (FIGS. 5B and 5C). Without wishing to be bound by theory, these data suggest that lung carcinoma cells that express Sox2 are particularly sensitive to LSD1 inactivation, whereas Sox2-negative cells are not. In addition, both Sox2-expressing H520 and A549 cells appeared to express higher levels of LSD1 (FIG. 5A).

6. Breast and Ovarian Carcinoma Cells can be Distinguished by their Sensitivity to LSD1 Inhibition Although LSD1 inhibitors specifically target lung carcinoma cells that overexpress Sox2, it remains unclear whether lung carcinoma cells are uniquely sensitive to LSD1 inhibition. Search of the Cancer Genome Anatomy Project database and published reports revealed that several breast and ovarian carcinoma cells may also express key pluripotent stem cell (PSC) proteins Oct4, Sox2, Lin28, Nanog, and Sal14 either alone or in combination (Leis, O., et al. (2012) Oncogene 31, 1354-1365; Peng, S., et al. (2008) Oncogene 29, 2153-2159; Zhong, X., et al. (2010) J. Biol. Chem. 285, 41961-41971). Therefore, a panel of ovarian, breast, and other carcinoma cells were examined for their response to LSD1 inhibition (see Table 1 above). Although the growth of some cells was not inhibited by LSD1 inhibitors such as human ovarian carcinoma cells OVCAR8, Hs28.T, and ES-2, and breast carcinoma cells MDA-MB-231, BT549, and SK-BR-3, several of them were highly sensitive to LSD1 inhibitors such as ovarian carcinoma cells OVCAR3, A2780, SKOV-3, and IGROV-1; ovarian teratocarcinoma PA-1 cells; and breast carcinoma cells MDA-MB-468, T47D, and MCF-7 (FIGS. 6A, 6B, 7A, 7B, and 8A-8C). The selective effects of LSD1 inhibitors were confirmed by ablation of LSD1 using LSD1 siRNAs (FIGS. 9A and 9C). Analysis of the cell-cycle effects by fluorescence-activated cell sorting (FACS) revealed that loss of LSD1 induced significant G1 cell-cycle arrest in cancer cells that are sensitive to LSD1 inhibition, such as A549, T47D, and IGROV1, which was associated with decreased expression of the cell-cycle regulatory proteins c-Myc and various cyclins, whereas such an arrest was not observed in cancer cells that are not sensitive to LSD1 inhibitors, such as H1437 (FIGS. 9A, 9B, and 9C).

Figure 6A:
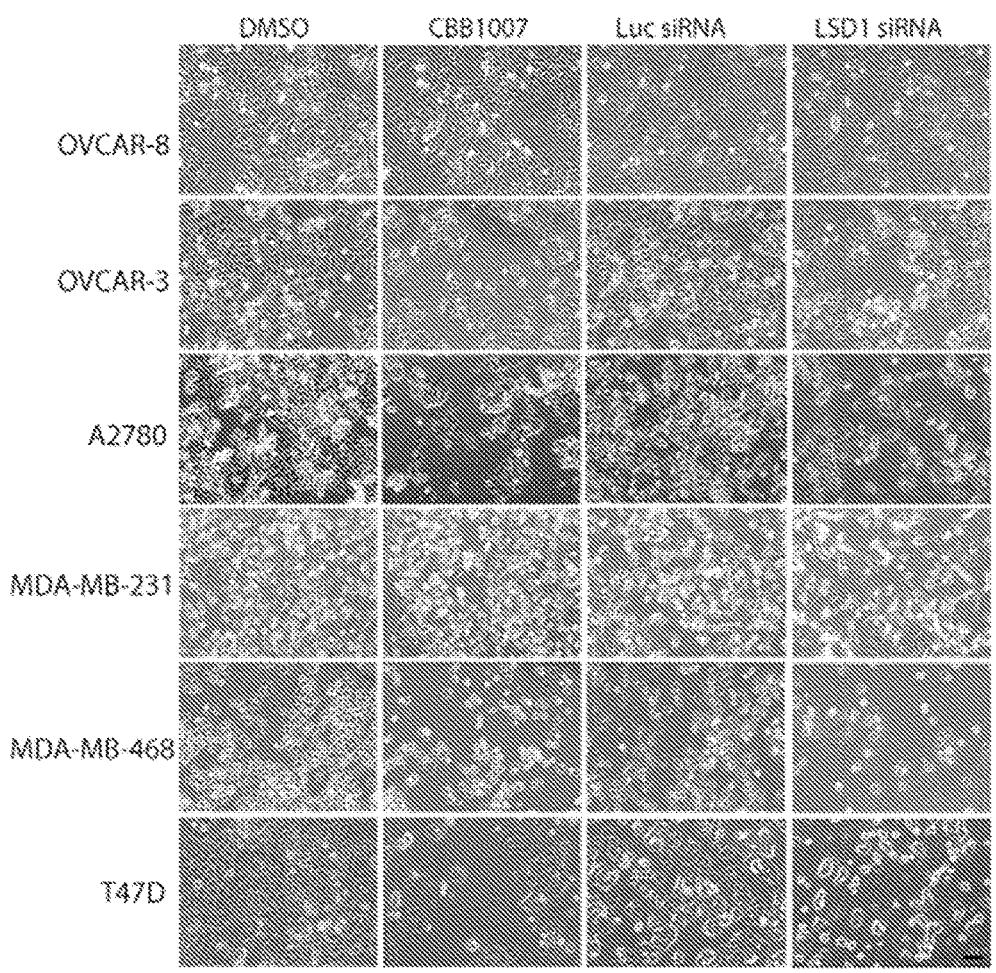
FIG. 6A-C show representative data pertaining to the sensitivity of a panel of breast, ovarian, and other human carcinoma cells to LSD1 inhibitors and LSD1 siRNA-mediated ablation.

Referring to FIG. 6A, the effects of LSD1 inhibitor CBB1007 and siRNAs on the growth of ovarian carcinoma OVCAR-8, OVCAR-3, and A2780 cells, and breast carcinoma MDA-MB-231, MDA-MB-468, and T47D cells are shown.

Figure 6B:
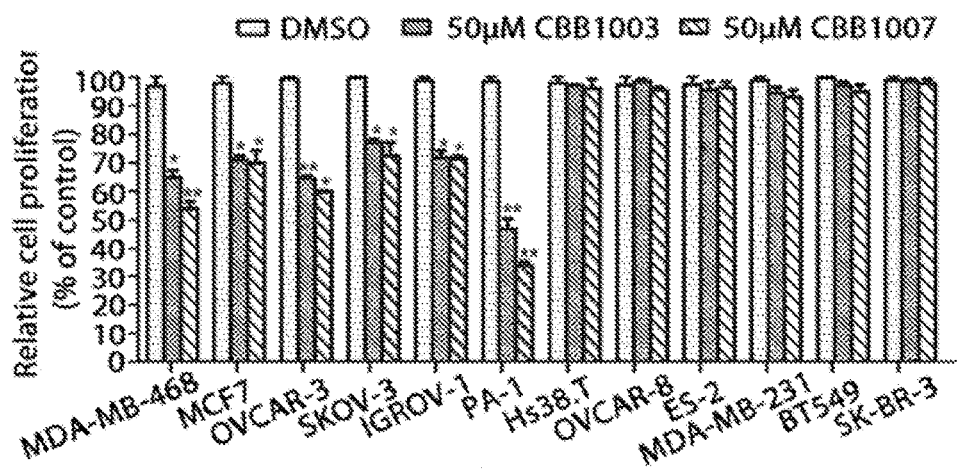
Figure 6C:
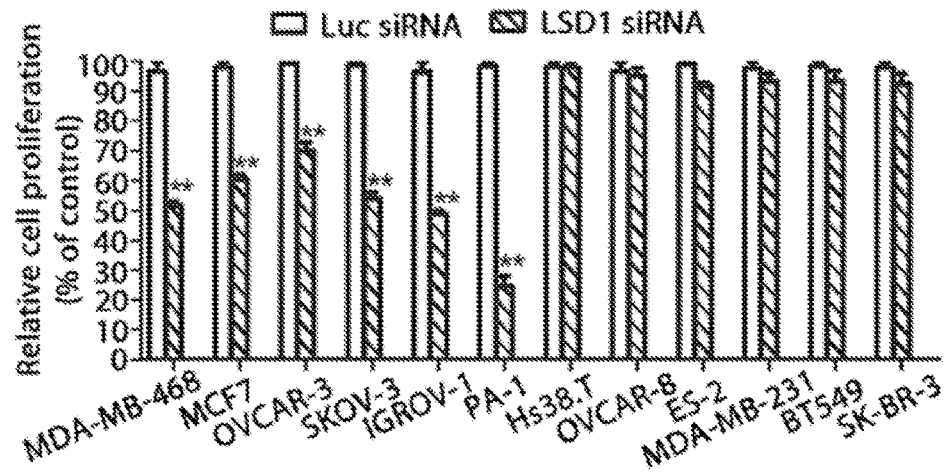

Referring to FIGS. 6B and 6C, quantitative analyses of the sensitivity of a panel of breast, ovarian, and other human carcinoma cells to LSD1 inhibitors (6B) and LSD1 siRNA-mediated ablation (6C) are shown. The statistical differences between inhibitor-treated and control groups were analyzed by one-way ANOVA (*$p<0.05$, **$p<0.01$).

Figure 7A:
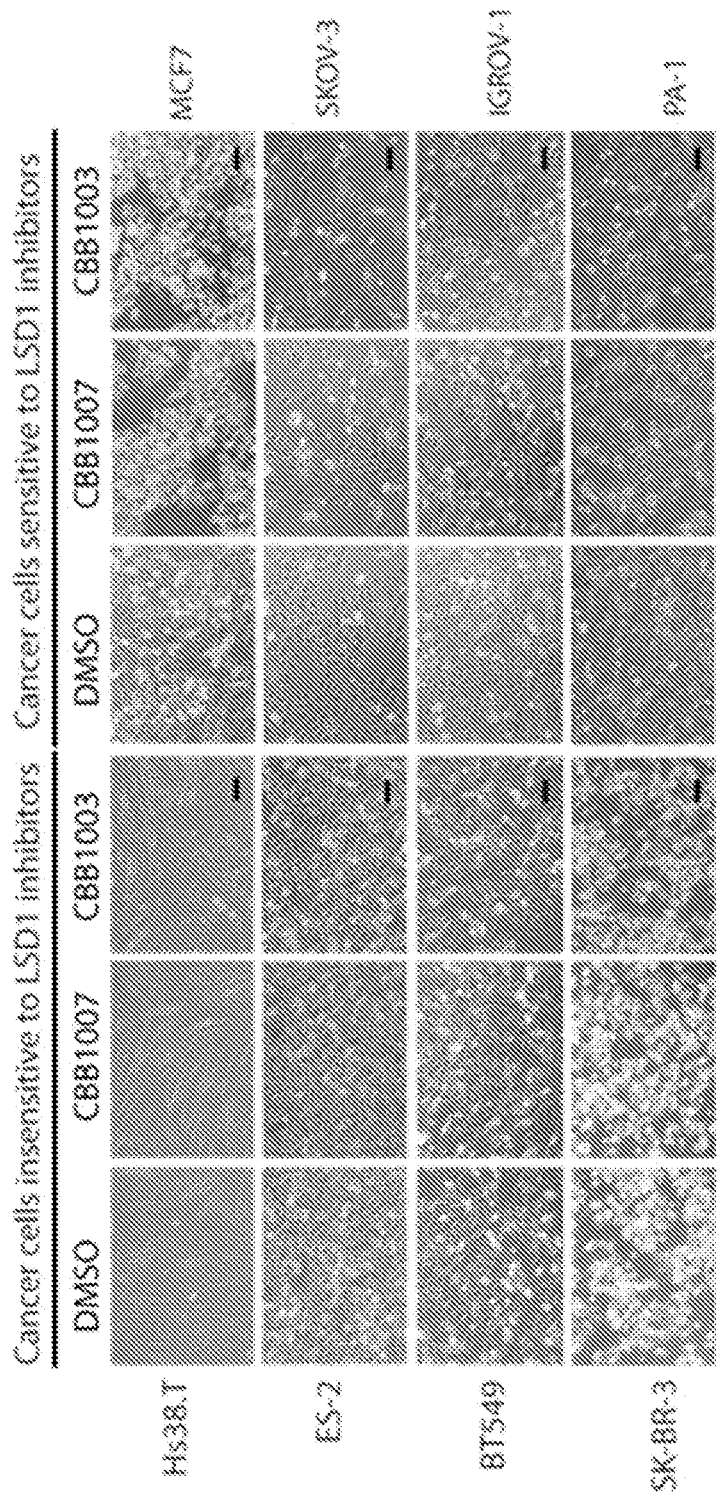
FIGS. 7A and 7B show representative data pertaining to the effects of LSD1 inhibitor CBB1007 and siRNAs on the growth of a panel of ovarian and breast carcinoma cells.

Referring to FIG. 7A, ovarian and breast cancer cells were treated with control (DMSO) or 50 μM LSD1 inhibitors CBB1003 and CBB1007 for 30 hours as indicated. Cell growth was monitored by microscopy (scale bar, 100 microns). While ovarian carcinoma Hs38.T and ES-2 and breast carcinoma BT549 and SK-BR-3 cells were not sensitive to LSD1 inhibitors, breast carcinoma MCF7 and ovarian carcinoma IGROV-1 and SKOV-3 cells, as well as ovarian teratocarcinoma PA-1 cells were sensitive to LSD1 inhibition.

Figure 7B:
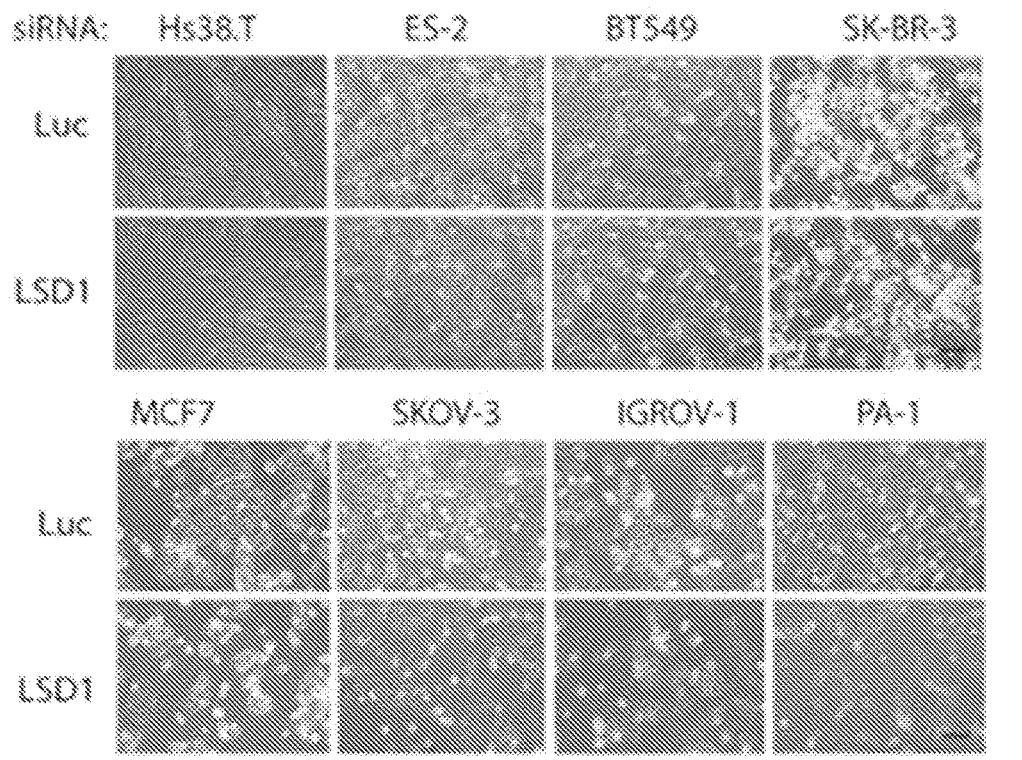
Figure 7B:
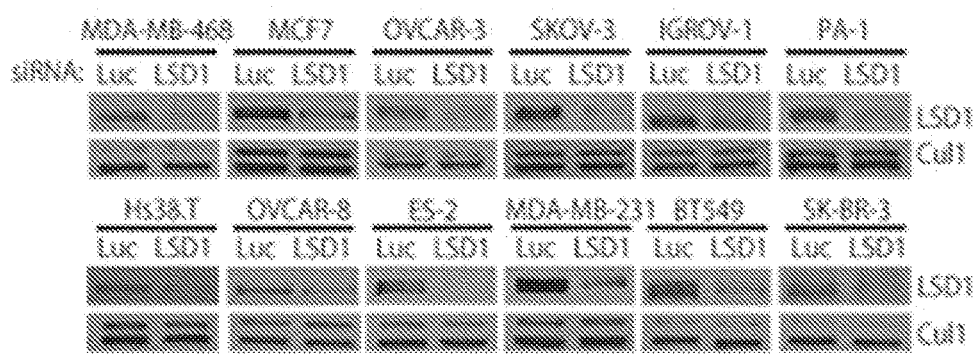

Referring to FIG. 7B, the indicated ovarian and breast cancer cells were transfected 50 nM luciferase (Luc) or LSD1 specific siRNAs for 60 hours and cell growth was monitored by microscopy and ablation efficiency by Western blotting.

Figure 8A:
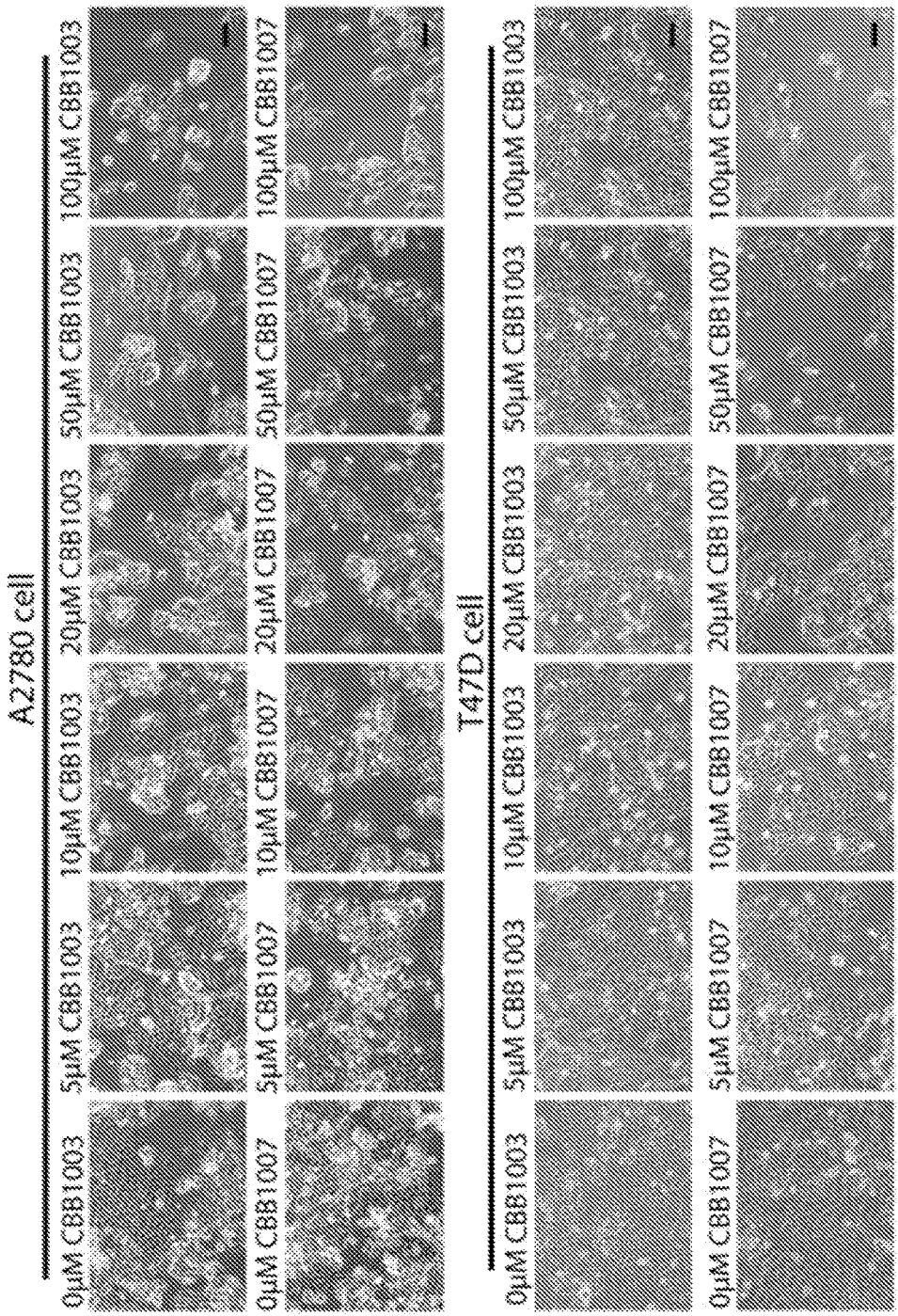
FIG. 8A-C show representative data demonstrating that loss of LSD1 activity causes growth inhibition in ovarian A2780, and breast T47D cells.
Figure 8C:
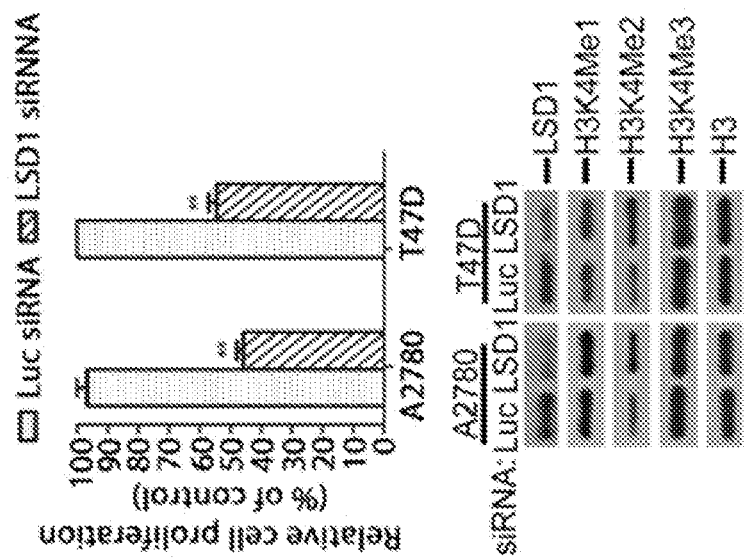
Figure 8B:
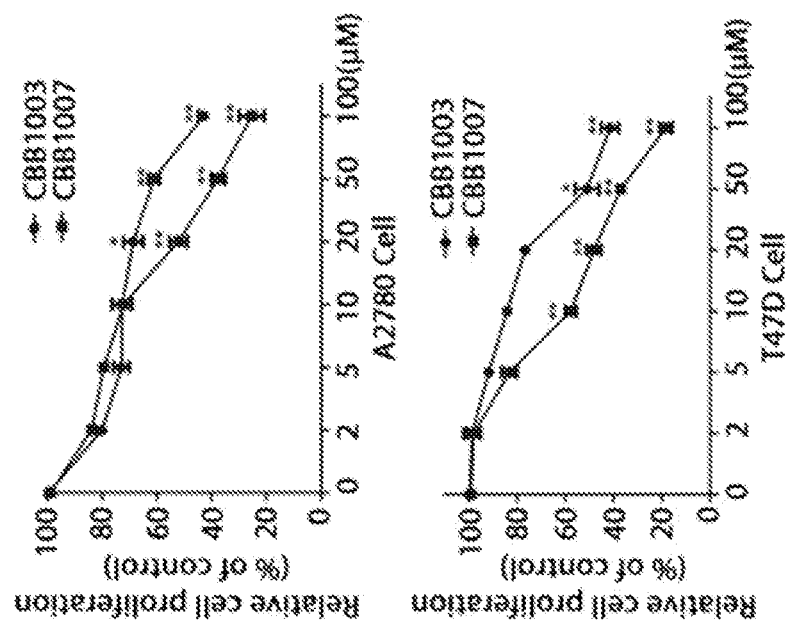
Figure 9A:
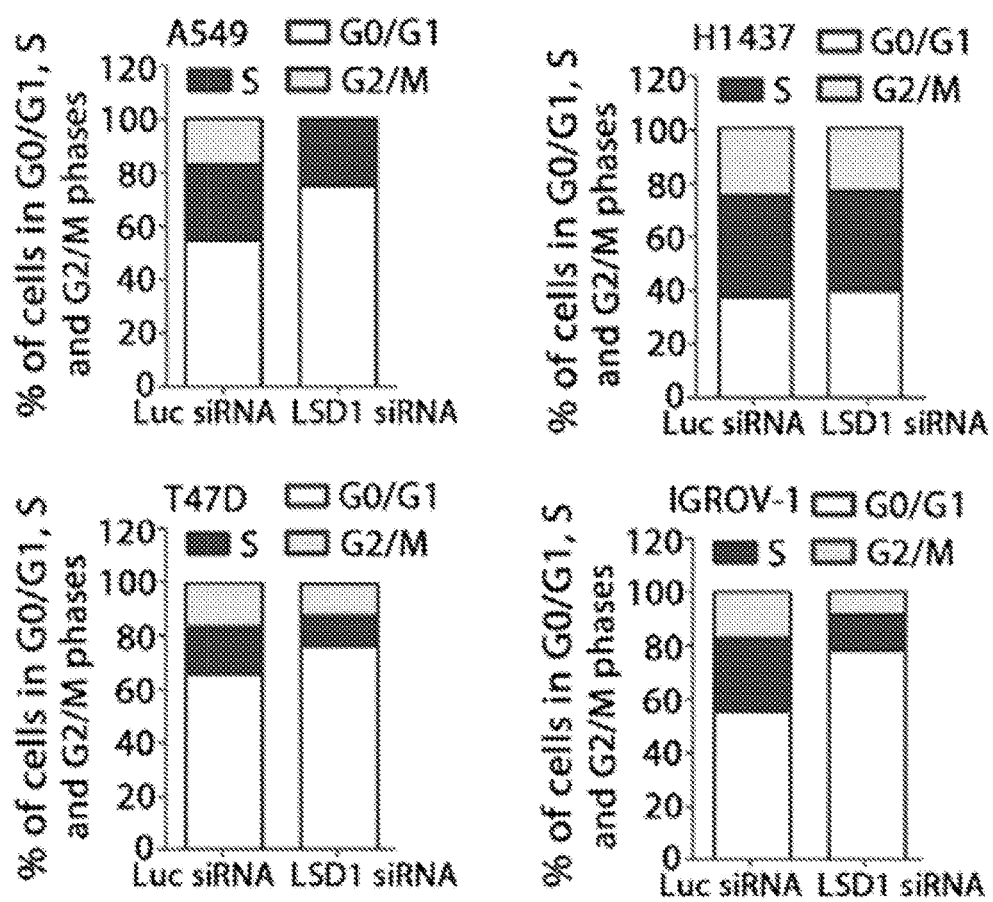
FIG. 9A-C show representative data pertaining to the ablation of LSD1 by specific siRNAs.
Figure 9B:
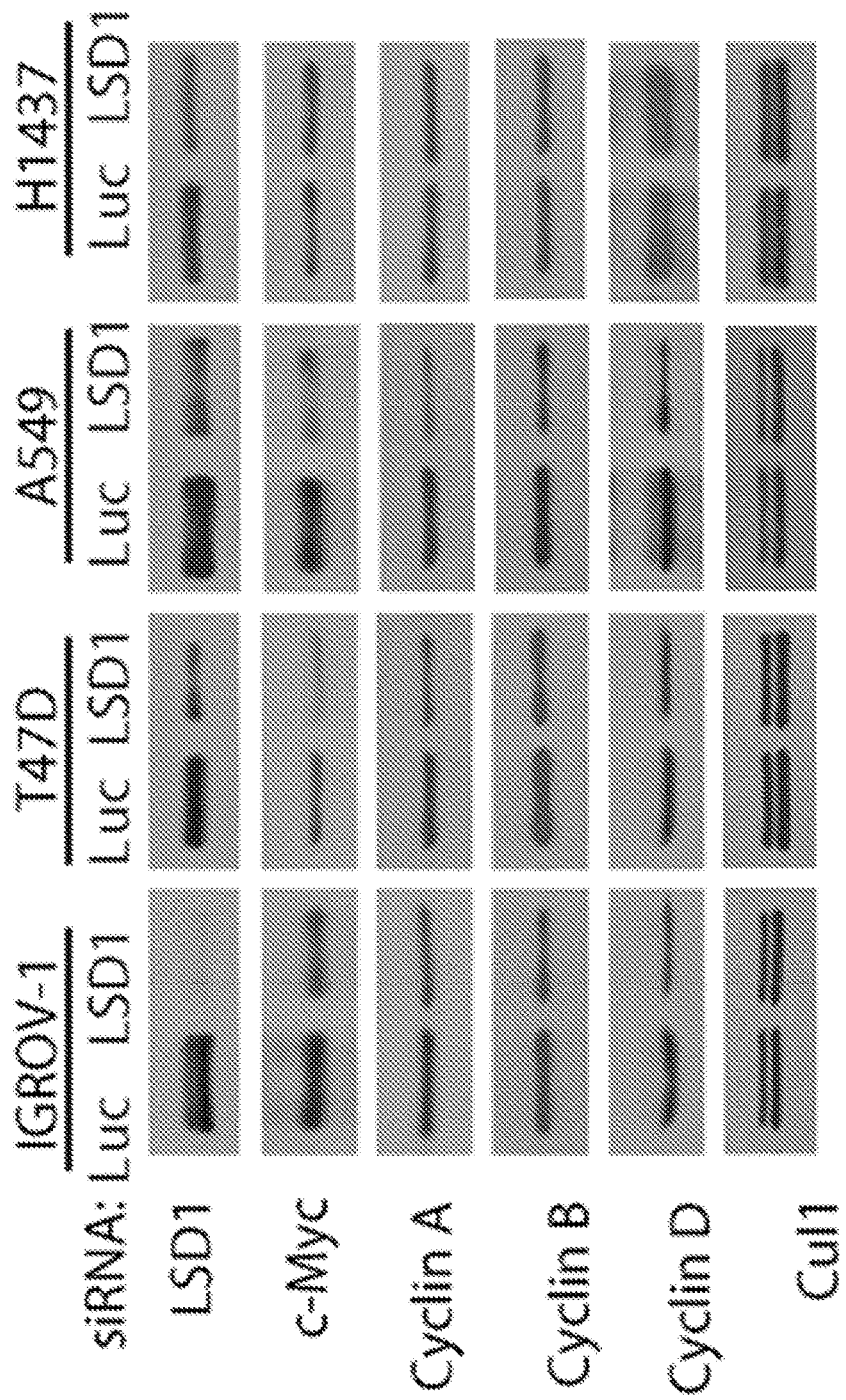
Figure 9C:
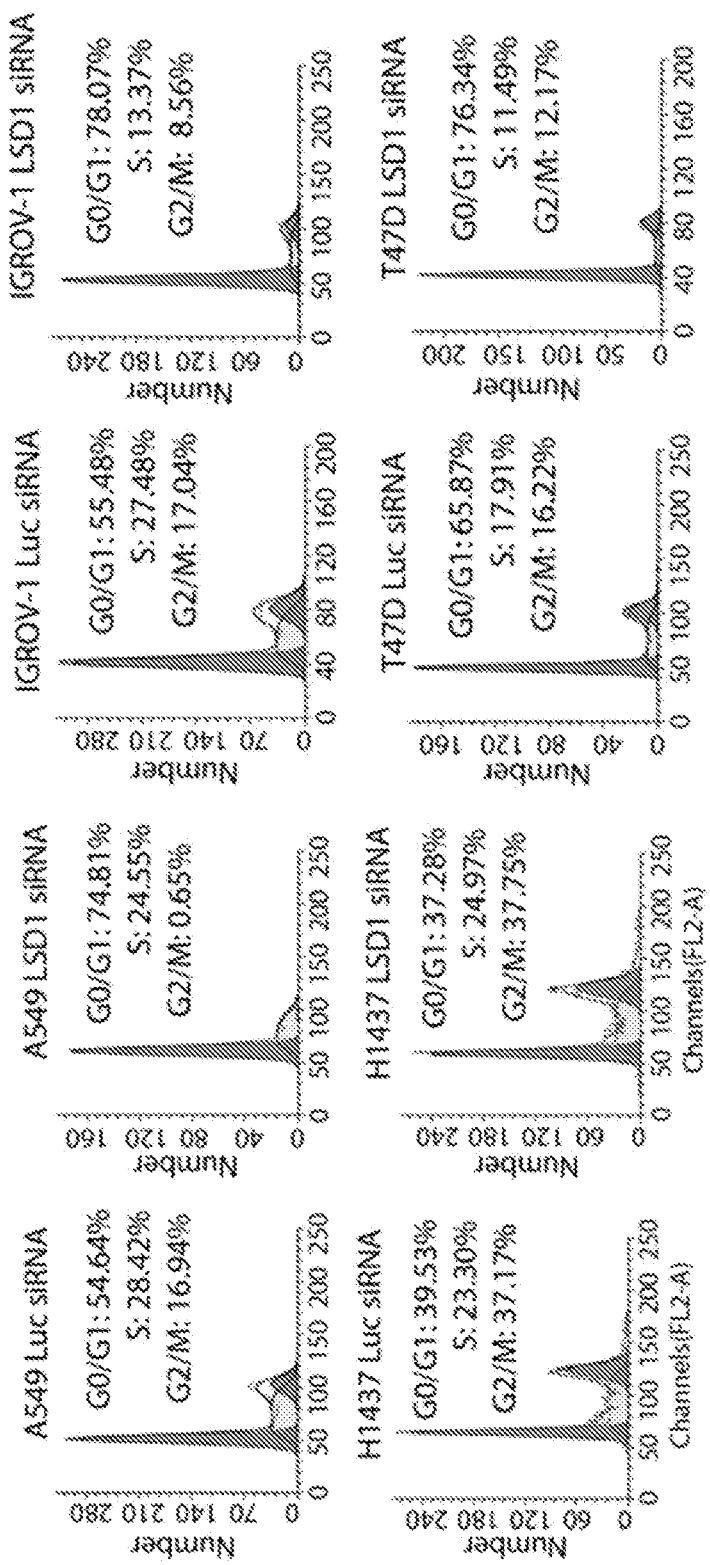

Referring to FIGS. 8A and 8B, ovarian A2780 and breast T47D carcinoma cells were treated with various concentrations of LSD1 inhibitors CBB1003 and CBB1007 for 30 hours as indicated. Cell growth was monitored (8A) and quantified by the MTT assay (8B). All error bars indicate mean±SD. *: p<0.05 and **: p<0.01.

Referring to FIG. 8C, A2780 and T47D cells were transfected with 50 nM luciferase or LSD1 specific siRNAs for 60 hours. Cell growth inhibition was analyzed by MTT. The effects of LSD1 siRNAs on LSD1 and methylations on histone H3K4 proteins were monitored by Western blotting using specific antibodies (right). **: p<0.01.

Referring to FIG. 9A, ablation of LSD1 by siRNAs induces G1 cell-cycle arrest in Sox2-expressing A549, T47D, and IGROV1 cells, but not in Sox2-negative H1437 carcinoma cells. The distributions of the cell cycle population were as follows: A549 cells, Luc siRNA: G0/G1: 54.64%, S: 28.42%, G2/M: 16.94%; and A549, LDS1 siRNA: G0/g1: 74.81%, S: 24.55%, G2/M: 0.65%. IGROV1 cells, Luc siRNA: G0/G1: 55.48%, S: 27.48%, G2/M: 17.04%; and IGROV1, LSD1 siRNA: G0/G1: 78.07%, S: 13.37%, G2/M: 8.56%. T47D cells, Luc: G0/G1: 65.87%, S: 17.91%, G2/M: 16.22%; and T47D, LSD1 siRNA: G0/G1: 76.34%, S: 11.49%, G2/M: 12.17%. H1437 cells, Luc siRNA: G0/G1: 39.53%, S: 23.30%, G2/M: 37.17%; and H1437 cells, LSD1 siRNA: G0/G1: 37.28%, S: 24.97%, G2/M: 37.75%.

Referring to FIG. 9B, the effects of LSD1 inactivation on the protein levels of c-Myc and cyclins are shown. The indicated cells were transfected with 50 nM Luc or LSD1 siRNAs, and histone methylation were analyzed.

Referring to FIG. 9C, Sox2-expressing A549, IGROV1, T47D and Sox2-negative H1437 cells were transfected with 50 nM luciferase (Luc) or LSD1 specific siRNAs for 60 hours and the cell cycle was analyzed by flow-cytometry (FACS). The Sox2-expressing cells were G1 cell cycle arrested by LSD1 inactivation but not Sox2-negative H1437 cells.

7. Sox2 is the Only PSC Protein Whose Expression Correlates with Sensitivity to LSD1 Inactivation in Carcinoma Cells Previous studies indicated that sensitivity to LSD1 inactivation is usually associated with cells derived from germ cell tumors that express PSC proteins (Wang, J., et al. (2011) Cancer Research 71, 7238-7249). As some of the breast and ovarian cancer cells in this collection were reported to express PSC proteins such as Oct4, Sox2, Lin28, Nanog, and/or Sal14 (Leis, O., et al. (2012) Oncogene 31, 1354-1365; Peng, S., et al. (2008) Oncogene 29, 2153-2159; Zhong, X., et al. (2010) J. Biol. Chem. 285, 41961-41971), a direct correlation between the expression of these proteins and the sensitivity to LSD1 inactivation has not been established. To determine the mechanism by which various carcinoma cells are sensitive to LSD1 inactivation, the expression of known PSC proteins in the collected cell lines was analyzed and their expression correlated with the sensitivity to LSD1 inactivation, using teratocarcinoma/embryonic carcinoma F9 and NTERA-2 cells and cervical carcinoma HeLa cells as controls (FIG. 10A; see Table 1 above) (Wang, J., et al. (2011) Cancer Research 71, 7238-7249).

Figure 10A:
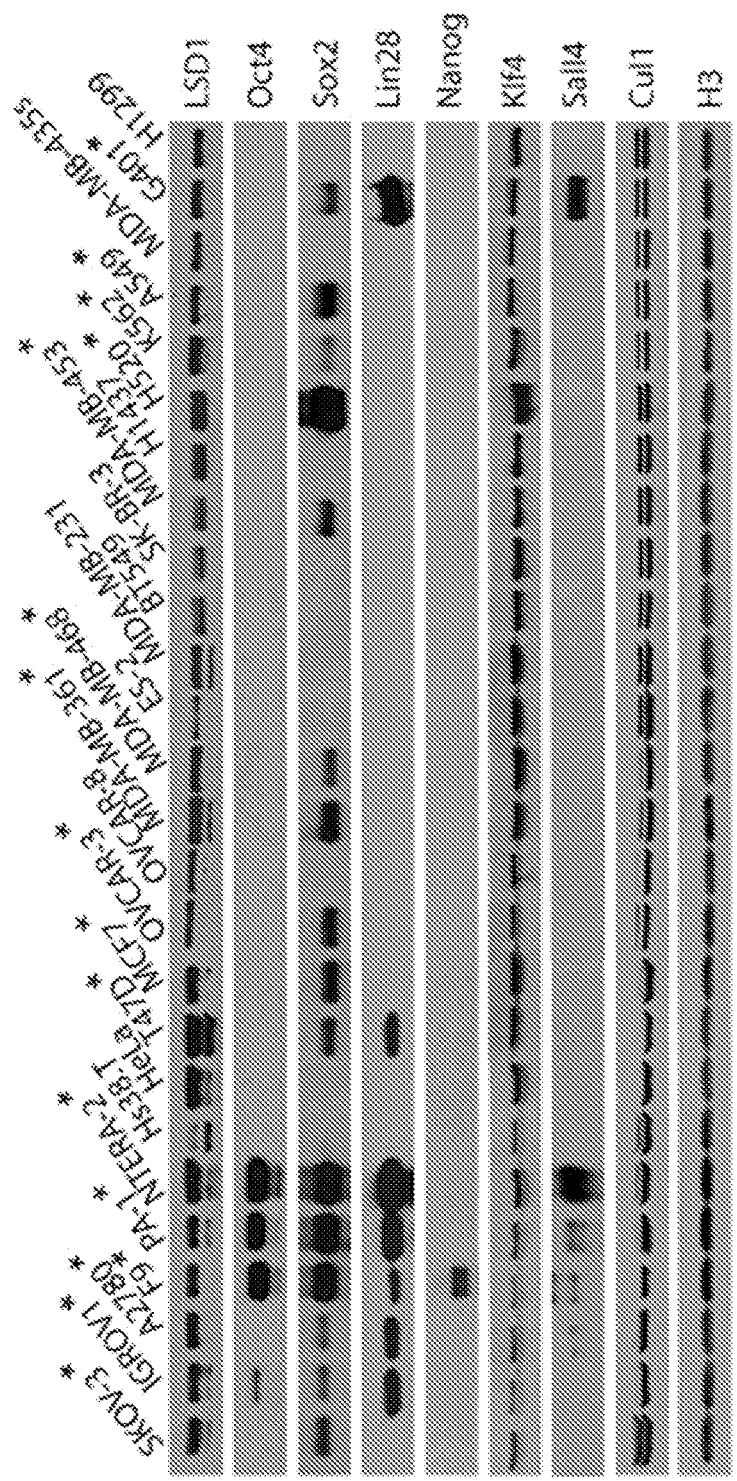
FIG. 10A-C show representative data pertaining to the expression of Oct 4, Sox2, Nano, Lin28, Sal14, and other proteins in lung, breast, ovarian, teratocarcinoma, embryonic carcinoma, and other carcinoma cells.

Referring to FIG. 10A, analysis of the expression of Oct4, Sox2, Nanog, Lin28, Sal14, and other proteins in lung, breast, ovarian, teratocarcinoma, embryonic carcinoma, and other carcinoma cells as indicated is shown. Cells that are sensitive to LSD1 inactivation are indicated by *. Among PSC proteins, only the expression of Sox2 correlates with the growth-inhibitory effects of LSD1 inactivation.

Several notable findings were revealed using this approach. First, it was determined that Oct4, Lin28, Sal14, and Nanog were each expressed in breast and ovarian carcinoma IGROV1, A2780, and T47D cells, and all teratocarcinoma/embryonic carcinoma F9, PA-1, and NTERA-2 cells (FIG. 10A). Not find a single cell line was found that expressed these PSC proteins independently of Sox2, suggesting the importance of Sox2. Second, Sox2 was the only PSC protein that was expressed alone and independently of other PSC proteins in SKOV-3, OVCAR-3, MCF-7, MDA-MB-361, MDA-MB-468, MDA-MB-453, NCI-H520, and A549 cells, again indicating that Sox2 is unique for these carcinoma cells. Third, and most importantly, these analyses revealed that all Sox2-expressing carcinoma cells were sensitive to LSD1 inactivation, whereas all Sox2-negative cancer cells were insensitive (FIG. 10A; Table 1). Consistently, it was also found that K562, a human myelogenous leukemia cell, and G401, a human rhabdoid-tumor-derived cell, also expressed Sox2, and both were sensitive to LSD1 inhibition, whereas MDA-MB-4355, a melanoma cell that does not express Sox2, was insensitive (FIGS. 10A, 10B, and 10C; Table 1). Whereas K652 cells only express Sox2, G401 cells also express Lin28 and Sal14. Without wishing to be bound by theory, these data suggest that there is a strong correlation between Sox2 expression and sensitivity to LSD1 inactivation.

Figure 10C:
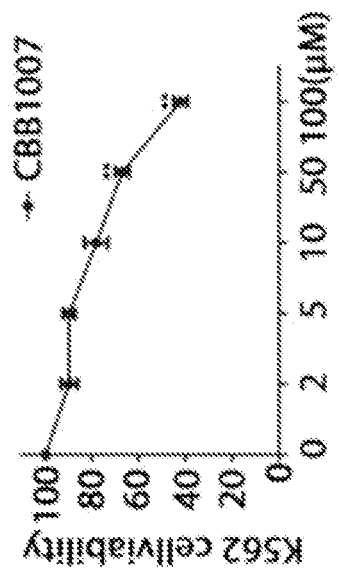
Figure 10B:
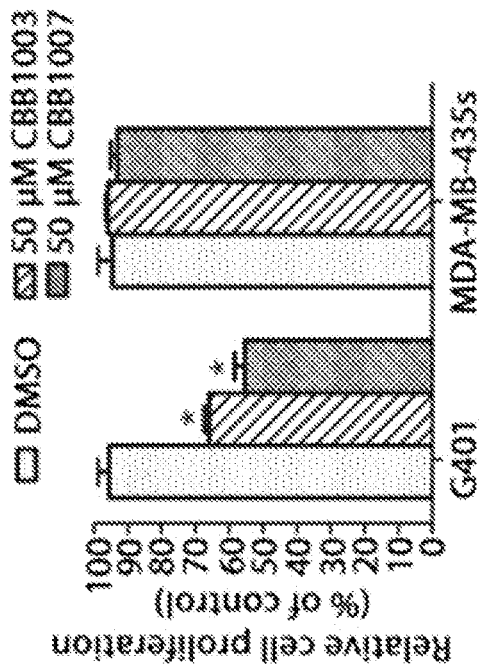

Referring to FIG. 10B, Sox2-expressing myelogenous leukemia and rhabdoid tumor cells were also sensitive to LSD1 inhibitors. The growth of human Sox2-expressing rhabdoid tumor G401 cells was inhibited after treatment of 50 µM CBB1007 or CBB1003 for 30 hours but not that of Sox2-negative melanoma MDA-MB-435s cells. The statistical differences between compound treated and control groups were analyzed by One-way ANOVA. *: p<0.05 and **: p<0.01.

Referring to FIG. 10C, human myelogenous leukemia K562 cells, which express Sox2, were treated with increasing concentrations of LSD1 inhibitor CBB1007 for 30 hours and relative cell viability of compound-treated and control groups was analyzed.

Figure 11A:
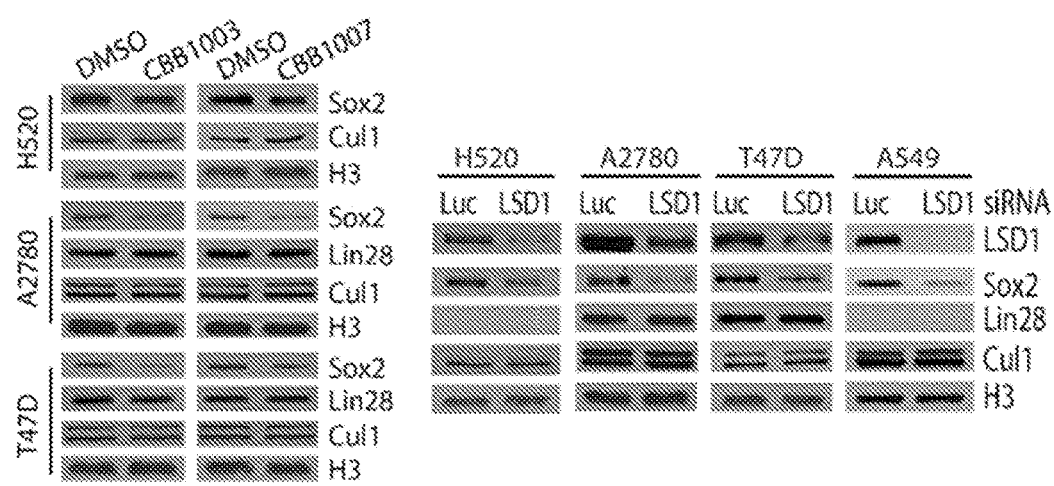
FIG. 11A-C show representative data pertaining to the regulation of Sox2 expression by LSD1.

8. LDS1 Inactivation of LSD1 Suppresses Sox2 Expression and Increases the Mono- and Dimethylation of H3K9 and Trimethylation of H3K27 Only in Sox2-Expressing Carcinoma Cells Analysis of the effects of LSD1 inactivation revealed that LSD1 inactivation consistently reduced the expression of Sox2 in H520, A2780, T47D (FIGS. 11A and 11B), and other Sox2-expressing cancer cells (FIG. 11C). In contrast, LSD1 inactivation did not change the levels of Lin28, another PSC protein, which is often co-expressed with Sox2 in a fraction of carcinoma cells (FIGS. 10A, 11A, and 11C). Without wishing to be bound by theory, these data suggest that LSD1 is required for the expression of Sox2 in these carcinoma cells.

Referring to FIG. 11A, inactivation of LSD1 by LSD1 inhibitors or siRNAs caused the downregulation of Sox2. The indicated carcinoma cells were treated with 50 mM of the LSD1 inhibitors CBB1007 and CBB1003 for 30 hr or with 50 nM of Luc or LSD1 siRNAs for 60 hr. The protein levels of LSD1, Sox2, Lin28, CUL1, and histone H3 were analyzed by western blotting.

Figure 11B:
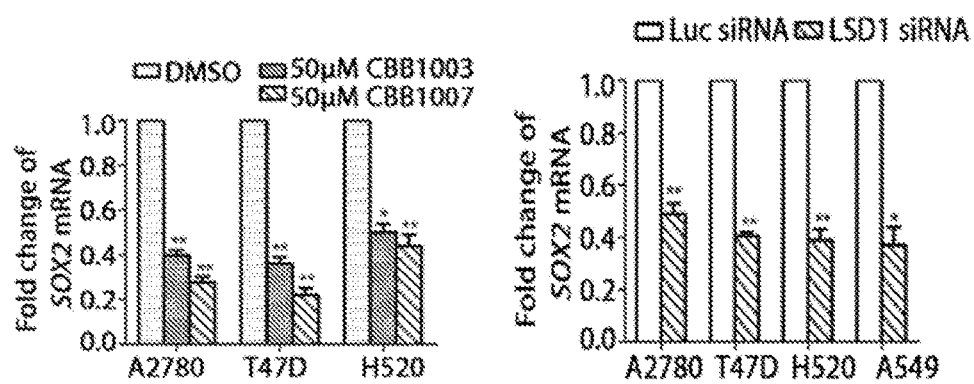
Figure 11C:
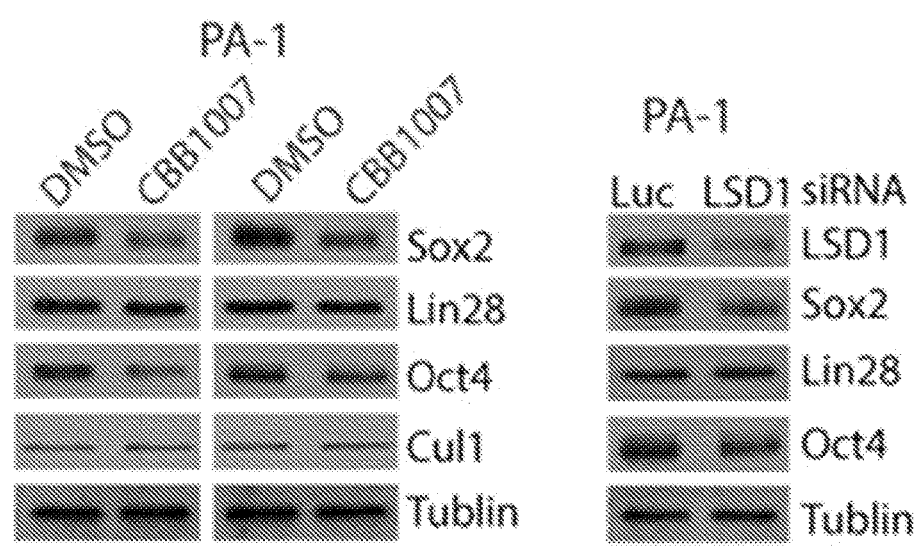

Referring to FIG. 11B, the mRNA levels of Sox2 were analyzed by real-time quantitative RT-PCR. Data are presented as mean±SD. **$p<0.01$.

Referring to FIG. 11C, ovarian teratocarcinoma PA-1 cells were either treated with 50 μM CBB1007 for 30 hours, or transfected with luciferase (Luc) or LSD1 specific siRNAs for 48 hours. The protein levels of Sox2, Oct4, Lin28 and control proteins CUL1 and tublin were monitored by Western blotting analysis with specific antibodies.

As LSD1 is a histone demethylase that removes the mono- and dimethyl groups from methylated H3K4 (H3K4me1/me2) (Shi, Y., et al. (2004) Cell 119, 941-953), LSD1 inactivation caused a dose dependent increase of H3K4me1/me2 in both Sox2-positive and -negative cells (FIGS. 8C, 12A, and 12B), indicating that the inhibitors specifically blocked LSD1 demethylase activity in all cancer cells.

Figure 12A:
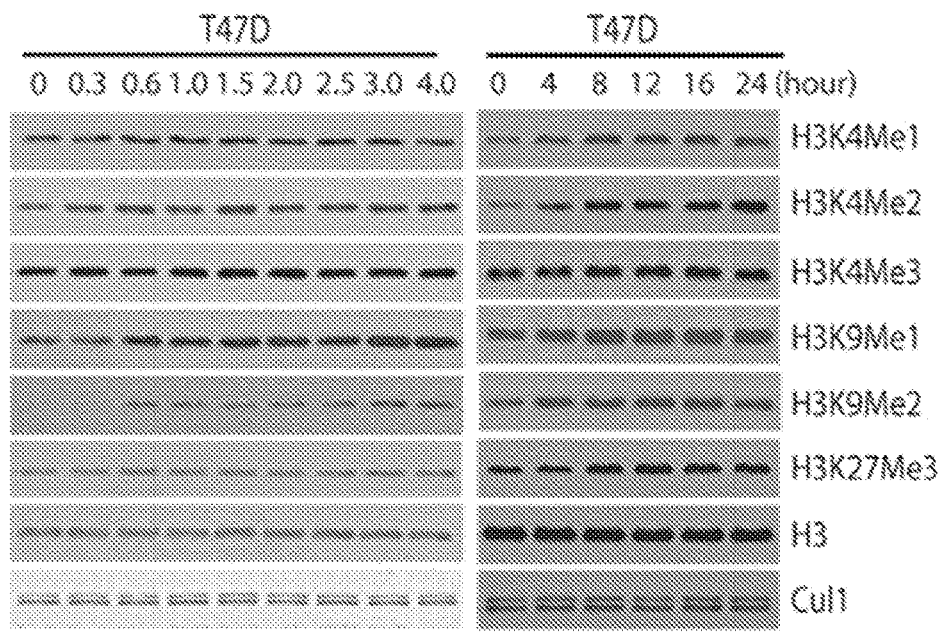
FIGS. 12A and 12B show representative data demonstrating that LSD1 regulates Sox2 expression by modulating bivalent H3K9 and H3K4 methylations.

Referring to FIG. 12A, T47D cells were treated with 50 mM CBB1007. They were subsequently harvested at various time points as indicated. The effects of the LSD1 inhibitor on H3K4, H3K9, and H3K27 methylations were examined.

Figure 12B:
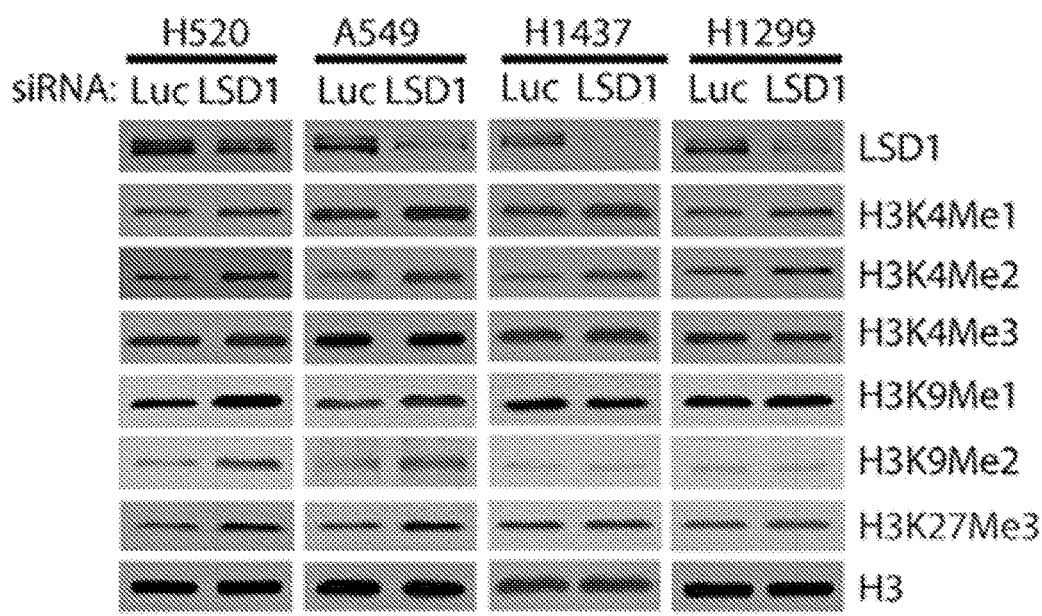

Referring to FIG. 12B, the indicated cells were transfected with 50 nM Luc or LSD1 siRNAs, and histone methylations were analyzed as above.

Because LSD1 interacts with the androgen receptor to act as an H3K9-specific demethylase to remove the mono- and dimethyl groups from methylated H3K9 (H3K9me1/me2) in certain prostate cancer cells (Metzger, E., et al. (2005) Nature, 437, 436-439), the effect of LSD1 inactivation on H3K9me1/me2 as well as the trimethylation of histone H3 at lysine 27 (H3K27me3), which is not a target of LSD1, was also examined Strikingly, LSD1 inactivation induced global increases of both H3K9me1/me2 and H3K27me3 only in Sox2-expressing carcinoma cells, but not in Sox2-negative cancer cells such as H1299 or H1437 (FIGS. 12A and 12B). A kinetic analysis of induction revealed that the increases of both H3K4me1/2 and H3K9me1/2 occurred early (<1 hr) and simultaneously, whereas H3K27me3 was induced much later (4-8 hr; FIG. 12A) after LSD1 inhibition, suggesting that the increases of H3K4me1/2- and H3K9me1/2 are likely a direct consequence of LSD1 inhibition, and H3K27me3 elevation may occur as a secondary event.

9. LSD1 Binds Directly to the Transcriptional Regulatory Region of Sox2 to Regulate Bivalent H3K4 and H3K9 Methylation Because LSD1 inactivation reduced Sox2 expression, in order to determine whether Sox2 is a direct target of LSD1, a chromatin immunoprecipitation (ChIP) assay (Whyte, W. A., et al. (2012) Nature 482, 221-225) was used to determine whether LSD1 binds to the Sox2 gene. ChIP analysis revealed that LSD1 is enriched in the transcriptional regulatory region (_3.0 to _4.0 kb) of the Sox2 gene (FIG. 13A) a region that was reported to act as a distal enhancer for Sox2 expression in breast cancer cells (Leis, O., et al. (2012) Oncogene 31, 1354-1365). This enrichment of LSD1 appears to be specific for Sox2, as no enrichment was observed on Lin28, Klf4, or the pericentromeric heterochromatin region (Dovey, O. M., et al. (2010) Proc. Natl. Acad. Sci. USA 107, 8242-8247; FIG. 13B), which are not regulated by LSD1.

Figure 13A:
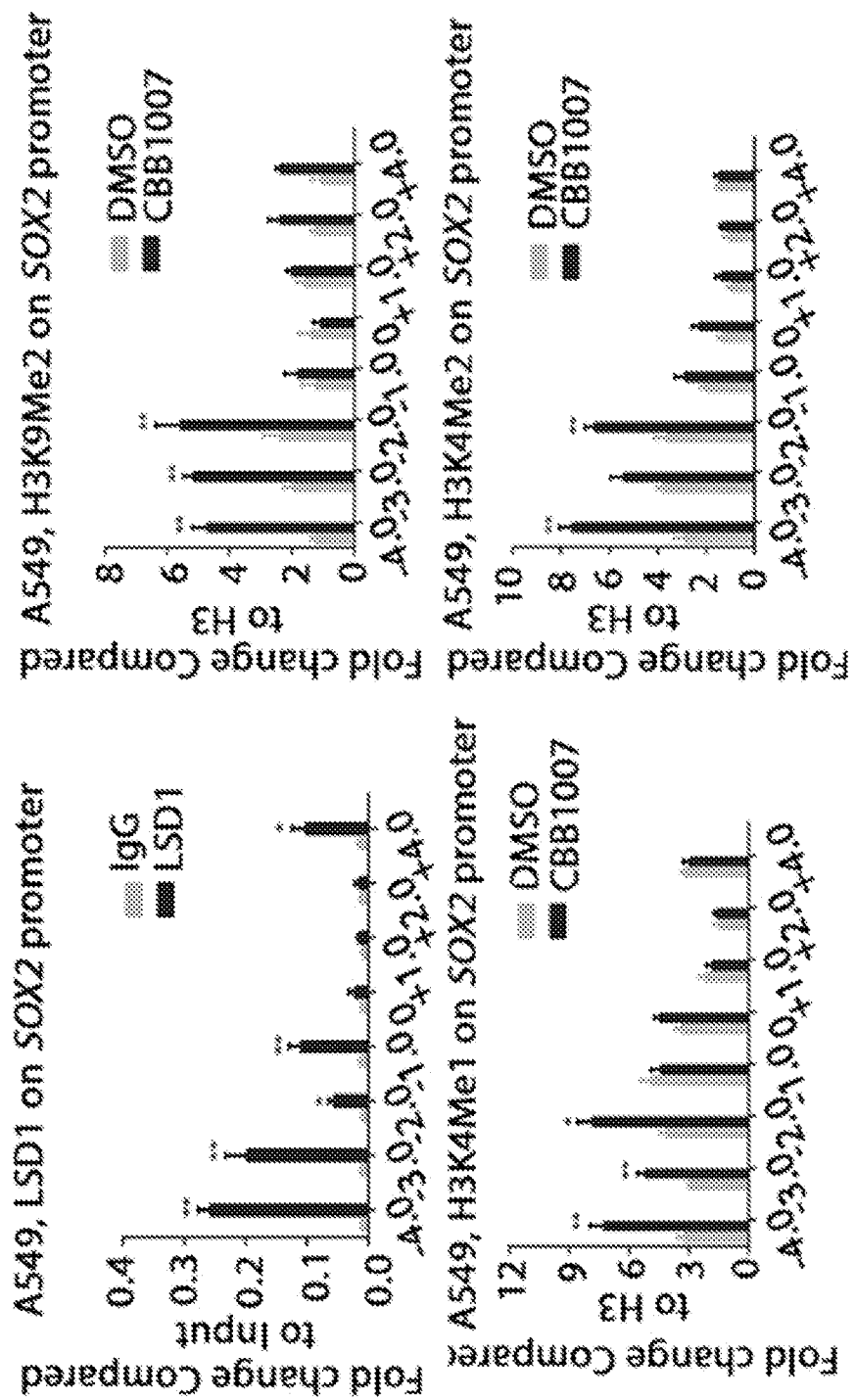
FIG. 13A-C show representative data pertaining to the presence of LSD1, H3K4me1/2, H3K9me2, and H3K27Me3 on either the Sox2 gene, the FoxA2 gene, the CyclinA gene, or SAT2 in A549 (13A-C) or A2780 (13C) cells.
Figure 13B:
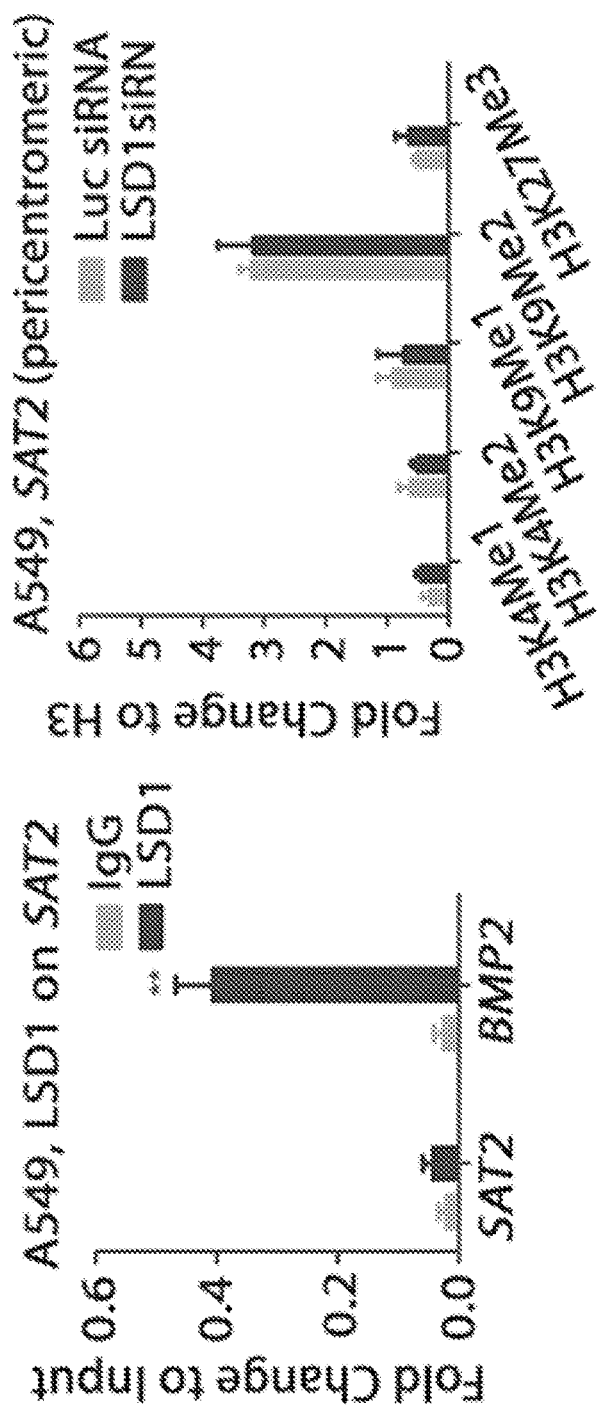

Referring to FIG. 13A, ChIP assays for the presence of LSD1, H3K4me1/2, and H3K9me2 on the Sox2 gene in A549 cells were performed. Chromatin-associated proteins were crosslinked to chromatin, sonicated (average 500-1,000 bp DNA), and immunoprecipitated with control rabbit immunoglobulin G (IgG), LSD1, or H3K9me2 antibodies as indicated. The DNA fragments were purified and used for real-time quantitative PCR with various primers along the Sox2 promoter. Data are presented as mean±SD. The statistical differences for increased H3K4 and H3K9 methylations along the Sox2 gene between inhibitor-treated and control groups were analyzed by one-way ANOVA. *$p<0.05$, **$p<0.01$.

Referring to FIG. 13B, ChIP assays for the presence of LSD1, H3K9me2, H3K4me1, and H3K4me2 on the pericentromeric heterochromatin region SAT2 and BMP2 genes after LSD1 inactivation in A549 cells. Chromatin fragments were immunoprecipitated with control rabbit IgG-, LSD1-, H3K9me2-, H3K4me1-, and H3K4me2-specific antibodies as indicated. The DNA fragments were purified and used for real-time quantitative PCR with various primers along the FOXA2 and cyclin A genes or the SAT2 and BMP2 regions. Data are presented as mean±SD.

Figure 13C:
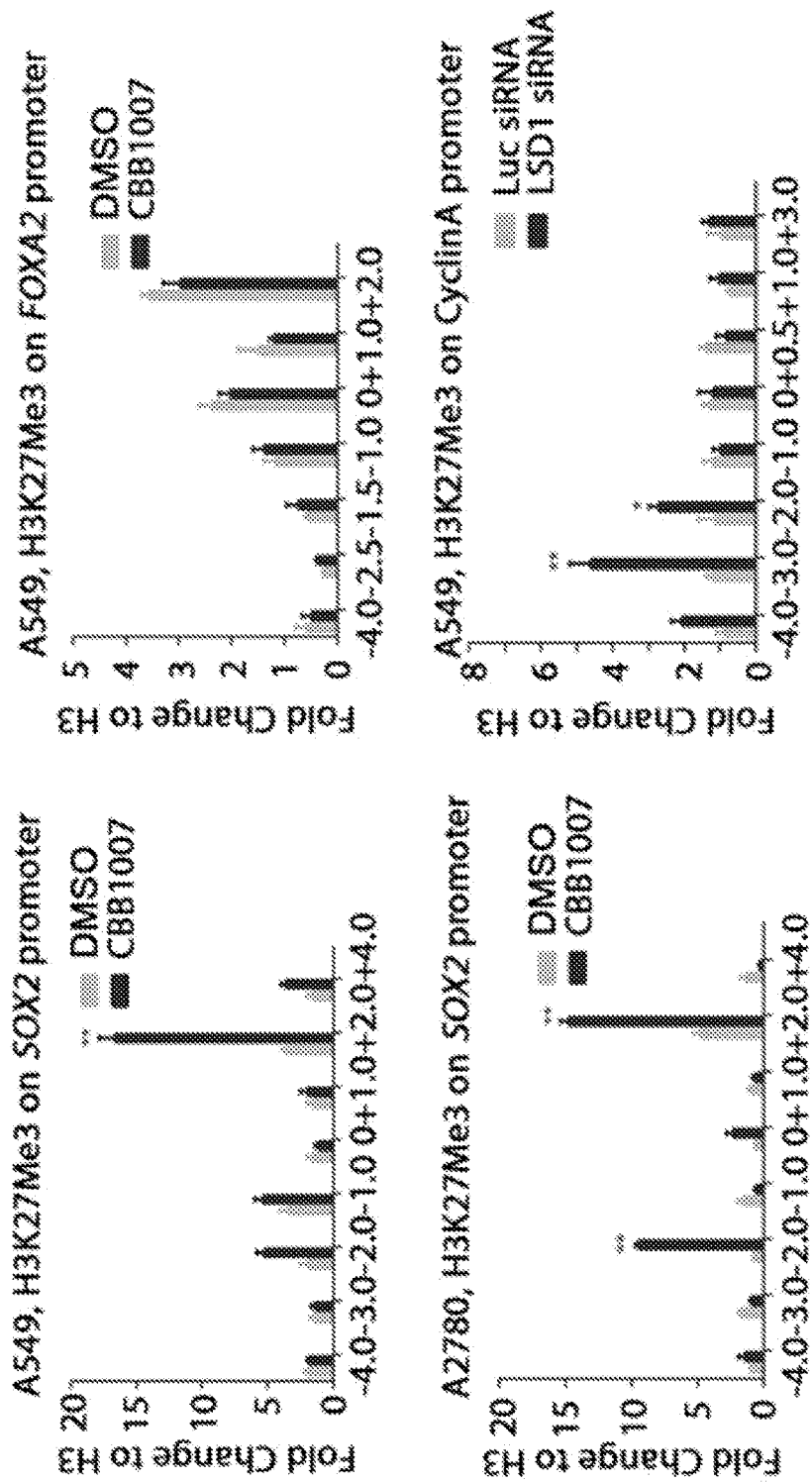

To determine whether LSD1 binding is associated with the demethylase activity on Sox2, the presence and changes of the characteristic H3K4me1/me2 and H3K9me1/me2 on Sox2 after LSD1 inactivation were examined Repeated ChIP analyses in Sox2-expressing cells, such as A2780 and A549 cells, consistently revealed that H3K9me2 (ChIPgrade H3K9me1 antibodies were not good) and H3K4me1/me2 were present in the Sox2 regulatory region, and inhibition of LSD1 caused significantly increased levels of both H3K9me2 and H3K4m1/me2 on Sox2 (FIG. 13A). Reciprocal re-ChIP of H3K9me2 or H3K4me2-enriched chromatin fragments revealed that H3K9me2 and H3K4me2 coexisted on the same Sox2 regulatory fragment. Although H3K27me3 was also induced on Sox2, the major site was located farther down the gene within the coding region (+2.0; FIG. 13C). Thus, without wishing to be bound by theory, these data suggest that the Sox2 regulatory region is regulated directly by the bivalent H3K4 and H3K9 methylations by LSD1 demethylase. Sox2 downregulation after LSD1 inactivation is likely to be directly caused by increased repressive H3K9 methylations on the Sox2 gene, even though H3K4me1/2 also increased on Sox2 (see below).

Referring to FIG. 13C, Sox2-expressing lung carcinoma A549 and ovarian carcinoma A2780 cells were treated with 50 μM CBB1007 for 30 hours or transfected with luciferase or LSD1 siRNAs for 48 hours as indicated. The changes of H3K27me3 along the transcriptional regulatory regions of Sox2, FOXA2, and cyclin A genes after LSD1 inactivation were analyzed using the ChIP assays.

Figure 14:
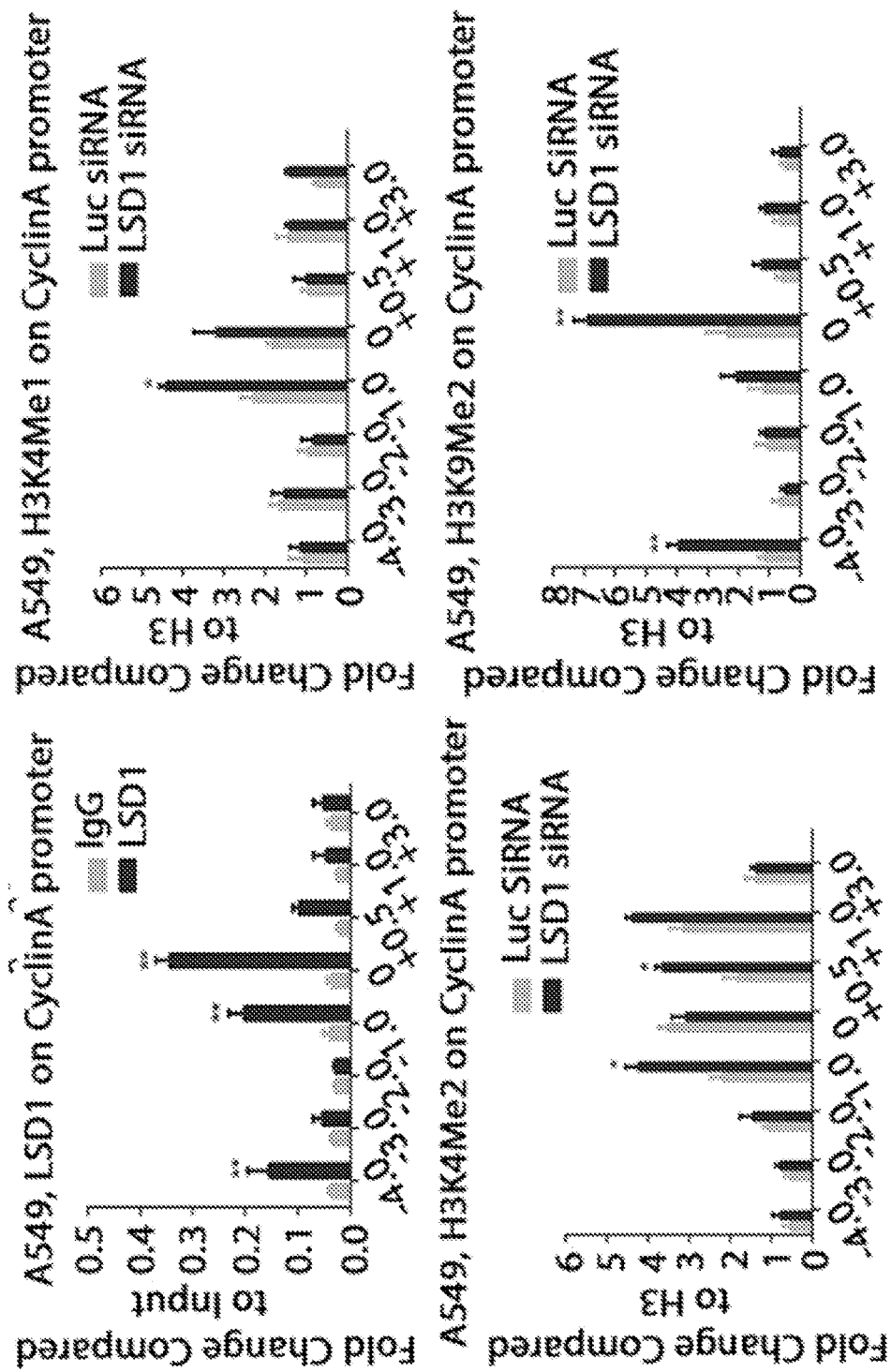
FIG. 14 shows representative data pertaining to the presence of LSD1, H3K4Me1 and H3K4Me2 on the CyclinA gene in A549 cells.

ChIP analysis also indicated that LSD1 also binds to the cyclin A, cyclin B, and cyclin D1 genes, and inactivation of LSD1 caused the increased levels of H3K4me1/me2, H3K9me2, and H3K27me3 on the cyclin promoters (FIGS. 13C and 14). Thus, without wishing to be bound by theory, these data suggest that increased levels of H3K9me2 on the cyclin genes may also repress the expression of cyclins, which may contribute to the G1 cell-cycle arrest after LSD1 inactivation (FIG. 9A-C).

Referring to FIG. 14, ChIP assays for the presence of LSD1, H3K9me2, H3K4me1, and H3K4me2 on the cyclin A gene after LSD1 inactivation in A549 cells. Chromatin fragments were immunoprecipitated with control rabbit IgG-, LSD1-, H3K9me2-, H3K4me1-, and H3K4me2-specific antibodies as indicated. The DNA fragments were purified and used for real-time quantitative PCR with various primers along the FOXA2 and cyclin A genes or the SAT2 and BMP2 regions. Data are presented as mean±SD.

10. Loss OF LSD1 Suppresses Sox2-Dependent Lineage-Specific Gene Expression

Figure 15A:
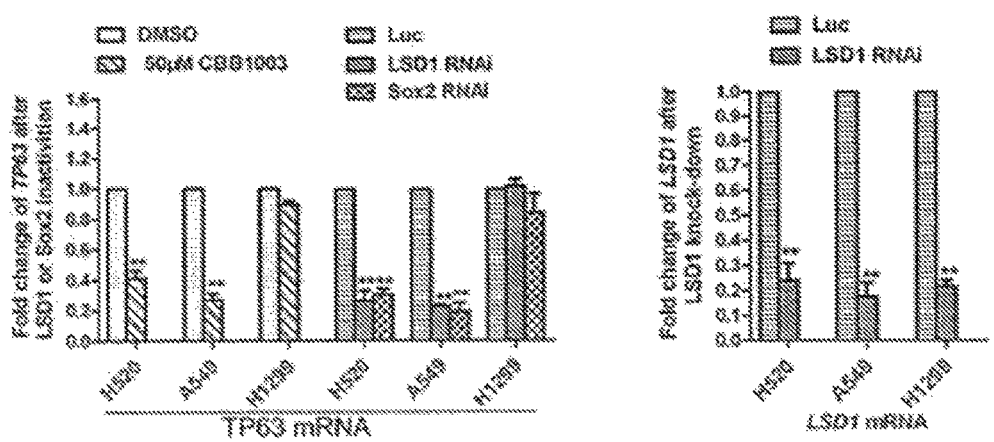
FIGS. 15A and 15B show representative data demonstrating that LSD1 deficiency suppresses the expression of Sox2-regulated lineage-specific genes.
Figure 15B:
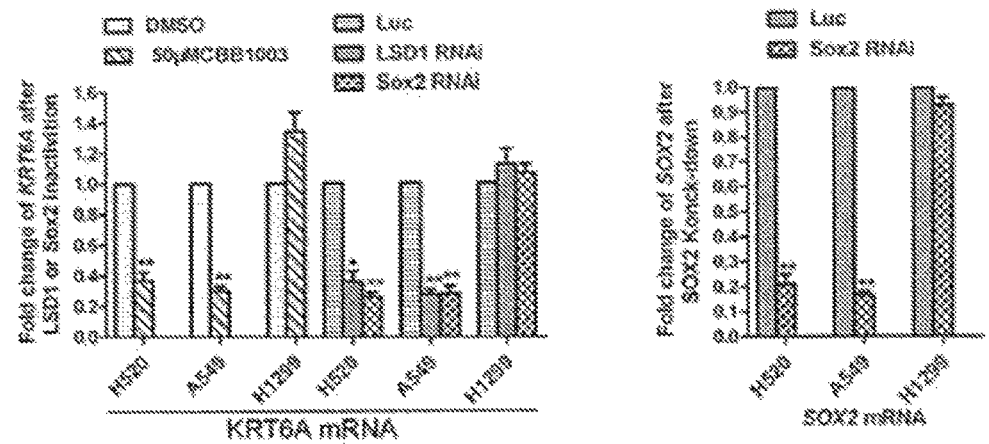

In lung squamous cell carcinomas, Sox2 acts as a lineage-survival oncogene and is required for the expression of lineage-specific genes such as TP63 and KRT6A (Bass, A. J., et al. (2009) Nat. Genet. 41, 1238-1242). To further analyze the functional correlation between LSD1 inhibition and Sox2 downregulation, the effects of LSD1 and Sox2 inactivation on the expression of lineage-specific TP63 and KRT6A genes in lung carcinoma cells were examined. It was found that loss of either LSD1 or Sox2 led to the down-regulation of PT63 and KRT6A expression in Sox2-expressing NCI-H520 and A549 lung carcinoma cells but not in Sox2-negative H1299 lung carcinoma cells (FIGS. 15A and 15B). As lineage-specific gene expression is regulated by Sox2 in Sox2-expressing lung carcinoma cells (Bass, A. J., et al. (2009) Nat. Genet. 41, 1238-1242), these data suggest that LSD1 directly acts on a Sox2-dependent stem cell regulatory transcriptional program to promote the lineage-survival oncogene function of Sox2.

Referring to FIGS. 15A and 15B, lineage-specific genes TP63 (15A) and KRT6A (15B) were down-regulated after the inactivation of LSD1 or Sox2. Left panels: lung carcinoma NCI-H520, A549, and H1299 cells were either treated with 50 µM CBB1003 for 30 hours or were transfected with Luc, LSD1, or Sox2 specific siRNAs for 48 hours as indicated. The mRNA levels of TP63 and KRT6A were down-regulated in Sox2-expressing H520 and A549 cells but not H1299 cells. The statistical differences between experimental and control groups were analyzed by one-way ANOVA (*: $p<0.05$ and **: $p<0.01$). Right panels: the ablation efficiency of LSD1 and Sox2 siRNAs was examined.

11. Loss of Sox2 Phenocopies the Growth-Inhibitory Effects of LSD1 Inactivation on Carcinoma Cells Although Sox2 acts as an amplified lineage-survival oncogene in lung SCCs (Bass, A. J., et al. (2009) Nat. Genet. 41, 1238-1242), the role of Sox2 in other carcinoma cells remains largely uncharacterized. Because LSD1 inactivation reduced Sox2 expression, the role of Sox2 in regulating cancer cell growth was further investigated. Ablation of Sox2 expression using specific siRNAs consistently showed that it caused G1 cell-cycle arrest and growth inhibition in Sox2-expressing carcinoma cells that are sensitive to LSD1 inactivation, but not in Sox2-negative cancer cells (FIGS. 16A-C, 17A, and 17B). Loss of Sox2 also downregulated c-Myc and cyclin A, cyclin B, and cyclin D1, and induced the expression of genes for differentiation, including FOXA2, HNF4A, BMP2, EOMES, and Sox17 (FIGS. 18A and 18B). However, loss of Sox2 increased only the levels of trimethylated H3K27, and not those of H3K4 and H3K9 methylations; without wishing to be bound by theory, this may suggest that induction of H3K27 trimethylation after LSD1 inactivation might be an indirect consequence of Sox2 downregulation (FIGS. 12A, 12B, and 18A). ChIP analysis revealed that Sox2 inactivation induced elevated H3K27me3 on Sox2 and cyclin promoters after Sox2 ablation, suggesting that increased H3K27me3 on these genes suppressed their expression. Thus, without wishing to be bound by theory, these data indicate that Sox2 serves as a primary and key direct target of LSD1 inactivation for growth inhibition and differentiation, because downregulation of Sox2 further amplifies and enhances the effects of LSD1 inactivation through the increased levels of H3K27me3. This observation is consistent with previous reports of critical thresholds and phenotypes associated with haploid insufficiency and hypomorphic mutations of Sox2 in animals and human diseases (Episkopou, V. (2005) Trends Neurosci. 28, 219-221). Mutations of human Sox2 that compromise one allele of the Sox2 genes were shown to cause anophthalmia-esophageal-genital (AEG) syndrome and exhibited neurological phenotypes, including seizures (Fantes, J., et al. (2003) Nat. Genet. 33, 461-463; Williamson, K. A., et al. (2006) Hum. Mol. Genet. 15, 1413-1422), whereas hypomorphic deletion of the enhancer of the mouse Sox2 genes, which reduced Sox2 mRNA and protein levels by 20%-30% compared with wild type levels, exhibited lower birth frequency and neurological phenotypes in the mouse (Ferri, A. L., et al. (2004) Development 131, 3805-3819).

Figure 16A:
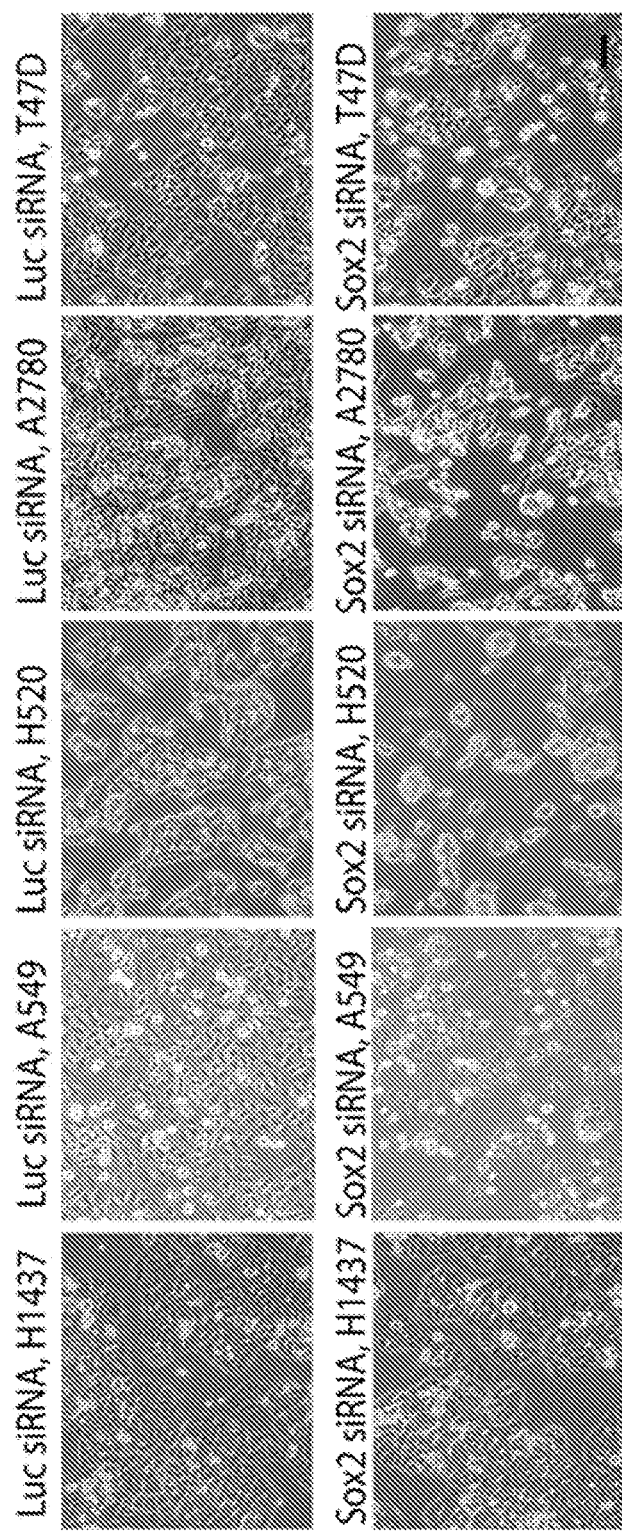
FIG. 16A-C show representative data demonstrating that inactivation of Sox2 causes $G_1$ cell-cycle arrest and inhibits the cell growth of Sox2-expressing carcinoma cells.

Referring to FIG. 16A, A549, NCI-H1437, T47D, and IGROV1 cells were transfected with 50 nM luciferase or Sox2 siRNAs for 60 hr and the cell growth of control and Sox2-ablated cells was examined by microscopy.

Figure 16B:
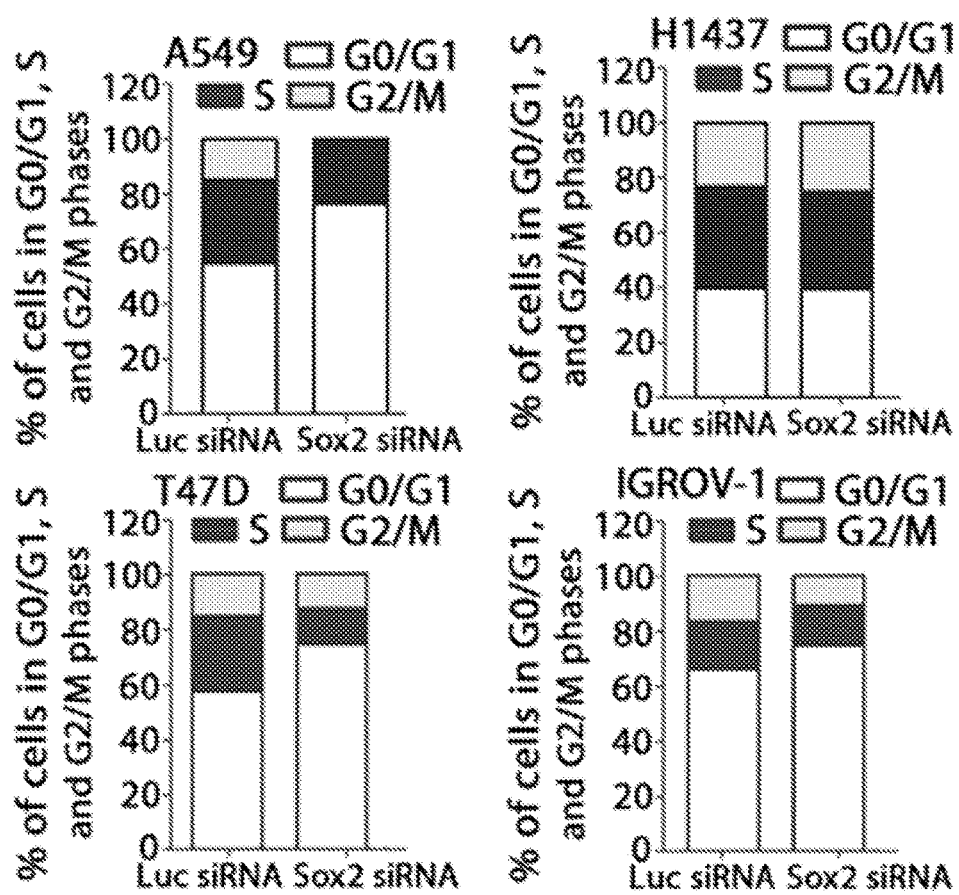

Referring to FIG. 16B, cell cycles after Sox2 inactivation were analyzed by FACS. The cell-cycle distribution of cells was as follows: A549 cells, Luc siRNA: G0/G1: 54.68%, S: 30.52%, G2/M: 14.80%; and A549, Sox2 siRNA: G0/G1: 76.40%, S: 23.41%, G2/M: 0.19%. H1437 cells, Luc siRNA: G0/G1: 39.69%, S: 23.11%, G2/M: 37.20%; and H1437 cells, Sox2 siRNA: G0/G1: 39.39%, S: 25.10%, G2/M: 35.51%. IGROV1 cells, Luc siRNA: G0/G1: 57.29%, S: 27.32%, G2/M: 15.39%; IGROV1, Sox2 siRNA: G0/G1: 74.62%, S: 12.87%, G2/M: 12.52%. T47D cells, Luc: G0/G1: 66.02%, S: 17.27%, G2/M: 16.71%, T47D, Sox2 siRNA: G0/G1: 74.65%, S: 14.48%, G2/M: 10.86%.

Figure 16C:
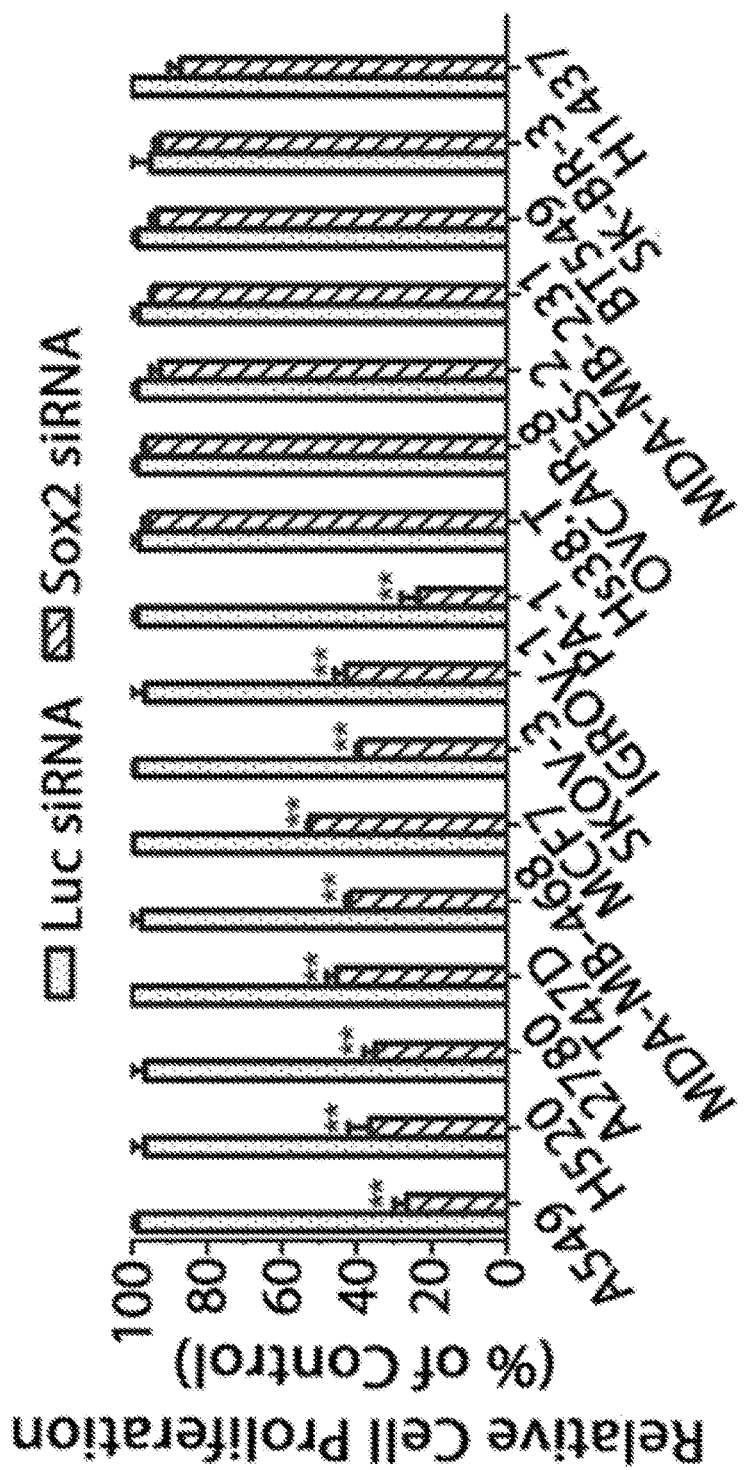

Referring to FIG. 16C, the indicated lung, breast, ovarian, and other carcinoma cells were transfected with 50 nM luciferase or Sox2 siRNAs for 48 hr and cell growth was monitored by MTT assay. *$p<0.05$, **$p<0.01$.

Figure 17A:
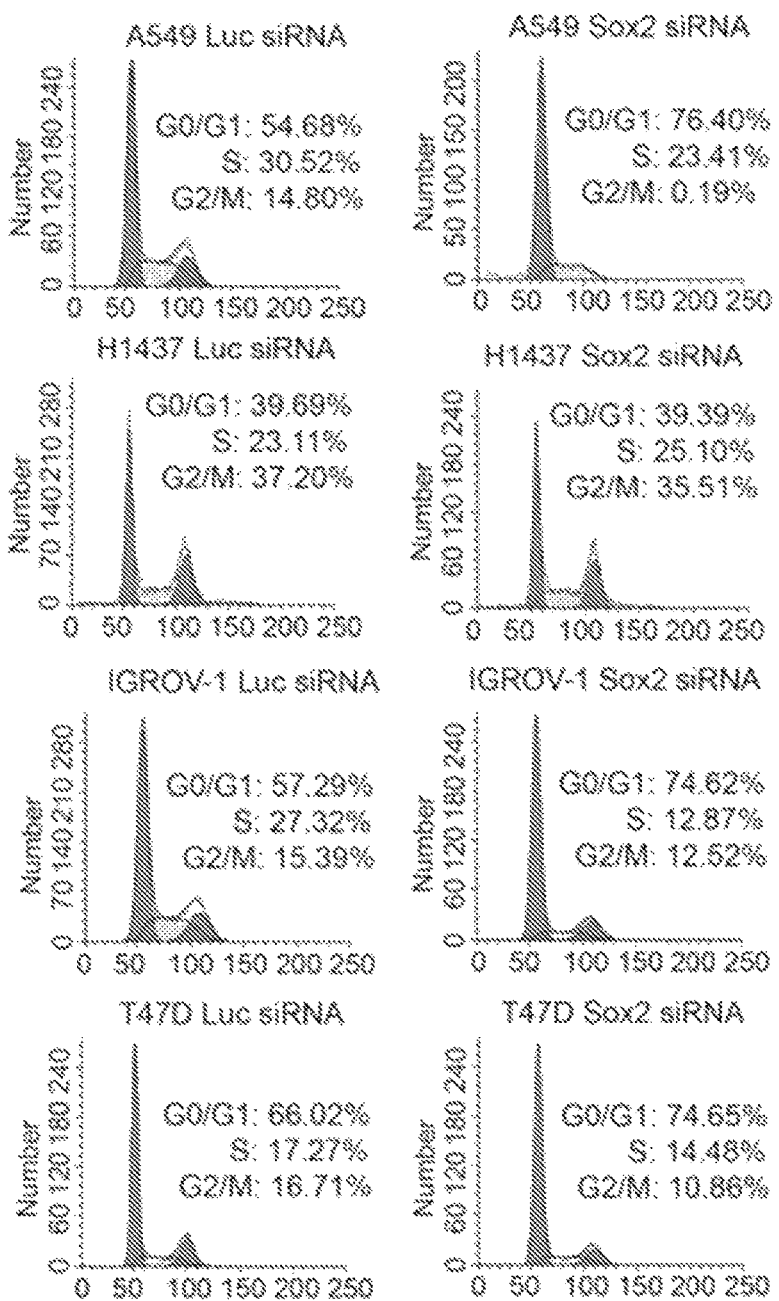
FIG. 17A shows representative data pertaining to the effect of $G_1$ cell cycle arrest on Sox2 in expression.
Figure 18A:
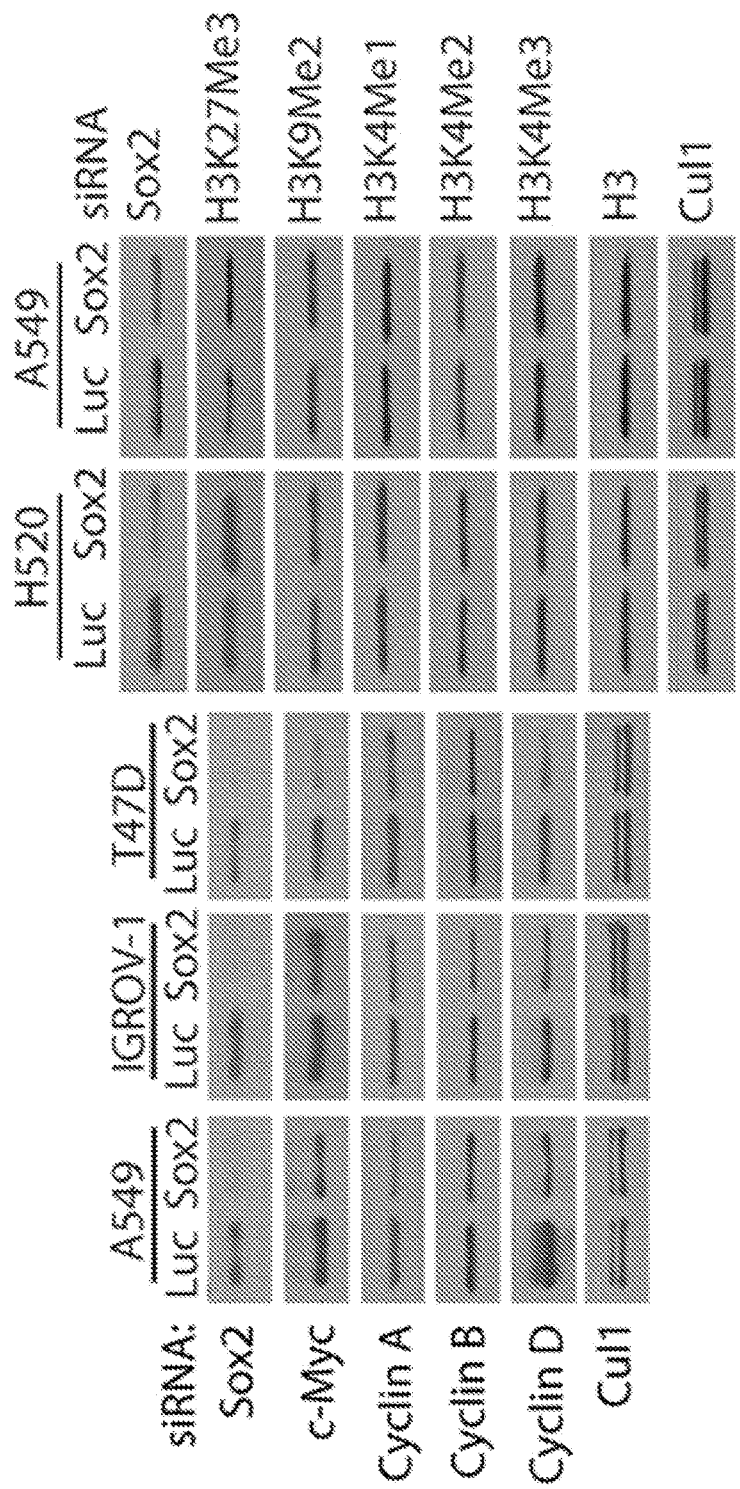
FIGS. 18A and 18B show representative data pertaining to the effects of Sox2 inactivation on cell cycles (18A) and the induction of differentiation genes (18B).
Figure 18B:
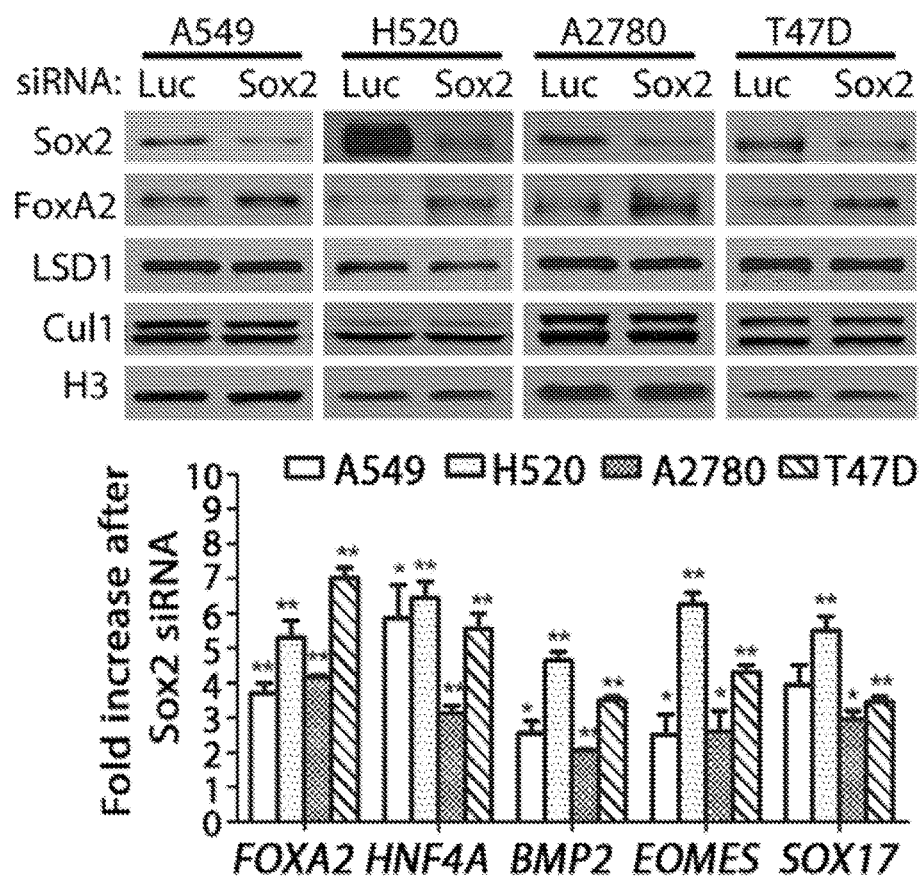

Referring to FIG. 17A, Sox2-expressing A549, IGROV1, and T47D and Sox2-negative H1437 cells were transfected with luciferase and Sox2 specific siRNAs for 48 hours. The cell cycles of these cells after Sox2 ablation were analyzed by flow-cytometry.

Figure 17B:
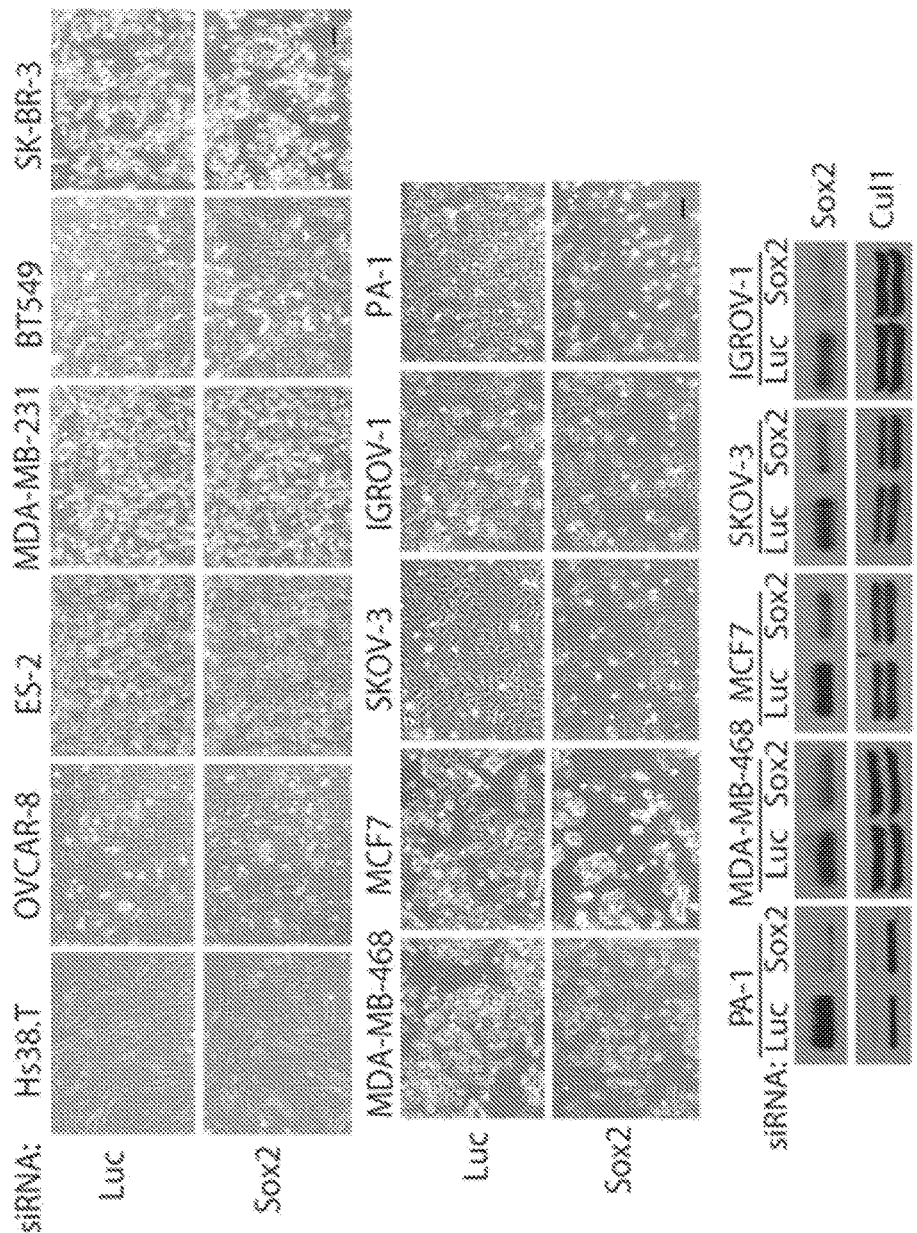
FIG. 17B shows representative data pertaining to the effect of ablation of Sox2 on cells that are sensitive to LSD1 inhibitors.

Referring to FIG. 17B, ablation of Sox2 induced growth inhibition in cells that are sensitive to LSD1 inhibitors, but not in insensitive cells. Ovarian and breast cancer cells were transfected with luciferase (Luc) or Sox2 specific siRNAs for 60 hours as indicated. Cell growth was monitored by microscopy. Scale bar: 100 microns. The effects of Sox2 siRNA were analyzed by Western blotting as indicated.

Referring to FIG. 18A, the effects of Sox2 inactivation as above on c-Myc, cyclins, and methylated H3K4, H3K9, and H3K27 proteins were analyzed by western blotting.

Referring to FIG. 18B, induction of differentiation genes FOXA2, HNF4A, BMP2, EOMES, and Sox17 by Sox2 deficiency in A549, H520, A2780, and T47D cells, analyzed by western blotting and real-time quantitative RT-PCR is shown.

Figures 19A, 19B:
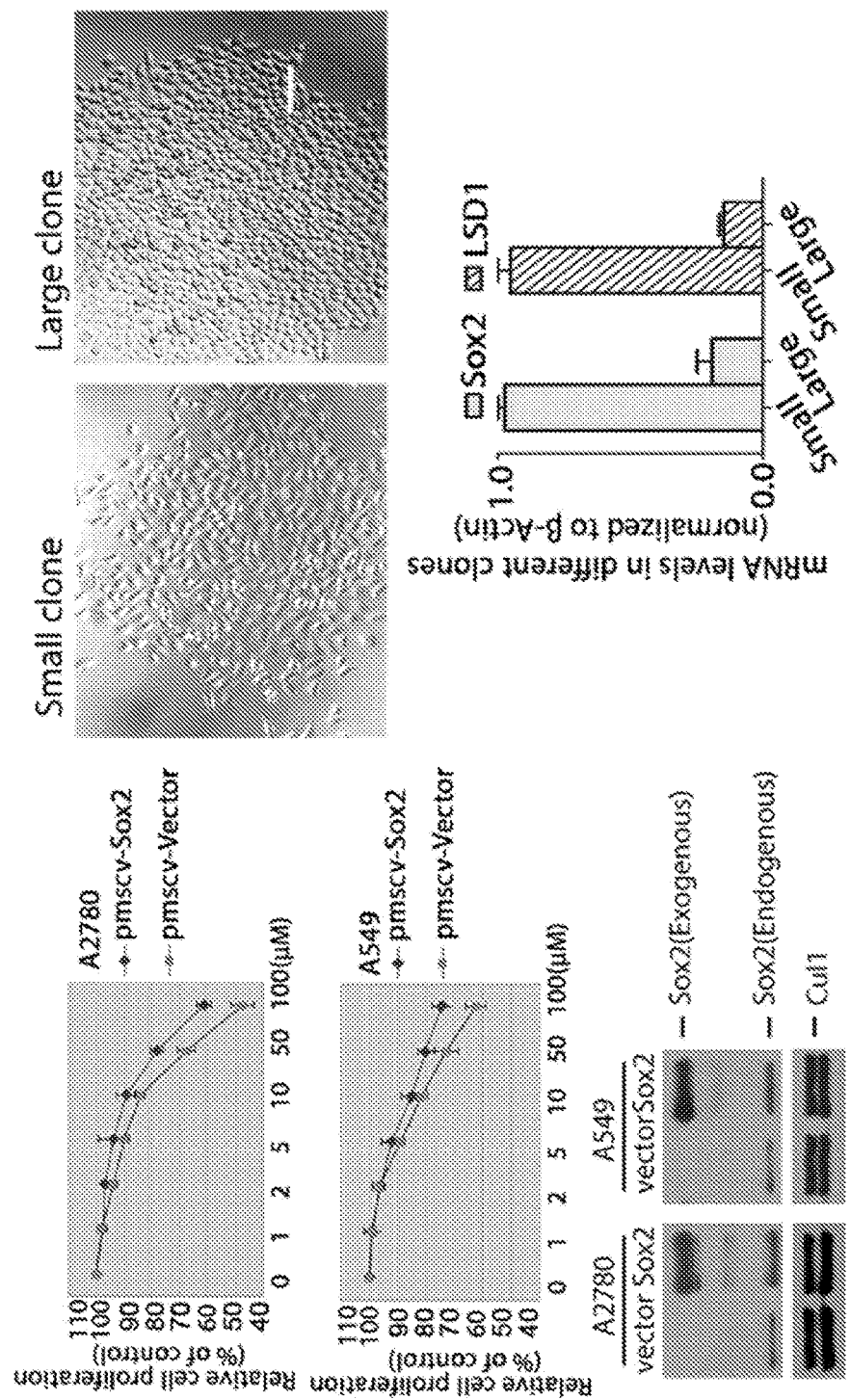
FIG. 19A-D show representative data demonstrating that Sox2 is a target of LSD1 inactivation in Sox2-expressing carcinoma cells.

12. Sox2 is Involved in Mediating the Growth-Inhibitory Effects of LSD1 Inactivation To further determine whether reduced expression of Sox2 is responsible for the growth inhibition caused by LSD1 inactivation, Sox2 was ectopically expressed in Sox2-expressing carcinoma cells. In both Sox2-expressing ovarian A2780 and lung A549 carcinoma cells, stable and ectopic expression of Sox2 led to a significant resistance of these cells to LSD1 inhibition as compared with control cells (FIG. 19A). Co-inactivation of Sox2 and LSD1 in Sox2-expressing cancer cells by siRNAs or LSD1 inhibitors also did not reveal any additive or synergetic effects on growth inhibition induced by the loss of LSD1 or Sox2 alone (FIGS. 19B and 19C), which may suggest that LSD1 and Sox2 act in the same pathway to control cell growth.

Referring to FIG. 19A, ectopic expression of Sox2 conferred resistance to LSD1 inhibitors. Human Sox2 cDNA was tagged with Flag epitope at the amino terminus and stably expressed in A2780 or A549 cells using the retroviral pMSCV vector. Control and Flag-Sox2-expressing cells were treated with various concentrations of CBB1007 for 30 hr, and cell viability was assayed and compared.

Referring to FIG. 19B, Sox2-expressing A549 carcinoma cells were separated by serial dilution into single cells. The single-cell clones were expanded and two representative clones are shown. The mRNA levels of Sox2 and LSD1 in the small and large clones were analyzed by real-time quantitative RT-PCR.

Figure 19C:
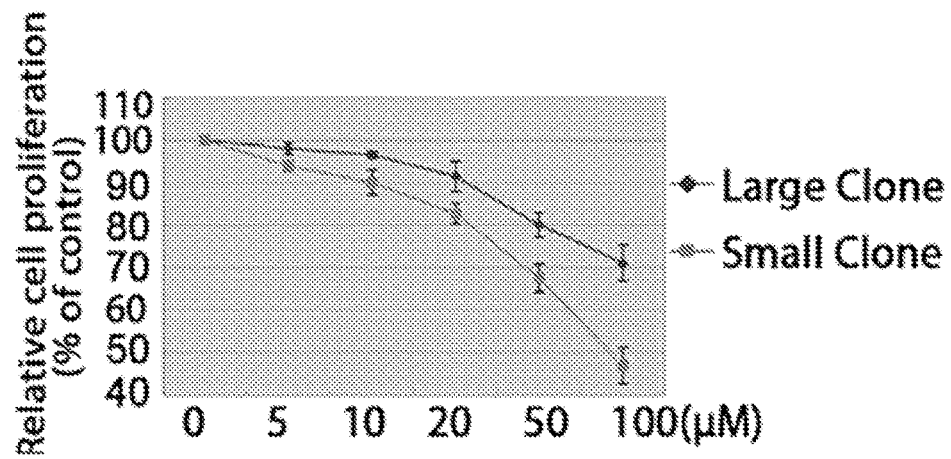

Referring to FIG. 19C, the responses of the single small and large clones of A549 carcinoma cells to various concentrations of CBB1007 were examined.

Figure 19D:
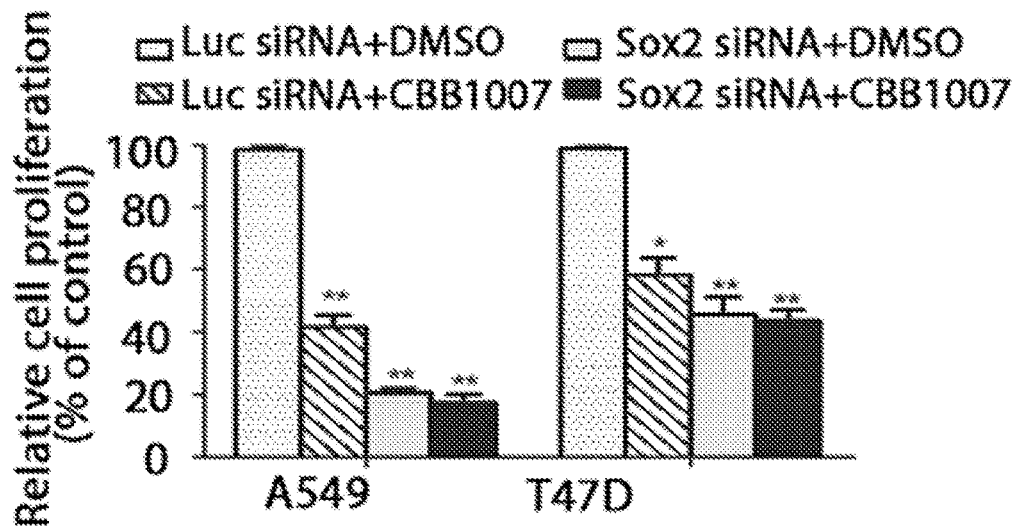
Figure 20A:
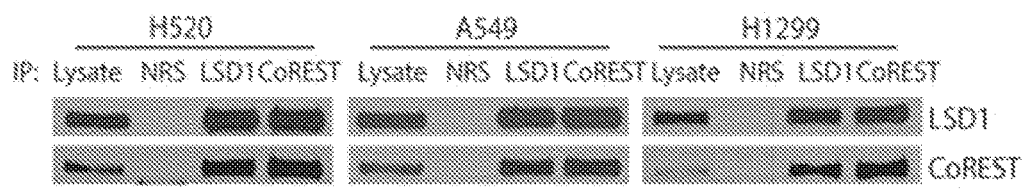
FIG. 20A-E show representative data demonstrating that LSD1 binds to CoREST and loss of CoREST phenocopies the selective growth inhibition of LSD1 inactivation in Sox2-expressing cancer cells.
Figure 20B:
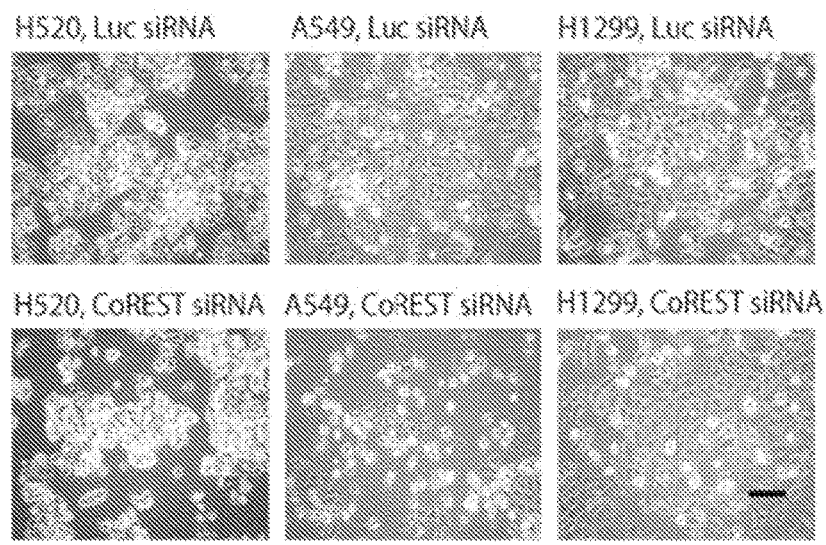
Figure 20C:
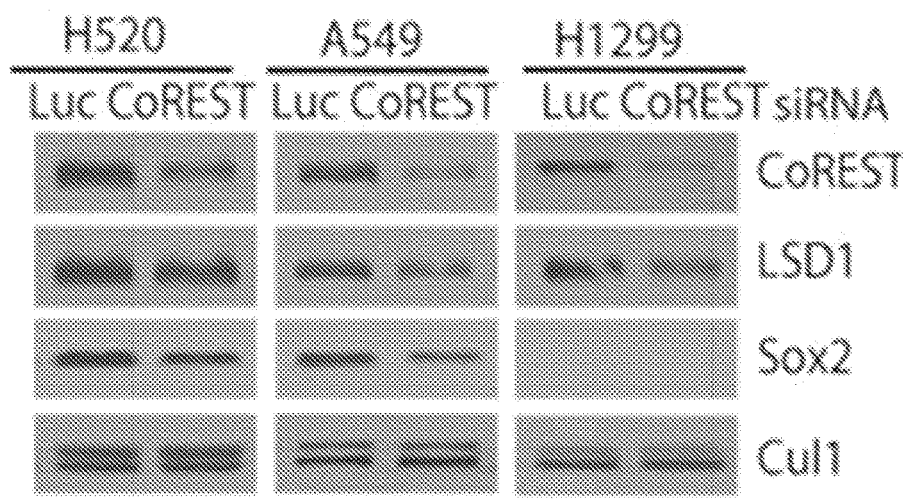
Figure 20D:
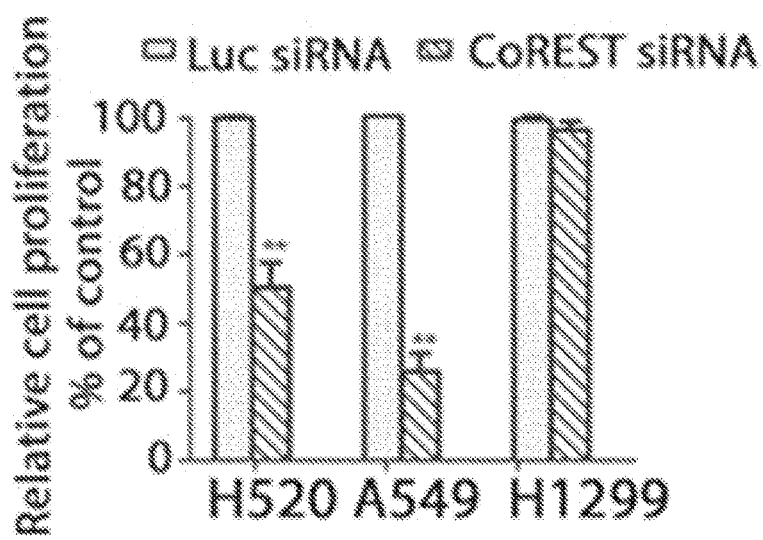
Figure 20E:
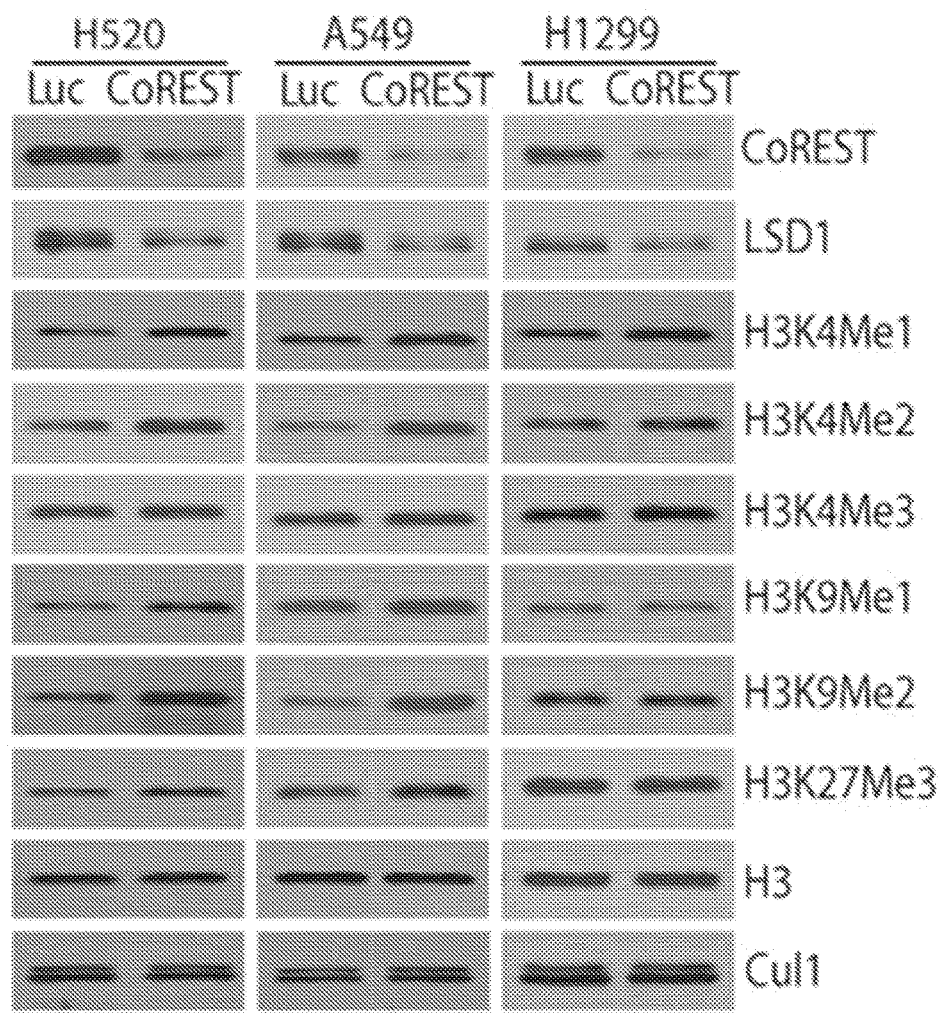

Referring to FIG. 19D, Sox2-expressing A549, T47D, or A2780 cells were treated with 50 mM CBB1007 for 30 hr and the effects on their growth were monitored and quantified.

LSD1 was shown to interact with several proteins, such as CoREST, in various cells (Shi, Y. J., et al. (2005) *Mol. Cell* 19, 857-864). To confirm that the effects of LSD1 inactivation are mediated through its interaction with cellular proteins, the expression of CoREST was also ablated. Loss of CoREST caused the same selective growth-inhibitory effects and induction of H3K4, H3K9, and H3K27 methylations on Sox2-expressing cancer cells, but not Sox2-negative cancer cells, as LSD1 inactivation (FIG. 20A-E). It is likely that LSD1 acts through the CoREST complex to selectively regulate the growth of Sox2-expressing cancer cells, although loss of CoREST slightly reduced the level of LSD1 protein, possibly because of their in vivo association.

Referring to FIG. 20A-E, LSD1 binds to CoREST and loss of CoREST phenocopies the selective growth inhibition of LSD1 inactivation in Sox2-expressing cancer cells. LSD1 binds to CoREST in NCI-H520, A549, and H1299 cells (20A). The LSD1 protein complexes were immunoprecipitated from the lysates of H520, A549 and H1299 cells and the complexes were blotted with anti-LSD1 and CoREST antibodies. Ablation of CoREST by specific siRNAs induced growth inhibition in Sox2-expressing H520 and A549 cells but not in Sox2-negative H1299 cells (20B). Indicated cells were transfected with luciferase (Luc) or CoREST specific siRNAs for 48 hours and cell growth were monitored by microscopy. Examination of ablation efficiency of CoREST and the effects of CoREST deficiency on LSD1 and Sox2 as above (20C). Quantitative analysis of cell growth inhibition in B by the MTT assay (20D). Association of CoREST and the changes of LSD1 binding and H3K4me1, H3K4me2, H3K9me2, and H3K27me3 with the transcriptional regulatory region of Sox in control (Luc) and CoREST ablated A549 cells by specific siRNAs were analyzed using the ChIP assays. CoREST inactivation phenocopied the effects of LSD1 inactivation on the methylations of H3K4, H3K9, and H3K27 on Sox2-expressing lung carcinoma NCI-H520 and A549 cells and Sox2-negative H1299 cells (20E).

13. Loss of LSD1 Suppresses Sox2-Dependent, Lineage-Specific Gene Expression and Reduces Sox2-Mediated Repression of Genes for Differentiation In lung SCCs, Sox2 acts as a lineage-survival oncogene that is required for the expression of lineage-specific genes such as TP63 and KRT6A (Bass, A. J., et al. (2009) *Nat. Genet.* 41, 1238-1242). These studies revealed that loss of either LSD1 or Sox2 led to the downregulation of TP63 and KRT6A expression in Sox2-expressing H520 and A549, but not in Sox2-negative H1299 lung carcinoma cells. Additionally, ChIP assays were used to determine whether LSD1 inactivation affects the ability of Sox2 to bind the promoters of TP63 and KRT6A. In H520 cells, Sox2 bound directly to the promoters of TP63 and KRT6A genes, and inhibition of LSD1 significantly reduced the binding of Sox2 to these lineage-specific genes.

These studies also revealed that ablation of Sox2 induced the expression of differentiation genes such as FOXA2 and Sox17 (FIG. 18B). ChIP assays indicated that Sox2 bound directly to these promoters and inactivation of LSD1 significantly decreased Sox2 binding to these promoters, suggesting that Sox2 normally acts as a repressor of these differentiation genes. Thus, without wishing to be bound by theory, these data suggest that LSD1 inactivation acts directly on a Sox2-dependent transcriptional program to reduce the lineage-survival oncogene function of Sox2 and to impair Sox2-mediated repression of differentiation genes.

14. Loss of LSD1 Induces the Expression of Genes for Differentiation by Selectively Increasing the Levels of Methylated H3K4, but not Methylated H3K9 or H3K27, on the Promoters LSD1 inactivation in germ tumor cells or ESCs induced the expression of genes for differentiation (Wang, J., et al. (2011) *Cancer Research* 71, 7238-7249). To determine whether the function of LSD1 is preserved in Sox2-expressing carcinoma cells, the effects of LSD1 inactivation on the expression of differentiation genes were analyzed. LSD1 inactivation led to the induction of differentiation genes such as FOXA2, HNF4A, BMP2, EOMES, and Sox17 only in Sox2-expressing cancer cells, and not in Sox2-negative cancer cells (FIG. 21A-D). Although loss of LSD1 caused G1 cell-cycle arrest (FIGS. 9A and 9C), the induction of differentiation genes did not appear to be the consequence of LSD1 inactivation-induced G1 cell-cycle arrest, as arresting Sox2-expressing A549 cells in the G1/S border alone did not promote the induction of differentiation genes or the suppression of Sox2 expression.

Figure 21A:
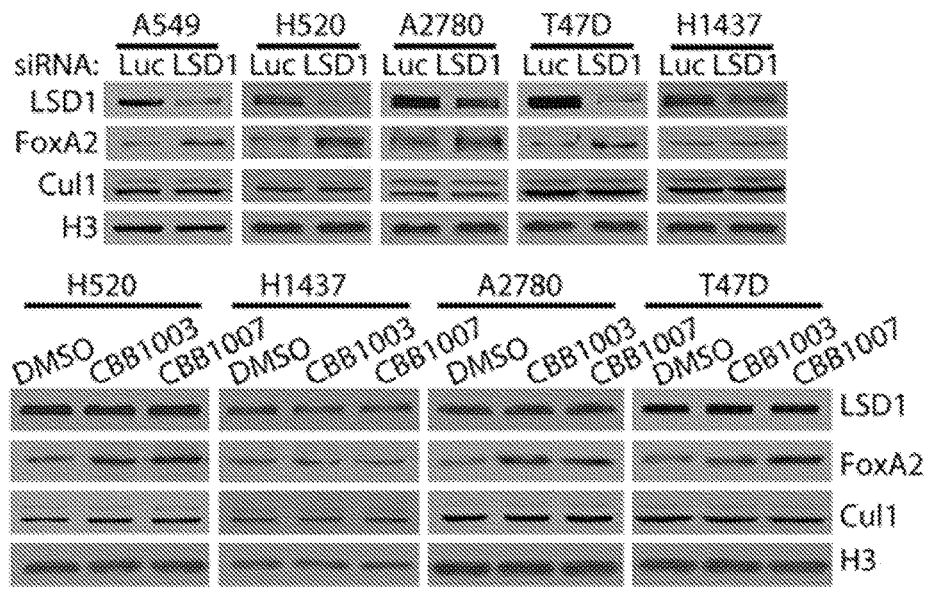
FIG. 21A-D show representative data demonstrating that inactivation of LSD1 induces the expression of differentiation genes.
Figure 21B:
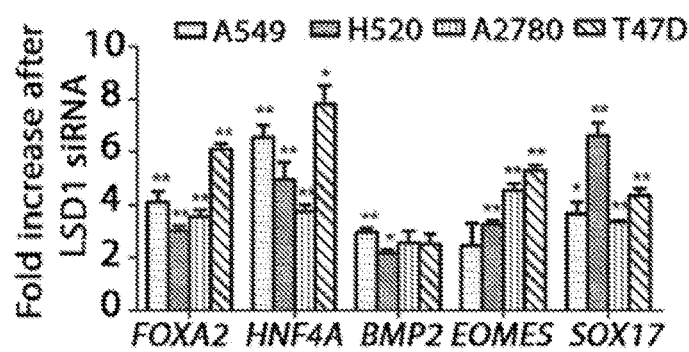
Figure 21C:
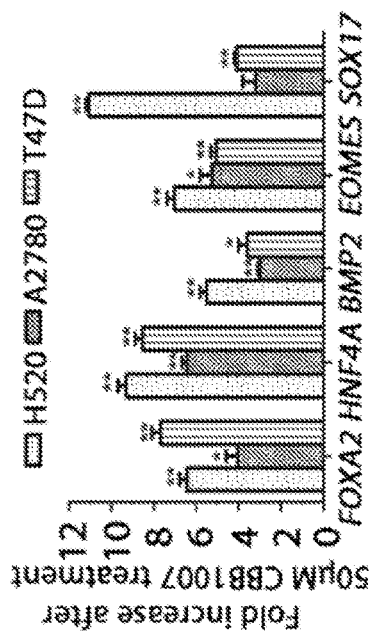

Referring to FIG. 21A-C, A549, NCI-H520, H1437, A2780, and T47D cells were transfected with 50 nM luciferase or LSD1 siRNAs for 48 hr or treated with 50 mM LSD1 inhibitors CBB1003 and 1007 for 30 hr. The effects of LSD1 inactivation on the induction of FOXA2 (21A) or on various differentiation genes (FOXA2, HNF4A, BMP2, EOMES, and Sox17 [21B and 21C]) were analyzed by western blotting (21A) or real-time quantitative RT-PCR (21B and 21C).

Figure 21D:
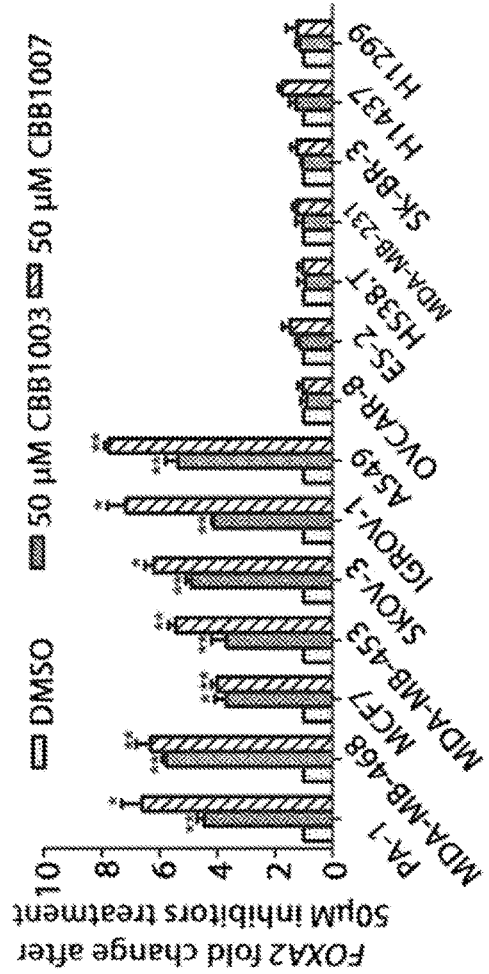

Referring to FIG. 21D, the indicated lung, breast, ovarian, and other carcinoma cells were treated with 50 mM CBB1003 or CBB1007 for 30 hr, and induced expression of FOXA2 mRNAs was monitored, quantified, and compared between control and inhibitor-treated cells using real-time quantitative RT-PCR. *p<0.05, **p<0.01.

Figure 22:
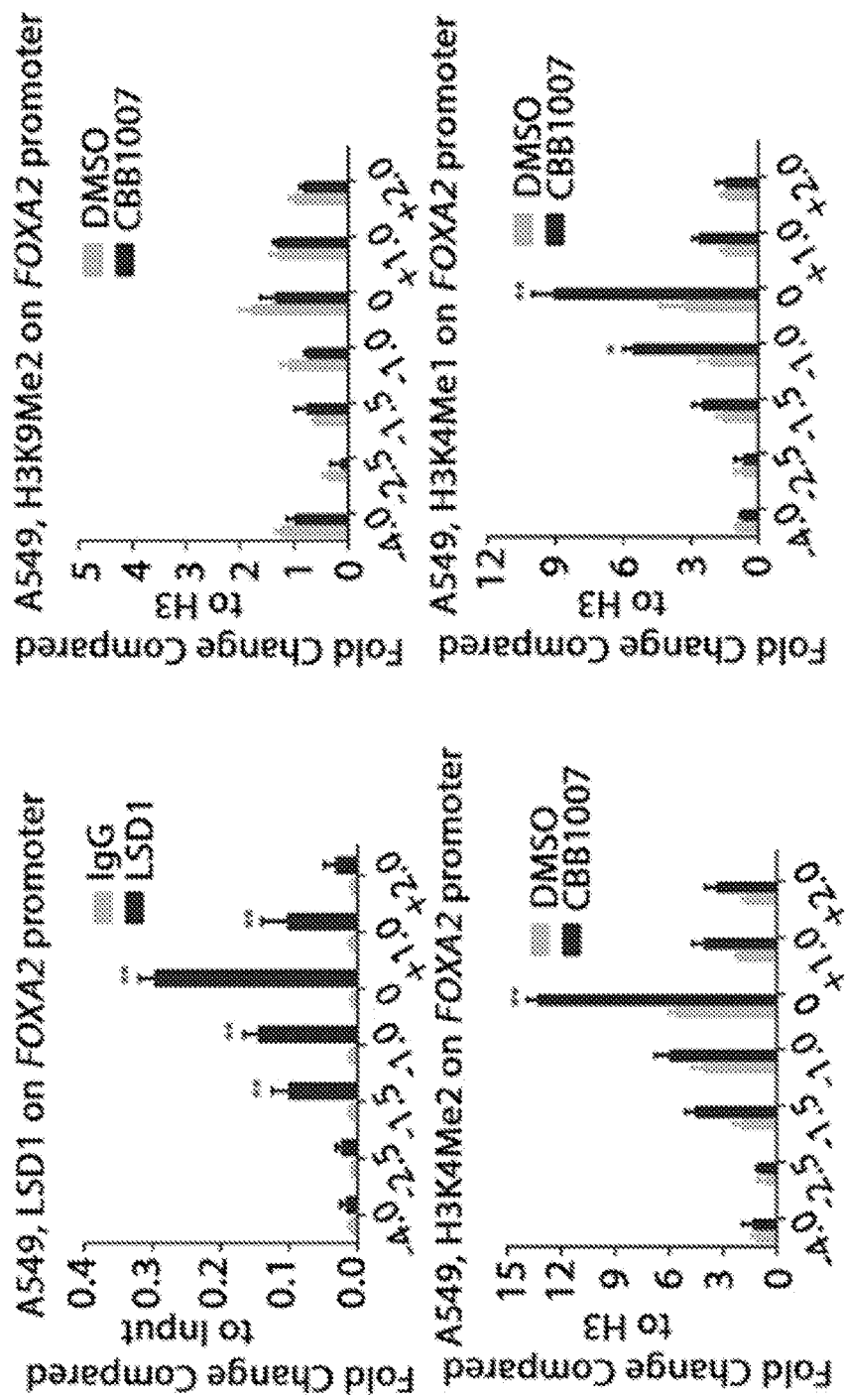
FIG. 22 shows representative data demonstrating that inactivation of LSD1 induces the expression of differentiation genes by increased methylation of H3K4, but not methylated H3K9, and suppression of the Cyclin A Gene by Increased H3K4me1/2 and H3K9me2.
Figures 23A, 23B:
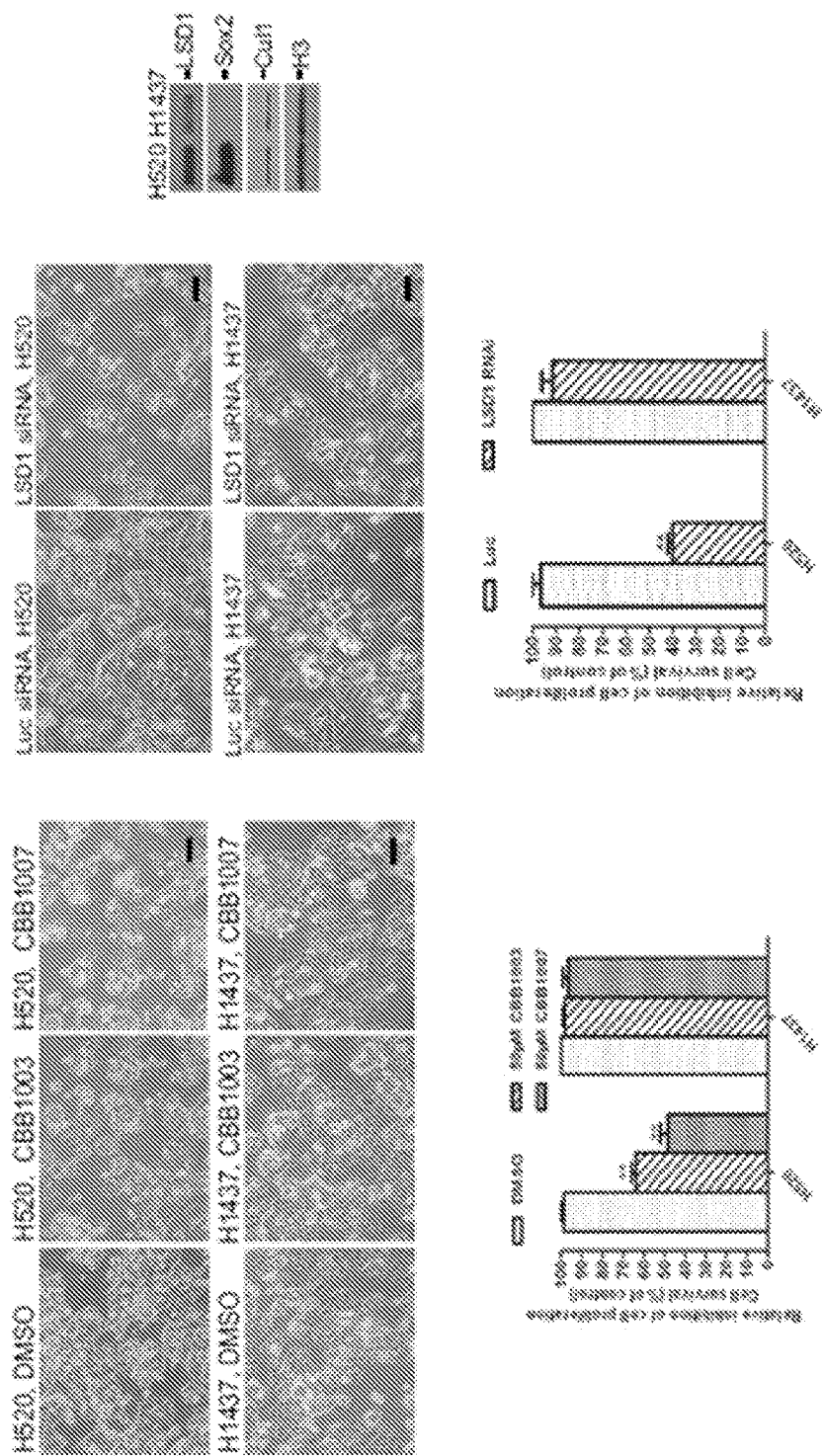
FIGS. 23A and 23B shows representative data demonstrating that LSD1 inhibitors CBB1003 and CBB1007 selectively block the growth of squamous carcinoma cells containing Sox2 gene amplification.
Figure 24B:
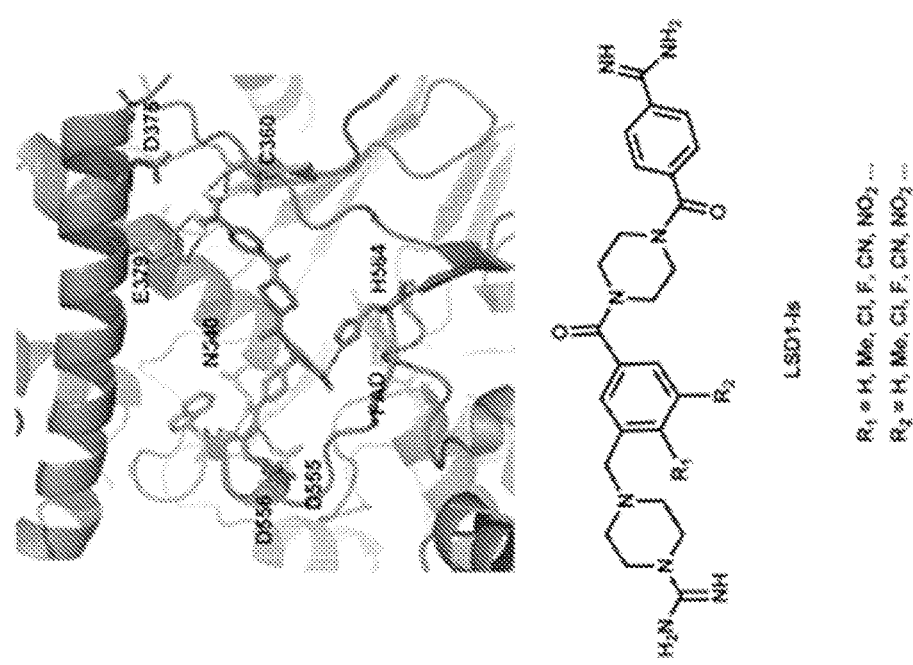
FIGS. 24A and 24B show representative data pertaining to the design of LSD1 inhibitors using a crystal structure of LSD1 and a pseudo-substrate.
Figure 24A:
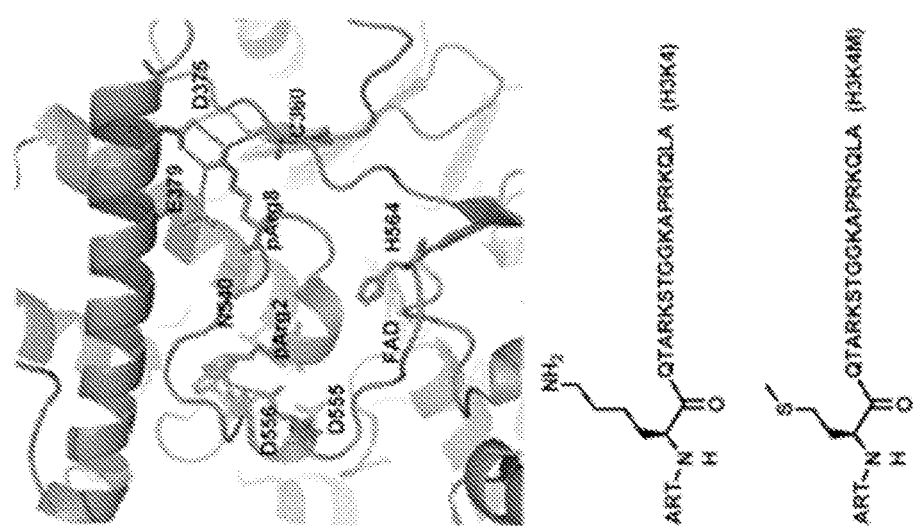
Figure 25:
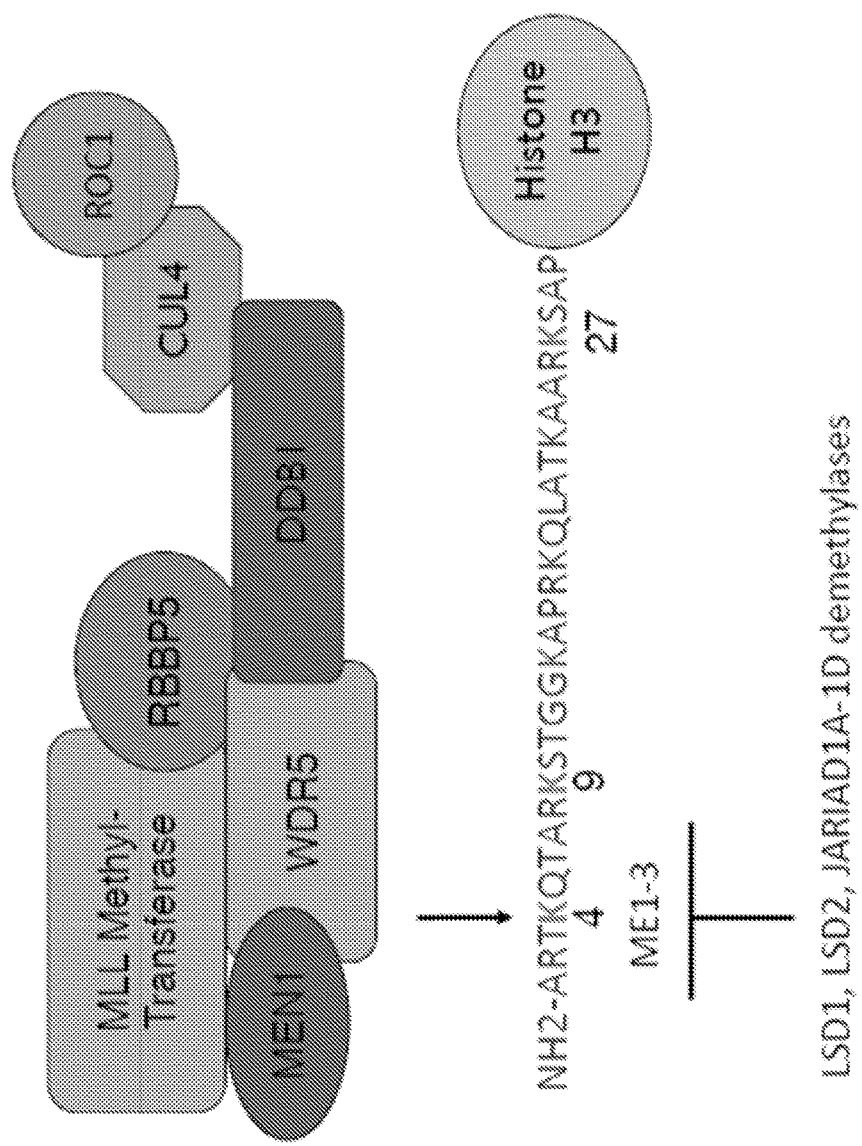
FIG. 25 shows a representative schematic illustrating that histone methylation at lysine 4 (H3K4) is dynamically regulated by MLL-WDR5-RBBP5 methyltransferases and LSD1/2 and JARIAD1A-1D demthylases.
Figure 26:
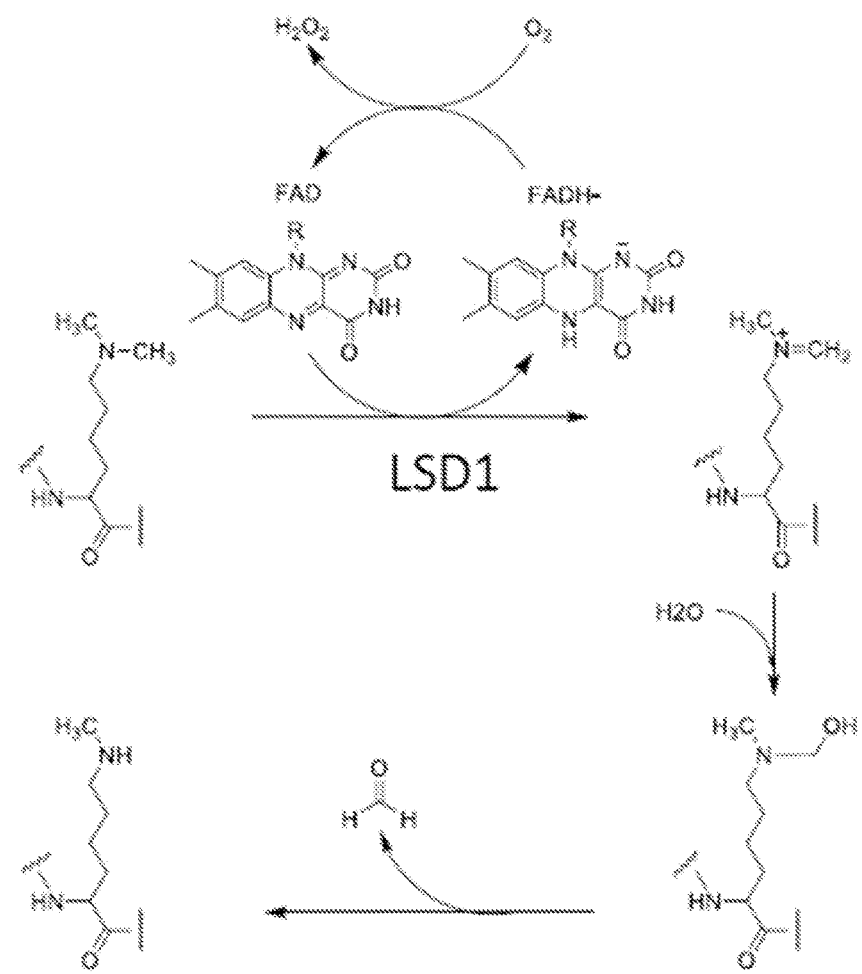
FIG. 26 shows a representative schematic illustrating the removal of H3K4 in histone 3 by an FAD-dependent oxidation catalyzed by LSD1.

Because LSD1 inactivation promotes the primary global methylations of H3K4me1/2, H3K9me1/2, and H3K27me3 in Sox2-expressing cancer cells (FIGS. 12A and 12B), and increased levels of these methylations on the promoters of Sox2 and cyclin genes (FIGS. 13A, 13C, and 14A), these methylations were examined in the regulatory regions of differentiation genes. In sharp contrast to the increased H3K4, H3K9, and H3K27 methylations on the Sox2 or cyclin genes after LSD1 inactivation, LSD1 inhibition consistently increased the mono- and dimethylations of H3K4 in the regulatory regions of FOXA2, BMP2, and Sox17 genes, but not the H3K9 and H3K27 methylations in Sox2-expressing carcinoma cells (FIG. 22). Thus, without wishing to be bound by theory, these data suggest a mechanism by which LSD1 inactivation suppresses the expression of Sox2 and cyclins by increased H3K9 and H3K27 methylations on their regulatory regions/promoters, whereas it causes the induction of differentiation genes by selectively elevating the levels of H3K4me1/me2 on differentiation genes, but not methylated H3K9 and H3K27. The effects of LSD1 inhibitors on differentiation may be enhanced by Sox2 downregulation, which de-represses Sox2-mediated suppression of differentiation genes and causes further cellular differentiation.

Referring to FIG. 22, ChIP assays for the presence of LSD1, H3K9me2, H3K4me1, and H3K4me2 in the regulatory regions of the differentiation gene FOXA2 with or without LSD1 inhibitors were performed for 30 hr.

15. LDS1 Forms a Complex with HDAC1, and Loss of HDAC1 Phenocopies the Selective Growth-Inhibitory Effects of LSD1 Inactivation in ES/EC Cells It was previously demonstrated that LSD1 inhibitors specifically block the growth of ES and EC cells and induce their differentiation but not that of nonpluripotent cells, such as HeLa, 293, or NIH 3T3 cells (Wang, J., et al. (2011) Cancer Research 71, 7238-7249). To investigate the mechanism by which LSD1 regulates the pluripotency of ES/EC cells, the proteins that interact with LSD1 in ES/EC cells were isolated, as LSD1 was reported to be a component of several repressor complexes (Shi, Y. J., et al. (2005) Nature 437, 432-435; Lee, M. G., et al. (2005) Nature 437, 432-435; Shi, Y., et al. (2003) Nature 422, 735-738; Wang, Y., et al. (2009) Cell 138, 660-672; Shi, Y. (2007) Nat. Rev. Genet. 8, 829-833). For this purpose, human LSD1 was epitope tagged with triple Flag and HA tags and stably expressed it in pluripotent mouse teratocarcinoma F9 cells. The LSD1 complexes were isolated by immunoprecipitation of anti-Flag and HA antibodies, and the associated proteins were identified by mass spectrometry analyses. This analysis revealed that LSD1 primarily associated with CoREST and HDAC1 in F9 cells (FIG. 27A). Independent immunoco-precipitation followed by Western blotting of LSD1 complexes confirmed that LSD1 forms a protein complex with HDAC1 and CoREST in F9 cells (FIG. 27B).

Referring to FIG. 27A, LSD1 formed a protein complex with CoREST and HDAC1. The 3XFlag/HA-tagged LSD1 protein complex was isolated by immunoprecipitation from F9 cells that stably expressed the tagged LSD1 using F9 cells as a control. LSD1, HDAC1, and CoREST were identified by mass spectrometry. Marker, molecular weight markers (in thousands).

Referring to FIG. 27B, the interactions among LSD1, HDAC1, and CoREST were confirmed by immunoprecipitation (IP), followed by Western blotting, as indicated. NRS, normal rabbit serum as a control.

Figure 27C:
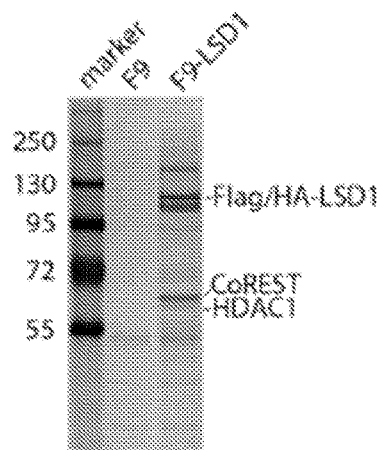
Figure 27C:
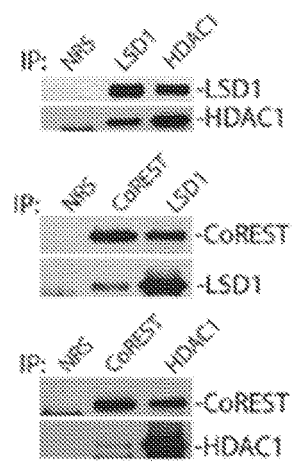
Figure 27C:
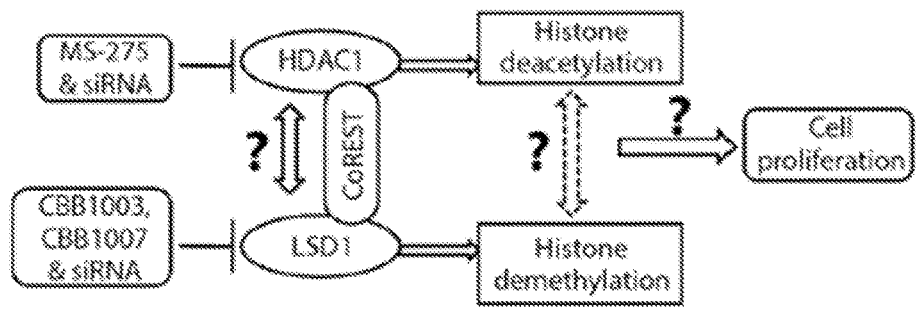
Figure 27D:
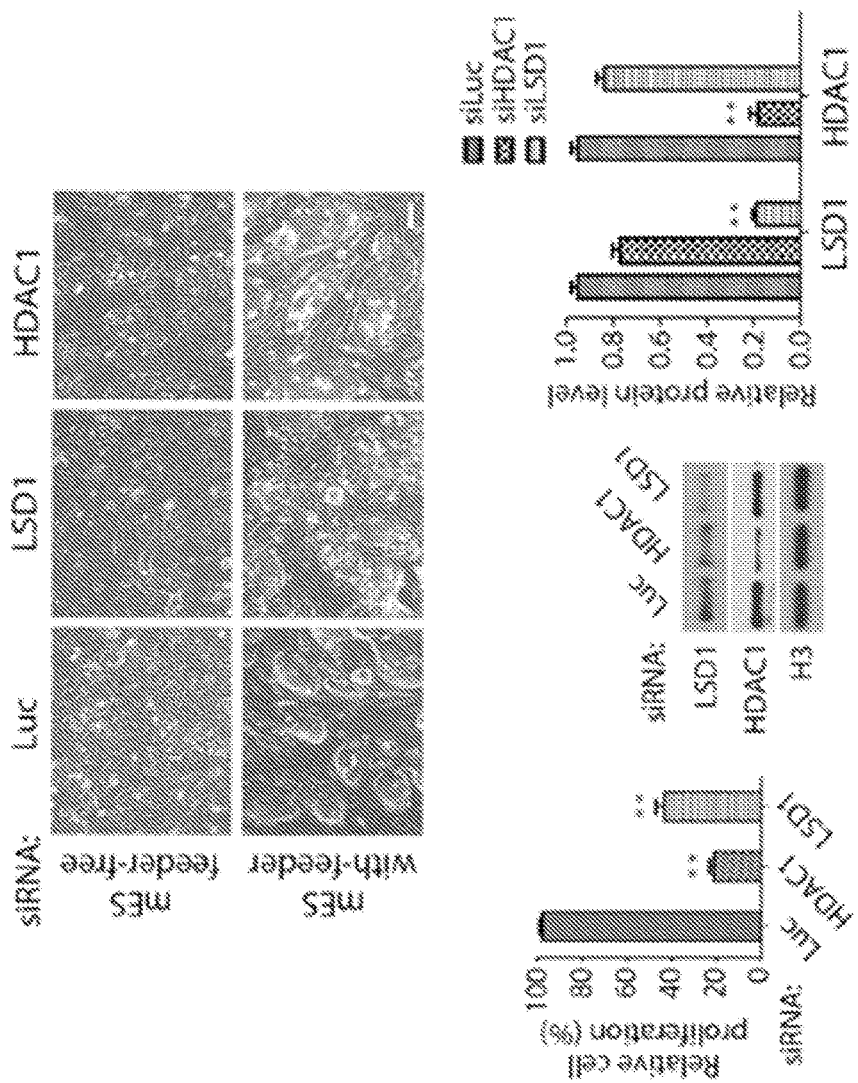
Figure 27E:
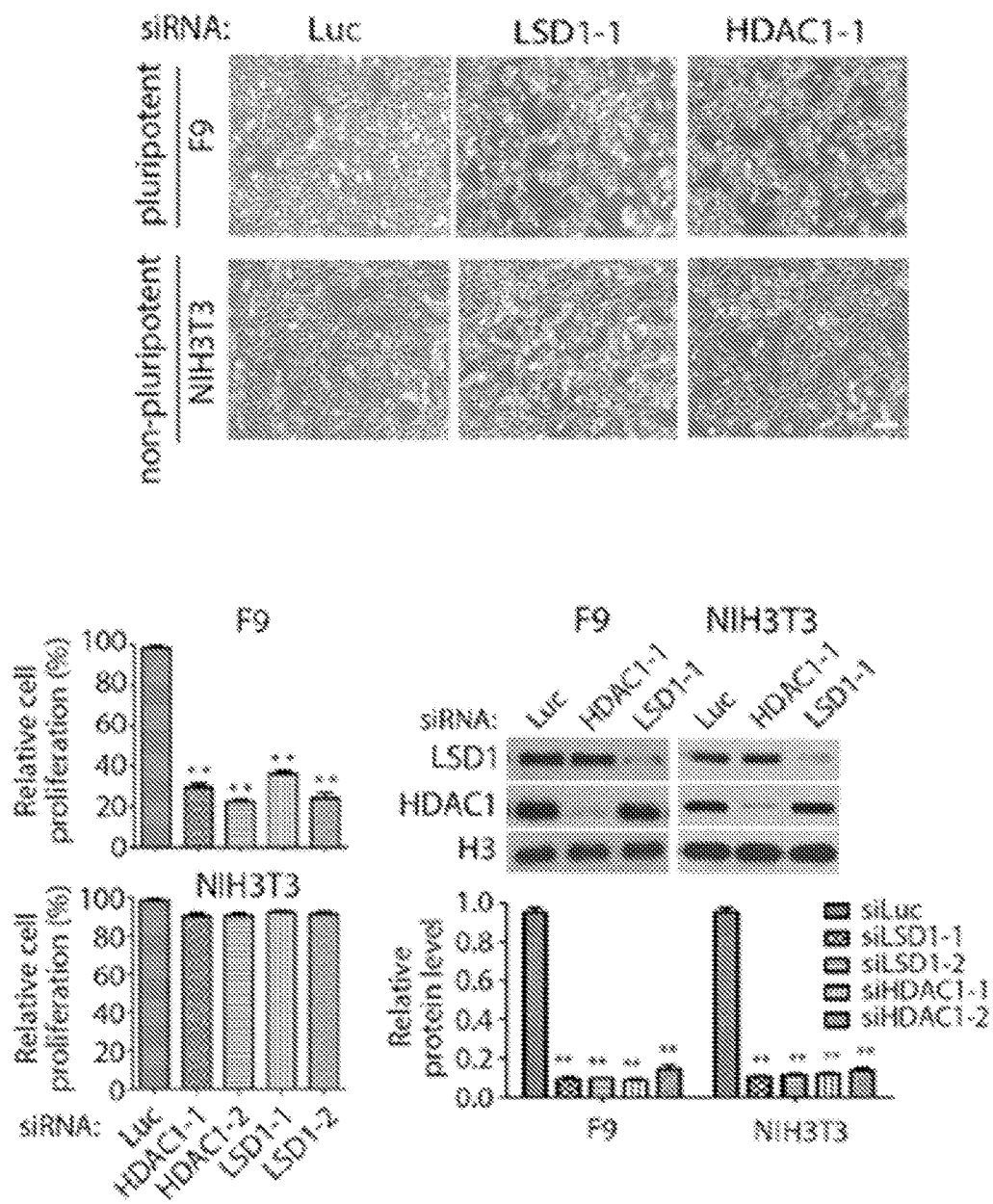
Figure 27F:
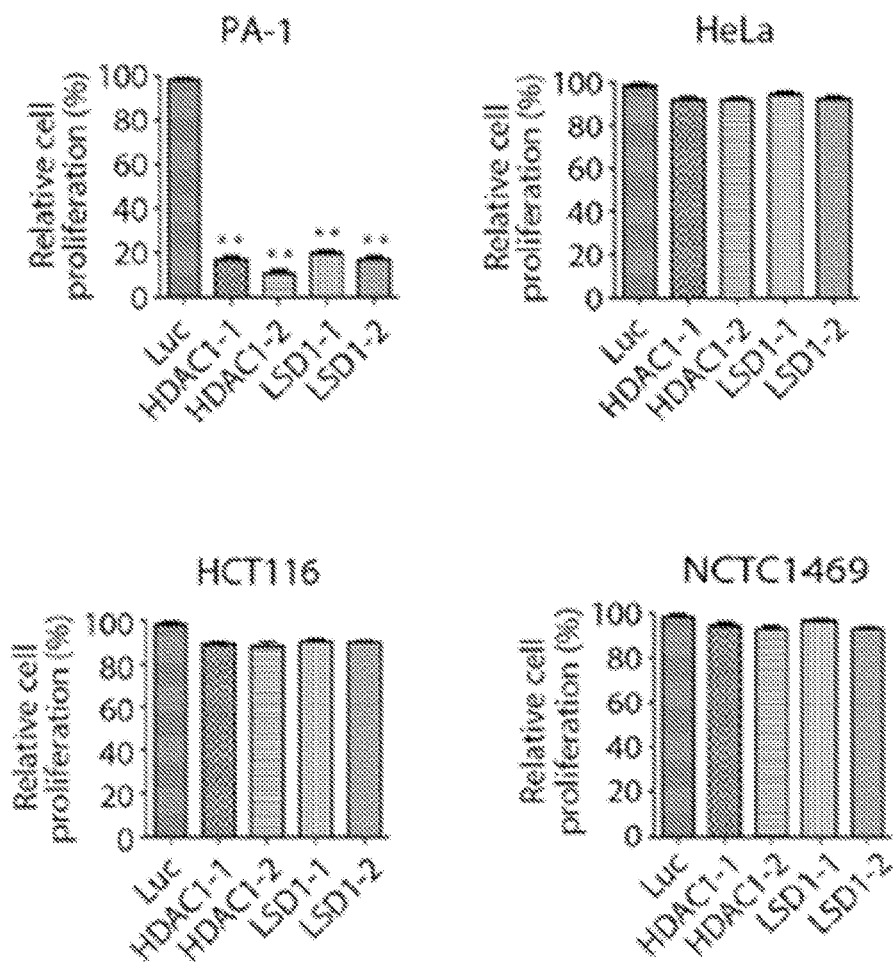

To determine the significance of the association between LSD1 and HDAC1 (FIG. 27C), the expression of LSD1 or HDAC1 was ablated by the use of specific siRNAs in pluripotent mouse ES (mES) and F9 cells and nonpluripotent mouse NIH 3T3 cells (FIGS. 27D and 27E). Consistent with previous findings (Wang, J., et al. (2011) Cancer Research 71, 7238-7249), loss of LSD1 led to profound and selective growth inhibition only of the pluripotent mES and F9 cells (FIGS. 27D and 27E), which expressed pluripotent stem cell proteins Sox2, Oct4, and Lin28 (Table 9), while LSD1 ablation had no significant effects on that of nonpluripotent NIH 3T3 cells (FIG. 27E). Notably, ablation of HDAC1 using specific siRNAs phenocopied the effects of LSD1 inactivation on the selective growth inhibition of pluripotent mES and F9 cells but not that of nonpluripotent NIH 3T3 cells (FIGS. 27D and 27E). These effects were specific to the loss of LSD1 or HDAC1, as inactivation using independent siRNAs against LSD1 or HDAC1 produced the same selective effects (FIG. 27E). Further examination of the effects of LSD1 and HDAC1 ablation by their specific siRNAs in pluripotent PA-1 human ovarian teratocarcinoma cells and nonpluripotent NCTC1469 normal mouse liver, HeLa, and HCT116 human colorectal carcinoma cells confirmed that inactivation of LSD1 or HDAC1 impaired the growth only of pluripotent PA-1 cells and not that of nonpluripotent cells (FIG. 27F).

TABLE 9

| Cell Line | Protein Expression[a] | | | | | |
|---|---|---|---|---|---|---|
|  | Oct4 | Sox2 | Klf4 | Lin28 | Nanog | Sall4 |
| mES | ✓ | ✓ | ✓ | ✓ | ✓ | ✓ |
| F9 | ✓ | ✓ | ✓ | ✓ | ✓ | ✓ |
| PA-1 | ✓ | ✓ | ✓ | ✓ | X | ✓ |
| NIH 3T3 | X | X | ✓ | X | X | X |
| NCTC1469 | X | X | ✓ | X | X | X |
| HeLa | X | X | ✓ | X | X | X |
| HCT116 | X | X | ✓ | X | X | X |

[a]✓, expression of proteins, as confirmed by Western blotting; X, no detectable expression of proteins.

Referring to FIG. 27C, a schematic of the experimental design for the functional relationship between LSD1, CoREST, and HDAC1 is shown.

Referring to FIG. 27D, ablation of HDAC1 or LSD1 inhibits the proliferation of pluripotent mES cells. The mES cells were transfected with luciferase, HDAC1, or LSD1 siRNA (siLuc, siHDAC1, and siLSD1, respectively), and the growth of mES cells was examined under a microscope and quantified by the MTT assay. The efficacy of the siRNAs was determined by Western blotting and quantified by the use of Gel-Pro Analyzer (version 4.0) software.

Referring to FIG. 27E, inactivation of LSD1 or HDAC1 specifically inhibits the proliferation of pluripotent F9 cells but not that of nonpluripotent NIH 3T3 cells. Cells were transfected with two sets of independent LSD1 and HDAC1 siRNAs for 48 h. Only one set of cell images is shown. The rest were quantified by MTT assay, as described above for FIG. 27D.

Referring to FIG. 27F, loss of LSD1 or HDAC1 by siRNA-mediated ablation also caused growth inhibition of pluripotent human PA-1 teratoma cells but not that of nonpluripotent HeLa, HCT116, or mouse NCTC1469 cells. All experiments were performed in duplicate with consistent results each time and repeated at least three times. Error bars represent SEMs for duplicates of the data. The statistical differences between experimental and control groups were analyzed by one-way ANOVA. **, P<0.01.

Figure 28A:
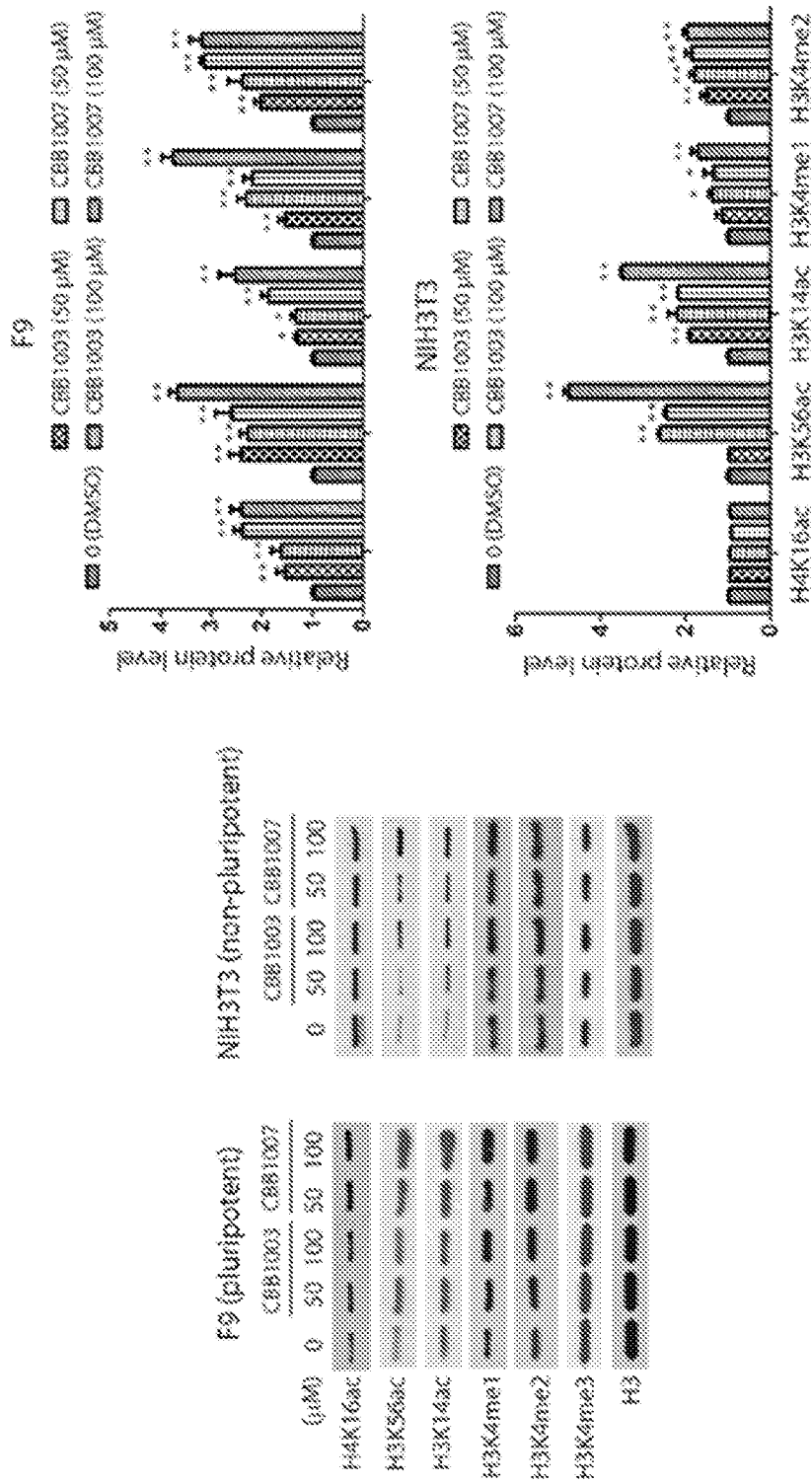
Figure 28B:
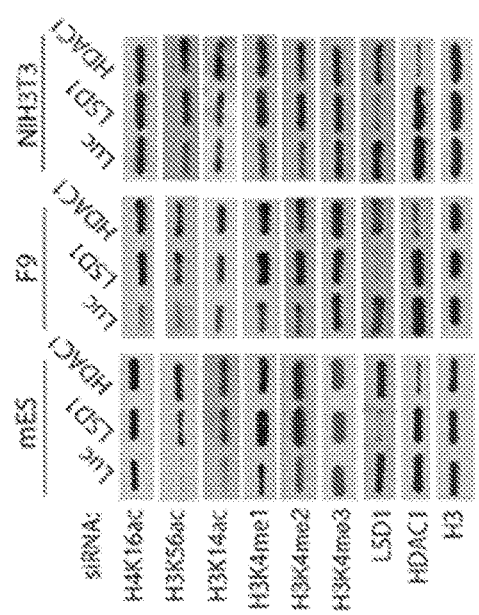

16. Inhibition of HDAC1 or LSD1 Increases Both H4K16 Acetylation and H3K4 Methylation in Cells Sensitive to LSD1 Inhibitors The similarity between the inhibitory effects of LSD1 and HDAC1 inactivation on the proliferation of pluripotent ES/EC cells and the interaction between LSD1 and HDAC1 in these cells raised the possibility that LSD1-regulated H3K4 methylation cross talks with the HDAC1-mediated histone acetylation in pluripotent ES/EC cells. To identify the potential link between these two pathways in pluripotent ES/EC cells, the changes of epigenetic modifications of histones H3 and H4 in pluripotent mES and F9 cells were examined and compared (FIGS. 28A and 28B). Inactivation of LSD1 by LSD1 inhibitors or specific siRNAs not only induced the accumulation of mono- and dimethylated H3K4 but also increased the levels of acetylated H4K16, H3K56, and H3K14 in these cells but not the level of trimethylated H3K4 (FIGS. 28A and 28B). Notably, a loss of HDAC1 caused the same patterns of accumulation of mono- and dimethylated H3K4 and acetylated H4K16, H3K56, and H3K14 in these pluripotent cells (FIG. 28B). These observations are consistent with the notion that LSD1 and HDAC1 may coordinate to regulate H3K4 methylation and histone acetylation in pluripotent cells.

Referring to FIG. 28A, F9 and NIH 3T3 cells were treated with the LSD1 inhibitors CBB1003 and CBB1007 for 24 h, and the acetylation and methylation of histones H3 and H4 were monitored by Western blotting and quantified by the use of Gel-Pro Analyzer (version 4.0) software using histone H3 as a loading control.

Referring to FIG. 28B, mES, F9, and NIH 3T3 cells were transfected with luciferase, LSD1, or HDAC1 siRNAs, and methylated and acetylated histones were analyzed and quantified as described for panel A.

As inactivation of both LSD1 and HDAC1 only selectively induced growth inhibition of pluripotent ES/EC cells and not that of nonpluripotent cells, the changes of histone methylation and acetylation between pluripotent and nonpluripotent cells were also compared. Strikingly, it was repeatedly observed that while inactivation of LSD1 or HDAC1 selectively caused the increased levels of acetylated H4K16 in pluripotent mES and F9 cells, such an increase in acetylated H4K16 did not happen in nonpluripotent NIH 3T3 cells (FIGS. 28A and 28B). It is possible that the loss of LSD1 caused secondary changes in histone modification when the cells were treated with LSD1 inhibitors or siRNAs for an extended time. Therefore, the time course of changes in histone modifications after treatment of F9 cells with the LSD1 inhibitor CBB1007 were monitored (FIGS. 28C and 28D). It was repeatedly found that the increases of acetylation at H4K16 and H3K56 and mono- and dimethylation at H3K4 occurred within 20 min after addition of CBB1007 in F9 cells, whereas the accumulation of H3K14 acetylation appeared to occur relatively late, at between 4 and 8 h. Without wishing to be bound by theory, these data suggest that the changes in histone modifications in H3K56ac, H4K16ac, and H3K4me1/me2 may be the primary effects of LSD1 inactivation.

Referring to FIG. 28C, time course analyses of the effects of 50 µM LSD1 inhibitor CBB1007 on histone modifications in F9 cells are shown.

Referring to FIG. 28D, time course analyses of the effects of 50 µM LSD1 inhibitor CBB1007 on histone modifications in F9 cells are shown, but with a shorter time course than above. The mean density of each band was quantified by the use of Gel-Pro Analyzer (version 4.0) software, and error bars represent SEMs for duplicate samples. All of the experiments were repeated more than three times, with similar results each time. The statistical differences were analyzed by one-way ANOVA. *, P_0.05; **, P_0.01.

17. Acetylated H4K16 is a Direct Substrate of HDAC1

Figures 29A, 29B, 29C, 29D:
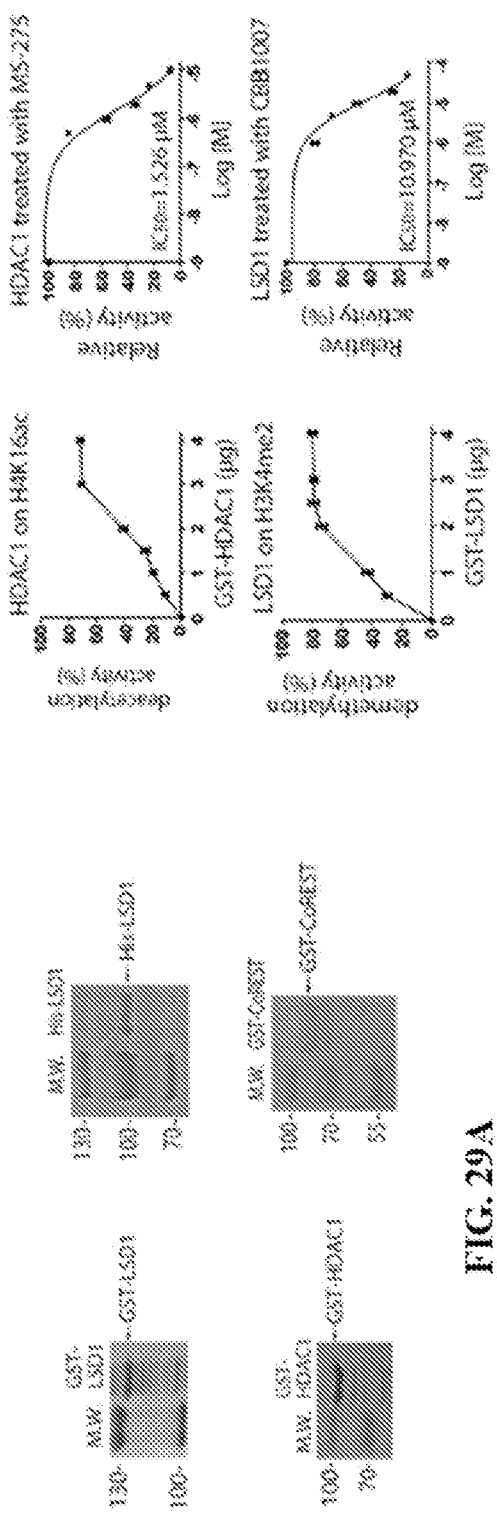
FIG. 29A-G show representative data pertaining to the regulation of LSD1 and HDAC1 by mutual activities in the LSD1-CoREST-HDAC1 complex.

As the effects of LSD1 and HDAC1 inactivation mirrored each other and affected both histone methylation and acetylation, it prompted further biochemical characterization of these effects in vitro using defined substrates and proteins. To determine whether acetylated H3K56, H4K16, and H3K14 are direct substrates of HDAC1, recombinant HDAC1 protein (FIG. 29A) was used to analyze its deacetylase activity against these acetylated bulk histones from F9 cells. GST-HDAC1 was found to remove the acetyl groups from the acetylated H3K56 and H4K16 but not the acetyl group of acetylated H3K14 (FIG. 29C). To further confirm that the acetylated H4K16 is a substrate of HDAC1, a synthetic H4K16ac that contains the acetylated H4K16 as a substrate was also used, and these studies showed that HDAC1 could deacetylate this peptide in a reaction that was inhibited by MS-275, an inhibitor of class I HDACs, which include HDAC1 (FIG. 29B). These observations, as well as the findings from the in vivo studies (FIGS. 29C and 29D), suggest that acetylated H3K56 and H4K16 are indeed the specific and direct substrates of HDAC1, while acetylated H3K14 is not.

Referring to FIG. 29A, purified recombinant GST-LSD1, 6-histidine-tagged LSD1 (His-LSD1), GST-HDAC1, and GST-CoREST proteins are shown. Lanes M. W., molecular weight markers (in thousands).

Referring to FIG. 29B, analysis of the activities of recombinant HDAC1 and LSD1 proteins on peptide substrates. (Left) Concentration-dependent GST-HDAC1 (top) and GST-LSD1 (bottom) activities using H4K16ac and H3K4me2 peptides as the substrates. The products were analyzed by mass spectrometry and quantified by GraphPad Prism (version 5) software. (Right) Determination of the 50% inhibitory concentration ($IC_{50}$) of MS-275 toward HDAC1 and that of CBB1007 toward LSD1.

Referring to FIG. 29C, GST-HDAC1 deacetylates H4K16ac and H3K56ac in acid-extracted histones.

Figure 28B:
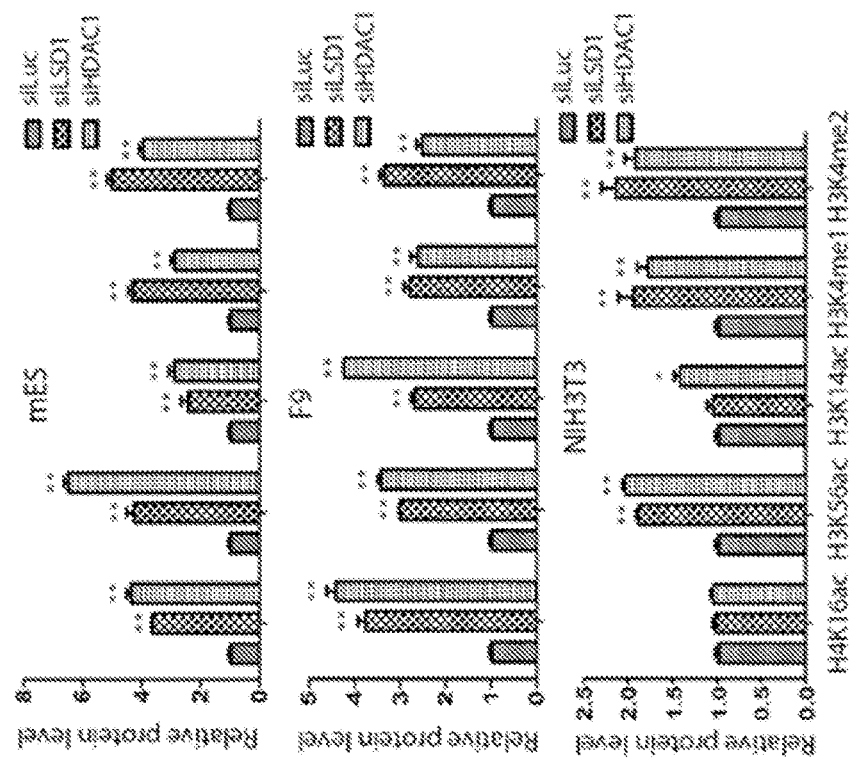
Figure 29E:
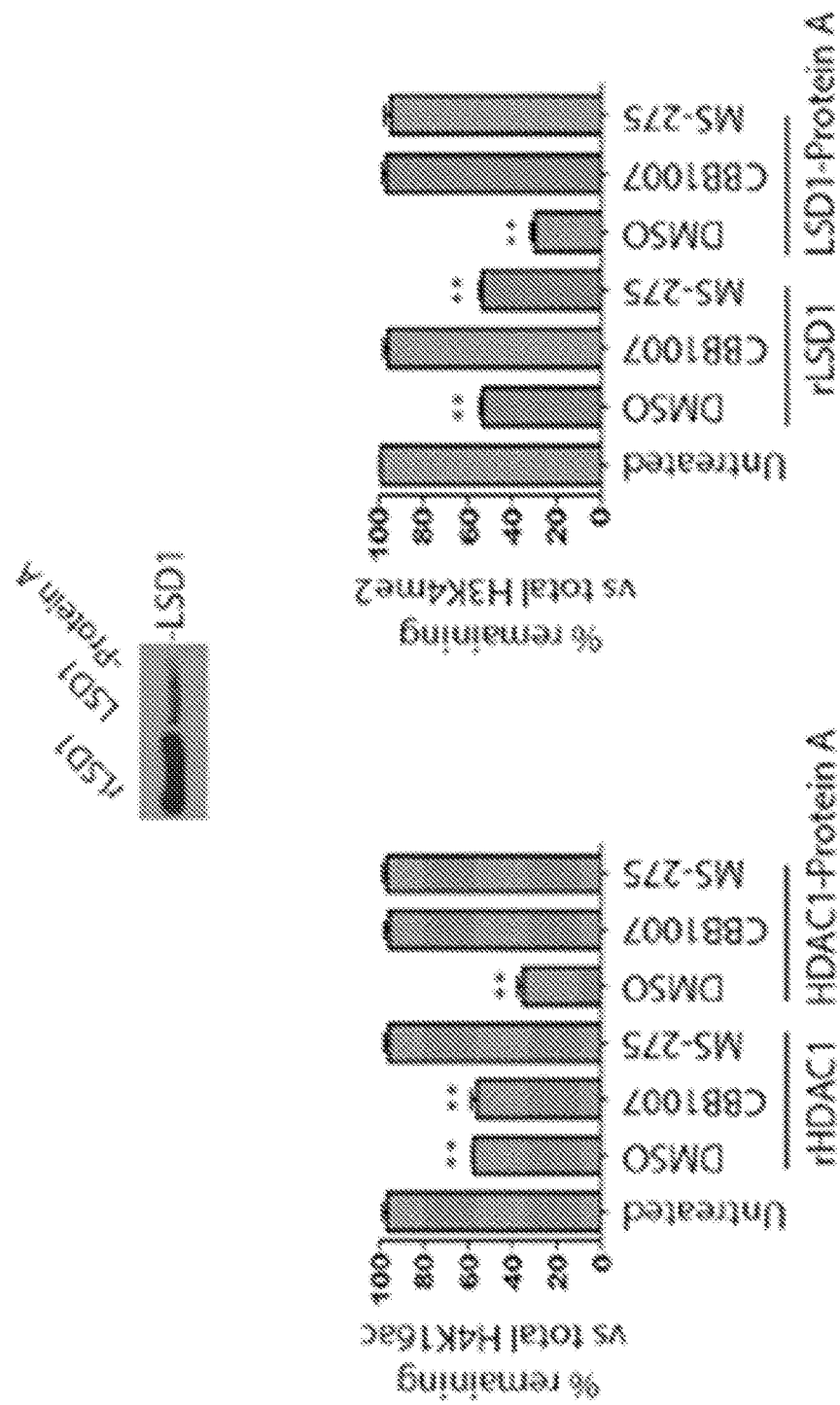

18. Regulation of LSD1 and HDAC1 by Mutual Activities in the LSD1-Corest-HDAC1 Complex To investigate the relationship between LSD1 and HDAC1, the activities of recombinant LSD1 and HDAC1 proteins were compared with those of LSD1-HDAC1 complexes isolated from F9 cells. Additionally, the sensitivity of recombinant LSD1 or HDAC1 proteins and isolated LSD1 or HDAC1 protein complexes to LSD1 or HDAC1 inhibitors in vitro was evaluated (FIGS. 29A and 29D). The LSD1-proteinA and HDAC1-proteinA complexes, which also contain CoREST, from F9 cells using anti-LSD1 and HDAC1 antibodies were also immunoaffinity purified (FIGS. 27A-B and 29E) to compare their activities with those of recombinant proteins. The substrate H4K16ac peptide was incubated with GST-HDAC1 and HDAC1-protein A. The substrate (acetylated H4K16) and product (nonacetylated H4K16) peptides were separated, resolved, and quantified by mass spectrometry (FIG. 29E, middle). Both GST-HDAC1 and HDAC1-protein A could remove the acetyl group from the H4K16ac peptide, and both were sensitive to MS-275, although the endogenous HDAC1 appeared to be more active, even though it consisted of about 2.5 times less protein (FIG. 29E, left and middle). Because H4K16ac in F9 cells is sensitive to LSD1 inhibitors (FIG. 28), the potential effects of LSD1 inhibitors in the HDAC1 assay were also evaluated in vitro. Strikingly, the LSD1 inhibitor CBB1007 was sufficient to inhibit the deacetylase activity of immuno affinity purified HDAC1 (HDAC1-protein A) but not that of GSTHDAC1 (FIG. 29E, middle) in the deacetylation reaction.

Referring to FIG. 29D, a schematic design to test whether inhibition of LSD1 blocks the activity of HDAC1 and vice versa is shown.

Referring to FIG. 29E, the activities of HDAC1 and LSD1 in the isolated endogenous protein complexes were sensitive to both MS-275 and CBB1007. (Left) Protein levels of recombinant HDAC1 and LSD1 (rHADC1 or rLSD1) and immunoaffinity-purified HDAC1 and LSD1 (HDAC1-protein A or LSD1-protein A complexes) from F9 cells. The GST tag of the GST-HDAC1 and GST-LSD1 proteins was removed prior to the reactions. (Middle) The endogenous HDAC1 in immunoprecipitated protein complexes was sensitive to both CBB1007 and MS-275, whereas rHDAC1 was sensitive only to MS-275. (Right) The activity of LSD1 in the isolated immunoprecipitated LSD1-protein A was inhibited by MS-275 and CBB1007, while the activity of rLSD1 was inhibited only by CBB1007.

As H3K4me1 and H3K4me2 were also sensitive to the inactivation of HDAC1 in pluripotent ES and EC cells (FIGS. 28A and 28B), the effects of MS-275 on the in vitro activities of recombinant and endogenous LSD1 complexes isolated from F9 cells using a dimethylated H3K4 peptide as a substrate were also evaluated (FIG. 29E). While both GST-LSD1 and the immunoaffinity-isolated LSD1 complexes from F9 cells (LSD1-protein A) could remove the methyl groups from the dimethylated H3K4 peptide and convert it into mono- and nonmethylated H3K4 peptides in a reaction that was sensitive to CBB1007 (FIGS. 29B and 29E, right), addition of HDAC inhibitor MS-275 in the demethylation reaction blocked the demethylation activity of immunoaffinity-purified LSD1 but not that of GST-LSD1 (FIG. 29E, right). Similar to the endogenous HDAC1, the immunoaffinity-purified LSD1 protein from F9 cells seemed to be more active, as 4 times less LSD1 protein was present in the LSD1-protein A complex (FIG. 29E). Without wishing to be bound by theory, these results suggest that, different from the recombinant LSD1 or HDAC1 proteins, the activities of LSD1 and HDAC1 are mutually dependent on each other in the protein complexes isolated from F9 cells, which is consistent with our observation that loss of LSD1 or HDAC1 selectively inhibited cell growth and increased H3K4me1/me2, H4K16ac, and H3K56ac levels in ES/EC cells (FIGS. 27 and 28).

Figure 29F:
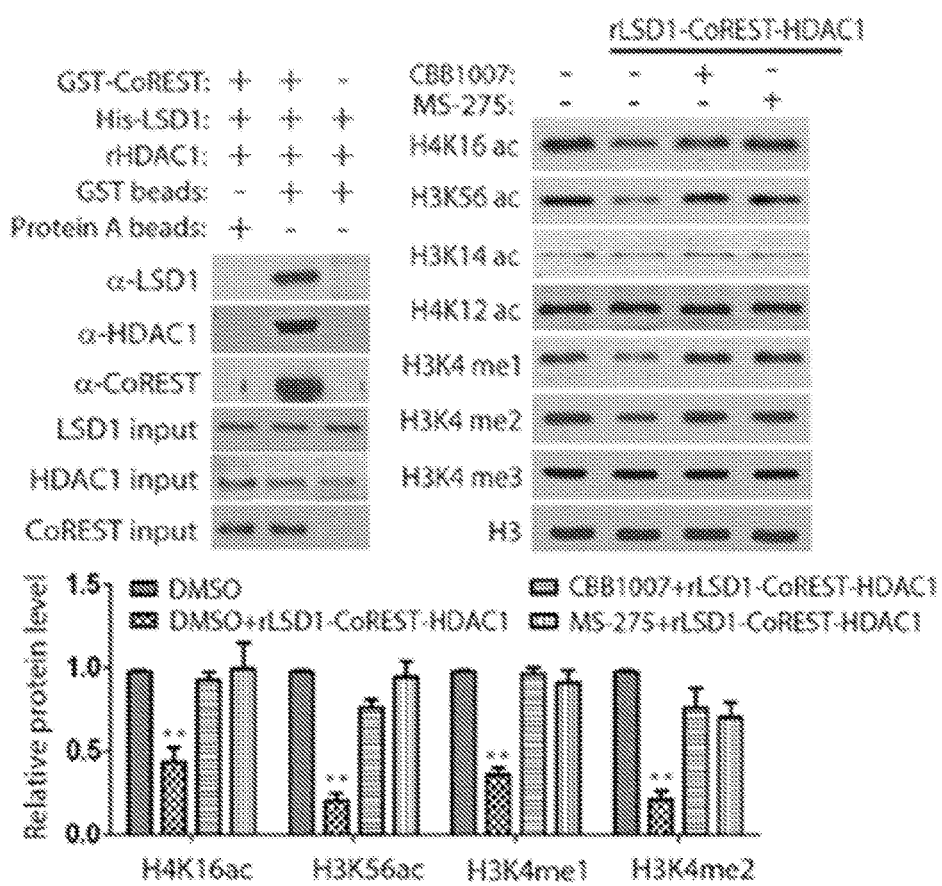
Figure 29G:
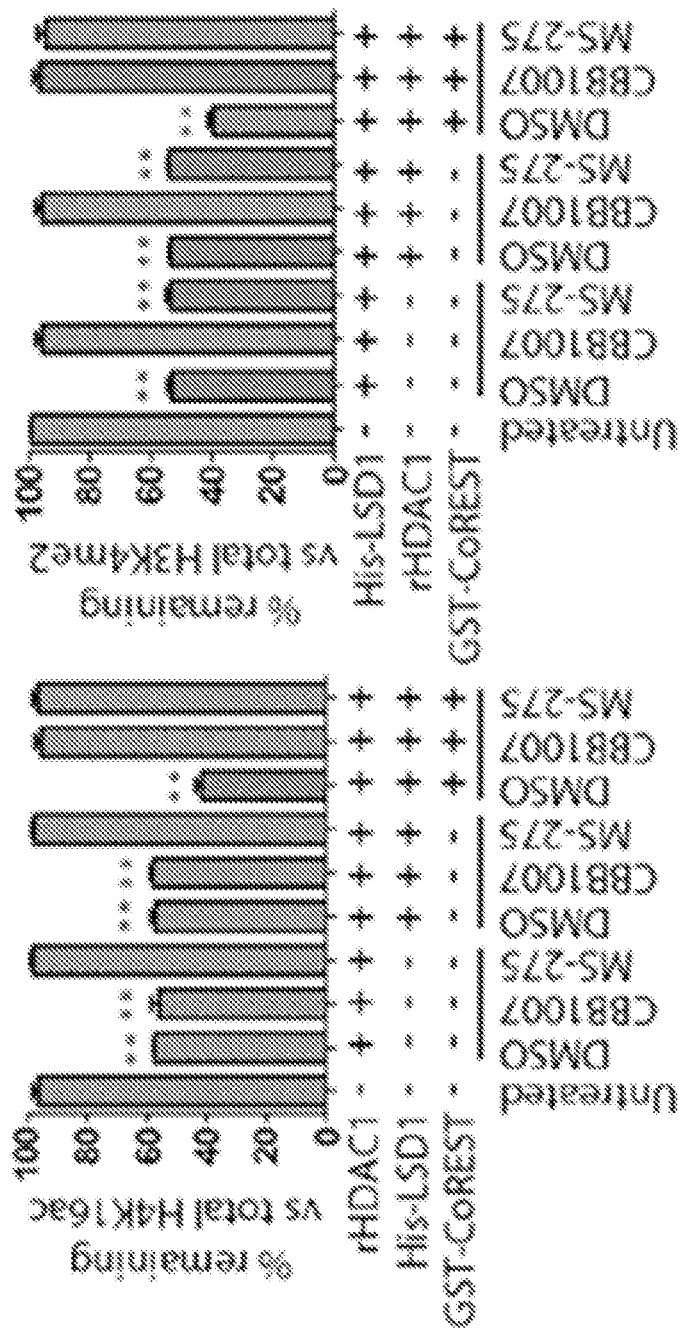

Because LSD1 and HDAC1 were both associated with CoREST in F9 cells (FIGS. 27A and 27B), it was hypothesized that the mutual requirements of LSD1 and HDAC1 activities may be due to their binding to the same CoREST complex. To validate this point, the recombinant proteins were used to reconstitute the LSD1-CoRESTHDAC1 protein complex (FIG. 29F, top left). The activities of the reconstituted complexes were then assayed using oligonucleosomal histones as the substrate which were extracted from F9 cells after micrococcal nuclease digestion, as recombinant LSD1 alone did not work on such a substrate (Shi, Y. J., et al. (2005) Mol. Cell 19, 857-864; Lee, M. G., et al. (2005) Nature 437, 432-435). These studies showed that the reconstituted LSD1-CoREST-HDAC1 complex could be assembled in vitro and the complex contained both demethylase and deacetylase activities toward the nucleosomal substrates (FIG. 29F, top right). Treatment of this complex with the LSD1 inhibitor CBB1007 not only inhibited the activity of LSD1 demethylase but also caused the partial inhibition of the HDAC1 deacetylase activity. Conversely, the HDAC inhibitor MS-275 could also partially inhibit the LSD1 demethylase activity by blocking the HDAC1 activity in the reconstituted LSD1-CoREST-HDAC1 complex (FIG. 29F, bottom). The formation of the LSD1 and HDAC1 complexes and the mutual sensitivities toward either LSD1 or HDAC1 inhibitors are dependent on CoREST. In the absence of CoREST, not only did the LSD1-HDAC1 complex not form but also the activity of LSD1 was independent of HDAC1 and vice versa for HDAC1 (FIGS. 29F and 29G). Without wishing to be bound by theory, these studies suggest that the allosteric effects of LSD1 and HDAC1 through their trimeric complex formation with CoREST to regulate their demethylase and deacetylase activities.

Referring to FIG. 29F, both LSD1 and HDAC1 in the reconstituted recombinant LSD1-CoREST-HDAC1 complex were partially sensitive to LSD1 or HDAC1 inhibitors. (Top left) The indicated recombinant LSD1, HDAC1, and GST-CoREST proteins were mixed, and the protein complexes were isolated by GST beads. The components in the isolated reconstituted complexes were examined by Western blotting. Protein A beads were used as a negative control. (Top right) The activity of the reconstituted LSD1-CoREST-HDAC1 complexes was measured using oligonucleosomes as the substrate either in the presence or in the absence of 50 μM CBB1007 or 2 μM MS-275. (Bottom) The protein levels in the top right panel were quantified using Gel-Pro Analyzer (version 4.0) software. The first lane in the top right panel contained oligonucleosomes only.

Referring to FIG. 29G, in the absence of CoREST, LSD1 was not sensitive to MS-275, while HDAC1 was not inhibited by CBB1007 using the H3K4me2 or H4K16ac peptide as the substrate. All experiments were conducted at least three times, and only the results of a representative experiment are shown. Error bars denote SEMs for duplicate samples. The statistical differences were analyzed by one-way ANOVA. **, $P<0.01$.

19. Regulation of LSD1 and HDAC1 Activities by Substrate Modification

Figure 30A:
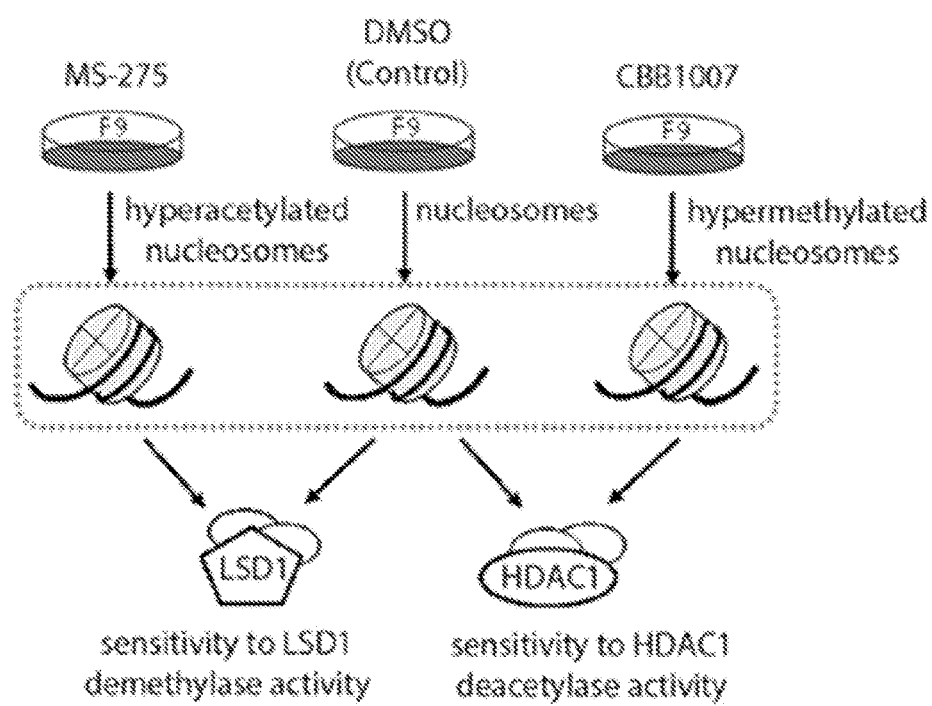
FIG. 30A-C show representative data pertaining to the regulation of LSD1 and HDAC1 activities by substrate modification.
Figure 30B:
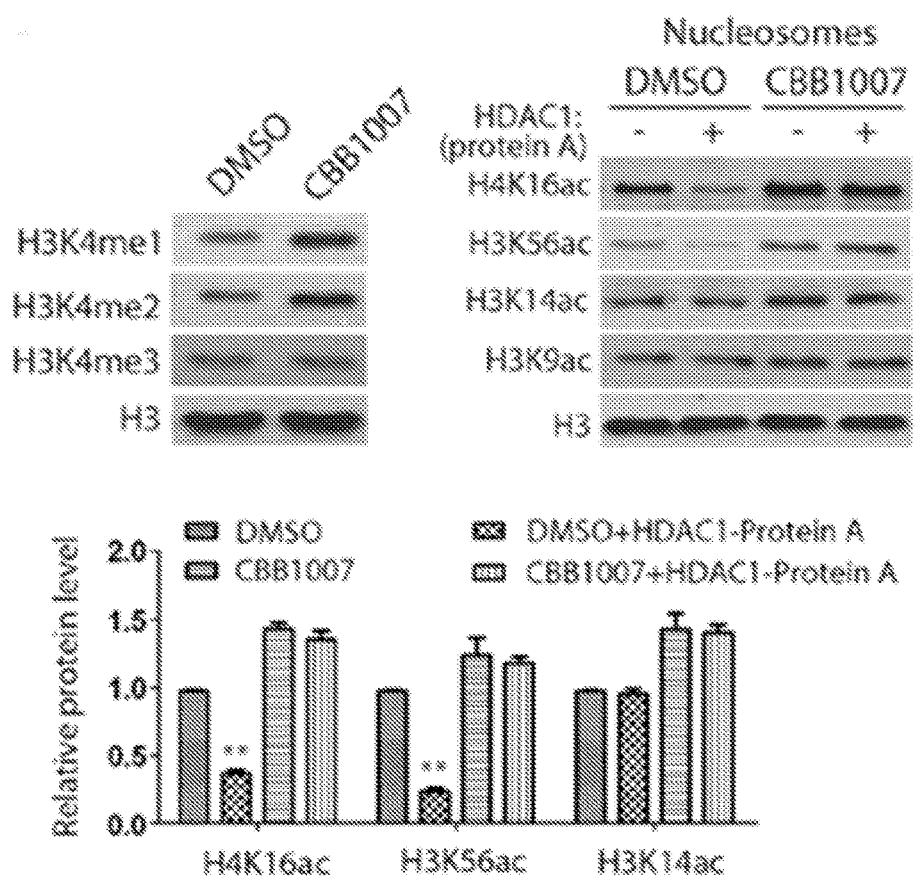

Because the loss of LSD1 or HDAC1 in ES/EC cells induces hypermethylated HsK4 or hyperacetylated H4K16 or H3K56, respectively (FIG. 28), whether the hypermethylated or hyperacetylated nucleosomes serve as optimal substrates for HDAC1 or LSD1 was investigated (FIG. 30A). To isolate hypermethylated or hyperacetylated nucleosomes, F9 cells were treated with either the LSD1 inhibitor CBB1007 or the HDAC inhibitor MS-275, and oligonucleosomes were subsequently isolated (FIGS. 30A and 30B, top, and C, left). The hypermethylated nucleosomes from CBB1007-treated cells were incubated with immunoaffinity-purified HDAC1 complex (HDAC1-protein A), and the efficiency of deacetylation was compared with that of dimethyl sulfoxide (DMSO)-treated nucleosomes (FIG. 30B). The HDAC1 complex could no longer efficiently deacetylate the H3K4 hypermethylated nucleosomes isolated from LSD1 inhibitor treated F9 cells (FIG. 30B, bottom). Conversely, when hyperacetylated nucleosomes isolated from MS-275-treated F9 cells were used as the substrates (FIG. 30C, left), the immunoaffinity-purified LSD1 complex (LSD1-protein A) could not utilize this substrate (FIG. 30C, right), consistent with the findings of previous TSA experiments (Shi, Y. J., et al. (2005) *Mol. Cell* 19, 857-864). Thus, without wishing to be bound by theory these studies suggest not only that LSD1 and HDAC1 can mutually regulate their activities through an allosteric effect in the CoREST complex but also that their activities are controlled by the preference for the hypomethylated or hypoacetylated nucleosomal substrates, respectively.

Referring to FIG. 30A, a schematic outline for the experimental design is shown. The hyperacetylated or hypermethylated nucleosomes were isolated from cells treated with either MS-275 or LSD1 inhibitors. The hyperacetylated or hypermethylated nucleosomes, as well as the control nucleosomes (DMSO treated), were subsequently used as the substrates for immunoaffinity-purified HDAC1 or LSD1 complexes to determine the substrate preferences.

Referring to FIG. 30B, HDAC1 was unable to use hypermethylated H3K4 oligonucleosomes as a substrate. (Top) Oligonucleosomes from CBB1007-treated F9 cells were hypermethylated on H3K4, and HDAC1 in the immunoprecipitated HDAC1-proteinA complexes could not efficiently use hypermethylated histones as a substrate; (bottom) the protein bands were quantified by the use of Gel-Pro Analyzer (version 4.0) software.

Figure 30C:
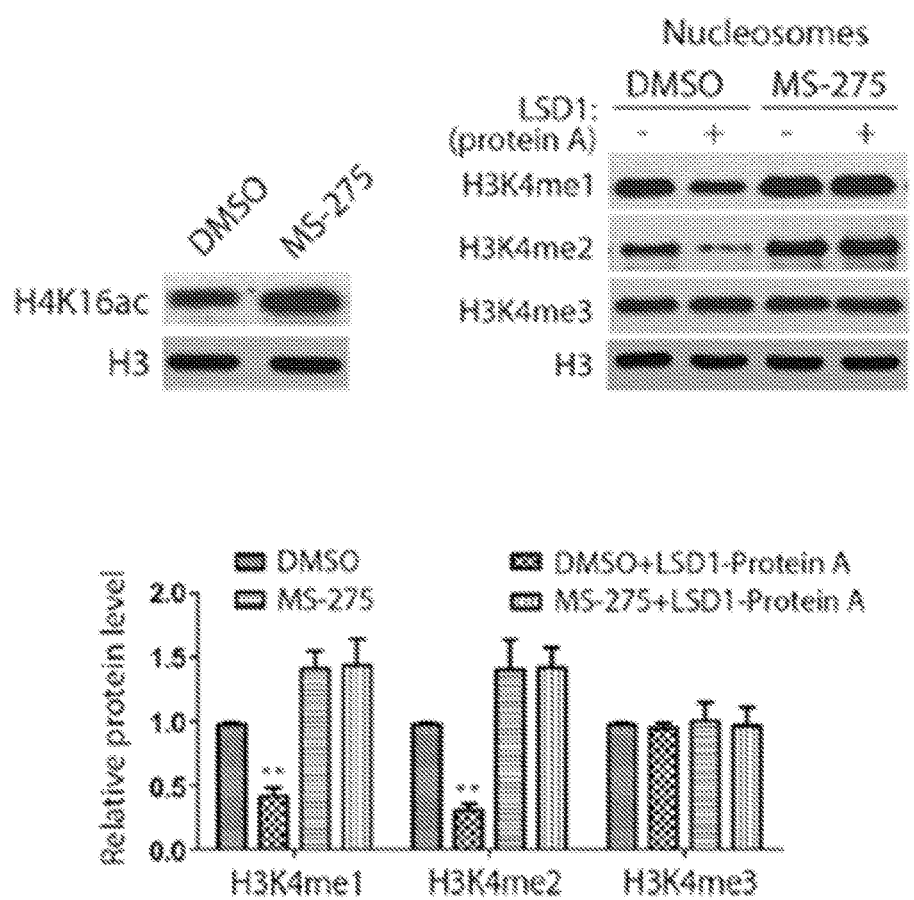

Referring to FIG. 30C, LSD1 preferred hypoacetylated oligonucleosomes as the substrate. Oligonucleosomes from MS-275-treated F9 cells were hyperacetylated on H4K16 (left), and they were resistant to the demethylase activity of LSD1 in the immunoprecipitated LSD1-protein A complex (right). Quantification was done as described in the legend to FIG. 27, and error bars denote SEMs for duplicate samples. Results are representative of those from three independent experiments. The statistical differences were analyzed by one-way ANOVA. **, P<0.01.

Figure 31A:
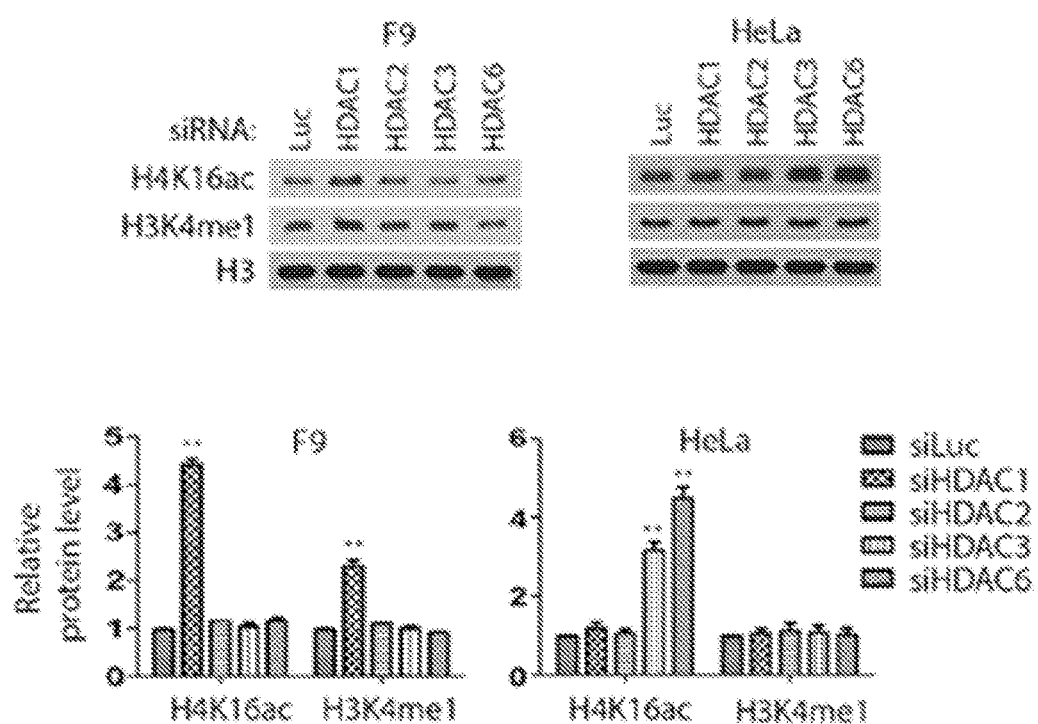
FIG. 31A-E show representative data pertaining to the regulation of H4K16 acetylation by elevated HDAC1 and LSD1 levels in ES/EC cells.
Figure 31B:
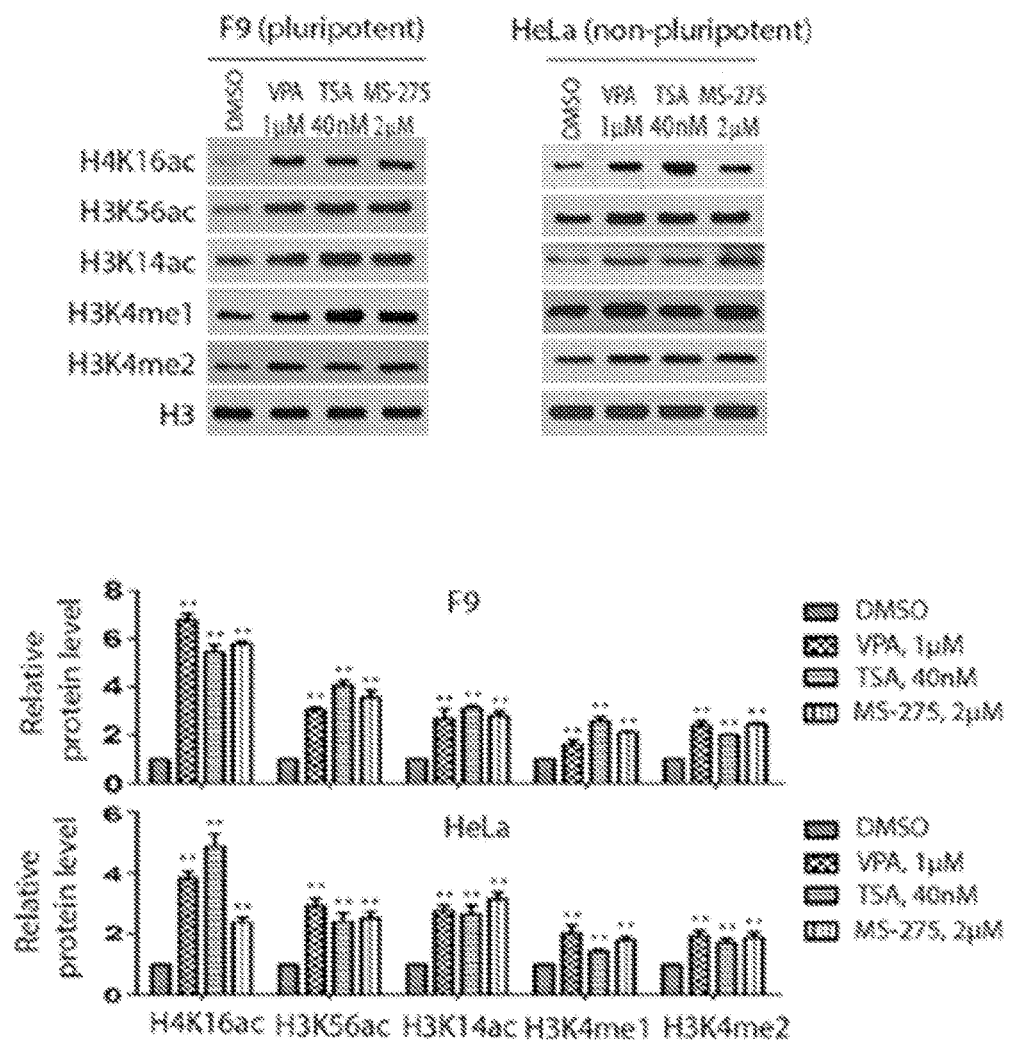

20. Multiple HDACs Regulate the Acetylation of Histone H4K16 in Nonpluripotent Cells These results indicated that the acetylated H4K16 is a substrate of HDAC1 (FIGS. 28 and 29). However, the loss of HDAC1 could induce the accumulation of acetylated H4K16 only in pluripotent ES/EC cells and not in nonpluripotent NIH 3T3 or HeLa cells (FIGS. 28A-B and 31A). HDAC1 belongs to the HDAC family, which has 18 members in the human genome. Because HDAC1 and HDAC2 were reported to play a redundant role in the proliferation of HeLa cells (Jurkin, J., et al. (2011) *Cell Cycle* 10, 406-412; Haberland, M., et al. (2009) *Proc. Natl. Acad. Sci. USA* 106, 7751-7755), it was hypothesized that acetylation of H4K16 may be regulated by multiple HDACs in nonpluripotent cells. To test this, HeLa cells were treated with various HDAC inhibitors, including valproic acid (VPA), trichostatin A (TSA), and MS-275 (FIG. 31B). It is known that MS-275 inhibits the activities of HDACs 1, 2, and 3 and VPA specifically targets HDACs 1, 2, 3, and 8, while TSA has a broader substrate specificity against class I and class II HDACs, including HDAC6 and HDAC10 (Witt, O., et al. (2009) *Cancer Lett.* 277, 8-21). Indeed, these pan-HDAC inhibitors induced the accumulation of acetylated H4K16 in HeLa cells (FIG. 31B); without wishing to be bound by theory, this may suggest that the deacetylation of H4K16 in nonpluripotent cells may be regulated by multiple HDACs, in addition to HDAC1.

Referring to FIG. 31A, F9 and HeLa cells were transfected with the indicated siRNAs, and histone modifications were analyzed and quantified.

Referring to FIG. 31B, the acetylation of H4K16 is sensitive to pan-HDAC inhibitors in HeLa cells. F9 and HeLa cells were treated with the HDAC inhibitor VPA (1 µM) or MS-275 (2 µM) for 24 h or TSA (40 nM) for 16 h. Methylated and acetylated histones H3 and H4 were blotted by specific antibodies, as indicated, and quantified by the use of Gel-Pro Analyzer (version 4.0) software.

Figure 31C:
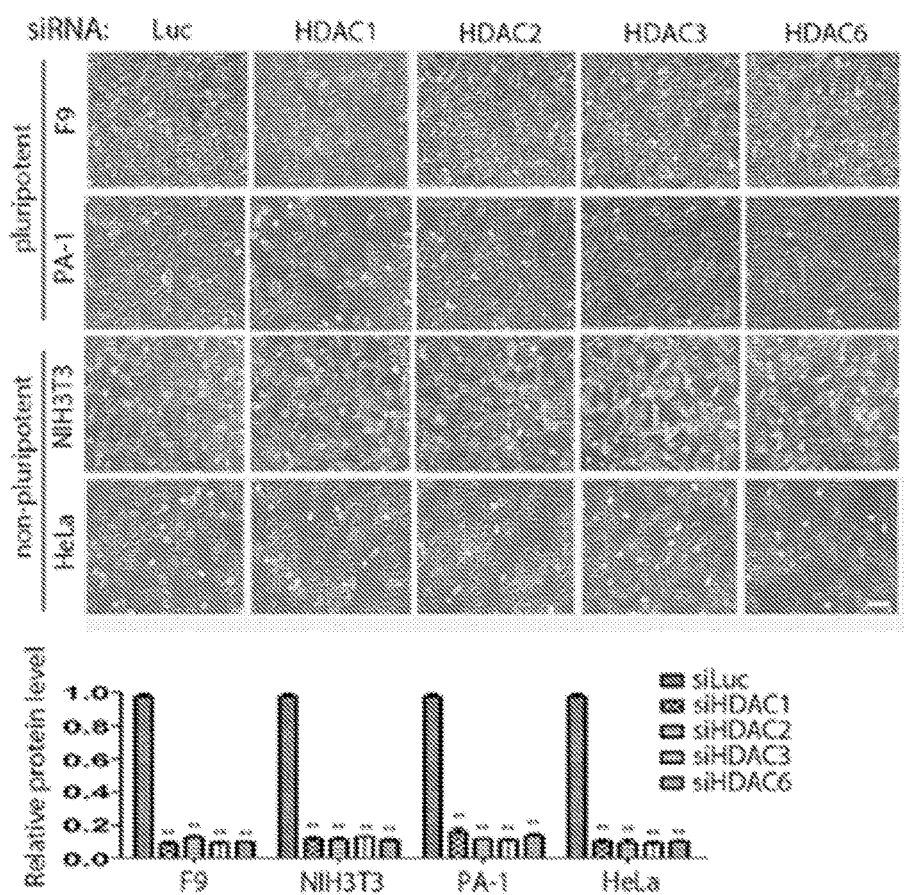

To determine whether additional HDACs are involved in the deacetylation of H4K16ac, the expression of HDACs 1 to 3 and 6 were individually ablated and their effects on the acetylation of H4K16 in nonpluripotent HeLa and pluripotent F9 cells was examined Loss of HDAC3 or HDAC6 alone was sufficient to induce the accumulation of acetylated H4K16 in HeLa cells, even though the loss of HDAC1 could sometimes cause a slight increase of this acetylation (FIG. 31A). However, the loss of HDAC3 and HDAC6 in pluripotent EC cells, such as F9 cells, did not induce the accumulation of acetylated H4K16 and cause growth inhibition of EC cells, such as PA-1 and F9 cells (FIGS. 31A and 31C), even though HDAC6 deficiency caused some growth inhibition in HeLa cells (FIG. 31C). Without wishing to be bound by theory, these studies suggest that HDAC1 is unique in regulating the acetylation of H4K16 in ES/EC cells (FIGS. 27, 28, and 31).

Referring to FIG. 31C, only the loss of HDAC1 causes inhibition of F9 and PA-1 cell growth. The cell growth was analyzed by microscopy, and proteins were analyzed by Western blotting and quantified by the use of Gel-Pro Analyzer (version 4.0) software.

Figure 31D:
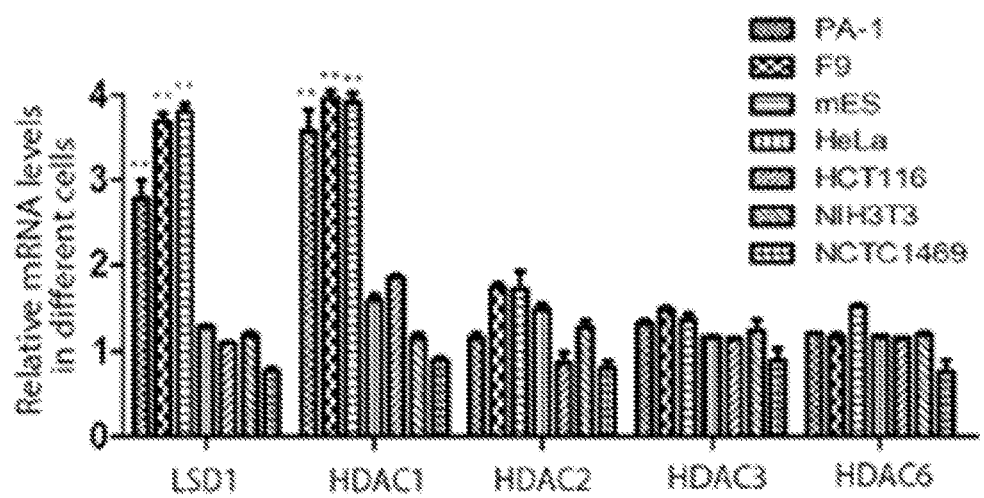

Referring to FIG. 31D, total mRNAs were isolated from pluripotent PA-1, F9, and mES cells and nonpluriptoent HeLa, HCT116, NIH 3T3, and NCTC1469 cells. The expression levels of LSD1, HDAC1, HDAC2, HDAC3, and HDAC6 were compared using quantitative real-time PCR (qPCR).

Figure 31E:
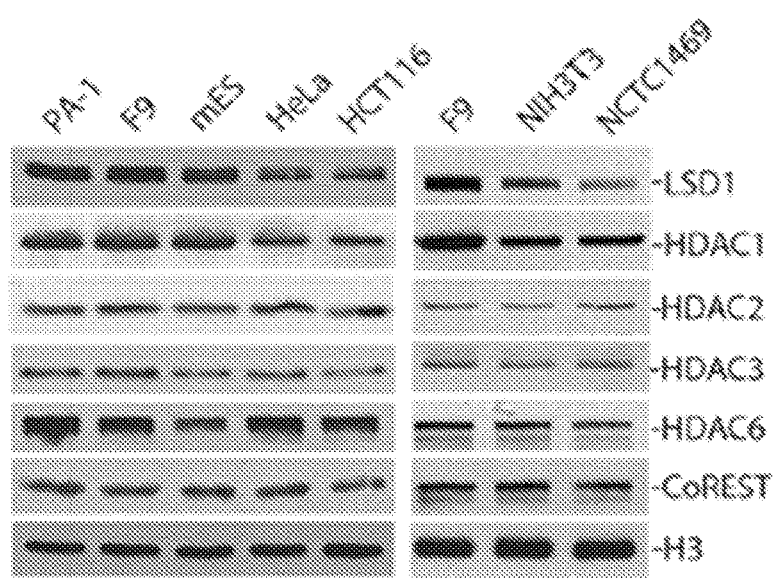

Referring to FIG. 31E, the levels of the HDAC1, HDAC2, HDAC3, and HDAC6, CoREST, and LSD1 proteins were compared between the various cell lines, as indicated. The RNA interference effects were confirmed in three independent experiments. The error bars denote SEMs for duplicate samples. The statistical differences were analyzed by one-way ANOVA. **, P<0.01.

21. Levels of Both HDAC1 and LSD1 are Significantly Elevated in ES/EC Cells

To determine the mechanism by which HDAC1 or LSD1 inactivation causes the accumulation of H4K16 acetylation only in pluripotent ES/EC cells (FIGS. 28 and 27A), the mRNA and protein levels of HDACs 1 to 3 and HDAC6 were examined in pluripotent ES/EC cells and nonpluripotent cells. RNA levels of HDAC1 and LSD1 are significantly elevated in pluripotent mES, F9, and PA-1 cells compared with their levels in nonpluripotent cells, such as HeLa, HCT116, NIH 3T3, and NCTC1469 cells (FIG. 27D).

Analysis of the levels of the HDAC1 and LSD1 proteins confirmed these observations (FIG. 27E). In contrast, the expression of HDAC2, HDAC3, and HDAC6, as well as that of CoREST, remained relatively constant in both pluripotent and nonpluripotent cells (FIGS. 27D and 27E). Without wishing to be bound by theory, these studies suggest that the elevated expression of HDAC1 and LSD1 and the formation of a predominant LSD1-HDAC1 protein complex in pluripotent ES/EC cells may account for the enhanced sensitivity of H4K16 acetylation to the changes of HDAC1 or LSD1, which is required for the proliferation of ES/EC cells. However, because of the relatively low levels of LSD1 and HDAC1 in nonpluripotent cells, other HDACs, such as HDAC3 and HDAC6, may play a major role in the removal of acetylated H4K16.

Figure 32A:
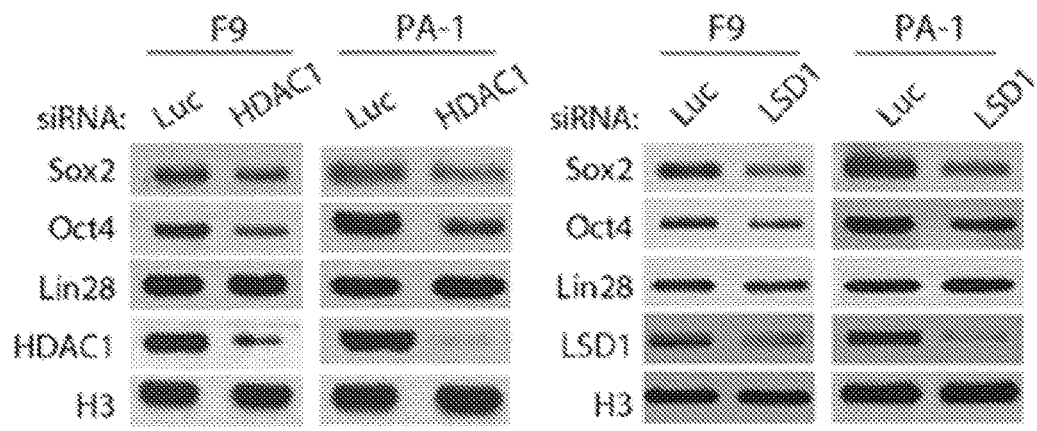
FIGS. 32A and 32B show representative data demonstrating that HDAC1 is required for the expression of Oct4 and Sox2 by directly binding to the regulatory regions.
Figure 32B:
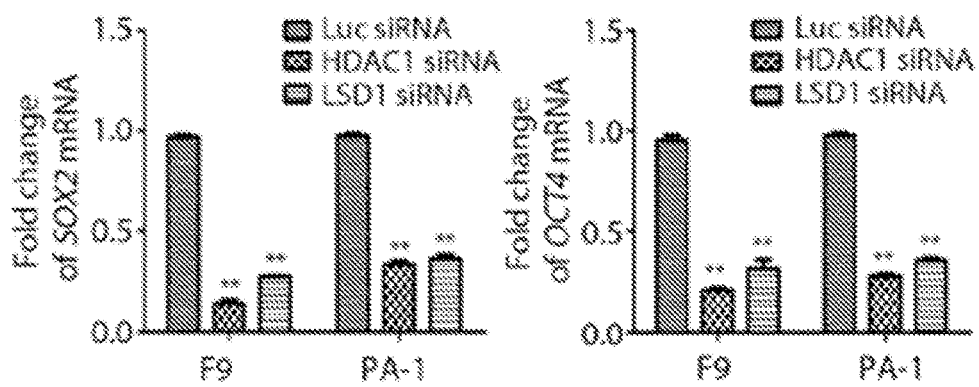

22. HDAC1 is Required for the Expression of Oct4 and Sox2 and for Suppressing Genes for Differentiation of ES/EC Cells Previous studies revealed that inhibition of LSD1 in ES/EC cells caused the downregulation of pluripotent stem cell proteins Oct4 and Sox2 (Wang, J. et al. (2011) *Cancer Research* 71, 7238-7249). Consistent with this observation, loss of HDAC1 in pluripotent F9 and PA-1 cells also reduced the expression of both Oct4 and Sox2 at the mRNA and protein levels (FIGS. 32A and 32B). In addition, inactivation of LSD1 can induce the expression of differentiation-associated genes in ES/EC cells (Adamo, A., et al. (2011) *Nat. Cell Biol.* 13, 652-659; Wang, J. et al. (2011) *Cancer Research* 71, 7238-7249). Ablation of either HDAC1 or LSD1 by specific siRNAs also induced the expression of differentiation genes, such as FOXA2, HNF4A, SOX17, BMP2, and EOMES, in F9 and PA-1 cells (FIG. 33A), consistent with the notion that LSD1 and HDAC1 act through the same pathway to regulate the pluripotency of ES/EC cells.

Referring to FIGS. 32A and 32B, inactivation of HDAC1 or LSD1 suppresses the expression of pluripotent stem cell proteins Oct4 and Sox2. F9 and PA-1 cells were transfected with siRNAs specific for HDAC1 or LSD1, and the effects of Oct4 and Sox2 on the protein (32A) and mRNA (32B) levels were analyzed by Western blotting and qPCR.

Figure 33A:
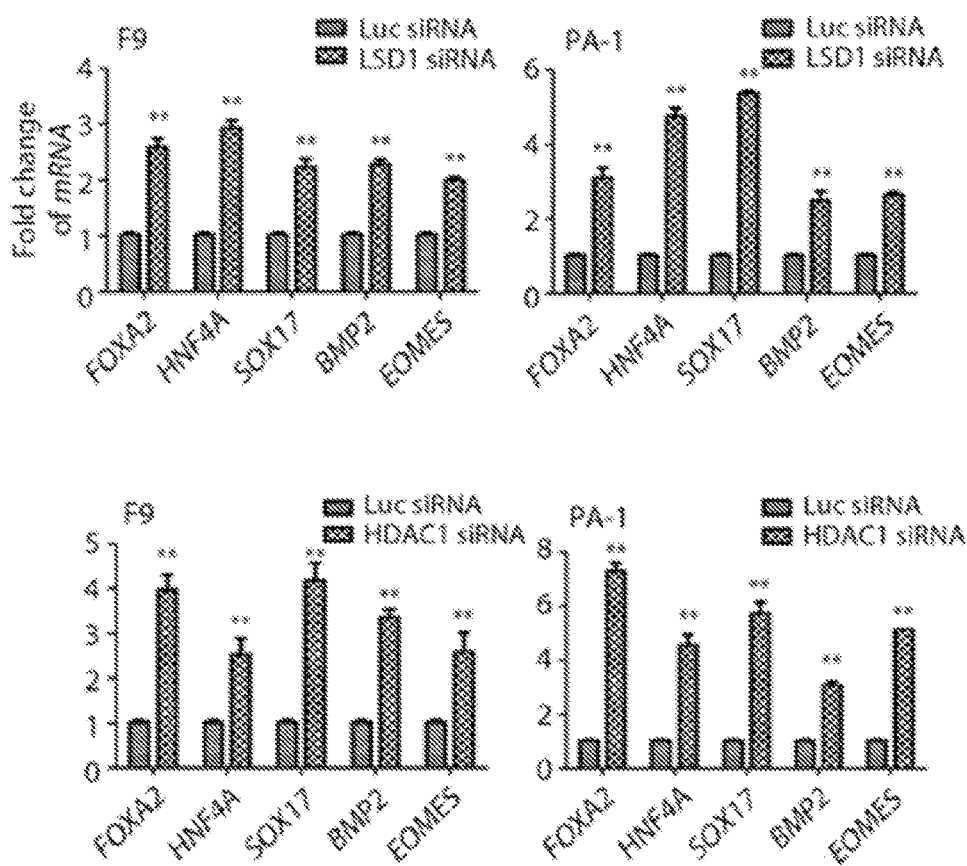
FIGS. 33A and 33B show representative data demonstrating that loss of HDAC1 or LSD1 induces the expression of genes for differentiation.

Referring to FIG. 33A, PA-1 and F9 cells were transfected with the indicated siRNAs. The mRNAs were isolated, and the levels of the differentiation genes FOXA2, HNF4A, SOX17, BMP2, and EOMES were analyzed using qPCR.

Figure 34A:
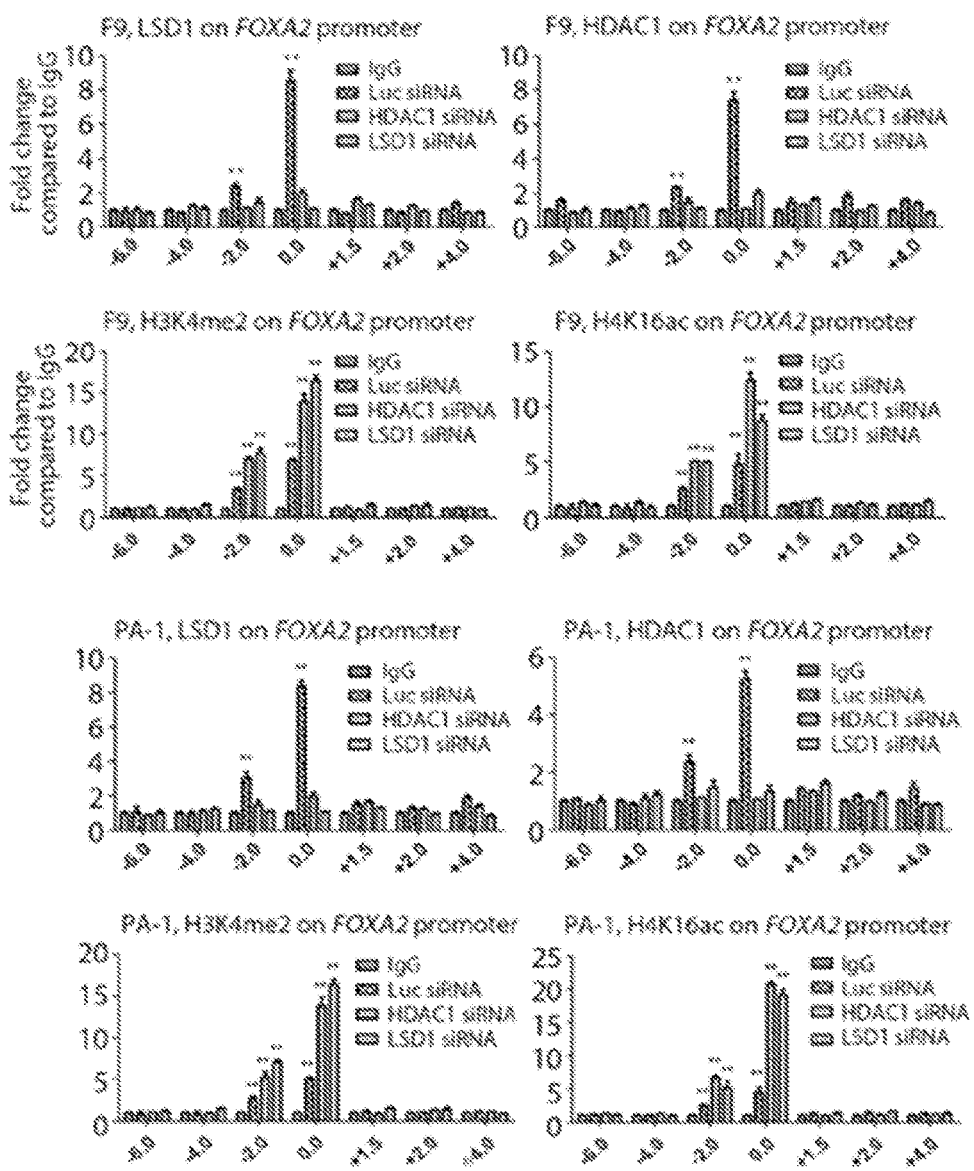
FIGS. 34A and 34B show representative data demonstrating that LSD1 or HDAC1 inactivation induces elevated levels of H3K4me2 and H4K16ac on the regulatory regions of differentiation genes.
Figure 34B:
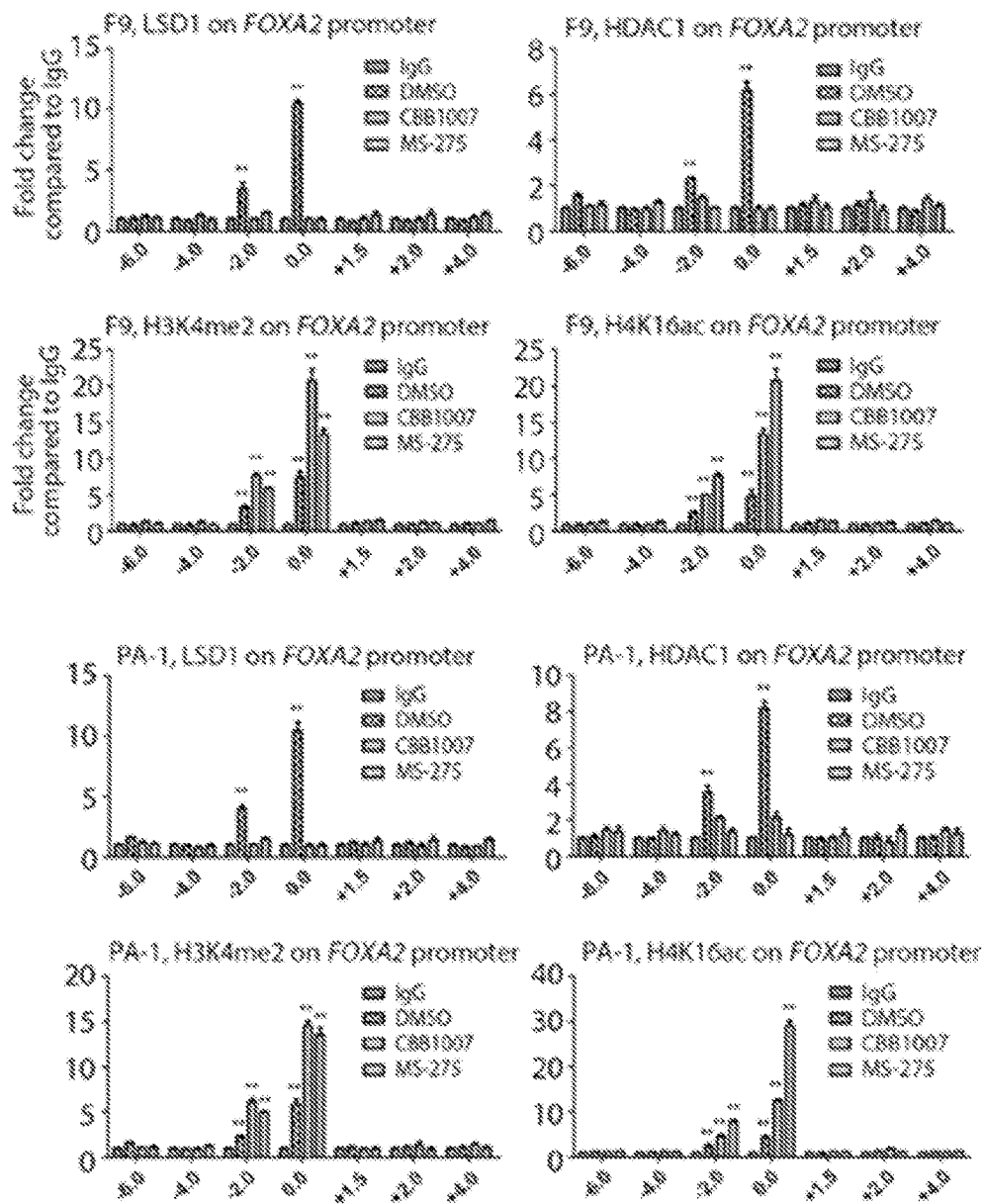

To further determine the roles of HDAC1 and LSD1 in regulating the expression of Oct4 and Sox2 and the genes for differentiation, the chromatin immunoprecipitation (ChIP) assay was carried out using antibodies specific for HDAC1, LSD1, H3K4me2, and H4K16ac and IgG as a control. The ChIP analysis allowed for mapping of the binding sites of HDAC1 and LSD1 and the presence of histone methylation/acetylation on the transcriptional regulatory regions of the target genes in F9 and PA-1 cells. Without wishing to be bound by theory, these data suggest that both HDAC1 and LSD1, as well as H3K4me2 and H4K16ac, are enriched and colocalized on the OCT4, SOX2, and FOXA2 upstream regulatory regions (FIG. 32B). Inactivation of LSD1 or HDAC1 activities by siRNAs or by LSD1 inhibitors reduced the binding of LSD1 or HDAC1 to the promoters of differentiation genes, such as the FOXA2 promoter, and induced elevated levels of H3K4me2 and H4K16ac on the FOXA2 regulatory region (FIGS. 34A and 34B). Without wishing to be bound by theory, these analyses suggest that LSD1 and HDAC1 directly regulate the expression of these genes in pluripotent EC cells.

Figure 33B:
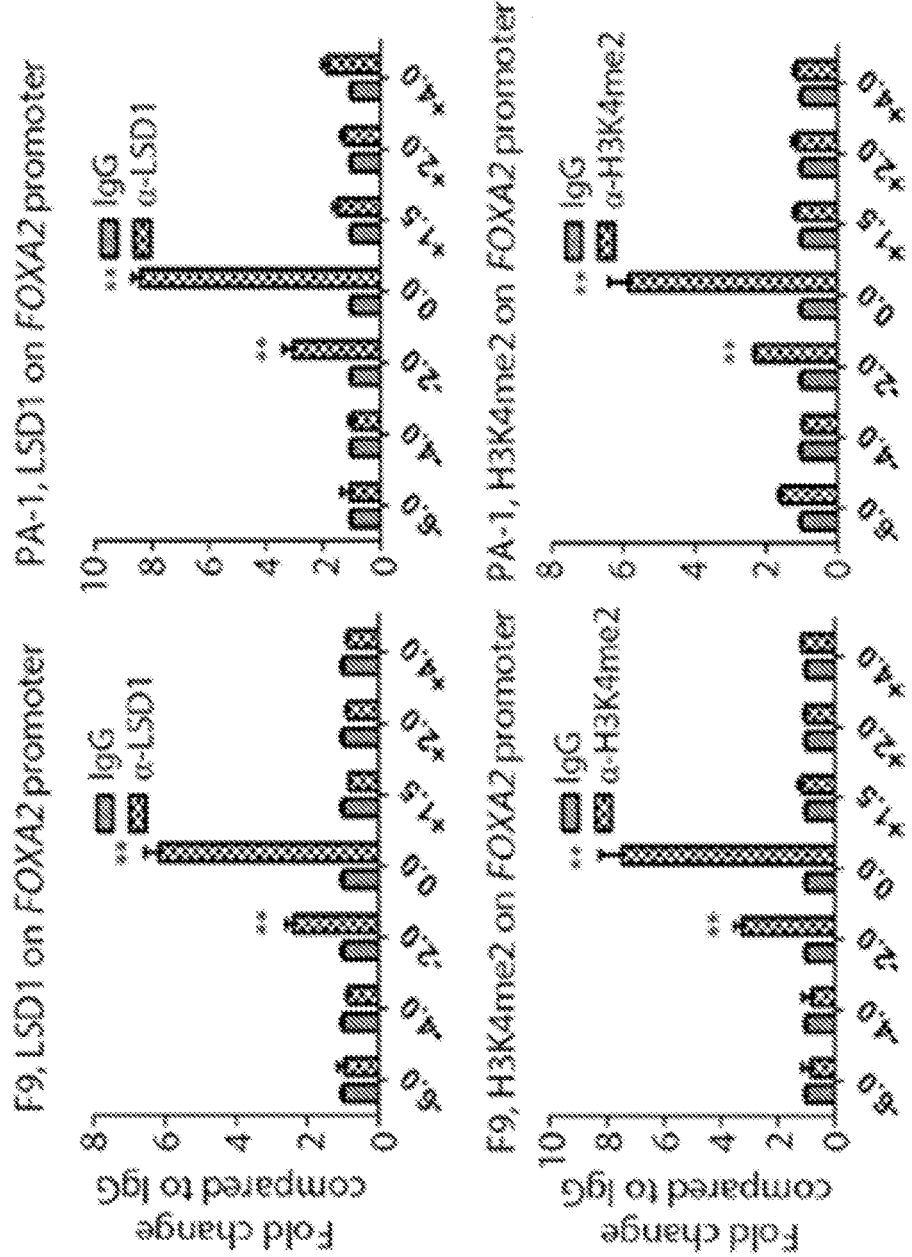
Figure 33B:
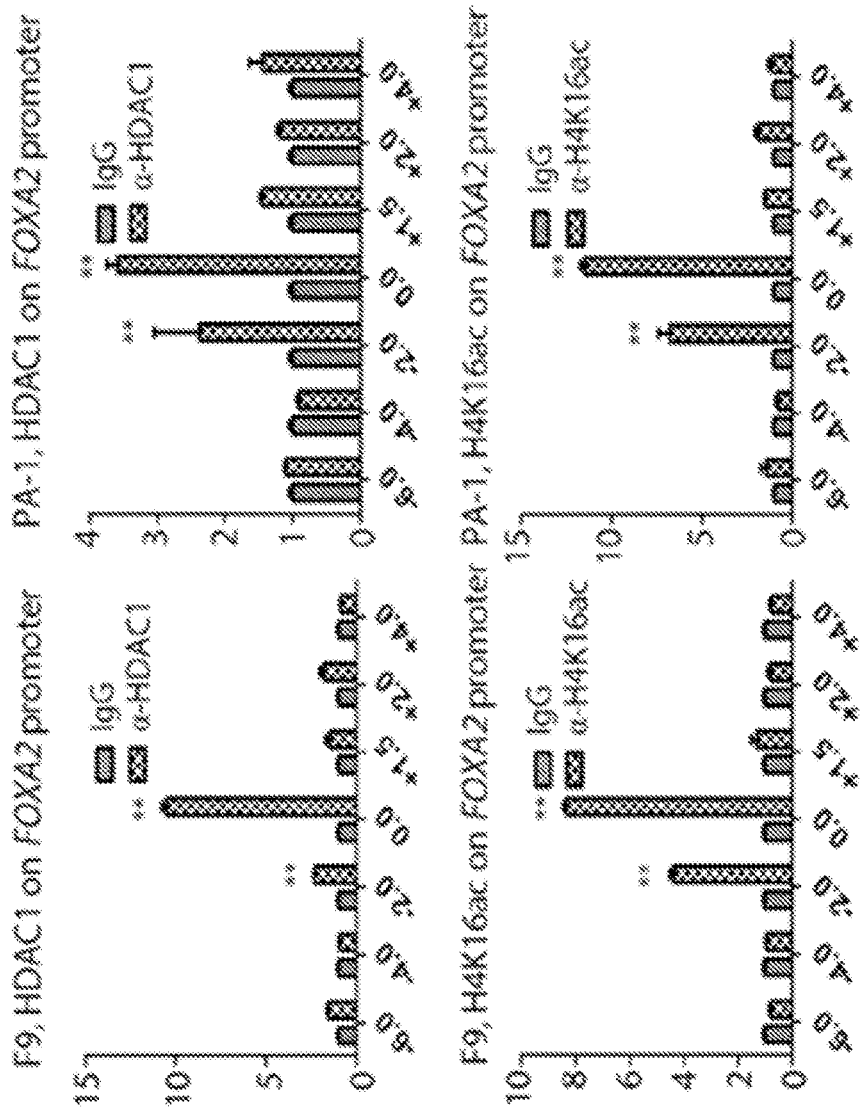

Referring to FIG. 33B, LSD1, HDAC1, H3K4me2, and H4K16ac colocalize to the regulatory regions of the differentiation gene FOXA2. The ChIP assay showed that LSD1, HDAC1, H3K4me2, and H4K16ac were enriched in the kb 0.0 to −2.0 upstream region of the FOXA2 gene in F9 and PA-1 cells. All experiments were conducted in triplicate, and the results were confirmed at least three times. Error bars denote SEMs for triplicate experiments. The statistical differences were analyzed by one-way ANOVA. **, $P<0.01$.

Referring to FIGS. 34A and 34B, F9 and PA-1 cells were transfected with siRNAs for 48 h (34A) or treated with CBB1007 or MS-275 for 30 h (34B), as indicated. The ChIP assay was performed to analyze the association of LSD1, HDAC1, H3K4me2, and H4K16ac with the transcriptional regulatory regions of FOXA2 in control and LSD1- or HDAC1-inactivated cells through qPCR in F9 and PA-1 cells. While the binding of LSD1 and HDAC1 was reduced when either LSD1 or HDAC1 was inactivated, the presence of H3K4me2 and H4K16ac was stimulated on the upstream regulatory region of the FOXA2 gene. All experiments were confirmed at least three times. The error bars represent SEMs for triplicate experiments. The statistical differences were analyzed by one-way ANOVA. **, $P<0.01$.

Figure 35A:
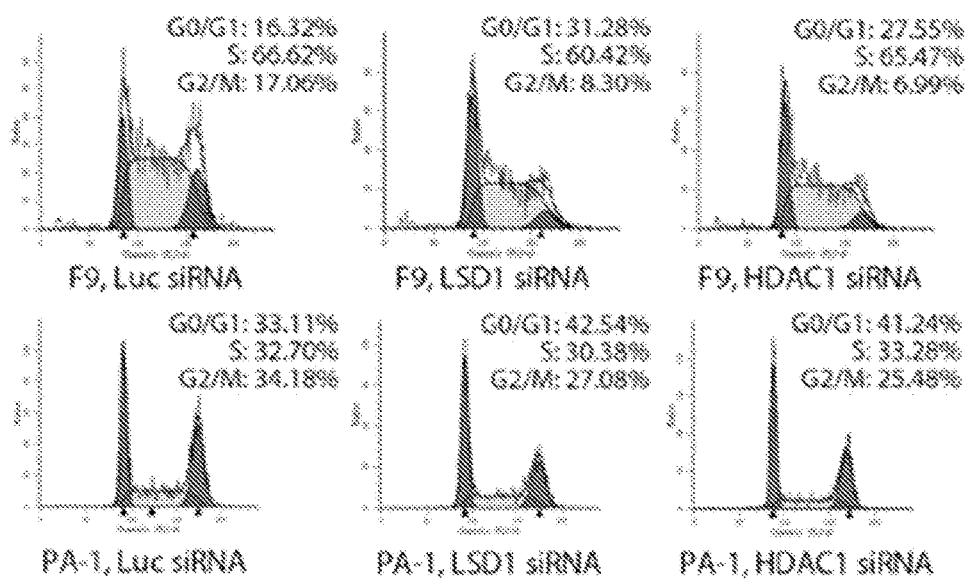
FIGS. 35A and 35B show representative data demonstrating that loss of LSD1 or HDAC1 induces $G_1$ cell cycle arrest in F9 and PA-1 cells.
Figure 35B:
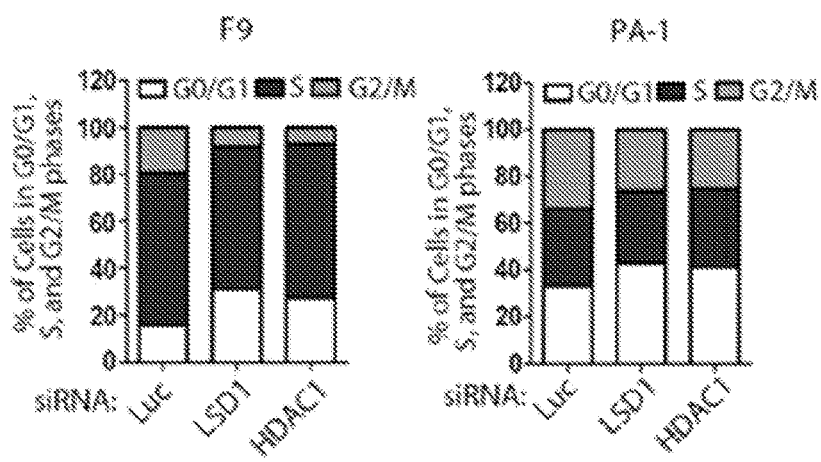

23. Loss of LSD1 or HDAC1 Causes $G_1$ Cell Cycle Arrest in Pluripotent EC Cells The cell cycle effects of F9 and PA-1 cells after LSD1 or HDAC1 inactivation were examined, using fluorescence activated cell sorting (FACS) analyses. Inactivation of LSD1 or HDAC1 consistently caused a profound $G_1$ cell cycle arrest in these EC cells (FIGS. 35A and 35B). Such a $G_1$ cell cycle arrest could also be induced by the treatment of these EC cells with retinoic acid (RA), a differentiation inducer. RA treatment also caused the reduction of pluripotent stem cell gene OCT4 and SOX2 levels and the induction of genes for differentiation, such as FOXA2 and BMP2. However, synchronization of F9 and PA-1 cells in the G1/S border by the double-thymidine-block method was insufficient to cause the downregulation of OCT4 and SOX2 and the induction of genes for differentiation. Without wishing to be bound by theory, these data suggest that the effects induced by inactivation of LSD1 or HDAC1 on the expression of Oct4, Sox2, and differentiation genes are similar to those induced by the differentiation agent RA, while G1 cell cycle arrest alone was not sufficient to induce effects similar to those induced by LSD1 or HDAC1 inactivation on F9 and PA-1 cells.

Referring to FIGS. 35A and 35B, F9 and PA-1 cells were transfected with the indicated siRNAs, and the cell cycle was analyzed by FACS. F9 and PA-1 cells were arrested in the $G_1$ cell cycle by LSD1 or HDAC1 inactivation.

24. HDAC1 is Unique in Coupling the Acetylation of H4K16 to the Methylation of H3K4 to Control the Proliferation of ES/EC Cells It was reported that Sirt1, another HDAC, interacts with histone H1 and removes the acetyl group from the acetylated H4K16 and H3K9 (Vaquero, A., et al. (2004) *Mol. Cell* 16, 93-105). Loss of Sirt1 did not cause growth inhibition of pluripotent F9 and PA-1 cells, even though the proliferation of NIH 3T3 cells was affected, indicating that Sirt1 deficiency did not have effects on pluripotent EC cells similar to those of HDAC1 inactivation. Examination of various chromatin modifications revealed that Sirt1 inactivation caused increased levels of acetylated H4K16 and H3K9 but not increased levels of H3K4me1/me2, while the loss of HDAC1 induced the accumulation of H4K16ac and H3K4me1/me2 but not that of acetylated H3K9. Without wishing to be bound by theory, these analyses suggest that Sirt1 inactivation induced patterns of histone modifications that are different from those induced by the loss of HDAC1 or LSD1, except for H4K16ac. Consistent with the differential histone modifications, the loss of Sirt1 also caused gene expression patterns in F9 and PA-1 cells different from those caused by HDAC1 inactivation. While the loss of HDAC1 caused the downregulation of OCT4 and SOX2 and induced the genes for differentiation, ablation of Sirt1 did not have similar effects on the expression of these genes. Rather, Sirt1 inactivation induced the expression of HES1, which was not regulated by HDAC1 in F9 and PA-1 cells. It is likely that Sirt1 and HDAC1 regulate distinct sets of target genes due to their differences in combinatorial chromatin modifications and, possibly, compositional differences in various protein complexes in F9 and PA-1 cells.

Figure 36A:
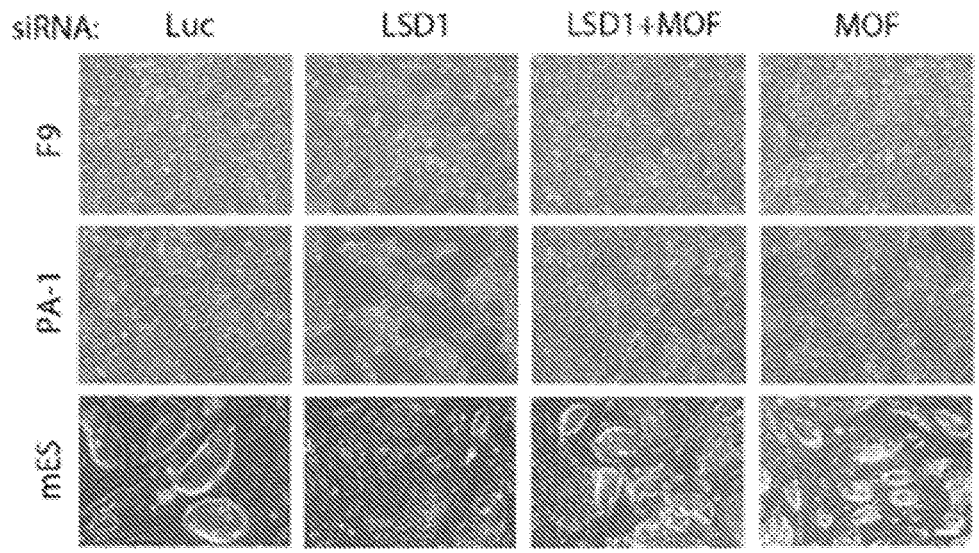
FIG. 36A-D show representative data demonstrating that HDAC1 and Sirt1 regulate the expression of different sets of genes.
Figure 36B:
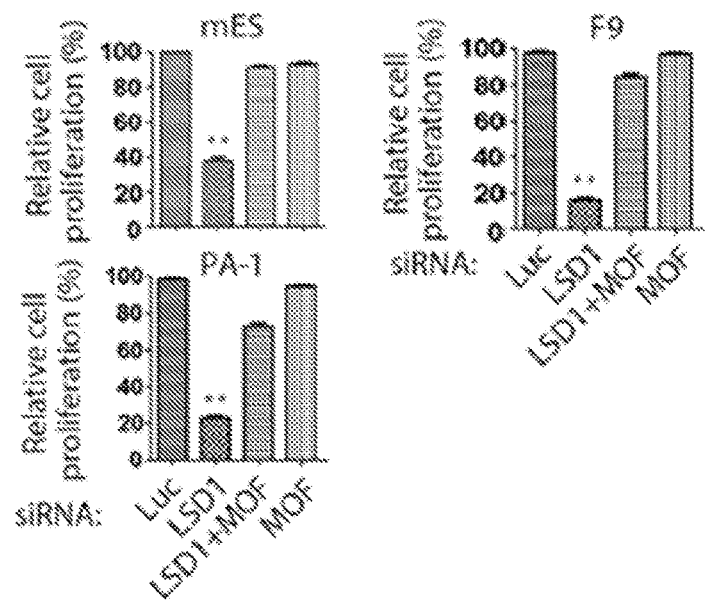
Figure 36C:
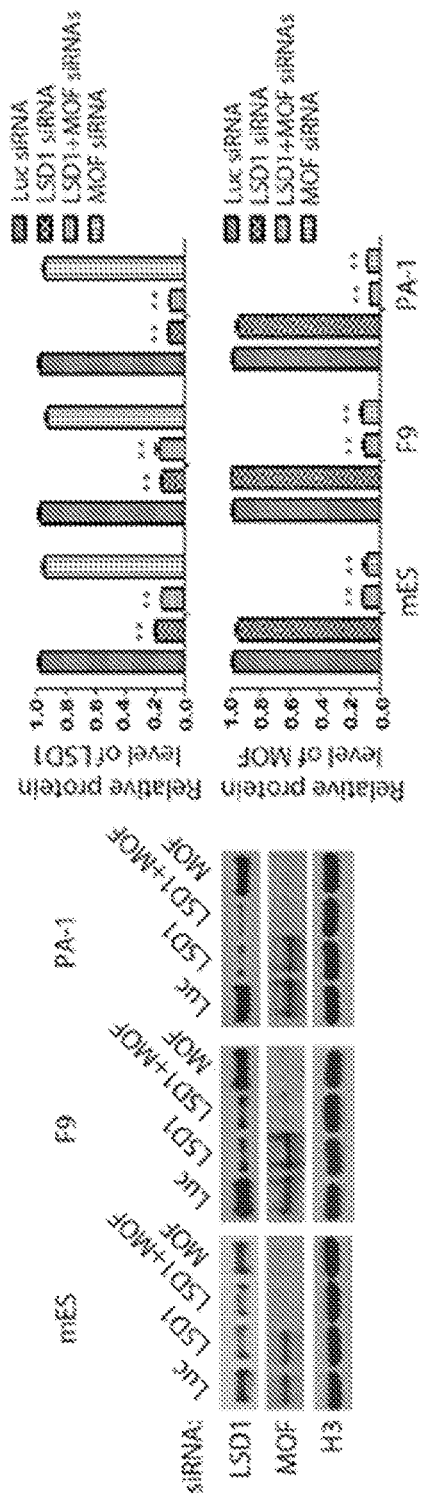

25. Loss of MOF Rescues Growth Inhibition of ES and EC Cells by LSD1 Inactivation Loss of LSD1 or HDAC1 caused the unique increase of H4K16 acetylation in ES/EC cells (FIG. 28A). If increased acetylation of H4K16 plays a critical role in the selective growth-inhibitory effects after LSD1 inhibition in ES/EC cells, reduction or elimination of the increased level of H4K16 acetylation should diminish the effects of LSD1 inactivation. To test this possibility, the effects of ablation of MOF on growth inhibition was examined after LSD1 inactivation in pluripotent mES, F9, and PA-1 cells. MOF is an acetyltransferase that usually associates with H3K4-specific methyltransferase MLL complexes to specifically acetylate H4K16 (Dou, Y., et al. (2005) *Cell* 121, 873-885). While the loss of LSD1 caused the marked growth inhibition of mES, F9, and PA-1 cells, coablation of LSD1 and MOF significantly rescued the growth inhibition caused by LSD1 deficiency in these ES/EC cells (FIG. 36A-C). However, the loss of MOF alone did not have discernible effects on the growth of ES/EC cells (FIGS. 36A and 36B).

Referring to FIG. 36A-C, F9, PA-1, and mES cells were transfected with siRNAs specific for luciferase, LSD1, LSD1 plus MOF, and MOF for 48 h. Cell growth was examined by microscopy (36A) and quantified by MTT assays (36B). Proteins were analyzed by Western blotting and quantified by the use of Gel-Pro Analyzer (version 4.0) software (33C).

Figure 36D:
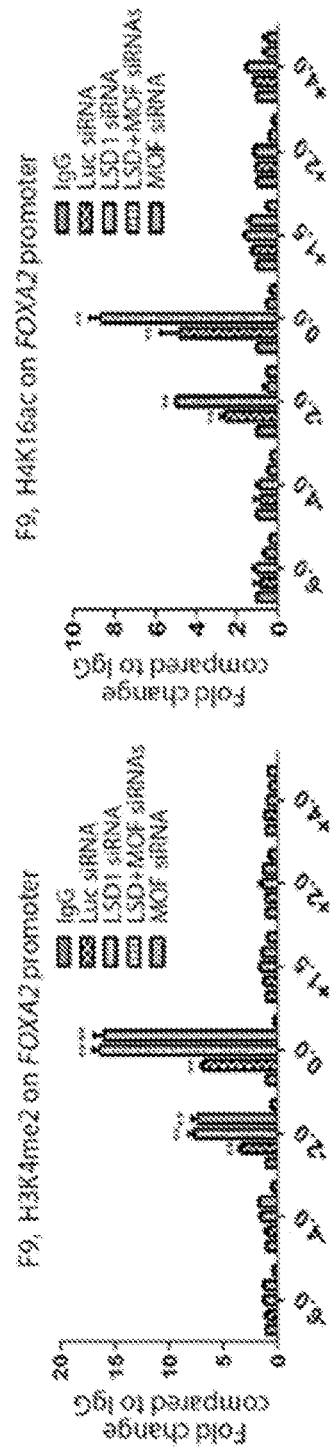
Figure 37A:
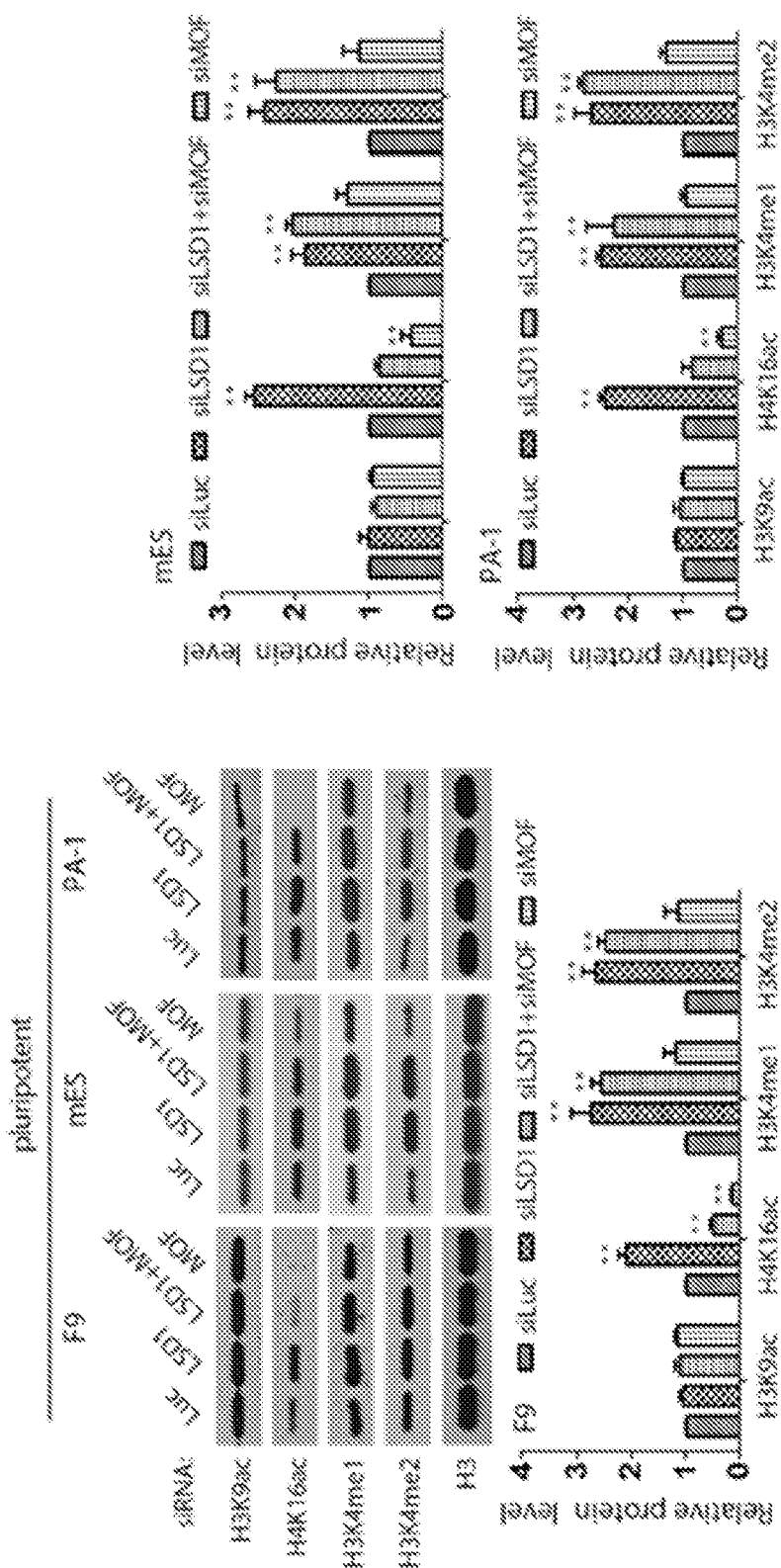

Examination of histone modifications showed that while the loss of LSD1 increased the levels of acetylated H4K16, coablation of LSD1 and MOF nearly restored the normal levels of acetylated H4K16 in LSD1-deficient cells (FIG. 37A). Interestingly, the loss of MOF did not appear to have significant effects on the global mono- and dimethylation of H3K4 or dimethylated H3K4 on the FOXA2 gene, even though it caused decreased levels of H4K16ac on FOXA2 (FIGS. 36D and 37A), suggesting that MOF acts through H4K16 acetylation to rescue the growth inhibition in ES/EC cells. Importantly, ablation of MOF is also sufficient to restore the down-regulated Oct4 and Sox2 levels in LSD1-deficient ES/EC cells (FIG. 37B) and partially suppressed the induction of differentiation genes FOXA2, HNF4A, BMP2, and EOMES in these cells (FIG. 37C). The rescuing effect is specific for MOF, as loss of another histone acetyltransferase, Tip60 (KAT5), could not rescue growth inhibition, the reduction of Oct4/Sox2, or the suppression of differentiation genes induced by LSD1 inactivation in F9 and PA-1 cells. Without wishing to be bound by theory, these studies suggest that LSD1 acts through the HDAC1- and MOF-mediated regulation of H4K16 acetylation to maintain the pluripotency of ES/EC cells.

Referring to FIG. 33D, the loss of MOF restored the levels of H4K16ac but not those of H3K4me2 on the FOXA2 gene. F9 cells were transfected with siRNAs, as indicated, and the presence of H3K4me2 and H4K16ac on FOXA2 was analyzed by ChIP using control IgG and anti-H3K4me2 and anti-H4K16ac antibodies. The results of the rescue experiments were independently confirmed three times. The error bars represent SEMs for duplicate samples. The statistical differences were analyzed by one-way ANOVA. **, P<0.01.

Referring to FIG. 37A, F9, mES, and PA-1 cells were transfected with the indicated siRNAs. Histone modifications of H3 and H4 were monitored by Western blotting and quantified by the use of Gel-Pro Analyzer (version 4.0) software. MOF inactivation reversed the increase in H4K16ac in LSD1-deficient cells.

Referring to FIGS. 37B and 37C, MOF inactivation restored the protein (12B) and mRNA (12C) levels of Oct4 and Sox2 and partially rescued the mRNA expression of differentiation genes FOXA2, BMP2, EOMES, and HNF4A in LSD1-deficient mES and F9 cells.

To eliminate the possibility of potential off-target effects of siRNAs, whether the effects of inactivation of LSD1, HDAC1, and MOF by siRNAs can be rescued by reexpression of LSD1, HDAC1, and MOF, respectively, were tested. While ablation of LSD1, HDAC1, or MOF expression using siRNAs specifically targeting the UTRs of their cognate mRNAs caused growth inhibition of F9 or PA-1 cells, re-expression of the coding cDNAs of LSD1, HDAC1, and MOF in these growth-inhibited cells restored their growth (FIG. 38). Without wishing to be bound by theory, these data suggest that LSD1, HDAC1, and MOF may indeed regulate pluripotency and cell cycle progression in these EC cells.

Figure 38A:
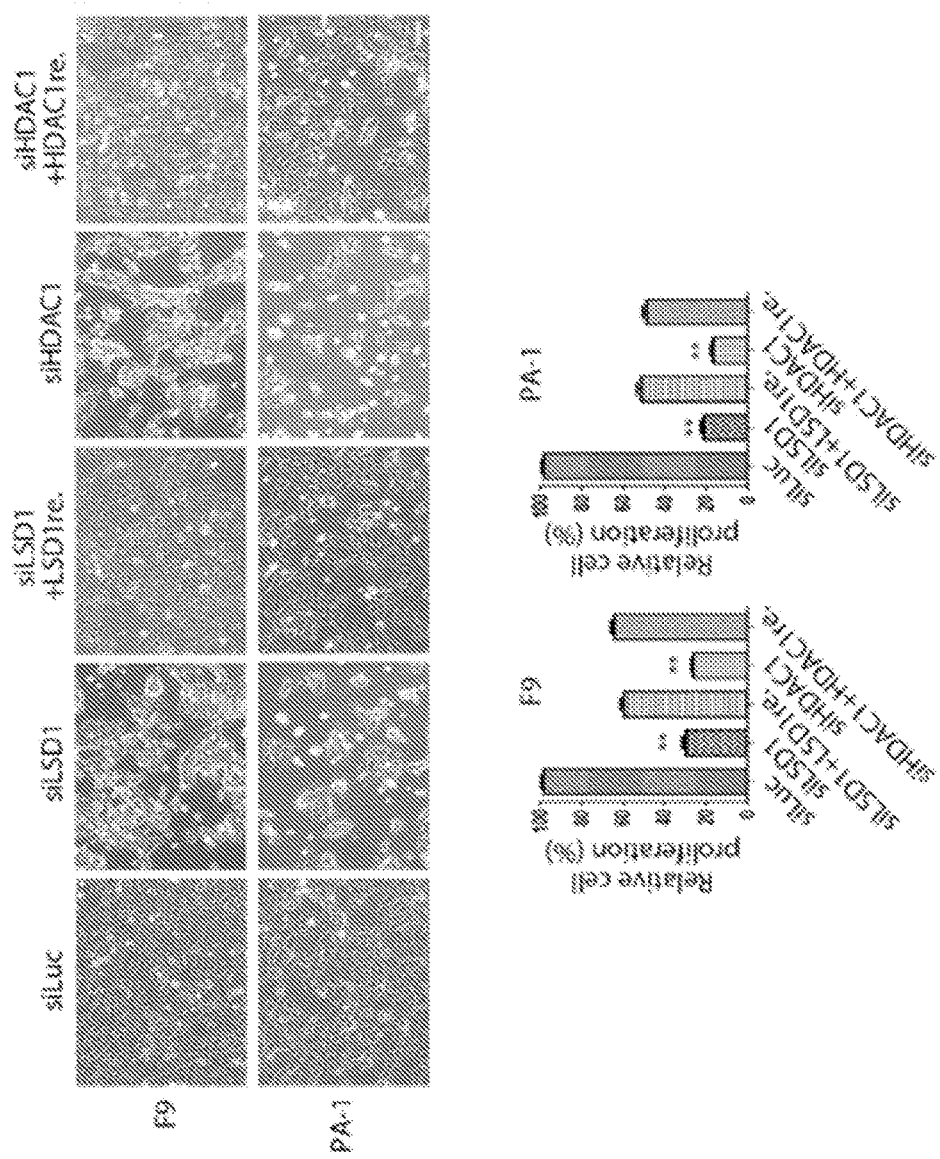
FIG. 38A-F show representative data pertaining to the restoration of LSD1, HDAC1, and MOF siRNA ablation effects by reexpression of cognate cDNAs.
Figure 38B:
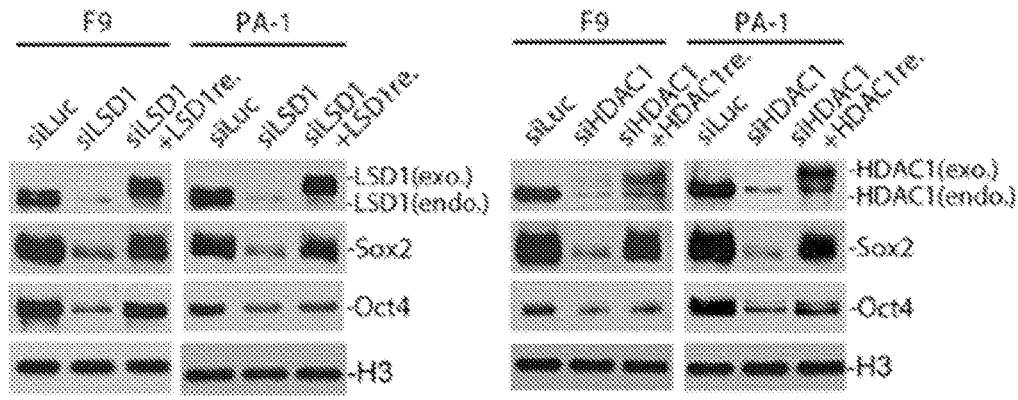
Figure 38C:
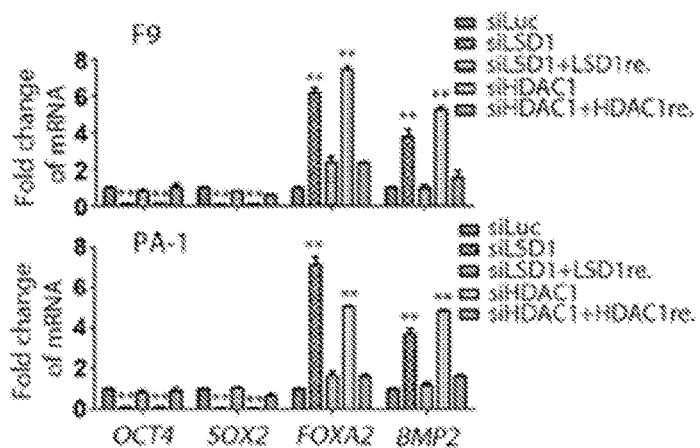

Referring to FIG. 38A-C, after they were transfected with siRNA specific for the LSD1 and HDAC1 5' or 3' UTR for 24 h, F9 and PA-1 cells were transfected with Flag-tagged LSD1 (LSD1re, where the suffix -re represents reexpression) or HDAC1 (HDAC1re) cDNA to express ectopic cDNAs for another 24 h. The transfection efficiency for re-expression was about 50 to 60%, using parallel expression of GFP on the same vector as a control. Cell growth (38A), proteins (38B), and mRNAs (38C) were analyzed to determine the effects of expression of exogenous (exo.) proteins after target gene ablation. endo., endogenous.

Figure 38D:
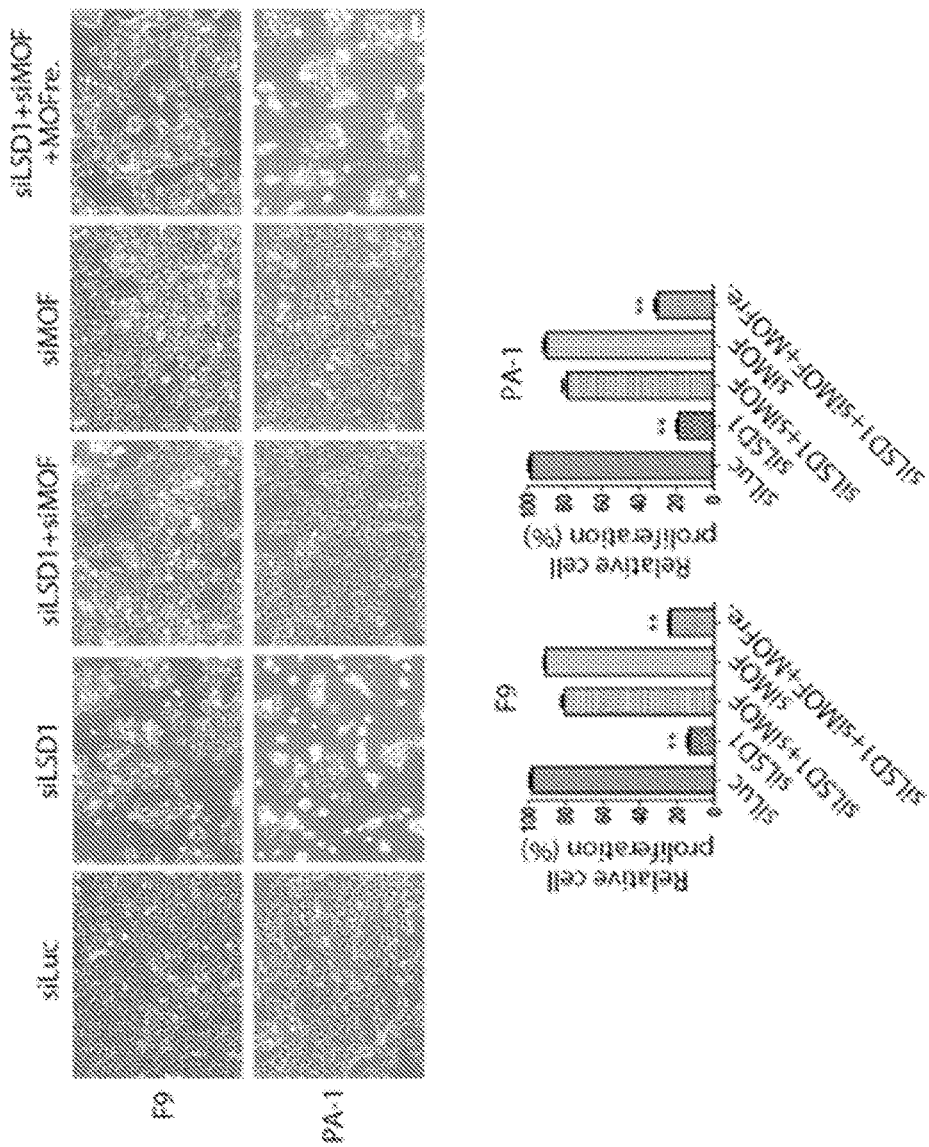
Figure 38E:
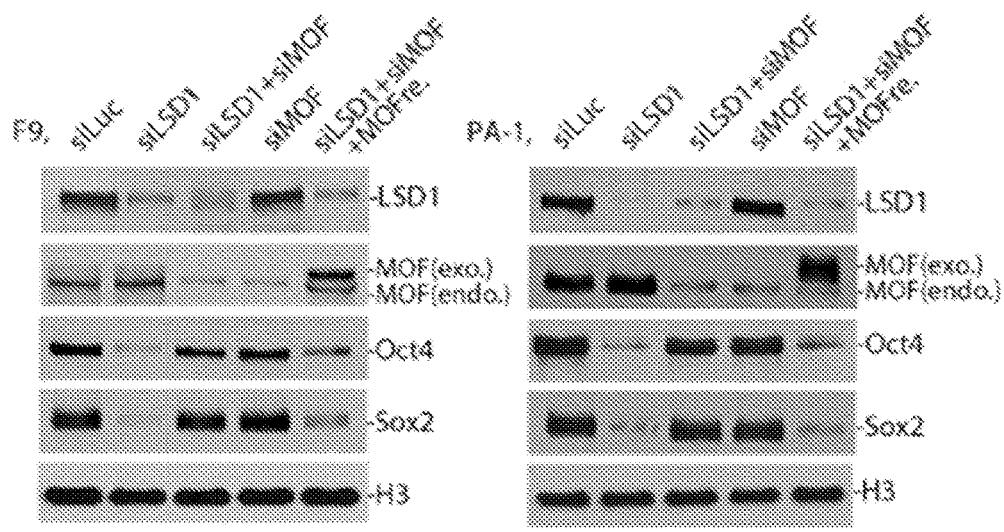
Figure 38F:
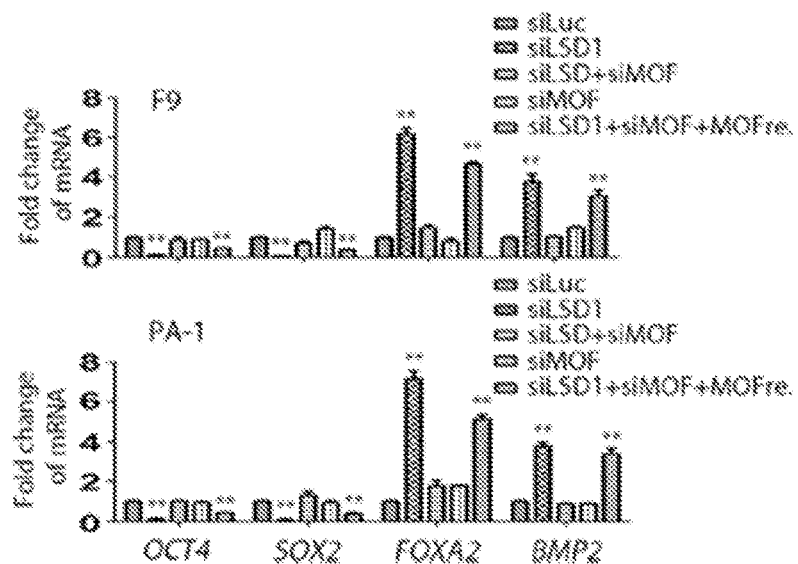
Figure 39:
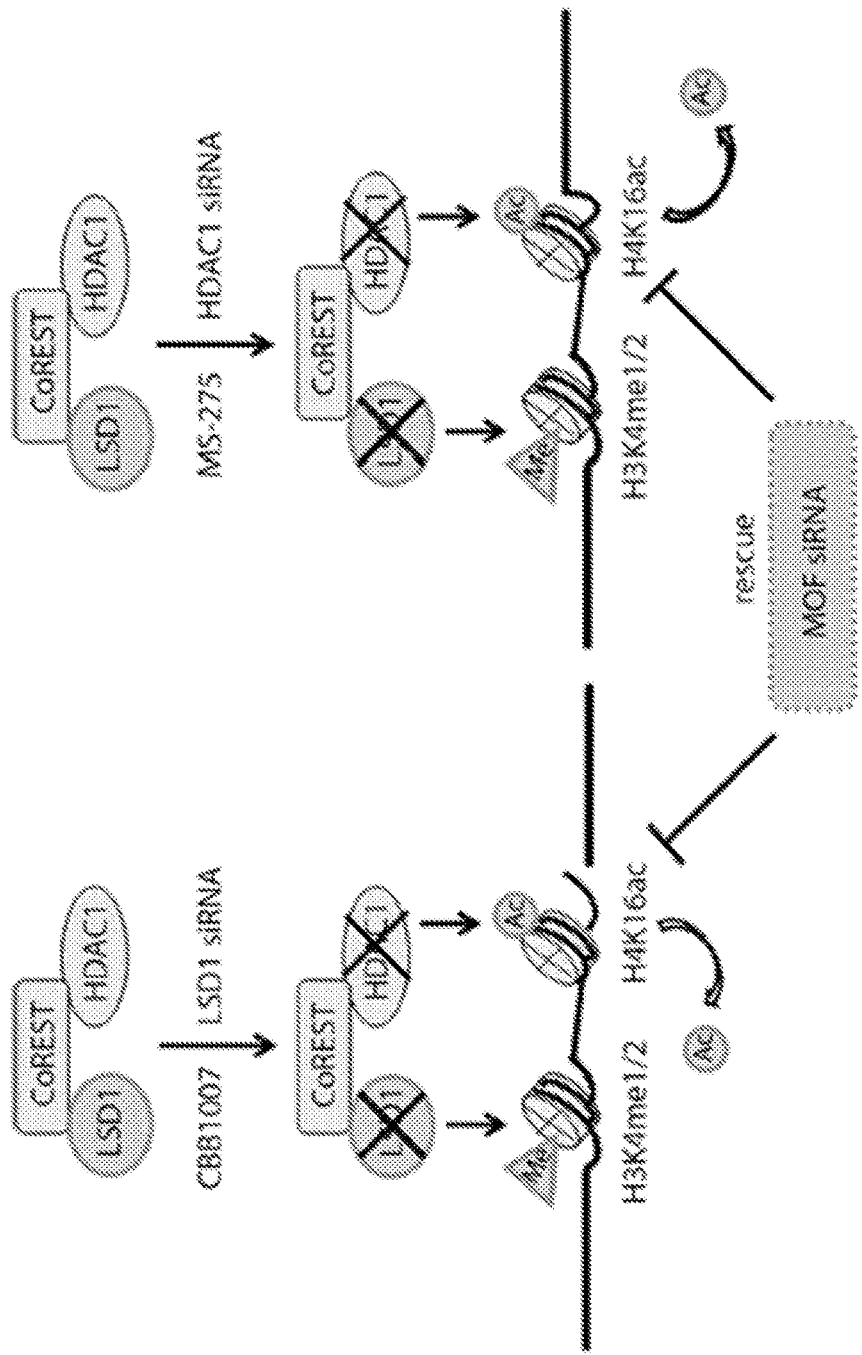
FIG. 39 shows a representative schematic summarizing LSD1- or HDAC1-regulated pluripotency of mES or EC cells through HDAC1-mediated H4K16 acetylation.
Figure 40:
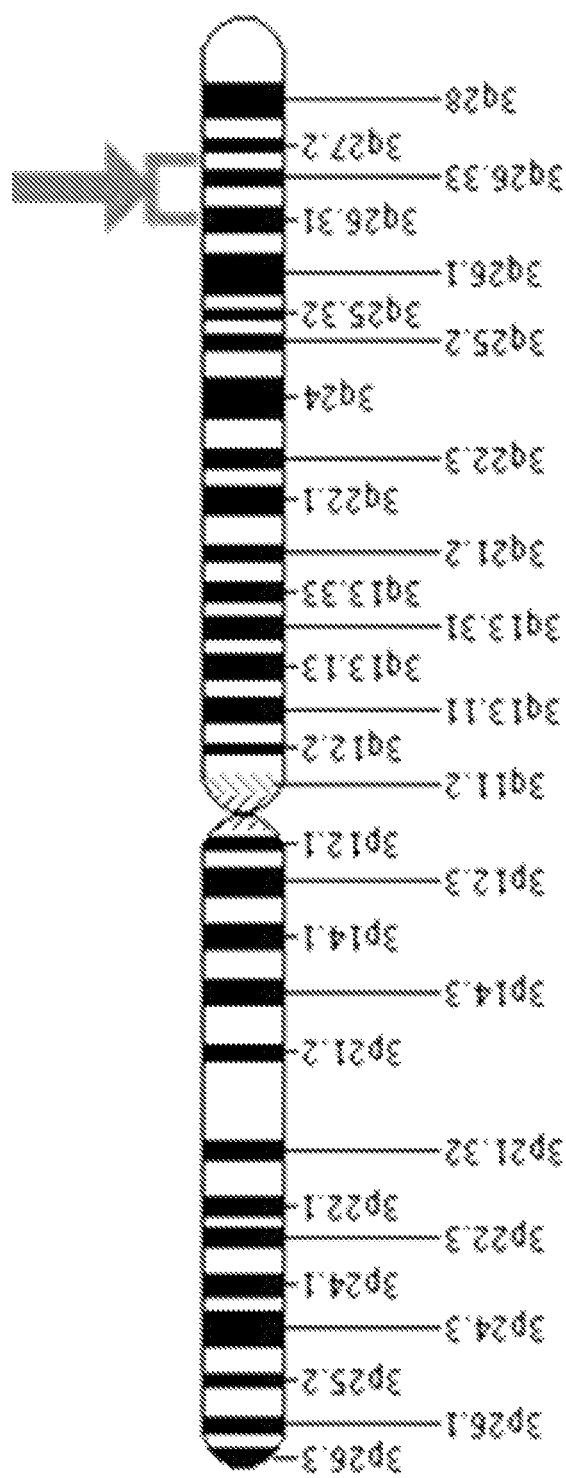
FIG. 40 shows the cytogenic location of the Sox2 configuration in the human genome.

Referring to FIG. 38D-F, the effects of re-expression of Flag-tagged MOF (MOFre) in LSD1- and MOF-ablated F9 and PA-1 cells are shown. siMOF, siRNA for MOF. Experiments were confirmed with three repeats. Error bars denote the SEMs for duplicate data. The statistical differences were analyzed by one-way ANOVA. **, P<0.01.

What is claimed is:

1. A compound having a structure represented by a formula:

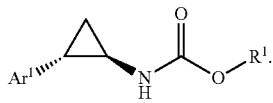

wherein $R^1$ is selected from C1-C8 alkyl, C1-C8 alkenyl, C1-C8 alkynyl, C1-C8 monohaloalkyl, C1-C8 polyhaloalkyl, C1-C8 hydroxyalkyl, $Ar^r$, and $Cy^1$;
  wherein $Ar^2$, when present, is selected from aryl and heteroaryl and wherein $Ar^2$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino;
  wherein $Cy^1$, when present, is selected from C3-C6 cycloalkyl and C2-C5 heterocycloalkyl and wherein $Cy^1$, when present, is substituted with 0, 1, 2, or 3 groups independently selected from halogen, —OH, —NH$_2$, —CN, C1-C3 alkyl, C1-C3 monohaloalkyl, C1-C3 polyhaloalkyl, C1-C3 alkoxy, C1-C3 hydroxyalkyl, C1-C3 monoalkylamino, and C1-C3 dialkylamino;
wherein $Ar^1$ is phenyl substituted with 1, 2, or 3 groups independently selected from —OR$^{12}$, —C(O)SR$^{17}$, —CONR$^{19a}$R$^{19b}$, and —SO$_2$NR$^{20a}$R$^{20b}$;
  wherein $R^{12}$, when present, is —CO$_2$R$^{21}$;
    wherein $R^{21}$, when present, is selected from hydrogen and C1-C4 alkyl;
  wherein each of $R^{17}$, $R^{19a}$, $R^{19b}$, $R^{20a}$, and $R^{20b}$, when present, is independently selected from hydrogen, C1-C4 alkyl, C1-C4 monohaloalkyl, and C1-C4 polyhaloalkyl;
or a pharmaceutically acceptable salt thereof.

2. The compound of claim 1, wherein $R^1$ is C1-C4 alkyl.

3. The compound of claim 1, wherein each of $R^{17}$, $R^{19a}$, $R^{19b}$, $R^{20a}$, and $R^{20b}$, when present, is independently selected from hydrogen and C1-C4 alkyl.

4. The compound of claim 1, wherein the compound has a structure represented by a formula:

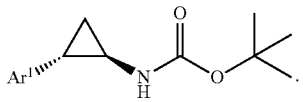

5. The compound of claim 1, wherein the compound has a structure represented by a formula:

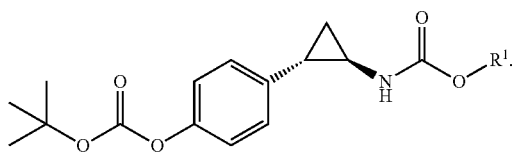

6. The compound of claim 1, wherein $R^1$ is C1-C8 alkyl.

7. The compound of claim 1, wherein $R^1$ is selected from C1-C4 alkyl, C1-C4 alkenyl, C1-C4 alkynyl, C1-C4 monohaloalkyl, C1-C4 polyhaloalkyl, C1-C4 hydroxyalkyl, $Ar^2$ and $Cy^2$.

8. The compound of claim 1, wherein $R^1$ is selected from C1-C4 alkyl, C1-C4 alkenyl, and C1-C4 alkynyl.

9. The compound of claim 1, wherein $R^1$ is selected from n-propyl, i-propyl, n-butyl, i-butyl, s-butyl, and t-butyl.

10. The compound of claim 1, wherein $R^1$ is selected from n-butyl, i-butyl, s-butyl, and t-butyl.

11. The compound of claim 1, wherein $Ar^1$ is phenyl monosubstituted with a group selected from —OR$^{12}$, —C(O)SR$^{17}$, —CONR$^{19a}$R$^{19b}$, and —SO$_2$NR$^{20a}$R$^{20b}$.

12. The compound of claim 1, wherein $Ar^1$ is phenyl substituted with 1, 2, or 3 —OCO$_2$R$^{21}$ groups.

13. The compound of claim 1, wherein $R^{21}$, when present, is C1-C4 alkyl.

14. The compound of claim 1, wherein $R^{21}$, when present, is selected from n-propyl, propyl, n-butyl, i-butyl, s-butyl, and t-butyl.

15. The compound of claim 1, wherein $R^{21}$, when present, is t-butyl.

16. The compound of claim 1, wherein each of $R^{17}$, $R^{19a}$, $R^{19b}$, $R^{20a}$, and $R^{20b}$, when present, is C1-C4 alkyl.

17. The compound of claim 1, wherein each of $R^{17}$, $R^{19a}$, $R^{19b}$, $R^{20a}$, and $R^{20b}$, when present, is independently selected from hydrogen, n-propyl, i-propyl, n-butyl, i-butyl, s-butyl, and t-butyl.

18. The compound of claim 1, wherein each of $R^{17}$, $R^{19a}$, $R^{19b}$, $R^{20a}$, and $R^{20b}$, when present, is independently selected from hydrogen and t-butyl.

19. The compound of claim 1, having a structure represented by a formula selected from:

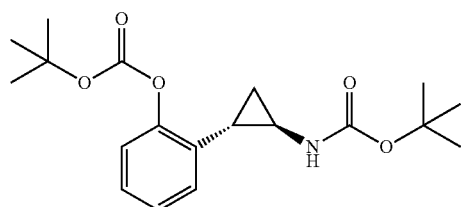

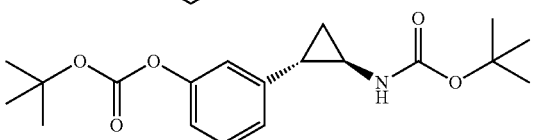

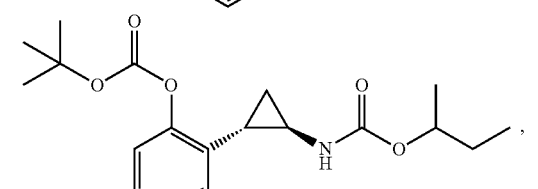

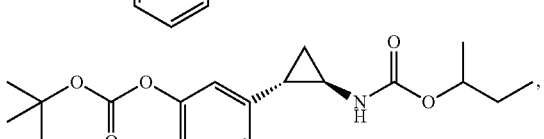

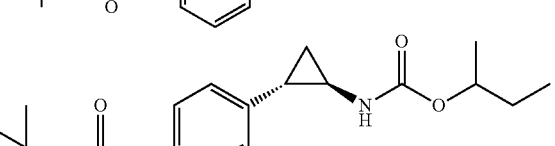

307
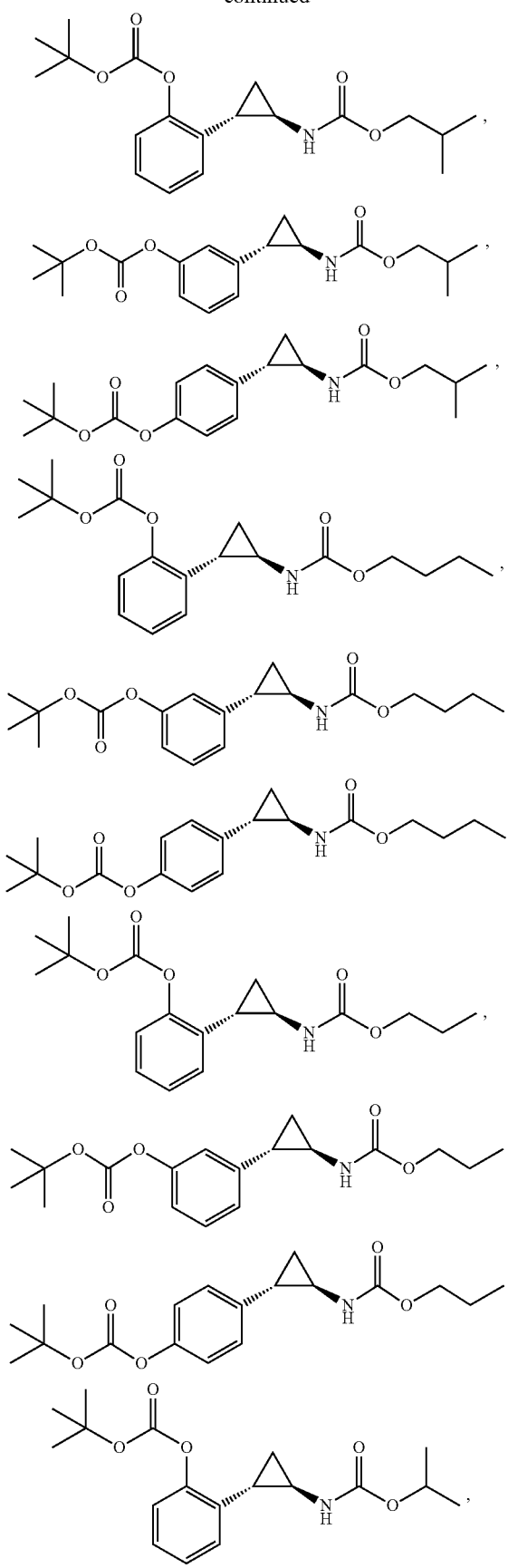
308
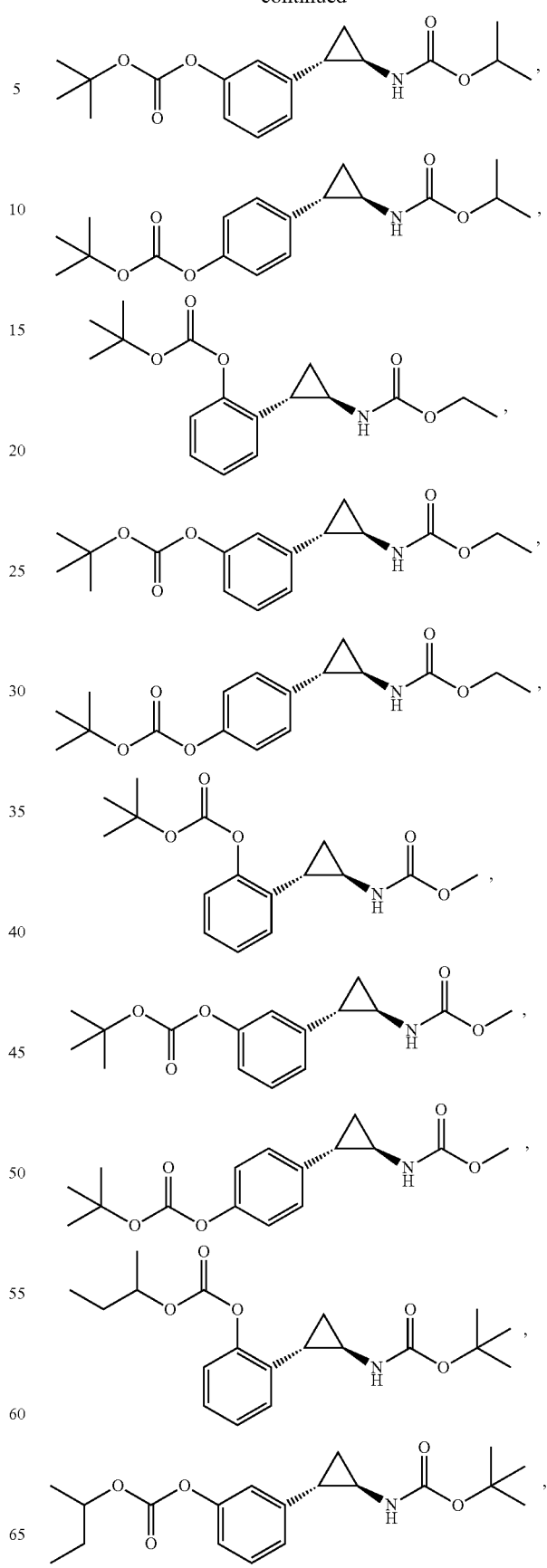

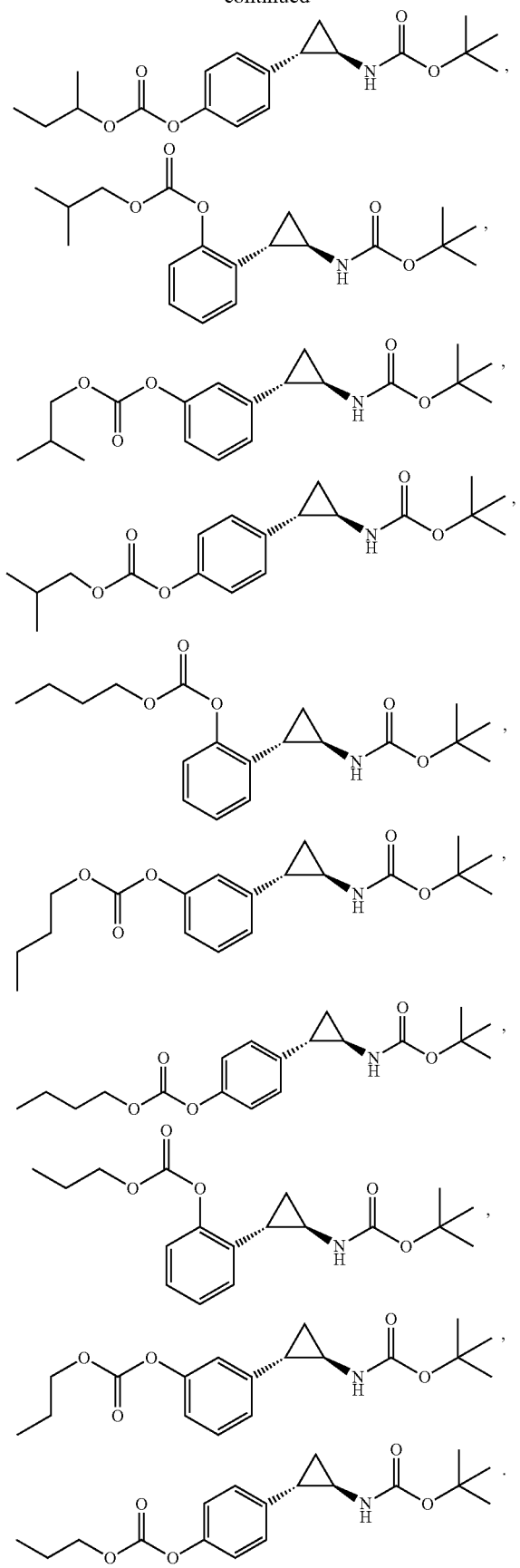
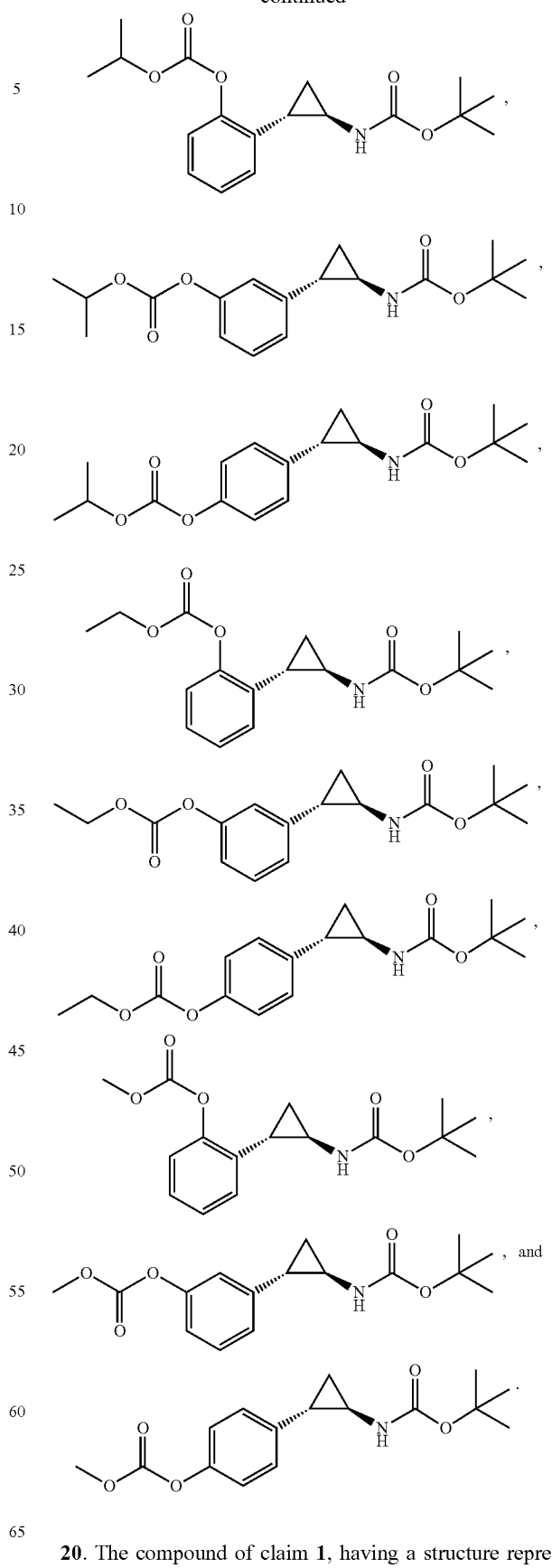
20. The compound of claim 1, having a structure represented by a formula:

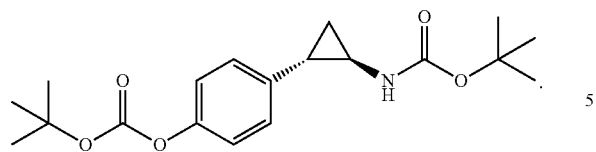
* * * * *